(12) United States Patent
Jadhav et al.

(10) Patent No.: US 7,858,769 B2
(45) Date of Patent: Dec. 28, 2010

(54) RNA INTERFERENCE MEDIATED INHIBITION OF GENE EXPRESSION USING MULTIFUNCTIONAL SHORT INTERFERING NUCLEIC ACID (MULTIFUNCTIONAL SINA)

(75) Inventors: Vasant Jadhav, Longmont, CO (US); Shawn Zinnen, Denver, CO (US)

(73) Assignee: Sirna Therapeutics, Inc., San Francisco, CA (US)

( * ) Notice: Subject to any disclaimer, the term of this patent is extended or adjusted under 35 U.S.C. 154(b) by 674 days.

(21) Appl. No.: 10/597,755

(22) PCT Filed: Feb. 9, 2005

(86) PCT No.: PCT/US2005/004270

§ 371 (c)(1), (2), (4) Date: May 22, 2007

(87) PCT Pub. No.: WO2005/078097

PCT Pub. Date: Aug. 25, 2005

(65) Prior Publication Data

US 2008/0039412 A1    Feb. 14, 2008

Related U.S. Application Data

(63) Continuation-in-part of application No. PCT/US2004/016390, filed on May 24, 2004.

(60) Provisional application No. 60/543,480, filed on Feb. 10, 2004.

(51) Int. Cl.
*C07H 21/04* (2006.01)

(52) U.S. Cl. .................. 536/24.5; 536/24.31; 536/24.1; 435/6; 435/325; 435/375; 514/44

(58) Field of Classification Search ........................ None
See application file for complete search history.

(56) References Cited

U.S. PATENT DOCUMENTS

| | | | |
|---|---|---|---|
| 5,587,471 A | 12/1996 | Cook et al. | |
| 5,814,620 A | 9/1998 | Robinson et al. | |
| 5,898,031 A | 4/1999 | Crooke | |
| 5,998,148 A | 12/1999 | Bennett et al. | |
| 5,998,203 A * | 12/1999 | Matulic-Adamic et al. | 435/325 |
| 5,998,206 A | 12/1999 | Cowsert | |
| 6,060,456 A | 5/2000 | Arnold et al. | |
| 6,107,094 A | 8/2000 | Crook | |
| 6,214,805 B1 | 4/2001 | Torrence et al. | |
| 6,346,398 B1 | 2/2002 | Pavco et al. | |
| 6,506,559 B1 | 1/2003 | Fire et al. | |
| 6,573,099 B2 | 6/2003 | Graham et al. | |
| 6,824,972 B2 | 11/2004 | Kenwrick et al. | |
| 7,022,828 B2 | 4/2006 | McSwiggen et al. | |
| 7,078,196 B2 | 7/2006 | Tuschl et al. | |
| 2002/0086356 A1 | 7/2002 | Tuschl et al. | |
| 2002/0151693 A1 | 10/2002 | Breaker et al. | |
| 2003/0059944 A1 | 3/2003 | Lois-Caballe et al. | |
| 2003/0064945 A1 | 4/2003 | Akhtar et al. | |
| 2003/0083294 A1 * | 5/2003 | Sullenger et al. | 514/44 |
| 2003/0143732 A1 | 7/2003 | Fosnaugh et al. | |
| 2003/0190635 A1 | 10/2003 | McSwiggen et al. | |
| 2003/0206887 A1 | 11/2003 | Morrissey et al. | |
| 2004/0019001 A1 | 1/2004 | McSwiggen et al. | |
| 2004/0053876 A1 * | 3/2004 | Turner et al. | 514/44 |
| 2004/0161844 A1 | 8/2004 | Baker et al. | |
| 2004/0259247 A1 * | 12/2004 | Tuschl et al. | 435/375 |
| 2005/0020521 A1 * | 1/2005 | Rana | 514/44 |
| 2005/0182005 A1 | 8/2005 | Tuschl et al. | |
| 2005/0227256 A1 | 10/2005 | Hutvagner et al. | |

FOREIGN PATENT DOCUMENTS

| | | |
|---|---|---|
| AU | 2001240375 | 3/2001 |
| CA | 2359180 | 8/2000 |
| EP | 1144623 B1 | 1/2002 |
| EP | 1325955 | 1/2002 |
| EP | 1389637 | 8/2002 |
| JP | 08208687 | 8/1996 |
| WO | 90/14090 | 11/1990 |
| WO | 94/01550 | 1/1994 |

(Continued)

OTHER PUBLICATIONS

Caplen NJ. RNAi as a Gene Therapy Approach. Expert Opinon. Biol. Thera. (2003) vol. 3(4) 575-586. Ashley Publications Ltd.*

(Continued)

*Primary Examiner*—Kimberly Chong

(57) ABSTRACT

The present invention concerns methods and nucleic acid based reagents useful in modulating gene expression in a variety of applications, including use in therapeutic, veterinary, agricultural, diagnostic, target validation, and genomic discovery applications. Specifically, the invention relates to multifunctional short interfering nucleic acid (multifunctional siNA) molecules that modulate the expression of one or more genes in a biologic system, such as a cell, tissue, or organism via RNA interference (RNAi). The bifunctional short interfering nucleic acid (multifunctional siNA) molecules of the invention can target more than one regions of nucleic acid sequence in a single target nucleic acid molecule or can target regions of nucleic acid sequence in differing target nucleic acid molecules. The self multifunctional siNA molecules are useful in the treatment of any disease or condition that responds to modulation of gene expression or activity in a cell, tissue, or organism.

16 Claims, 11 Drawing Sheets

FOREIGN PATENT DOCUMENTS

| | | |
|---|---|---|
| WO | 95/04142 | 2/1995 |
| WO | 99/04819 | 2/1999 |
| WO | 99/07409 | 2/1999 |
| WO | 99/14226 | 3/1999 |
| WO | 99/32619 | 7/1999 |
| WO | 99/49029 | 9/1999 |
| WO | 99/53050 | 10/1999 |
| WO | 99/55857 | 11/1999 |
| WO | 99/61631 | 12/1999 |
| WO | 00/01846 | 1/2000 |
| WO | 00/21560 | 4/2000 |
| WO | 00/44895 | 8/2000 |
| WO | 00/44914 | 8/2000 |
| WO | 00/49035 | 8/2000 |
| WO | 00/63364 | 10/2000 |
| WO | 01/04313 | 1/2001 |
| WO | 01/29058 | 4/2001 |
| WO | 01/36646 | 5/2001 |
| WO | 01/38551 | 5/2001 |
| WO | 01/42443 | 6/2001 |
| WO | 01/49844 | 7/2001 |
| WO | 01/53475 | 7/2001 |
| WO | 01/68836 | 9/2001 |
| WO | 01/70944 | 9/2001 |
| WO | 01/70949 | 9/2001 |
| WO | 01/72774 | 10/2001 |
| WO | 01/75164 | 10/2001 |
| WO | 01/92513 | 12/2001 |
| WO | 01/96584 | 12/2001 |
| WO | 01/97850 | 12/2001 |
| WO | 02/07747 | 1/2002 |
| WO | 02/55692 | 1/2002 |
| WO | 02/55693 | 1/2002 |
| WO | 02/10378 | 2/2002 |
| WO | 02/22636 | 3/2002 |
| WO | 02/38805 | 5/2002 |
| WO | 02/44321 | 6/2002 |
| WO | 03/044188 | 11/2002 |
| WO | 02/096927 | 12/2002 |
| WO | 03/064625 | 8/2003 |
| WO | 03/064626 | 8/2003 |
| WO | 03/068797 | 8/2003 |
| WO | 03/070887 | 8/2003 |
| WO | 03/070896 | 8/2003 |
| WO | 03/070910 | 8/2003 |
| WO | 03/070918 | 8/2003 |
| WO | 03/074654 | 9/2003 |
| WO | 03/080638 | 10/2003 |
| WO | 2004/029212 | 4/2004 |
| WO | 2004/043977 | 5/2004 |
| WO | 2004/048566 | 6/2004 |
| WO | 2004/072261 | 8/2004 |
| WO | 2004/090105 | 10/2004 |
| WO | 2005/019453 | 3/2005 |
| WO | 2005/049821 | 6/2005 |

OTHER PUBLICATIONS

Parrish et al. Functional Anatomy of a dsRNA trigger: differential requirements for the two trigger strands in RNA interference. Molecular Cell, 2000, vol. 6: 1077-1087.*

Braasch et al. Novel Antisense and Peptide Nucleic Acid Strategies for Controlling Gene Expression. Biochemistry 2002, Vo. 41(14): 4503-4510.*

Pieken et al. Kinetic Characterization of Ribonuclease-Resistant 2'-Modified Hammerhead Ribozymes. Science, 1991, vol. 253: pp. 314-317.*

Adah et al., "Chemistry and Biochemistry of 2',5'-Oligoadenylate-Based Antisense Strategy," *Current Medicinal Chemistry*, 8, 1189-1212 (2001).

Alexeev et al., "Localized in vivo genotypic and phentypic correction of the albino mutation in skin by Rna-Dna oligonucleotide," *Nature Biotechnology*, 18:43-47 (2000).

Bahramian et al., "Transcriptional and Posttranscriptional Silencing of Rodent α1(I) Collagen by a Homologous Transcriptionally Self-Silenced Transgene," *Molecular and Cellular Biology*, 274-283 (1999).

Bass, "Double-Stranded RNA as a Template for Gene Silencing," *Cell*, 101, 235-238 (2000).

Bass, "The short answer," *Nature* 411:428-429 (2001).

Bayard et al., "Increased stability and antiviral activity of 2'-O-phosphoglyceryl derivatives of (2'-5')oligo(adenylate)," *Eur. J. Biochem.*, 142(29):291-298 (1984).

Beigelman et al., "Chemical Modification of Hammerhead Ribozymes," *The Journal of Biological Chemistry* 270:25702-25708 (1995).

Bellon et al., "4-Thio-oligo-β-D-ribonucleotides: synthesis of β-4'-thio-oligouridylates, nuclease resistance, base pairing properties, and interaction with HIV-1 reverse transcriptase," *Nucleic Acids Research*, 21(7):1587-1593 (1993).

Bernstein et al., "Role for a Bidentate Ribonuclease in the Initiation Step of RNA Interference," Nature 409:363-366 (2001).

Bernstein et al., "The rest is silence," *RNA*, 7:1509-1521 (2001).

Bitko et al., "Phenotypic silencing of cytoplasmic genes using sequence-specific double-stranded short interfering RNA and its application in the reverse genetics of wild type negative-strand RNA viruses," *BMC Microbiology*, 1:34 (11 pgs) (2001).

Braasch et al., "Novel Antisense and Peptide Nucleic Acid Strategies for Controlling Gene Expression," *Biochemistry*, 31:14, 4503-4510 (2002).

Braasch et al., "RNA Inteference in Mammalian Cells by Chemically-Modified RNA," *Biochemistry*, 42, 7967-7975 (2003).

Caplen, Natasha J., "RNAi as a gene therapy approach," *Expert Opin. Biol. Ther.*, 3(4):575-586 (2003).

Chiu et al., "siRNA function in RNAi: A chemical modification analysis," RNA, 9:1034-1048 (2003).

Claverie, Jean-Michel, "Fewer Genes, More Noncoding RNA," *Science*, 309, 1529-1530 (2005).

Clemens et al., "The Double-Stranded RNA-Dependent Protein Kinase PKR: Structure and Function," *Journal of Interferon and Cytokine Research*, 17:503-524 (1997).

Czech, Michael P., "MicroRNAs as Therapeutic Targets," *The New England Journal of Medicine*, 354, 1194-1195 (2006).

Elbashir et al., "Analysis of gene function in somatic mammalian cells using small interfering RNAs," *Methods*, 26:199-213 (2002).

Elbashir et al., "Duplexes of 21-nucleotide RNAs mediate RNA interference in cultured mammalian cells," *Nature* 411:494-498 (2001).

Elbashir et al., "RNA Interference is Mediated by 21—and 22-Nucleotide RNAs," Genes and Development 15:188-200 (2001).

Fire et al., "Potent and Specific Genetic Interference by Double-Stranded RNA in *Caenorhabditis elegans*," Nature 391:806-811(1998).

Fire, "RNA-triggered Gene Silencing," *TIG* 15:358-363(1999).

Futami et al., "Induction of Apoptosis in HeLa Cells with siRNA Expression Vector Targeted Against bcl-2," *Nucleic Acids Research Supplement* 2:251-252 (2002).

Hamasaki et al., "Short interfering RNA-directed inhibition of hepatitis B virus replication," *FEBS Letters*, 543:51-54 (2003).

Hamilton, et al., "A Species of Small Antisense RNA in Post-transcriptional Gene Silencing in Plants," *Science*, 286, 950-952 (1999)).

Hammond et al., "An RNA-Directed Nuclease Mediates Post-Transcriptional Gene Silencing in *Drosophila* Cells," Nature 404:293-296 (2000).

Hammond et al., "Post-Transcriptional Gene Silencing by Double-Stranded RNA," *Nature*, 2:110-119 (2001).

Harborth et al., "Sequence, Chemical, and Structural Variation of Small Interfering RNAs and Short Hairpin RNAs and the Effect on Mammalian Gene Silencing," *Antisense and Nucleic Acid Drug Development*, 13:83-105 (2003).

Hasan et al., "VEGF antagonists," *Oncologic, Metabolic & Endocrine*, 703-718 (2001).

Holen et al., "Positional effects of short interfering RNAs targeting the human coagulation trigger Tissue Factor," *Nucleic Acids Research*, 30:8, 1757-1766 (2002).

Hornung et al., "Sequence-specific potent induction of IFN-α by short interfering RNA in plasmacytoid dendritic cells through TLR7," *Nature Medicine*, 11, 263-270 (2005).

Hutvagner et al., "A Cellular Function for the RNA-Interference Enzyme Dicer in the Maturation of the let-7 Small Temporal RNA," Science 293:834-838 (2001).

Jen et al., "Suppression of gene Expression by Targeted Disruption of Messenger RNA: Available Options and Current Strategies," Stem Cells, 18:307-319 (2000).

Judge et al., "Sequence-dependent stimulation of the mammalian innate immune response by synthetic siRNA," *Nature Biotechnology*, 23(4):457-462 (2005).

Kawaski et al., "Uniformly Modified 2'-Modified 2'-Deoxy-2'-fluoro Phosphorothioate Oligonucleotides as Nuclease-Resistant Antisense Compounds with High Affinity and Specificity for RNA Targets," *J. Med. Chem.*, 36, 831-841 (1993).

Kuwabara et al., "A C. elegans patched gene, ptc-1, functions in germ-line cytokinesis," *Genes and Development*, 14(15):1933-1944 (2000).

Lin et al., "A Novel mRNA-cRNA Interference Phenomenon for Silencing bcl-2 Expression in Human LNCaP Cells," Biochemical and Biophysical Research Communications, 281, 639-644 (2001).

Lin et al., "Policing rogue genes," Nature, 402, 128-129 (1999).

Martinez et al., "Single-Stranded Antisense siRNAs Guide Target RNA Cleavage in RNAi," *Cell* 110:563-574 (2002).

Mattick, John S., "The Functional Genomics of Noncoding RNA", Science, 309, 1527-1528 (2005).

McCaffrey et al., "RNA interference in adult mice," Nature, 148, 38-39 (2002).

Monia et al., "Evaluation of 2'-Modified Oligonucleotides Containing 2'-Deoxy Gaps as Antisense Inhibitors of Gene Expression," *J. Biol. Chem.* 268:14514-14522 (1993).

Morvan et al., "Comparative Evaluation of Seven Oligonucleotide Analogues as Potential Antisense Agents," *J. Med. Chem.*, 36, 280-287 (1993).

Olie et al., "Analysis of ribosyl-modified, mixed backbone analogs of a bcl-2/bcl-xL antisense oligonucleotide," *Biochimica et Biophysica Acta*, 1576, 101-109 (2002).

Opalinska et al., "Nucleic-Acid Therapeutics: Basic Principles and Recent Applications," *Nature Reviews Drug Discovery*, (1):503-514 (2002).

Parrish, "Functional Anatomy of a dsRNA Trigger: Differential Requirement for the Two Trigger Strands in RNA Interference," Molecular Cell 6:1077-1087 (2000).

Schmidt et al., "Base and sugar requirements for RNA cleavage of essential nucleoside residues in internal loop B of the hairpin ribozyme: implications for secondary structure," *Nucleic Acids Research* 24:573-581 (1996).

Sethupathy et al., "TarBase: A comprehensive database of experimentally supported animal microRNA targets," *RNA*, 12:192-197 (2006).

Sharp et al., "RNAi and double-strand RNA," *Genes & Development*, 13:139-141 (1999).

Strauss, Evelyn, "Molecular Biology: Candidate 'Gene Silencers' Found," Molecular Biology, vol. 286, No. 5441, p. 886 (1999) [sometimes mistakenly referred to as being published in *Science*].

Thomson et al., "Activity of hammerhead ribozymes containing non-nucleotidic linkers," *Nucleic Acids Research* 21:5600-5603 (1993) (May Be Referred to as Thompson).

Tuschl et al., "Small Interfering RNAs: A Revolutionary Tool for Analysis of Gene Function and Gene Therapy," Molecular Interventions, 295, 3, 158-167 (2002).

Tuschl et al., "Targeted mRNA Degradation by Double-Stranded RNA In Vitro," *Genes & Development* 13: 3191-3197 (1999).

Tuschl, "RNA Interference and Small Interfering RNAs," *Chembiochem* 2:239-245 (2001).

Vickers et al., "Efficient Reduction of Target RNAs by Small Interfering RNA and RNase H-dependent Antisense Agents," *Journal of Biological Chemistry*, 278, 7108-7118 (2003).

Waterhouse et al., "Virus resistance and gene silencing in plants can be induced by simultaneous expression of sense and antisense RNA," Proc. Natl. Acad. Sci. USA, 95, 13959-13964 (1998).

Wianny and Zernicka-Goetz et al., "Specific Interference with Gene Function by Double-Stranded RNA in Early Mouse Development," *Nature Cell Biology* 2:70-75 (2000).

Zamore et al., "RNAi: Double-Stranded RNA Directs the ATP-Dependent Cleavage of mRNA at 21 to 23 Nucleotide Intervals," *Cell* 101:25-33 (2000).

Zhang et al., "Single Processing Center Models for Human Dicer and Bacterial RNase III," *Cell*, 118:57-68 (2004).

Anderson et al., "Bispecific Short Hairpin siRNA Constructs Targeted to CD4, CXCR4, and CCR5 Confer HIV-1 Resistance," Oligonucleotides, 13:303-312 (2003).

Elbashir et al., "Functional Anatomy of siRNAs for Mediating Efficient RNAi in Drosophila Melanogaster Embryo Lysate," The EMBO Journal 20:6877-6888 (2001).

Leirdal et al., "Gene silencing in mammalian cells by preformed RNA duplexes," Biochemical and Biophysical Research Communications, 295, 744-748 (2002).

* cited by examiner

Figure 1: Examples of double stranded multifunctional siNA constructs with distinct complementary regions
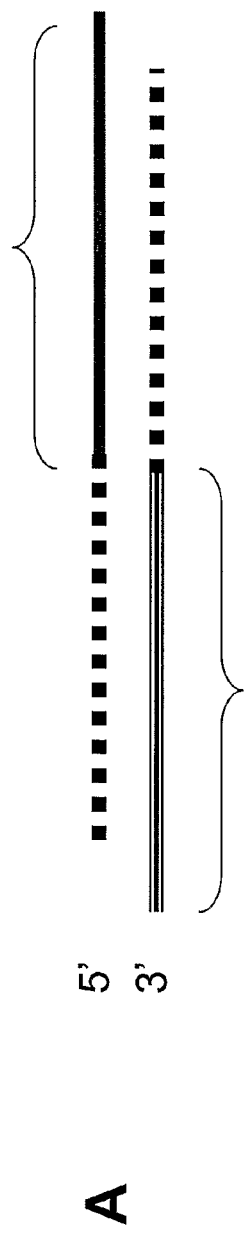
A
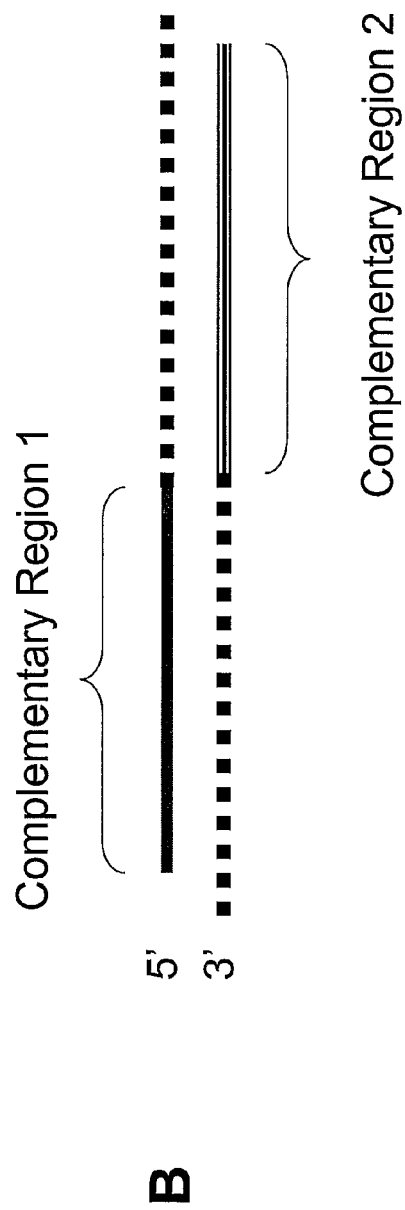
B

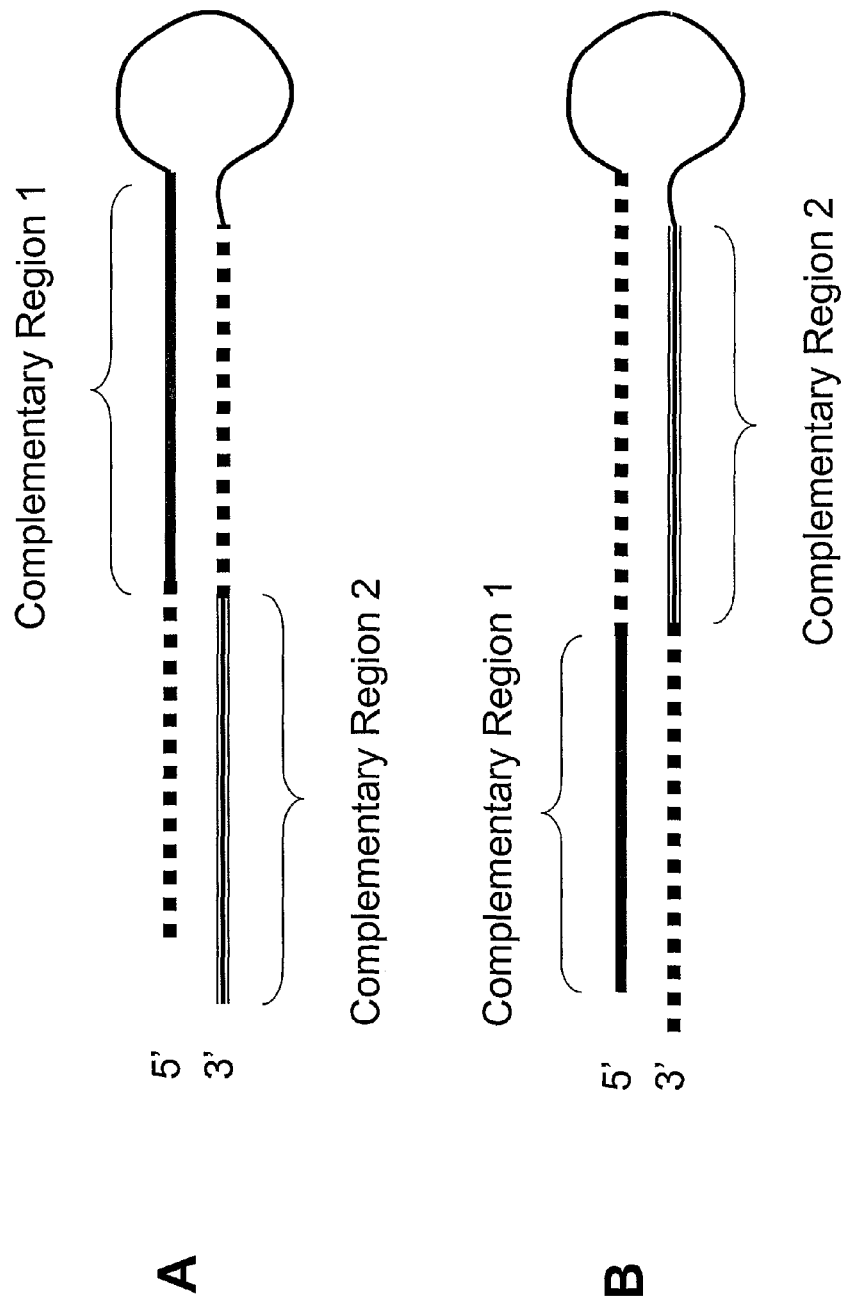
Figure 2: Examples of hairpin multifunctional siNA constructs with distinct complementary regions

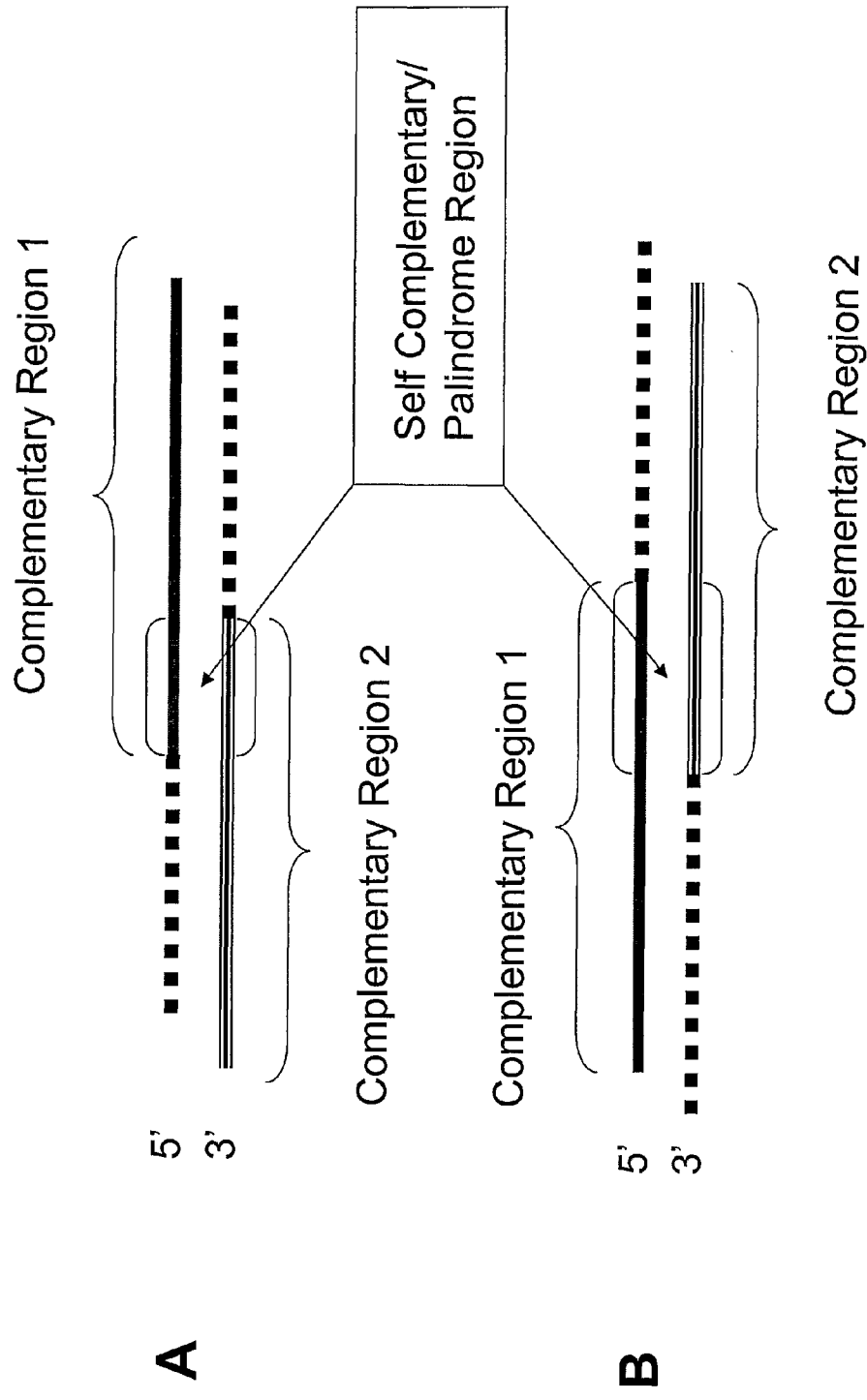
Figure 3: Examples of double stranded multifunctional siNA constructs with distinct complementary regions and a self complementary/palindrome region

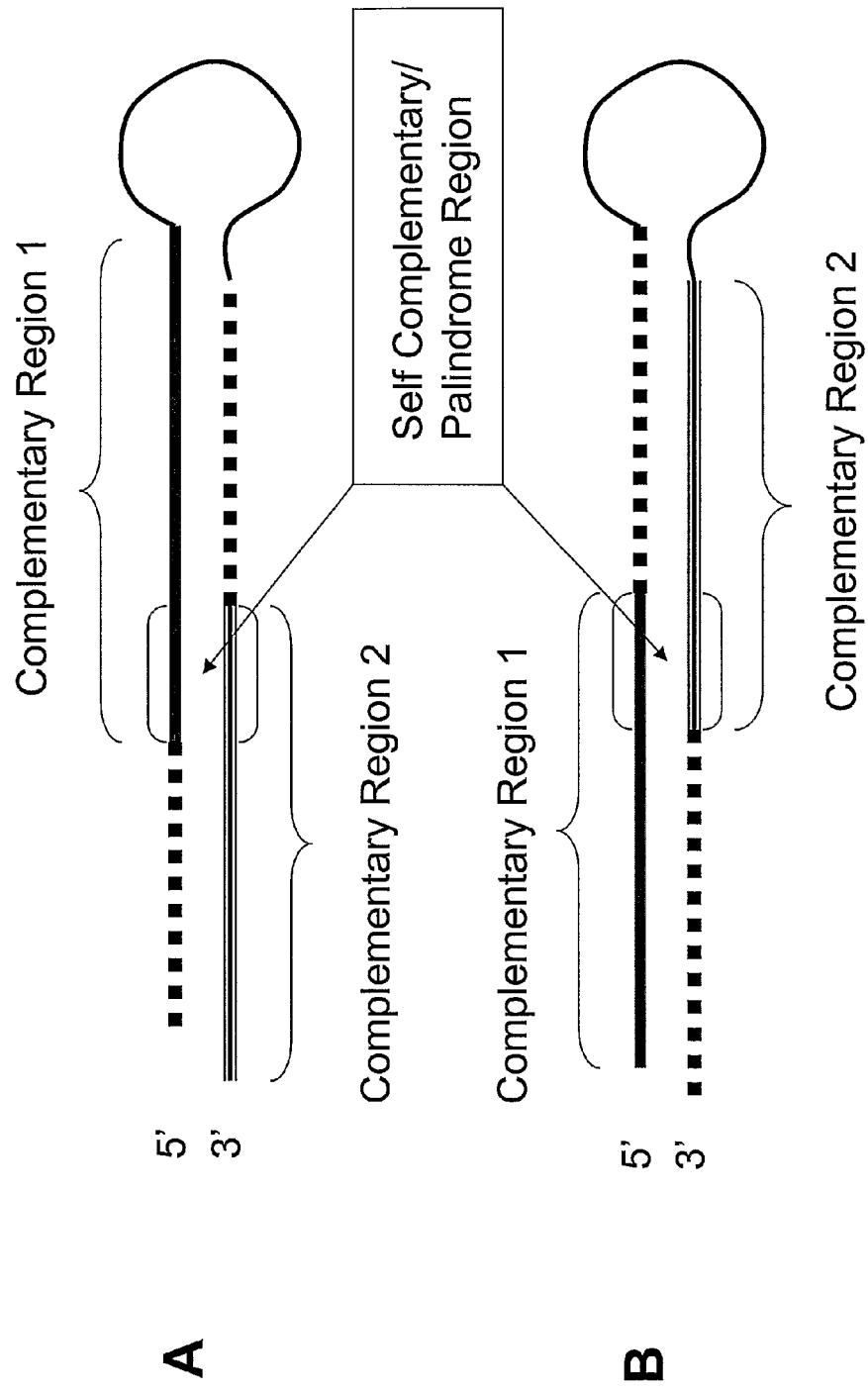
Figure 4: Examples of hairpin multifunctional siNA constructs with distinct complementary regions and a self complementary/palindrome region

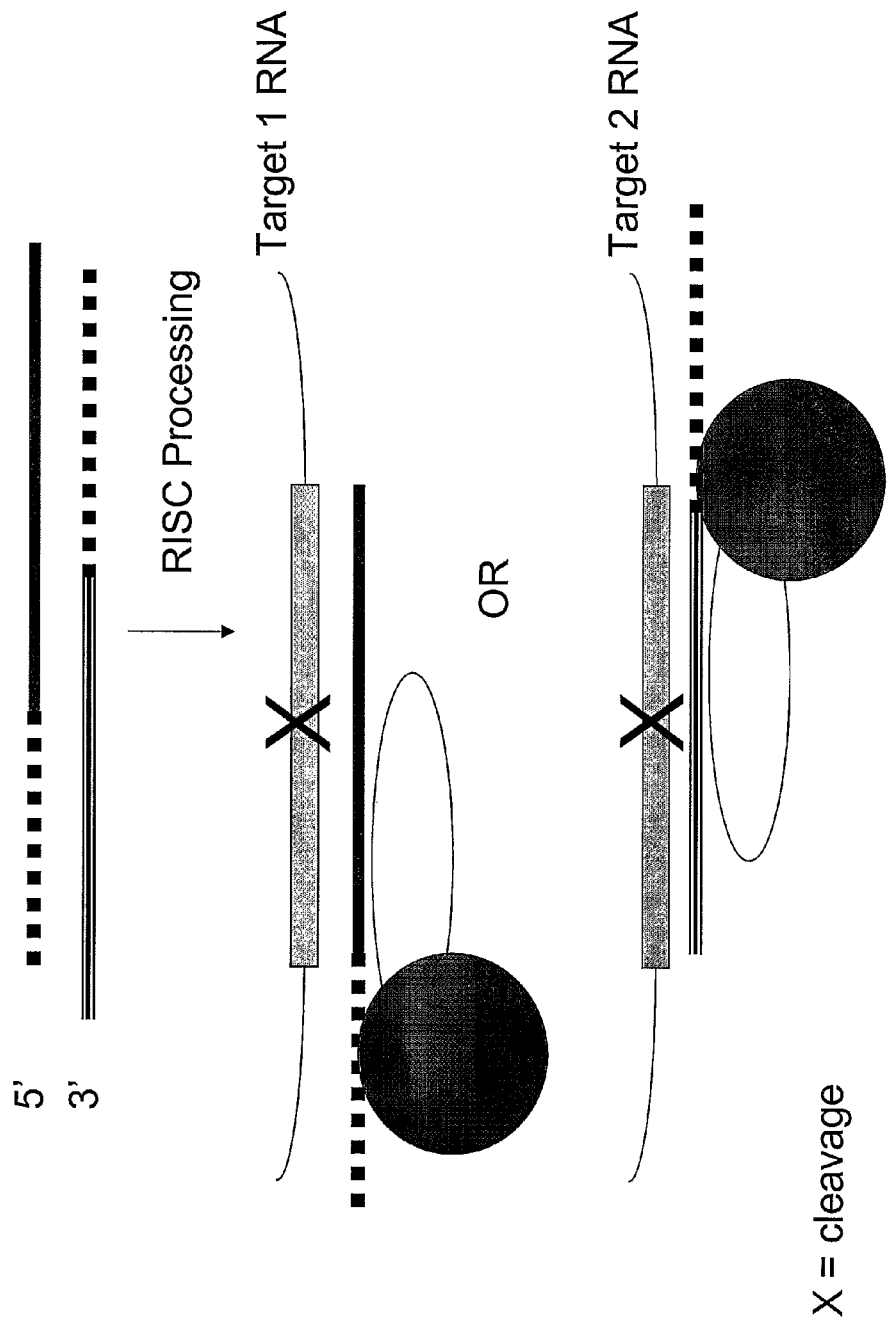

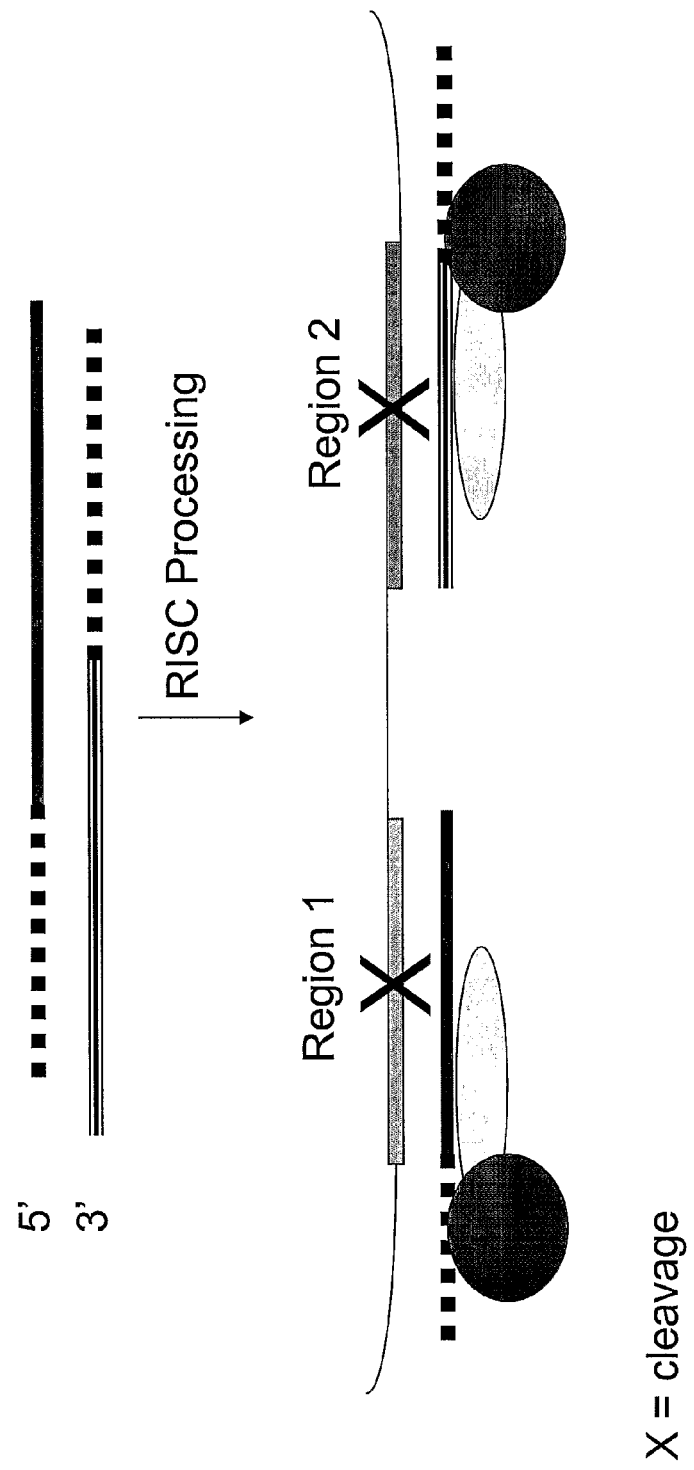
Figure 6: Example of multifunctional siNA targeting two regions within the same target nucleic acid sequence

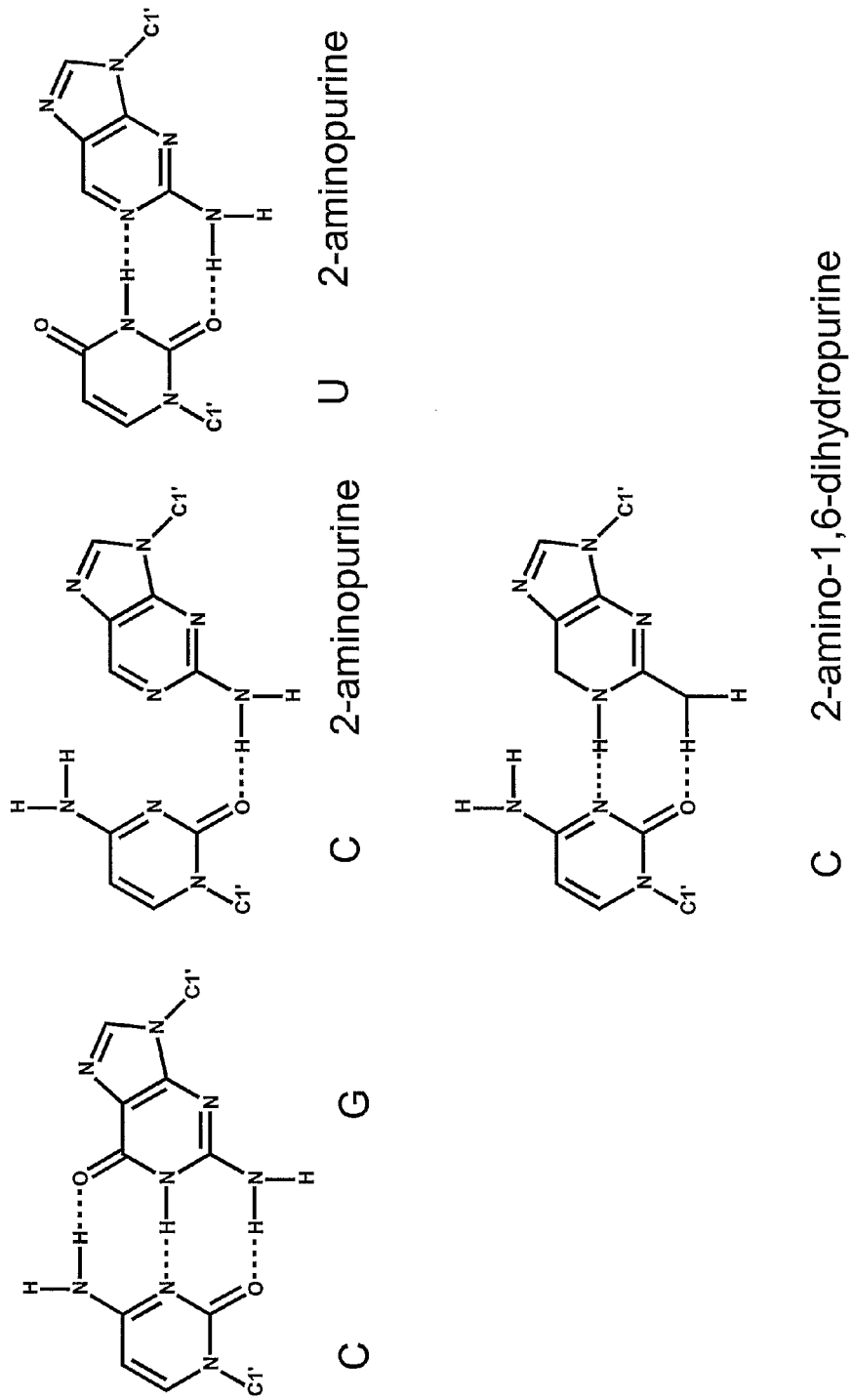
Figure 7: Examples of artificial complementary/palindromic sites generated using Modified nucleotides

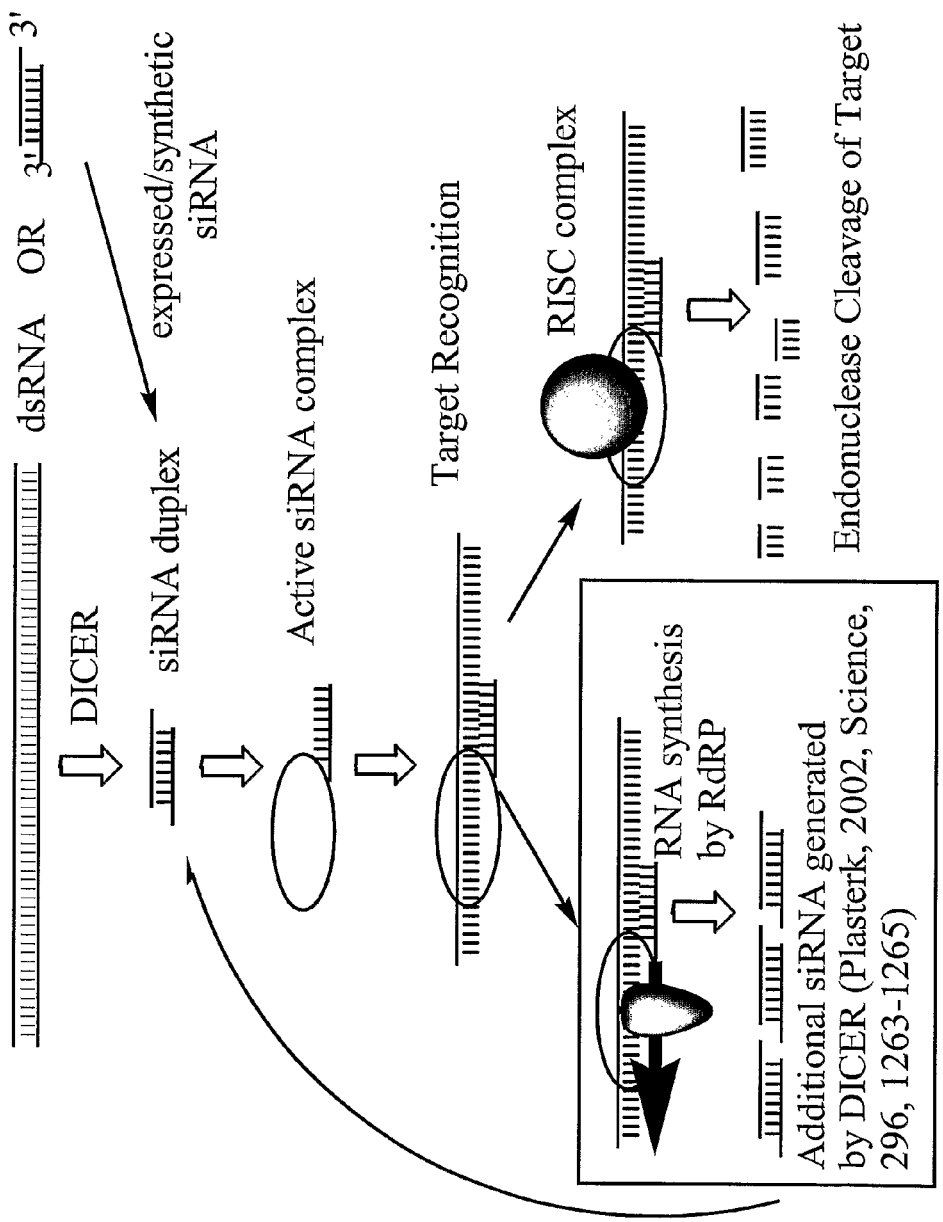
Figure 8: Example of Proposed Mechanism of RNAi

Figure 10: 5'-phosphate modifications

US 7,858,769 B2

RNA INTERFERENCE MEDIATED INHIBITION OF GENE EXPRESSION USING MULTIFUNCTIONAL SHORT INTERFERING NUCLEIC ACID (MULTIFUNCTIONAL SINA)

This application claims the benefit of U.S. Provisional Application No. 60/543,480, filed Feb. 10, 2004, and is a continuation-in-part of international application PCT/US04/016390, filed May 24, 2004. Both of these applications are incorporated by reference in their entirety.

SEQUENCE LISTING

The sequence listing submitted via EFS, in compliance with 37 CFR §1.52(e)(5), is incorporated herein by reference. The sequence listing text file submitted via EFS contains the file "SequenceListing4USPCT," created on Oct. 19, 2010, which is 49,445 bytes in size.

FIELD OF THE INVENTION

The present invention concerns methods and reagents useful in modulating gene expression in a variety of applications, including use in therapeutic, veterinary, agricultural, diagnostic, target validation, and genomic discovery applications. Specifically, the invention relates to multifunctional short interfering nucleic acid (multifunctional siNA) molecules that modulate the expression of more than one gene and methods of generating such siNA molecules.

BACKGROUND OF THE INVENTION

The following is a discussion of relevant art pertaining to nucleic acid molecules that modulate gene expression. The discussion is provided only for understanding of the invention that follows. The summary is not an admission that any of the work described below is prior art to the claimed invention.

Various single strand, double strand, and triple strand nucleic acid molecules are presently known that possess biological activity. Examples of single strand nucleic acid molecules that have biologic activity to mediate alteration of gene expression include antisense nucleic acid molecules, enzymatic nucleic acid molecules or ribozymes, and 2'-5'-oligoadenylate nucleic acid molecules. Examples of triple strand nucleic acid molecules that have biologic activity to mediate alteration of gene expression include triplex forming oligonucleotides. Examples of double strand nucleic acid molecules that have biologic activity to mediate alteration of gene expression include dsRNA and siRNA. For example, interferon mediated induction of protein kinase PKR is known to be activated in a non-sequence specific manner by long double stranded RNA (see for example Wu and Kaufman, 1997, J. Biol. Chem., 272, 1921-6). This pathway shares a common feature with the 2',5'-linked oligoadenylate (2-5A) system in mediating RNA cleavage via RNaseL (see for example Cole et al., 1997, J. Biol. Chem., 272, 19187-92). Whereas these responses are intrinsically sequence-non-specific, inhibition of gene expression via short interfering RNA mediated RNA interference (RNAi) is known to be highly sequence specific (see for example Elbashir et al., 2001, Nature, 411, 494-498).

RNA interference refers to the process of sequence-specific post-transcriptional gene silencing in animals mediated by short interfering RNAs (siRNAs) (Zamore et al., 2000, Cell, 101, 25-33; Fire et al., 1998, Nature, 391, 806; Hamilton et al., 1999, Science, 286, 950-951). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., 1999, Trends Genet., 15, 358). Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA. The presence of dsRNA in cells triggers the RNAi response though a mechanism that has yet to be fully characterized. This mechanism appears to be different from the interferon response that results from dsRNA-mediated activation of protein kinase PKR and 2',5'-oligoadenylate synthetase resulting in non-specific cleavage of mRNA by ribonuclease L.

The presence of long dsRNAs in cells stimulates the activity of a ribonuclease III enzyme referred to as dicer. Dicer is involved in the processing of the dsRNA into short pieces of dsRNA known as short interfering RNAs (siRNAs) (Hamilton et al., supra; Zamore et al., 2000, Cell, 101, 25-33; Berstein et al., 2001, Nature, 409, 363). Short interfering RNAs derived from dicer activity are typically about 21 to about 23 nucleotides in length and comprise about 19 base pair duplexes (Hamilton et al., supra; Elbashir et al., 2001, Genes Dev., 15, 188). Dicer has also been implicated in the excision of 21- and 22-nucleotide small temporal RNAs (stRNAs) from precursor RNA of conserved structure that are implicated in translational control (Hutvagner et al., 2001, Science, 293, 834). The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex (Elbashir et al., 2001, Genes Dev., 15, 188).

RNAi has been studied in a variety of systems. Fire et al., 1998, Nature, 391, 806, were the first to observe RNAi in C. elegans. Bahramian and Zarbl, 1999, Molecular and Cellular Biology, 19, 274-283 and Wianny and Goetz, 1999, Nature Cell Biol., 2, 70, describe RNAi mediated by dsRNA in mammalian systems. Hammond et al., 2000, Nature, 404, 293, describe RNAi in Drosophila cells transfected with dsRNA. Elbashir et al., 2001, Nature, 411, 494 and Tuschl et al., International PCT Publication No. WO 01/75164, describe RNAi induced by introduction of duplexes of synthetic 21-nucleotide RNAs in cultured mammalian cells including human embryonic kidney and HeLa cells. Recent work in Drosophila embryonic lysates (Elbashir et al., 2001, EMBO J., 20, 6877 and Tuschl et al., International PCT Publication No. WO 01/75164) has revealed certain requirements for siRNA length, structure, chemical composition, and sequence that are essential to mediate efficient RNAi activity. These studies have shown that 21-nucleotide siRNA duplexes are most active when containing 3'-terminal dinucleotide overhangs. Furthermore, complete substitution of one or both siRNA strands with 2'-deoxy (2'-H) or 2'-O-methyl nucleotides abolishes RNAi activity, whereas substitution of the 3'-terminal siRNA overhang nucleotides with 2'-deoxy nucleotides (2'-H) was shown to be tolerated. Single mismatch sequences in the center of the siRNA duplex were also shown to abolish RNAi activity. In addition, these studies also indicate that the position of the cleavage site in the target RNA is defined by the 5'-end of the siRNA guide sequence rather than the 3'-end of the guide sequence (Elbashir et al., 2001, *EMBO J.*, 20, 6877). Other studies have indicated that a 5'-phosphate on the target-complementary strand of a siRNA duplex is required for siRNA activity and that ATP is utilized to maintain the 5'-phosphate moiety on the siRNA (Nykanen et al., 2001, *Cell*, 107, 309).

Studies have shown that replacing the 3'-terminal nucleotide overhanging segments of a 21-mer siRNA duplex having two-nucleotide 3'-overhangs with deoxyribonucleotides does not have an adverse effect on RNAi activity. Replacing up to four nucleotides on each end of the siRNA with deoxyribonucleotides has been reported to be well tolerated, whereas complete substitution with deoxyribonucleotides results in no RNAi activity (Elbashir et al., 2001, *EMBO J.*, 20, 6877 and Tuschl et al., International PCT Publication No. WO 01/75164). In addition, Elbashir et al., supra, also report that substitution of siRNA with 2'-O-methyl nucleotides completely abolishes RNAi activity. Li et al., International PCT Publication No. WO 00/44914, and Beach et al., International PCT Publication No. WO 01/68836 preliminarily suggest that siRNA may include modifications to either the phosphate-sugar backbone or the nucleoside to include at least one of a nitrogen or sulfur heteroatom, however, neither application postulates to what extent such modifications would be tolerated in siRNA molecules, nor provides any further guidance or examples of such modified siRNA. Kreutzer et al., Canadian Patent Application No. 2,359,180, also describe certain chemical modifications for use in dsRNA constructs in order to counteract activation of double-stranded RNA-dependent protein kinase PKR, specifically 2'-amino or 2'-O-methyl nucleotides, and nucleotides containing a 2'-O or 4'-C methylene bridge. However, Kreutzer et al. similarly fails to provide examples or guidance as to what extent these modifications would be tolerated in dsRNA molecules.

Parrish et al., 2000, *Molecular Cell*, 6, 1077-1087, tested certain chemical modifications targeting the unc-22 gene in *C. elegans* using long (>25 nt) siRNA transcripts. The authors describe the introduction of thiophosphate residues into these siRNA transcripts by incorporating thiophosphate nucleotide analogs with T7 and T3 RNA polymerase and observed that RNAs with two phosphorothioate modified bases also had substantial decreases in effectiveness as RNAi. Further, Parrish et al. reported that phosphorothioate modification of more than two residues greatly destabilized the RNAs in vitro such that interference activities could not be assayed. Id. at 1081. The authors also tested certain modifications at the 2'-position of the nucleotide sugar in the long siRNA transcripts and found that substituting deoxynucleotides for ribonucleotides produced a substantial decrease in interference activity, especially in the case of Uridine to Thymidine and/or Cytidine to deoxy-Cytidine substitutions. Id. In addition, the authors tested certain base modifications, including substituting, in sense and antisense strands of the siRNA, 4-thiouracil, 5-bromouracil, 5-iodouracil, and 3-(aminoallyl)uracil for uracil, and inosine for guanosine. Whereas 4-thiouracil and 5-bromouracil substitution appeared to be tolerated, Parrish reported that inosine produced a substantial decrease in interference activity when incorporated in either strand. Parrish also reported that incorporation of 5-iodouracil and 3-(aminoallyl)uracil in the antisense strand resulted in a substantial decrease in RNAi activity as well.

The use of longer dsRNA has been described. For example, Beach et al., International PCT Publication No. WO 01/68836, describes specific methods for attenuating gene expression using endogenously-derived dsRNA. Tuschl et al., International PCT Publication No. WO 01/75164, describe a *Drosophila* in vitro RNAi system and the use of specific siRNA molecules for certain functional genomic and certain therapeutic applications; although Tuschl, 2001, *Chem. Biochem.*, 2, 239-245, doubts that RNAi can be used to cure genetic diseases or viral infection due to the danger of activating interferon response. Li et al., International PCT Publication No. WO 00/44914, describe the use of specific long (141 bp-488 bp) enzymatically synthesized or vector expressed dsRNAs for attenuating the expression of certain target genes. Zernicka-Goetz et al., International PCT Publication No. WO 01/36646, describe certain methods for inhibiting the expression of particular genes in mammalian cells using certain long (550 bp-714 bp), enzymatically synthesized or vector expressed dsRNA molecules. Fire et al., International PCT Publication No. WO 99/32619, describe particular methods for introducing certain long dsRNA molecules into cells for use in inhibiting gene expression in nematodes. Plaetinck et al., International PCT Publication No. WO 00/01846, describe certain methods for identifying specific genes responsible for conferring a particular phenotype in a cell using specific long dsRNA molecules. Mello et al., International PCT Publication No. WO 01/29058, describe the identification of specific genes involved in dsRNA-mediated RNAi. Deschamps Depaillette et al., International PCT Publication No. WO 99/07409, describe specific compositions consisting of particular dsRNA molecules combined with certain anti-viral agents. Waterhouse et al., International PCT Publication No. 99/53050, describe certain methods for decreasing the phenotypic expression of a nucleic acid in plant cells using certain dsRNAs. Driscoll et al., International PCT Publication No. WO 01/49844, describe specific DNA expression constructs for use in facilitating gene silencing in targeted organisms.

Others have reported on various RNAi and gene-silencing systems. For example, Parrish et al., 2000, *Molecular Cell*, 6, 1077-1087, describe specific chemically-modified dsRNA constructs targeting the unc-22 gene of *C. elegans*. Grossniklaus, International PCT Publication No. WO 01/38551, describes certain methods for regulating polycomb gene expression in plants using certain dsRNAs. Churikov et al., International PCT Publication No. WO 01/42443, describe certain methods for modifying genetic characteristics of an organism using certain dsRNAs. Cogoni et al., International PCT Publication No. WO 01/53475, describe certain methods for isolating a *Neurospora* silencing gene and uses thereof. Reed et al., International PCT Publication No. WO 01/68836, describe certain methods for gene silencing in plants. Honer et al., International PCT Publication No. WO 01/70944, describe certain methods of drug screening using transgenic nematodes as Parkinson's Disease models using certain dsRNAs. Deak et al., International PCT Publication No. WO 01/72774, describe certain *Drosophila*-derived gene products that may be related to RNAi in *Drosophila*. Arndt et al., International PCT Publication No. WO 01/92513 describe certain methods for mediating gene suppression by using factors that enhance RNAi. Tuschl et al., International PCT Publication No. WO 02/44321, describe certain synthetic siRNA constructs. Pachuk et al., International PCT Publication No. WO 00/63364, and Satishchandran et al., International PCT Publication No. WO 01/04313, describe certain methods and compositions for inhibiting the function of certain polynucleotide sequences using certain long (over 250 bp), vector expressed dsRNAs. Echeverri et al., International PCT Publication No. WO 02/38805, describe certain *C. elegans* genes identified via RNAi. Kreutzer et al., International PCT Publications Nos. WO 02/055692, WO 02/055693, and EP 1144623 B1 describes certain methods for inhibiting gene expression using dsRNA. Graham et al., International PCT Publications Nos. WO 99/49029 and WO 01/70949, and AU 4037501 describe certain vector expressed siRNA molecules. Fire et al., U.S. Pat. No. 6,506,559, describe certain methods for inhibiting gene expression in vitro using certain long dsRNA (299 bp-1033 bp) constructs that mediate RNAi. Martinez et al., 2002, Cell, 110, 563-574, describe certain single stranded siRNA constructs, including certain 5'-phosphorylated single stranded siRNAs that mediate RNA interference in Hela cells. All of these references describe double stranded nucleic acid constructs where one of the two strands (the antisense strand) is complementary to the target RNA and the other strand (sense strand) is complementary to the antisense strand.

SUMMARY OF THE INVENTION

This invention relates to nucleic acid-based compounds, compositions, and methods useful for modulating RNA function and/or gene expression in a cell. Specifically, the instant invention features multifunctional short interfering nucleic acid (multifunctional siNA) molecules that modulate the expression of one or more genes in a biologic system, such as a cell, tissue, or organism. The multifunctional short interfering nucleic acid (multifunctional siNA) molecules of the invention can target more than one region of the target nucleic acid sequence or can target sequences of more than one distinct target nucleic acid molecules. The multifunctional siNA molecules of the invention can be chemically synthesized or expressed from transcription units and/or vectors. The multifunctional siNA molecules of the instant invention provide useful reagents and methods for a variety of therapeutic, diagnostic, agricultural, veterinary, target validation, genomic discovery, genetic engineering and pharmacogenomic applications.

Applicant demonstrates herein that certain oligonucleotides, referred to herein for convenience but not limitation as multifunctional short interfering nucleic acid or multifunctional siNA molecules, are potent mediators of sequence specific regulation of gene expression. The multifunctional siNA molecules of the invention are distinct from other nucleic acid sequences known in the art (e.g., siRNA, miRNA, stRNA, shRNA, antisense oligonucleotides, etc.) in that they represent a class of polynucleotide molecules that are designed such that each strand in the multifunctional siNA construct comprises nucleotide sequence that is complementary to a distinct nucleic acid sequence in one or more target nucleic acid molecules. A single multifunctional siNA molecule of the invention can thus target more than one (e.g., 2, 3, 4, 5, or more) differing target nucleic acid target molecules. Nucleic acid molecules of the invention can also target more than one (e.g., 2, 3, 4, 5, or more) region of the same target nucleic acid sequence. As such multifunctional siNA molecules of the invention are useful in down regulating or inhibiting the expression of one or more target nucleic acid molecules. For example, a multifunctional siNA molecule of the invention can target nucleic acid molecules encoding a cytokine and its corresponding receptor(s), nucleic acid molecules encoding a virus or viral proteins and corresponding cellular proteins required for viral infection and/or replication, or differing strains of a particular virus. By reducing or inhibiting expression of more than one target nucleic acid molecule with one multifunctional siNA construct, multifunctional siNA molecules of the invention represent a class of potent therapeutic agents that can provide simultaneous inhibition of multiple targets within a disease related pathway. Such simultaneous inhibition can provide synergistic therapeutic treatment strategies without the need for separate preclinical and clinical development efforts or complex regulatory approval process.

Use of multifunctional siNA molecules that target more then one region of a target nucleic acid molecule (e.g., messenger RNA) is expected to provide potent inhibition of gene expression. For example, a single multifunctional siNA construct of the invention can target both conserved and variable regions of a target nucleic acid molecule, thereby allowing down regulation or inhibition of different splice variants encoded by a single gene, or allowing for targeting of both coding and non-coding regions of a target nucleic acid molecule.

Generally, double stranded oligonucleotides are formed by the assembly of two distinct oligonucleotide sequences where the oligonucleotide sequence of one strand is complementary to the oligonucleotide sequence of the second strand; such double stranded oligonucleotides are generally assembled from two separate oligonucleotides (e.g., siRNA), or from a single molecule that folds on itself to form a double stranded structure (e.g. shRNA or short hairpin RNA). These double stranded oligonucleotides known in the art all have a common feature in that each strand of the duplex has a district nucleotide sequence, wherein only one nucleotide sequence region (guide sequence or the antisense sequence) has complementarity to a target nucleic acid sequence and the other strand (sense sequence) comprises nucleotide sequence that is homologous to the target nucleic acid sequence. Generally, the antisense sequence is retained in the active RISC complex and guides the RISC to the target nucleotide sequence by means of complementary base-pairing of the antisense sequence with the target sequence for mediating sequence-specific RNA interference. It is known in the art that in some cell culture systems, certain types of unmodified siRNAs can exhibit "off target" effects. It is hypothesized that this off-target effect involves the participation of the sense sequence instead of the antisense sequence of the siRNA in the RISC complex (see for example Schwarz et al., 2003, Cell, 115, 199-208). In this instance the sense sequence is believed to direct the RISC complex to a sequence (off-target sequence) that is distinct from the intended target sequence, resulting in the inhibition of the off-target sequence. In these double stranded nucleic acid molecules, each strand is complementary to a distinct target nucleic acid sequence. However, the off-targets that are affected by these dsRNAs are not entirely predictable and are non-specific.

Distinct from the double stranded nucleic acid molecules known in the art, the applicants have developed a novel, potentially cost effective and simplified method of down regulating or inhibiting the expression of more than one target nucleic acid sequence using a single multifunctional siNA construct. The multifunctional siNA molecules of the invention are designed such that a portion of each strand or region of the multifunctional siNA is complementary to a target nucleic acid sequence of choice. As such, the multifunctional siNA molecules of the invention are not limited to targeting sequences that are complementary to each other, but rather to any two differing target nucleic acid sequences. Multifunctional siNA molecules of the invention are designed such that each strand or region of the multifunctional siNA molecule that is complementary to a given target nucleic acid sequence is of length suitable (e.g., from about 16 to about 28 nucleotides in length, preferably from about 18 to about 28 nucleotides in length) for mediating RNA interference against the target nucleic acid sequence. The multifunctional siNA of the invention is expected to minimize off-target effects seen with certain siRNA sequences, such as those described in (Schwarz et al., supra).

It has been reported that dsRNAs of length between 29 base pairs and 36 base pairs (Tuschl et al., International PCT Publication No. WO 02/44321) do not mediate RNAi. One reason these dsRNAs are inactive may be the lack of turnover or dissociation of the strand that interacts with the target RNA sequence, such that the RISC complex is not able to efficiently interact with multiple copies of the target RNA resulting in a significant decrease in the potency and efficiency of the RNAi process. Applicant has surprisingly found that the multifunctional siNAs of the invention can overcome this hurdle and are capable of enhancing the efficiency and potency of RNAi process. As such, in certain embodiments of the invention, multifunctional siNAs of length between about 29 to about 36 base pairs can be designed such that, a portion of each strand of the multifunctional siNA molecule comprises a nucleotide sequence region that is complementary to a target nucleic acid of length sufficient to mediate RNAi efficiently (e.g., about 15 to about 23 base pairs) and a nucleotide sequence region that is not complementary to the target nucleic acid. By having both complementary and non-complementary portions in each strand of the multifunctional siNA, the multifunctional siNA can mediate RNA interference against a target nucleic acid sequence without being prohibitive to turnover or dissociation (e.g., where the length of each strand is too long to mediate RNAi against the respective target nucleic acid sequence). Furthermore, design of multifunctional siNA molecules of the invention with internal overlapping regions allows the multifunctional siNA molecules to be of favorable (decreased) size for mediating RNA interference and of size that is well suited for use as a therapeutic agent (e.g., wherein each strand is independently from about 18 to about 28 nucleotides in length). Non-limiting examples are illustrated in the enclosed FIGS. 1-6.

In one embodiment, a multifunctional siNA molecule of the invention comprises a first region and a second region, where the first region of the multifunctional siNA comprises nucleotide sequence complementary to a nucleic acid sequence of a first target nucleic acid molecule, and the second region of the multifunctional siNA comprises nucleic acid sequence complementary to a nucleic acid sequence of a second target nucleic acid molecule. In one embodiment, a multifunctional siNA molecule of the invention comprises a first region and a second region, where the first region of the multifunctional siNA comprises nucleotide sequence complementary to a nucleic acid sequence of the first region of a target nucleic acid molecule, and the second region of the multifunctional siNA comprises nucleotide sequence complementary to a nucleic acid sequence of a second region of a the target nucleic acid molecule. In another embodiment, the first region and second region of the multifunctional siNA can comprise separate nucleic acid sequences that share some degree of complementarity (e.g., from about 1 to about 10 complementary nucleotides). In certain embodiments, multifunctional siNA constructs comprising separate nucleic acid sequences cam be readily linked post-synthetically by methods and reagents known in the art and such linked constructs are within the scope of the invention. Alternately, the first region and second region of the multifunctional siNA can comprise a single nucleic acid sequence having some degree of self complementarity, such as in a hairpin or stem-loop structure. Non-limiting examples of such double stranded and hairpin multifunctional short interfering nucleic acids are illustrated in FIGS. 1 and 2 respectively. These multifunctional short interfering nucleic acids (multifunctional siNAs) can optionally include certain overlapping nucleotide sequence where such overlapping nucleotide sequence is present in between the first region and the second region of the multifunctional siNA (see for example FIGS. 3 and 4).

In one embodiment, the invention features a multifunctional short interfering nucleic acid (multifunctional siNA) molecule, wherein each strand of the multifunctional siNA independently comprises a first region of nucleic acid sequence that is complementary to a distinct target nucleic acid sequence and the second region of nucleotide sequence that is not complementary to the target sequence. The target nucleic acid sequence of each strand is in the same target nucleic acid molecule or different target nucleic acid molecules.

In another embodiment, the multifunctional siNA comprises two strands, where: (a) the first strand comprises a region having sequence complementarity to a target nucleic acid sequence (complementary region 1) and a region having no sequence complementarity to the target nucleotide sequence (non-complementary region 1); (b) the second strand of the multifunction siNA comprises a region having sequence complementarity to a target nucleic acid sequence that is distinct from the target nucleotide sequence complementary to the first strand nucleotide sequence (complementary region 2), and a region having no sequence complementarity to the target nucleotide sequence of complementary region 2 (non-complementary region 2); (c) the complementary region 1 of the first strand comprises nucleotide sequence that is complementary to nucleotide sequence in the non-complementary region 2 of the second strand and the complementary region 2 of the second strand comprises nucleotide sequence that is complementary to nucleotide sequence in the non-complementary region 1 of the first strand. The target nucleic acid sequence of complementary region 1 and complementary region 2 is in the same target nucleic acid molecule or different target nucleic acid molecules.

In another embodiment, the multifunctional siNA comprises two strands, where: (a) the first strand comprises a region having sequence complementarity to a target nucleic acid sequence derived from a gene (e.g., mammalian gene, viral gene or genome, bacterial gene or a plant gene) (complementary region 1) and a region having no sequence complementarity to the target nucleotide sequence of complementary region 1 (non-complementary region 1); (b) the second strand of the multifunction siNA comprises a region having sequence complementarity to a target nucleic acid sequence derived from a gene that is distinct from the gene of complementary region 1 (complementary region 2), and a region having no sequence complementarity to the target nucleotide sequence of complementary region 2 (non-complementary region 2); (c) the complementary region 1 of the first strand comprises nucleotide sequence that is complementary to nucleotide sequence in the non-complementary region 2 of the second strand and the complementary region 2 of the second strand comprises nucleotide sequence that is complementary to nucleotide sequence in the non-complementary region 1 of the first strand.

In another embodiment, the multifunctional siNA comprises two strands, where: (a) the first strand comprises a region having sequence complementarity to target nucleic acid sequence derived from a gene (e.g., mammalian gene, viral gene or genome, bacterial gene or a plant gene) (complementary region 1) and a region having no sequence complementarity to the target nucleotide sequence of complementary region 1 (non-complementary region 1); (b) the second strand of the multifunction siNA comprises a region having sequence complementarity to a target nucleic acid sequence distinct from the target nucleic acid sequence of complementary region 1 (complementary region 2), provided however, the target nucleic acid sequence for complementary region 1 and target nucleic acid sequence for complementary region 2 are both derived from the same gene, and a region having no sequence complementarity to the target nucleotide sequence of complementary region 2 (non-complementary region 2); (c) the complementary region 1 of the first strand comprises nucleotide sequence that is complementary to nucleotide sequence in the non-complementary region 2 of the second strand and the complementary region 2 of the second strand comprises nucleotide sequence that is complementary to nucleotide sequence in the non-complementary region 1 of the first strand.

In one embodiment, the invention features a multifunctional short interfering nucleic acid (multifunctional siNA) molecule, wherein the multifunctional siNA comprises two complementary nucleic acid sequences in which the first sequence comprises a first region having nucleotide sequence complementary to nucleotide sequence within a target nucleic acid molecule, and in which the second sequence comprises a first region having nucleotide sequence complementary to a distinct nucleotide sequence within the same target nucleic acid molecule. Preferably, the first region of the first sequence is also complementary to the nucleotide sequence of the second region of the second sequence, and where the first region of the second sequence is complementary to the nucleotide sequence of the second region of the first sequence, In one embodiment, the invention features a multifunctional short interfering nucleic acid (multifunctional siNA) molecule, wherein the multifunctional siNA comprises two complementary nucleic acid sequences in which the first sequence comprises a first region having nucleotide sequence complementary to nucleotide sequence within a first target nucleic acid molecule, and in which the second sequence comprises a first region having nucleotide sequence complementary to a distinct nucleotide sequence within a second target nucleic acid molecule. Preferably, the first region of the first sequence is also complementary to the nucleotide sequence of the second region of the second sequence, and where the first region of the second sequence is complementary to the nucleotide sequence of the second region of the first sequence, In one embodiment, the invention features a multifunctional siNA molecule comprising a first region and a second region, where the first region comprises nucleic acid sequence having between about 18 to about 28 nucleotides complementary to a nucleic acid sequence within a first target nucleic acid molecule, and the second region comprises nucleotide sequence having between about 18 to about 28 nucleotides complementary to a distinct nucleic acid sequence within a second target nucleic acid molecule.

In one embodiment, the invention features a multifunctional siNA molecule comprising a first region and a second region, where the first region comprises nucleic acid sequence having between about 18 to about 28 nucleotides complementary to a nucleic acid sequence within a target nucleic acid molecule, and the second region comprises nucleotide sequence having between about 18 to about 28 nucleotides complementary to a distinct nucleic acid sequence within the same target nucleic acid molecule.

In one embodiment, the invention features a double stranded multifunctional short interfering nucleic acid (multifunctional siNA) molecule, wherein one strand of the multifunctional siNA comprises a first region having nucleotide sequence complementary to a first target nucleic acid sequence, and the second strand comprises a first region having nucleotide sequence complementary to a second target nucleic acid sequence. The first and second target nucleic acid sequences can be present in separate target nucleic acid molecules or can be different regions within the same target nucleic acid molecule. As such, multifunctional siNA molecules of the invention can be used to target the expression of different genes, splice variants of the same gene, both mutant and conserved regions of one or more gene transcripts, or both coding and non-coding sequences of the same or differing genes or gene transcripts.

In one embodiment, a target nucleic acid molecule of the invention encodes a single protein. In another embodiment, a target nucleic acid molecule encodes more than one protein (e.g., 1, 2, 3, 4, 5 or more proteins). As such, a multifunctional siNA construct of the invention can be used to down regulate or inhibit the expression of several proteins. For example, a multifunctional siNA molecule comprising a region in one strand having nucleotide sequence complementarity to a first target nucleic acid sequence derived from a gene encoding one protein (e.g., a cytokine, such as vascular endothelial growth factor or VEGF) and the second strand comprising a region with nucleotide sequence complementarity to a second target nucleic acid sequence present in target nucleic acid molecules derived from genes encoding two proteins (e.g., two differing receptors, such as VEGF receptor 1 and VEGF receptor 2, for a single cytokine, such as VEGF) can be used to down regulate, inhibit, or shut down a particular biologic pathway by targeting, for example, a cytokine and receptors for the cytokine, or a ligand and receptors for the ligand.

In one embodiment the invention takes advantage of conserved nucleotide sequences present in different isoforms of cytokines or ligands and receptors for the cytokines or ligands. By designing multifunctional siNAs in a manner where one strand includes sequence that is complementary to target nucleic acid sequence conserved among various isoforms of a cytokine and the other strand includes sequence that is complementary to target nucleic acid sequence conserved among the receptors for the cytokine, it is possible to selectively and effectively modulate or inhibit a biological pathway or multiple genes in a biological pathway using a single multifunctional siNA.

In another nonlimiting example, a multifunctional siNA molecule comprising a region in one strand having nucleotide sequence complementarity to a first target nucleic acid sequence present in target nucleic acid molecules encoding two proteins (e.g., two isoforms of a cytokine such as VEGF, including for example any of VEGF-A, VEGF-B, VEGF-C, and/or VEGF-D) and the second strand comprising a region with nucleotide sequence complementarity to a second target nucleic acid sequence present in target nucleotide molecules encoding two additional proteins (e.g., two differing receptors for the cytokine, such as VEGFR1, VEGFR2, and/or VEGFR3) can be used to down regulate, inhibit, or shut down a particular biologic pathway by targeting different isoforms of a cytokine and receptors for such cytokines.

In another non-limiting example, a multifunctional siNA molecule comprising a region in one strand having nucleotide sequence complementarity to a first target nucleic acid sequence derived from a target nucleic acid molecule encoding a virus or a viral protein (e.g., HIV) and the second strand comprising a region having nucleotide sequence complementarity to a second target nucleic acid sequence present in target nucleic acid molecule encoding a cellular protein (e.g., a receptor for the virus, such as CCR5 receptor for HIV) can be used to down regulate, inhibit, or shut down the viral replication and infection by targeting the virus and cellular proteins necessary for viral infection or replication.

In another nonlimiting example, a multifunctional siNA molecule comprising a region in one strand having nucleotide sequence complementarity to a first target nucleic acid sequence (e.g. conserved sequence) present in a target nucleic acid molecule such as a viral genome (e.g., HIV genomic RNA) and the second strand comprising a region having nucleotide sequence complementarity to a second target nucleic acid sequence (e.g. conserved sequence) present in target nucleic acid molecule derived from a gene encoding a viral protein (e.g., HIV proteins, such as TAT, REV, ENV or NEF) to down regulate, inhibit, or shut down the viral replication and infection by targeting the viral genome and viral encoded proteins necessary for viral infection or replication.

In one embodiment the invention takes advantage of conserved nucleotide sequences present in different strains, isotypes or forms of a virus and genes encoded by these different strains, isotypes and forms of the virus. By designing multifunctional siNAs in a manner where one strand includes sequence that is complementary to target nucleic acid sequence conserved among various strains, isotypes or forms of a virus and the other strand includes sequence that is complementary to target nucleic acid sequence conserved in a protein encoded by the virus, it is possible to selectively and effectively inhibit viral replication or infection using a single multifunctional siNA.

In one embodiment, a multifunctional short interfering nucleic acid (multifunctional siNA) of the invention comprises a region in each strand, wherein the region in one strand comprises nucleotide sequence complementary to a cytokine and the region in the second strand comprises nucleotide sequence complementary to a corresponding receptor for the cytokine. Non-limiting examples of cytokines include vascular endothelial growth factors (e.g., VEGF-A, VEGF-B, VEGF-C, VEGF-D), interleukins (e.g., IL-1alpha, IL-1beta, IL-2, IL-3, IL-4, IL-5, IL-6, IL-7, IL-8, IL-9, IL-10, IL-11, IL-12, IL-13), tumor necrosis factors (e.g., TNF-alpha, TNF-beta), colony stimulating factors (e.g., CSFs), interferons (e.g., IFN-gamma), nerve growth factors (e.g., NGFs), epidermal growth factors (e.g., EGF), platelet derived growth factors (e.g., PDGF), fibroblast growth factors (e.g., FGF), transforming growth factors (e.g., TGF-alpha and TGF-beta), erythropoietins (e.g., Epo), and Insulin like growth factors (e.g., IGF-1, IGF-2) and non-limiting examples of cytokine receptors include receptors for each of the above cytokines.

In one embodiment, a multifunctional short interfering nucleic acid (multifunctional siNA) of the invention comprises a first region and a second region, wherein the first region comprises nucleotide sequence complementary to a viral RNA of a first viral strain and the second region comprises nucleotide sequence complementary to a viral RNA of a second viral strain. In one embodiment, the first and second regions can comprise nucleotide sequence complementary to shared or conserved RNA sequences of differing viral strains or classes or viral strains. Non-limiting examples of viruses include Hepatitis C Virus (HCV), Hepatitis B Virus (HBV), Human Immunodeficiency Virus type 1 (HIV-1), Human Immunodeficiency Virus type 2 (HIV-2), West Nile Virus (WNV), cytomegalovirus (CMV), respiratory syncytial virus (RSV), influenza virus, rhinovirus, papillomavirus (HPV), Herpes Simplex Virus (HSV), severe acute respiratory virus (SARS), and other viruses such as HTLV.

In one embodiment, a multifunctional short interfering nucleic acid (multifunctional siNA) of the invention comprises a first region and a second region, wherein the first region comprises nucleotide sequence complementary to a viral RNA encoding one or more viruses (e.g., one or more strains of virus) and the second region comprises nucleotide sequence complementary to a viral RNA encoding one or more interferon agonist proteins. In one embodiment, the first region can comprise nucleotide sequence complementary to shared or conserved RNA sequences of differing viral strains or classes or viral strains. Non-limiting examples of viruses include Hepatitis C Virus (HCV), Hepatitis B Virus (HBV), Human Immunodeficiency Virus type 1 (HIV-1), Human Immunodeficiency Virus type 2 (HIV-2), West Nile Virus (WNV), cytomegalovirus (CMV), respiratory syncytial virus (RSV), influenza virus, rhinovirus, papillomavirus (HPV), Herpes Simplex Virus (HSV), severe acute respiratory virus (SARS), and other viruses such as HTLV. Non-limiting example of interferon agonist proteins include any protein that is capable of inhibition or suppressing RNA silencing (e.g., RNA binding proteins such as E3L or NS1 or equivalents thereof, see for example Li et al., 2004, *PNAS,* 101, 1350-1355)

In one embodiment, a multifunctional short interfering nucleic acid (multifunctional siNA) of the invention comprises a first region and a second region, wherein the first region comprises nucleotide sequence complementary to a viral RNA and the second region comprises nucleotide sequence complementary to a cellular RNA that is involved in viral infection and/or replication. Non-limiting examples of viruses include Hepatitis C Virus (HCV), Hepatitis B Virus (HBV), Human Immunodeficiency Virus type 1 (HIV-1), Human Immunodeficiency Virus type 2 (HIV-2), West Nile Virus (WNV), cytomegalovirus (CMV), respiratory syncytial virus (RSV), influenza virus, rhinovirus, papillomavirus (HPV), Herpes Simplex Virus (HSV), severe acute respiratory virus (SARS), and other viruses such as HTLV. Non-limiting examples of cellular RNAs involved in viral infection and/or replication include cellular receptors, cell surface molecules, cellular enzymes, cellular transcription factors, and/or cytokines, second messengers, and cellular accessory molecules including, but not limited to, interferon agonist proteins (e.g., E3L or NS1 or equivalents thereof, see for example Li et al., 2004, *PNAS,* 101, 1350-1355), interferon regulatory factors (IRFs); cellular PKR protein kinase (PKR); human eukaryotic initiation factors 2B (e1F2B gamma and/or e1F2gamma); human DEAD Box protein (DDX3); and cellular proteins that bind to the poly(U) tract of the HCV 3'-UTR, such as polypyrimidine tract-binding protein, CD4 receptors, CXCR4 (Fusin; LESTR; NPY3R); CCR5 (CKR-5, CMKRB5); CCR3 (CC-CKR-3, CKR-3, CMKBR3); CCR2 (CCR2b, CMKBR2); CCR1 (CKR1, CMKBR1); CCR4 (CKR-4); CCR8 (ChemR1, TER1, CMKBR8); CCR9 (D6); CXCR2 (IL-8RB); STRL33 (Bonzo; TYMSTR); US28; V28 (CMKBRL1, CX3CR1, GPR13); GPR1; GPR15 (BOB); Apj (AGTRL1); ChemR23 receptors, Heparan Sulfate Proteoglycans, HSPG2; SDC2; SDC4; GPC1; SDC3; SDC1; Galactoceramides; Erythrocyte-expressed Glycolipids; N-myristoyltransferase (NMT, NMT2); Glycosylation Enzymes; gp-160 Processing Enzymes (PCSK5); Ribonucleotide Reductase; Polyamine Biosynthesis enzymes; SP-1; NF-kappa B (NFKB2, RELA, and NFKB1); Tumor Necrosis Factor-alpha (TNF-alpha); Interleukin 1 alpha (IL-1 alpha); Interleukin 6 (IL-6); Phospholipase C(PLC); Protein Kinase C(PKC), Cyclophilins, (PPID, PPIA, PPIE, PPIB, PPIF, PPIG, and PPIC); Mitogen Activated Protein Kinase (MAP-Kinase, MAPK1); and Extracellular Signal-Regulated Kinase (ERK-Kinase), (see for example Schang, 2002, *Journal of Antimicrobial Chemotherapy,* 50, 779-792 and Ludwig et al., 2003, *Trends. Mol. Med.,* 9, 46-52).

In one embodiment, a double stranded multifunctional siNA molecule of the invention comprises a structure having Formula I(a):

5'-p-XZX'-3'

3'-Y'ZY-p-5' wherein each 5'-p-XZX'-3' and 5'-p-YZY'-3' are independently an oligonucleotide of length between about 20 nucleotides and about 300 nucleotides, preferably between about 20 and about 200 nucleotides, about 20 and about 100 nucleotides, about 20 and about 40 nucleotides, about 20 and about 40 nucleotides, about 24 and about 38 nucleotides, or about 26 and about 38 nucleotides; XZ comprises a nucleic acid sequence that is complementary to a first target nucleic acid sequence; YZ is an oligonucleotide comprising nucleic acid sequence that is complementary to a second target nucleic acid sequence; Z comprises nucleotide sequence of length about 1 to about 24 nucleotides (e.g. about 1, 2, 3, 4, 5, 6, 7, 8, 9, 10, 11, 12, 13, 14, 15, 16, 17, 18, 19, 20, 21, 22, 23, or 24 nucleotides) that is complementary between regions XZ and YZ; X comprises nucleotide sequence of length about 1 to about 100 nucleotides, preferably about 1 to about 21 nucleotides (e.g., about 1, 2, 3, 4, 5, 6, 7, 8, 9, 10, 11, 12, 13, 14, 15, 16, 17, 18, 19, 20, or 21 nucleotides) that is complementary to nucleotide sequence present in region Y'; Y comprises nucleotide sequence of length about 1 to about 100 nucleotides, preferably about 1- about 21 nucleotides (e.g., about 1, 2, 3, 4, 5, 6, 7, 8, 9, 10, 11, 12, 13, 14, 15, 16, 17, 18, 19, 20 or 21 nucleotides) that is complementary to nucleotide sequence present in region X'; p comprises a terminal phosphate group that can independently be present or absent; each XZ and YZ independently is of length sufficient to stably interact (i.e., base pair) with the first and second target nucleic acid sequence, respectively, or a portion thereof. For example, each sequence X and Y can independently comprise sequence from about 12 to about 21 or more nucleotides (e.g., about 12, 13, 14, 15, 16, 17, 18, 19, 20, 21, or more) nucleotides in length that is complementary to a target nucleotide sequence in different target nucleic acid molecules, such as target RNAs or a portion thereof. In another non-limiting example, the length of the nucleotide sequence of X and Z together that is complementary to the first target nucleic acid sequence (e.g., RNA) or a portion thereof is from about 12 to about 21 or more nucleotides (e.g., about 12, 13, 14, 15, 16, 17, 18, 19, 20, 21, or more). In another non-limiting example, the length of the nucleotide sequence of Y and Z together, that is complementary to the second target nucleic acid sequence (e.g., RNA) or a portion thereof is from about 12 to about 21 or more nucleotides (e.g., about 12, 13, 14, 15, 16, 17, 18, 19, 20, 21, or more). In one embodiment, the first target nucleic acid sequence and the second target nucleic acid sequence are present in the same target nucleic acid molecule. In another embodiment, the first target nucleic acid sequence and the second target nucleic acid sequence are present in different target nucleic acid molecules. In one embodiment, Z comprises a palindrome or a repeat sequence. In one embodiment, the lengths of oligonucleotides X and X' are identical. In another embodiment, the lengths of oligonucleotides X and X' are not identical. In one embodiment, the lengths of oligonucleotides Y and Y' are identical. In another embodiment, the lengths of oligonucleotides Y and Y' are not identical. In one embodiment, the double stranded oligonucleotide construct of Formula I(a) includes one or more, specifically 1, 2, 3 or 4, mismatches, to the extent such mismatches do not significantly diminish the ability of the double stranded oligonucleotide to inhibit target gene expression.

In one embodiment, a multifunctional siNA molecule of the invention comprises structure having Formula II(a):

5'-p-XX'-3'

3'-Y'Y-p-5' wherein each 5'-p-XX'-3' and 5'-p-YY'-3' are independently an oligonucleotide of length between about 20 nucleotides and about 300 nucleotides, preferably between about 20 and about 200 nucleotides, about 20 and about 100 nucleotides, about 20 and about 40 nucleotides, about 20 and about 40 nucleotides, about 24 and about 38 nucleotides, or about 26 and about 38 nucleotides; X comprises a nucleic acid sequence that is complementary to a first target nucleic acid sequence; Y is an oligonucleotide comprising nucleic acid sequence that is complementary to a second target nucleic acid sequence; X comprises nucleotide sequence of length about 1 to about 100 nucleotides, preferably about 1 to about 21 nucleotides (e.g., about 1, 2, 3, 4, 5, 6, 7, 8, 9, 10, 11, 12, 13, 14, 15, 16, 17, 18, 19, 20, or 21 nucleotides) that is complementary to nucleotide sequence present in region Y'; Y comprises nucleotide sequence of length about 1 to about 100 nucleotides, preferably about 1 to about 21 nucleotides (e.g., about 1, 2, 3, 4, 5, 6, 7, 8, 9, 10, 11, 12, 13, 14, 15, 16, 17, 18, 19, 20 or 21 nucleotides) that is complementary to nucleotide sequence present in region X'; p comprises a terminal phosphate group that can independently be present or absent; each X and Y independently is of length sufficient to stably interact (i.e., base pair) with the first and second target nucleic acid sequence, respectively, or a portion thereof. For example, each sequence X and Y can independently comprise sequence from about 12 to about 21 or more nucleotides (e.g., about 12, 13, 14, 15, 16, 17, 18, 19, 20, 21, or more) nucleotides in length that is complementary to a target nucleotide sequence in different target nucleic acid molecules, such as target RNAs or a portion thereof. In one embodiment, the first target nucleic acid sequence and the second target nucleic acid sequence are present in the same target nucleic acid molecule. In another embodiment, the first target nucleic acid sequence and the second target nucleic acid sequence are present in different target nucleic acid molecules. In one embodiment, Z comprises a palindrome or a repeat sequence. In one embodiment, the lengths of oligonucleotides X and X' are identical. In another embodiment, the lengths of oligonucleotides X and X' are not identical. In one embodiment, the lengths of oligonucleotides Y and Y' are identical. In another embodiment, the lengths of oligonucleotides Y and Y' are not identical. In one embodiment, the double stranded oligonucleotide construct of Formula I(a) includes one or more, specifically 1, 2, 3 or 4, mismatches, to the extent such mismatches do not significantly diminish the ability of the double stranded oligonucleotide to inhibit target gene expression.

In one embodiment, regions X and Y of multifunctional siNA molecule of the invention (e.g., having any of Formula I or II), are complementary to different target nucleic acid sequences that are portions of the same target nucleic acid molecule. In one embodiment, such as target nucleic acid sequences are at different locations within the coding region of a RNA transcript. In one embodiment, such target nucleic acid sequences comprise coding and non-coding regions of the same RNA transcript. In one embodiment, such target nucleic acid sequences comprise regions of alternately spliced transcripts or precursors of such alternately spliced transcripts.

In one embodiment, a multifunctional siNA molecule having any of Formula I or II can comprise chemical modifications as described herein without limitation, such as, for example, nucleotides having any of Formulae III-IX described herein, stabilization chemistries as described in Table VIII, or any other combination of modified nucleotides and non-nucleotides as described in the various embodiments herein.

In one embodiment, the palindrome or repeat sequence or modified nucleotide (e.g. nucleotide with a modified base, such as 2-amino purine or a universal base) in Z of multifunctional siNA constructs having Formula I(a) or I(b), comprises chemically modified nucleotides that are able to interact with a portion of the target nucleic acid sequence (e.g., modified base analogs that can form Watson Crick base pairs or non-Watson Crick base pairs).

In one embodiment, a multifunctional siNA molecule of the invention, for example each strand of a multifunctional siNA having Formula I or II, independently comprises about 15 to about 40 nucleotides (e.g., about 15, 16, 17, 18, 19, 20, 21, 22, 23, 24, 25, 26, 27, 28, 29, 30, 31, 32, 33, 34, 35, 36, 37, 38, 39, or 40 nucleotides). In one embodiment, a multifunctional siNA molecule of the invention comprises one or more chemical modifications. In a non-limiting example, the introduction of chemically modified nucleotides and/or non-nucleotides into nucleic acid molecules of the invention provides a powerful tool in overcoming potential limitations of in vivo stability and bioavailability inherent to unmodified RNA molecules that are delivered exogenously. For example, the use of chemically modified nucleic acid molecules can enable a lower dose of a particular nucleic acid molecule for a given therapeutic effect since chemically modified nucleic acid molecules tend to have a longer half-life in serum or in cells or tissues. Furthermore, certain chemical modifications can improve the bioavailability and/or potency of nucleic acid molecules by not only enhancing half-life but also facilitating the targeting of nucleic acid molecules to particular organs, cells or tissues and/or improving cellular uptake of the nucleic acid molecules. Therefore, even if the activity of a chemically modified nucleic acid molecule is reduced in vitro as compared to a native/unmodified nucleic acid molecule, for example when compared to an unmodified RNA molecule, the overall activity of the modified nucleic acid molecule can be greater than the native or unmodified nucleic acid molecule due to improved stability, potency, duration of effect, bioavailability and/or delivery of the molecule.

In one embodiment, the invention features chemically modified multifunctional siNA constructs having specificity for more than one target nucleic acid molecules, such as in an in vitro system, cell or organism. Non-limiting examples of such chemical modifications independently include without limitation phosphate backbone modification (e.g. phosphorothioate internucleotide linkages), nucleotide sugar modification (e.g., 2'-O-methyl nucleotides, 2'-O-allyl nucleotides, 2'-deoxy-2'-fluoro nucleotides, 2'-deoxyribonucleotides), nucleotide base modification (e.g., "universal base" containing nucleotides, 5-C-methyl nucleotides), and non-nucleotide modification (e.g., abasic nucleotides, inverted deoxyabasic residue) or a combination of these modifications. These and other chemical modifications, when used in various multifunctional siNA constructs, can preserve biological activity of the multifunctional siNAs in vivo while at the same time, dramatically increasing the serum stability, potency, duration of effect and/or specificity of these compounds.

In one embodiment, a multifunctional siNA molecule of the invention can generally comprise modified nucleotides from about 5 to about 100% of the nucleotide positions (e.g., 5%, 10%, 15%, 20%, 25%, 30%, 35%, 40%, 45%, 50%, 55%, 60%, 65%, 70%, 75%, 80%, 85%, 90%, 95% or 100% of the nucleotide positions may be modified). The actual percentage of modified nucleotides present in a given multifunctional siNA molecule depends on the total number of nucleotides present in the multifunctional siNA. If the multifunctional siNA molecule is single stranded, the percent modification can be based upon the total number of nucleotides present in the single stranded multifunctional siNA molecules. Likewise, if the multifunctional siNA molecule is double stranded, the percent modification can be based upon the total number of nucleotides present in both strands. In addition, the actual percentage of modified nucleotides present in a given multifunctional siNA molecule can also depend on the total number of purine and pyrimidine nucleotides present in the multifunctional siNA, for example, wherein all pyrimidine nucleotides and/or all purine nucleotides present in the multifunctional siNA molecule are modified.

In one embodiment, a multifunctional siNA duplex molecule can comprise mismatches (e.g., 1, 2, 3, 4 or 5 mismatches), bulges, loops, or wobble base pairs, for example, to modulate or regulate the ability of the multifunctional siNA molecule to mediate inhibition of gene expression. Mismatches, bulges, loops, or wobble base pairs can be introduced into the multifunctional siNA duplex molecules to the extent such mismatches, bulges, loops, or wobble base pairs do not significantly impair the ability of the multifunctional siNAs to mediate inhibition of target gene expression. Such mismatches, bulges, loops, or wobble base pairs can be present in regions of the multifunctional siNA duplex that do not significantly impair the ability of such multifunctional siNAs to mediate inhibition of gene expression, for example, mismatches can be present at the terminal regions of the duplex or at one or positions in the internal regions of the duplex. Similarly, the wobble base pairs can, for example, be at the terminal base paired region(s) of the duplex or in the internal regions or in the regions where self complementary, palindromic, or repeat sequences are present within the multifunctional siNA.

In one embodiment, a multifunctional siNA molecule of the invention can comprise one or more (e.g., about 1, 2, 3, 4, or 5) phosphorothioate internucleotide linkages at the 3'-end of the multifunctional siNA molecule.

In one embodiment, a multifunctional siNA molecule of the invention comprises a 3' nucleotide overhang region, which includes one or more (e.g., about 1, 2, 3, 4) unpaired nucleotides when the multifunctional siNA is in duplex form. In a non-limiting example, the multifunctional siNA duplex with overhangs includes a fewer number of base pairs than the number of nucleotides present in each strand of the multifunctional siNA molecule (e.g., a multifunctional siNA 18 nucleotides in length forming a 16 base-paired duplex with 2 nucleotide overhangs at the 3' ends). Such blunt-end multifunctional siNA duplex may optionally include one or more mismatches, wobble base-pairs or nucleotide bulges. The 3'-terminal nucleotide overhangs of a multifunctional siNA molecule of the invention can comprise ribonucleotides or deoxyribonucleotides that are chemically-modified at a nucleic acid sugar, base, or phosphate backbone. The 3'-terminal nucleotide overhangs can comprise one or more universal base nucleotides. The 3'-terminal nucleotide overhangs can comprise one or more acyclic nucleotides or non-nucleotides.

In one embodiment, a multifunctional siNA molecule of the invention in duplex form comprises blunt ends, i.e., the ends do not include any overhanging nucleotides. For example, a multifunctional siNA duplex molecule of the invention comprising modifications described herein (e.g., comprising modifications having Formulae III-IX or multifunctional siNA constructs comprising Stab1-Stab22 or any combination thereof) and/or any length described herein, has blunt ends or ends with no overhanging nucleotides.

In one embodiment, any multifunctional siNA duplex of the invention can comprise one or more blunt ends, i.e. where a blunt end does not have any overhanging nucleotides. In a non-limiting example, a blunt ended multifunctional siNA duplex includes the same number of base pairs as the number of nucleotides present in each strand of the multifunctional siNA molecule (e.g., a multifunctional siNA 18 nucleotides in length forming an 18 base-paired duplex). Such blunt-end multifunctional siNA duplex may optionally include one or more mismatches, wobble base-pairs or nucleotide bulges.

By "blunt ends" is meant symmetric termini or termini of a multifunctional siNA duplex having no overhanging nucleotides. The two strands of a multifunctional siNA duplex molecule align with each other without over-hanging nucleotides at the termini. For example, a blunt ended multifunctional siNA duplex comprises terminal nucleotides that are complementary between the two strands of the multifunctional siNA duplex.

In one embodiment, a multifunctional siNA molecule of the invention comprises no ribonucleotides and is capable of down-regulating expression of more than one target gene in vitro or in vivo.

In one embodiment, a multifunctional siNA molecule of the invention comprises sequence wherein one or more pyrimidine nucleotides present in the multifunctional siNA sequence is a 2'-deoxy-2'-fluoro pyrimidine nucleotide. In another embodiment, a multifunctional siNA molecule of the invention comprises sequence wherein all pyrimidine nucleotides present in the multifunctional siNA sequence are 2'-deoxy-2'-fluoro pyrimidine nucleotides. Such multifunctional siNA sequences can further comprise differing nucleotides or non-nucleotide caps described herein, such as deoxynucleotides, inverted nucleotides, abasic moieties, inverted abasic moieties, and/or any other modification shown in FIG. 10 or those modifications generally known in the art that can be introduced into nucleic acid molecules, to the extent any modification to the multifunctional siNA molecule does not significantly impair the ability of the multifunctional siNA molecule to mediate inhibition of gene expression.

In one embodiment, a multifunctional siNA molecule of the invention comprises sequence wherein one or more purine nucleotides present in the multifunctional siNA sequence is a 2'-sugar modified purine, (e.g., 2'-O-methyl purine nucleotide, 2'-O-allyl purine nucleotide, or 2'-methoxy-ethoxy purine nucleotides). In another embodiment, a multifunctional siNA molecule of the invention comprises sequence wherein all purine nucleotides present in the multifunctional siNA sequence are 2'-sugar modified purines, (e.g., 2'-O-methyl purine nucleotides, 2'-O-allyl purine nucleotides, or 2'-methoxy-ethoxy purine nucleotides).

In one embodiment, a multifunctional siNA molecule of the invention comprises sequence wherein one or more purine nucleotides present in the multifunctional siNA sequence is a 2'-deoxy purine nucleotide. In another embodiment, a multifunctional siNA molecule of the invention comprises sequence wherein all purine nucleotides present in the multifunctional siNA sequence are 2'-deoxy purine nucleotides.

In one embodiment, a multifunctional siNA molecule of the invention comprises sequence wherein one or more purine nucleotides present in the multifunctional siNA sequence is a 2'-deoxy-2'-fluoro purine nucleotide. In another embodiment, a multifunctional siNA molecule of the invention comprises sequence wherein all purine nucleotides present in the multifunctional siNA sequence are 2'-deoxy-2'-fluoro purine nucleotides.

In one embodiment, a multifunctional siNA molecule of the invention comprises sequence wherein the multifunctional siNA sequence includes a terminal cap moiety at the 3'-end of one or both of the multifunctional siNA sequences. In another embodiment, the terminal cap moiety is an inverted deoxy abasic moiety or any other modification shown in FIG. 9 or those modifications generally known in the art that can be introduced into nucleic acid molecules, to the extent any modification to the multifunctional siNA molecule does not significantly impair the ability of the multifunctional siNA molecule to mediate inhibition of gene expression.

In one embodiment, a multifunctional siNA molecule of the invention comprises sequence wherein the multifunctional siNA sequence includes a terminal cap moiety at the 3' end of the multifunctional siNA sequence. In another embodiment, the terminal cap moiety is an inverted deoxy abasic moiety or any other modification shown in FIG. 9 or those modifications generally known in the art that can be introduced into nucleic acid molecules, to the extent any modification to the multifunctional siNA molecule does not significantly impair the ability of the multifunctional siNA molecule to mediate inhibition of gene expression.

In one embodiment, a multifunctional siNA molecule of the invention has activity that modulates expression of RNA encoded by more than one gene. Because many genes can share some degree of sequence homology with each other, multifunctional siNA molecules can be designed to target a class of genes (and associated receptor or ligand genes) or alternately specific genes by selecting sequences that are either shared amongst different gene targets or alternatively that are unique for a specific gene target. Therefore, in one embodiment, each complementary region of a multifunctional siNA molecule of the invention can be designed to target conserved regions of a RNA sequence having homology between several genes or genomes (e.g. viral genome, such as HIV, HCV, HBV, SARS and others) so as to target several genes or gene families (e.g., different gene isoforms, splice variants, mutant genes etc.) with one multifunctional siNA molecule. In another embodiment, each complementary region of a multifunctional siNA molecule of the invention can be designed to target a sequence that is unique to a specific RNA sequence of a specific gene or genome (e.g. viral genome, such as HIV, HCV, HBV, SARS and others). The expression of any target nucleic acid having known sequence can be modulated by multifunctional siNA molecules of the invention (see for example McSwiggen et al., WO 03/74654 incorporated by reference herein in its entirety for a list of mammalian and viral targets).

In one embodiment, a multifunctional siNA molecule of the invention does not contain any ribonucleotides. In another embodiment, a multifunctional siNA molecule of the invention comprises one or more ribonucleotides.

In one embodiment, the multifunctional siNA molecule of the invention does not include any chemical modification. In another embodiment, the multifunctional siNA molecule of the invention is RNA comprising no chemical modifications. In another embodiment, the multifunctional siNA molecule of the invention is RNA comprising two deoxyribonucleotides at the 3'-end. In another embodiment, the multifunctional siNA molecule of the invention is RNA comprising a 3'-cap structure (e.g., inverted deoxynucleotide, inverted deoxy abasic moiety, a thymidine dinucleotide residues or a thymidine dinucleotide with a phosphorothioate internucleotide linkage, and the like).

In one embodiment of the present invention, each sequence of a multifunctional siNA molecule is independently about 18 to about 300 nucleotides in length, in specific embodiments about 18-200 nucleotides in length, preferably 18-150 nucleotides in length, more specifically 18-100 nucleotides in length. In another embodiment, the multifunctional siNA duplexes of the invention independently comprise about 18 to about 300 base pairs (e.g., about 18-200, 18-150, 18-100, 18-75, 18-50, 18-34 or 18-30 base pairs).

In one embodiment, the invention features a multifunctional siNA molecule that inhibits the replication of a virus (e.g, as plant virus such as tobacco mosaic virus, or mammalian virus, such as hepatitis C virus, human immunodeficiency virus, hepatitis B virus, herpes simplex virus, cytomegalovirus, human papilloma virus, rhino virus, respiratory syncytial virus, SARS, or influenza virus).

In one embodiment, the invention features a medicament comprising a multifunctional siNA molecule of the invention.

In one embodiment, the invention features an active ingredient comprising a multifunctional siNA molecule of the invention.

In one embodiment, the invention features the use of a multifunctional siNA molecule of the invention to down-regulate expression of a target gene.

In one embodiment, the invention features a composition comprising a multifunctional siNA molecule of the invention and a pharmaceutically acceptable carrier or diluent.

In one embodiment, the invention features a method of increasing the stability of a multifunctional siNA molecule against cleavage by ribonucleases or other nucleases, comprising introducing at least one modified nucleotide into the multifunctional siNA molecule, wherein the modified nucleotide is for example a 2'-deoxy-2'-fluoro nucleotide. In another embodiment, all pyrimidine nucleotides present in the multifunctional siNA are 2'-deoxy-2'-fluoro pyrimidine nucleotides. In another embodiment, the modified nucleotides in the multifunctional siNA include at least one 2'-deoxy-2'-fluoro cytidine or 2'-deoxy-2'-fluoro uridine nucleotide. In another embodiment, the modified nucleotides in the multifunctional siNA include at least one 2'-fluoro cytidine and at least one 2'-deoxy-2'-fluoro uridine nucleotides. In another embodiment, all uridine nucleotides present in the multifunctional siNA are 2'-deoxy-2'-fluoro uridine nucleotides. In another embodiment, all cytidine nucleotides present in the multifunctional siNA are 2'-deoxy-2'-fluoro cytidine nucleotides. In another embodiment, all adenosine nucleotides present in the multifunctional siNA are 2'-deoxy-2'-fluoro adenosine nucleotides. In another embodiment, all guanosine nucleotides present in the multifunctional siNA are 2'-deoxy-2'-fluoro guanosine nucleotides. The multifunctional siNA can further comprise at least one modified internucleotidic linkage, such as phosphorothioate linkage or phosphorodithioate linkage. In another embodiment, the 2'-deoxy-2'-fluoronucleotides are present at specifically selected locations in the multifunctional siNA that are sensitive to cleavage by ribonucleases or other nucleases, such as locations having pyrimidine nucleotides or terminal nucleotides. The multifunctional siNA molecules of the invention can be modified to improve stability, pharmacokinetic properties, in vitro or in vivo delivery, localization and/or potency by methods generally known in the art (see for example Beigelman et al., WO 03/70918 incorporated by reference herein in its entirety including the drawings).

In one embodiment, a multifunctional siNA molecule of the invention comprises nucleotide sequence having complementarity to nucleotide sequence of RNA or a portion thereof encoded by the target nucleic acid or a portion thereof.

In one embodiment, the invention features a multifunctional siNA molecule having a first region and a second region, wherein the second region comprises nucleotide sequence that is an inverted repeat sequence of the nucleotide sequence of the first region, wherein the first region is complementary to nucleotide sequence of a target nucleic acid (e.g., RNA) or a portion thereof (see for example FIGS. 1 and 2 for an illustration of non-limiting examples of multifunctional siNA molecules of the instant invention).

One embodiment of the invention provides an expression vector comprising a nucleic acid sequence encoding at least one multifunctional siNA molecule of the invention in a manner that allows expression of the multifunctional siNA sequence. Another embodiment of the invention provides a mammalian cell comprising such an expression vector. The mammalian cell can be a human cell.

In one embodiment, a multifunctional siNA molecule of the invention comprises one or more (e.g., about 1, 2, 3, 4, 5, 6, 7, 8, 9, 10, or more) nucleotides comprising a backbone modified internucleotide linkage having Formula III:

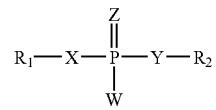

wherein each R1 and R2 is independently any nucleotide, non-nucleotide, or polynucleotide which can be naturally-occurring or chemically-modified, each X and Y is independently O, S, N, alkyl, or substituted alkyl, each Z and W is independently O, S, N, alkyl, substituted alkyl, O-alkyl, S-alkyl, alkaryl, or aralkyl, and wherein W, X, Y, and Z are optionally not all O. In another embodiment, a backbone modification of the invention comprises a phosphonoacetate and/or thiophosphonoacetate internucleotide linkage (see for example Sheehan et al., 2003, Nucleic Acids Research, 31, 4109-4118).

The chemically-modified internucleotide linkages having Formula III, for example, wherein any Z, W, X, and/or Y independently comprises a sulphur atom, can be present anywhere in the multifunctional siNA sequence. Non-limiting examples of such phosphate backbone modifications are phosphorothioate and phosphorodithioate. The multifunctional siNA molecules of the invention can comprise one or more (e.g., about 1, 2, 3, 4, 5, 6, 7, 8, 9, 10, or more) chemically-modified internucleotide linkages having Formula III at the 3'-end, the 5'-end, or both of the 3' and 5'-ends of the multifunctional siNA sequence. In another non-limiting example, an exemplary multifunctional siNA molecule of the invention can comprise one or more (e.g., about 1, 2, 3, 4, 5, 6, 7, 8, 9, 10, or more) pyrimidine nucleotides with chemically-modified internucleotide linkages having Formula III. In yet another non-limiting example, an exemplary multifunctional siNA molecule of the invention can comprise one or more (e.g., about 1, 2, 3, 4, 5, 6, 7, 8, 9, 10, or more) purine nucleotides with chemically-modified internucleotide linkages having Formula III. In another embodiment, a multifunctional siNA molecule of the invention having internucleotide linkage(s) of Formula III also comprises a chemically-modified nucleotide or non-nucleotide having any of Formulae III-IX.

In one embodiment, a multifunctional siNA molecule of the invention comprises one or more (e.g., about 1, 2, 3, 4, 5, 6, 7, 8, 9, 10, or more) nucleotides or non-nucleotides having Formula IV:

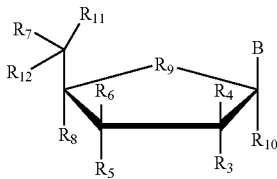

wherein each R3, R4, R5, R6, R7, R8, R10, R11 and R12 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-OSH, alkyl-OH, O-alkyl-OH, O-alkyl-SH, S-alkyl-OH, S-alkyl-SH, alkyl-5-alkyl, alkyl-O-alkyl, ONO2, NO2, N3, NH2, aminoalkyl, aminoacid, aminoacyl, ONH2, O-aminoalkyl, O-aminoacid, O-aminoacyl, heterocycloalkyl, heterocycloalkaryl, aminoalkylamino, polyalklylamino, substituted silyl, or group having Formula III or IV; R9 is O, S, CH2, S=O, CHF, or CF2, and B is a nucleosidic base such as adenine, guanine, uracil, cytosine, thymine, 2-aminoadenosine, 5-methylcytosine, 2,6-diaminopurine, 2-aminopurine, 2-amino-1,6-dihydropurine or any other non-naturally occurring base that can be complementary or non-complementary to target RNA or a non-nucleosidic base such as phenyl, naphthyl, 3-nitropyrrole, 5-nitroindole, nebularine, pyridone, pyridinone, or any other non-naturally occurring universal base that can be complementary or non-complementary to target RNA.

The chemically-modified nucleotide or non-nucleotide of Formula IV can be present anywhere in the multifunctional siNA sequence. The multifunctional siNA molecules of the invention can comprise one or more chemically-modified nucleotide or non-nucleotide of Formula IV at the 3'-end, the 5'-end, or both of the 3' and 5'-ends of the multifunctional siNA sequence. For example, an exemplary multifunctional siNA molecule of the invention can comprise about 1 to about 5 or more (e.g., about 1, 2, 3, 4, 5, or more) chemically-modified nucleotides or non-nucleotides of Formula IV at the 5'-end of the multifunctional siNA sequence. In another non-limiting example, an exemplary multifunctional siNA molecule of the invention can comprise about 1 to about 5 or more (e.g., about 1, 2, 3, 4, 5, or more) chemically-modified nucleotides or non-nucleotides of Formula IV at the 3'-end of the multifunctional siNA sequence.

In one embodiment, a multifunctional siNA molecule of the invention comprises one or more (e.g., about 1, 2, 3, 4, 5, 6, 7, 8, 9, 10, or more) nucleotides or non-nucleotides having Formula V:

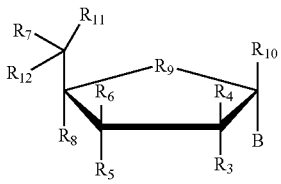

wherein each R3, R4, R5, R6, R7, R8, R10, R11 and R12 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-OSH, alkyl-OH, O-alkyl-OH, O-alkyl-SH, S-alkyl-OH, S-alkyl-SH, alkyl-5-alkyl, alkyl-O-alkyl, ONO2, NO2, N3, NH2, aminoalkyl, aminoacid, aminoacyl, ONH2, O-aminoalkyl, O-aminoacid, O-aminoacyl, heterocycloalkyl, heterocycloalkaryl, aminoalkylamino, polyalklylamino, substituted silyl, or group having Formula III or IV; R9 is O, S, CH2, S=O, CHF, or CF2, and B is a nucleosidic base such as adenine, guanine, uracil, cytosine, thymine, 2-aminoadenosine, 5-methylcytosine, 2,6-diaminopurine, or any other non-naturally occurring base that can be employed to be complementary or non-complementary to target RNA or a non-nucleosidic base such as phenyl, naphthyl, 3-nitropyrrole, 5-nitroindole, nebularine, pyridone, pyridinone, or any other non-naturally occurring universal base that can be complementary or non-complementary to target RNA.

The chemically-modified nucleotide or non-nucleotide of Formula V can be present anywhere in the multifunctional siNA sequence. The multifunctional siNA molecules of the invention can comprise one or more chemically-modified nucleotide or non-nucleotide of Formula V at the 3'-end, the 5'-end, or both of the 3' and 5'-ends of the multifunctional siNA sequence. For example, an exemplary multifunctional siNA molecule of the invention can comprise about 1 to about 5 or more (e.g., about 1, 2, 3, 4, 5, or more) chemically-modified nucleotide(s) or non-nucleotide(s) of Formula V at the 5'-end of multifunctional siNA sequence. In anther non-limiting example, an exemplary multifunctional siNA molecule of the invention can comprise about 1 to about 5 or more (e.g., about 1, 2, 3, 4, 5, or more) chemically-modified nucleotide or non-nucleotide of Formula V at the 3'-end of the multifunctional siNA sequence.

In another embodiment, a multifunctional siNA molecule of the invention comprises a nucleotide having Formula IV or V, wherein the nucleotide having Formula IV or V is in an inverted configuration. For example, the nucleotide having Formula IV or V is connected to the multifunctional siNA construct in a 3'-3', 3'-2', 2'-3', or 5'-5' configuration, such as at the 3'-end, the 5'-end, or both of the 3' and 5'-ends of one or both multifunctional siNA strands.

In one embodiment, a multifunctional siNA molecule of the invention comprises a 5'-terminal phosphate group having Formula VI:

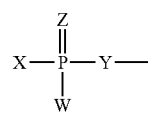

wherein each X and Y is independently O, S, N, alkyl, substituted alkyl, or alkylhalo; wherein each Z and W is independently O, S, N, alkyl, substituted alkyl, O-alkyl, S-alkyl, alkaryl, aralkyl, or alkylhalo or acetyl; and/or wherein W, X, Y and Z are optionally not all O.

In another embodiment, a multifunctional siNA molecule of the invention comprises one or more (e.g., 1, 2, 3, 4, 5, 6, 7, 8, 9, 10 or more) 2'-5' internucleotide linkages. The 2'-5' internucleotide linkage(s) can be anywhere in the multifunctional siNA sequence. In addition, the 2'-5' internucleotide linkage(s) can be present at various other positions within the multifunctional siNA sequence, for example, about 1, 2, 3, 4, 5, 6, 7, 8, 9, 10, or more including every internucleotide linkage of a pyrimidine nucleotide in the multifunctional siNA molecule can comprise a 2'-5' internucleotide linkage, or about 1, 2, 3, 4, 5, 6, 7, 8, 9, 10, or more including every internucleotide linkage of a purine nucleotide in the multifunctional siNA molecule can comprise a 2'-5' internucleotide linkage.

In one embodiment, a multifunctional siNA molecule of the invention comprises at least one (e.g., about 1, 2, 3, 4, 5, 6, 7, 8, 9, 10, or more) abasic moiety, for example a compound having Formula VII:

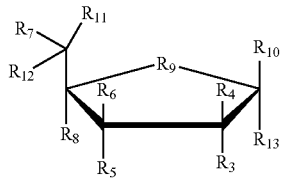

wherein each R3, R4, R5, R6, R7, R8, R10, R11, R12, and R13 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-OSH, alkyl-OH, O-alkyl-OH, O-alkyl-SH, S-alkyl-OH, S-alkyl-SH, alkyl-5-alkyl, alkyl-O-alkyl, ONO2, NO2, N3, NH2, aminoallyl, aminoacid, aminoacyl, ONH2, O-aminoalkyl, O-aminoacid, O-aminoacyl, heterocycloalkyl, heterocycloalkaryl, aminoalkylamino, polyalklylamino, substituted silyl, or group having Formula III or IV; R9 is O, S, CH2, S=O, CHF, or CF2.

In one embodiment, a multifunctional siNA molecule of the invention comprises at least one (e.g., about 1, 2, 3, 4, 5, 6, 7, 8, 9, 10, or more) inverted nucleotide or abasic moiety, for example a compound having Formula VIII:

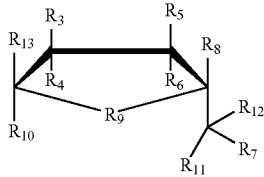

wherein each R3, R4, R5, R6, R7, R8, R10, R11, R12, and R13 is independently H, OH, alkyl, substituted allyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, allyl-OSH, alkyl-OH, O-allyl-OH, O-alkyl-SH, S-alkyl-OH, S-alkyl-SH, alkyl-5-alkyl, allyl-O-alkyl, ONO2, NO2, N3, NH2, aminoalkyl, aminoacid, aminoacyl, ONH2, O-aminoalkyl, O-aminoacid, O-aminoacyl, heterocycloalkyl, heterocycloalkaryl, aminoalkylamino, polyalklylamino, substituted silyl, or group having Formula III or IV; R9 is O, S, CH2, S=O, CHF, or CF2, and either R3, R5, R8 or R13 serve as points of attachment to the multifunctional siNA molecule of the invention.

In another embodiment, a multifunctional siNA molecule of the invention comprises at least one (e.g., about 1, 2, 3, 4, 5, 6, 7, 8, 9, 10, or more) substituted polyalkyl moieties, for example a compound having Formula IX:

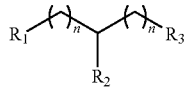

wherein each n is independently an integer from 1 to 12, each R1, R2 and R3 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-OSH, alkyl-OH, O-alkyl-OH, O-alkyl-SH, S-alkyl-OH, S-alkyl-SH, alkyl-5-alkyl, alkyl-O-alkyl, ONO2, NO2, N3, NH2, aminoalkyl, aminoacid, aminoacyl, ONH2, O-aminoalkyl, O-aminoacid, O-aminoacyl, heterocycloalkyl, heterocycloalkaryl, aminoalkylamino, polyalklylamino, substituted silyl, or a group having Formula III, and R1, R2 or R3 serves as points of attachment to the multifunctional siNA molecule of the invention.

In another embodiment, the invention features a compound having Formula IX, wherein R1 and R2 are hydroxyl (OH) groups, n=1, and R3 comprises O and is the point of attachment to the 3'-end, the 5'-end, or both of the 3' and 5'-ends of one or both strands of a multifunctional siNA molecule of the invention. This modification is referred to herein as "glyceryl" (for example modification 6 in FIG. 9).

In another embodiment, a moiety having any of Formula VII, VIII or IX of the invention is at the 3'-end, the 5'-end, or both of the 3' and 5'-ends of a multifunctional siNA molecule of the invention. In another embodiment, a moiety having any of Formula VII, VIII or IX of the invention is at the 3'-end of a multifunctional siNA molecule of the invention.

In another embodiment, a multifunctional siNA molecule of the invention comprises an abasic residue having Formula VII or VIII, wherein the abasic residue having Formula VII or VIII is connected to the multifunctional siNA construct in a 3-3', 3-2',2-3', or 5-5' configuration, such as at the 3'-end, the 5'-end, or both of the 3' and 5'-ends of the multifunctional siNA molecule. In another embodiment, a multifunctional siNA molecule of the invention comprises an abasic residue having Formula VII or VIII, wherein the abasic residue having Formula VII or VIII is connected to the multifunctional siNA construct in a 3-3' or 3-2' configuration at the 3'-end of the multifunctional siNA molecule.

In one embodiment, a multifunctional siNA molecule of the invention comprises one or more (e.g., about 1, 2, 3, 4, 5, 6, 7, 8, 9, 10, or more) locked nucleic acid (LNA) nucleotides, for example at the 5'-end, the 3'-end, both of the 5' and 3'-ends, or any combination thereof, of the multifunctional siNA molecule.

In another embodiment, a multifunctional siNA molecule of the invention comprises one or more (e.g., about 1, 2, 3, 4, 5, 6, 7, 8, 9, 10, or more) acyclic nucleotides, for example at the 5'-end, the 3'-end, both of the 5' and 3'-ends, or any combination thereof, of the multifunctional siNA molecule. In another embodiment, a multifunctional siNA molecule of the invention comprises one or more (e.g., about 1, 2, 3, 4, 5, 6, 7, 8, 9, 10, or more) acyclic nucleotides at the 3'-end of the multifunctional siNA molecule.

In one embodiment, a multifunctional siNA molecule of the invention comprises a terminal cap moiety, (see for example FIG. 9) such as an inverted deoxyabasic moiety or inverted nucleotide, at the 3'-end of one or both strands of the multifunctional siNA molecule.

In one embodiment, a multifunctional siNA molecule of the invention comprises sequence wherein any (e.g., one or more or all) pyrimidine nucleotides present in the multifunctional siNA are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and where any (e.g., one or more or all) purine nucleotides present in the multifunctional siNA are 2'-deoxy purine nucleotides (e.g., wherein all purine nucleotides are 2'-deoxy purine nucleotides or alternately a plurality of purine nucleotides are 2'-deoxy purine nucleotides). The multifunctional siNA can further comprise terminal cap modifications as described herein.

In one embodiment, a multifunctional siNA molecule of the invention comprises sequence wherein any (e.g., one or more or all) pyrimidine nucleotides present in the multifunctional siNA are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and where any (e.g., one or more or all) purine nucleotides present in the multifunctional siNA are 2'-O-methyl purine nucleotides (e.g., wherein all purine nucleotides are 2'-O-methyl purine nucleotides or alternately a plurality of purine nucleotides are 2'-O-methyl purine nucleotides). The multifunctional siNA can further comprise terminal cap modifications as described herein.

In one embodiment, a multifunctional siNA molecule of the invention comprises sequence wherein any (e.g., one or more or all) pyrimidine nucleotides present in the multifunctional siNA are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any (e.g., one or more or all) purine nucleotides present in the multifunctional siNA are selected from the group consisting of 2'-deoxy nucleotides, locked nucleic acid (LNA) nucleotides, 2'-methoxyethyl nucleotides, 4'-thionucleotides, and 2'-O-methyl nucleotides (e.g., wherein all purine nucleotides are selected from the group consisting of 2'-deoxy nucleotides, locked nucleic acid (LNA) nucleotides, 2'-methoxyethyl nucleotides, 4'-thionucleotides, and 2'-O-methyl nucleotides or alternately a plurality of purine nucleotides are selected from the group consisting of 2'-deoxy nucleotides, locked nucleic acid (LNA) nucleotides, 2'-methoxyethyl nucleotides, 4'-thionucleotides, and 2'-O-methyl nucleotides).

In another embodiment, a multifunctional siNA molecule of the invention comprises modified nucleotides having properties or characteristics similar to naturally occurring ribonucleotides. For example, the invention features multifunctional siNA molecules including modified nucleotides having a Northern conformation (e.g., Northern pseudorotation cycle, see for example Saenger, *Principles of Nucleic Acid Structure*, Springer-Verlag ed., 1984). As such, chemically modified nucleotides present in the multifunctional siNA molecules of the invention are resistant to nuclease degradation while at the same time maintaining the capacity to modulate gene expression. Non-limiting examples of nucleotides having a northern configuration include locked nucleic acid (LNA) nucleotides (e.g., 2'-O,4'-C-methylene-(D-ribofuranosyl) nucleotides); 2'-methoxyethoxy (MOE) nucleotides; 2'-methyl-thio-ethyl, 2'-deoxy-2'-fluoro nucleotides, 2'-deoxy-2'-chloro nucleotides, 2'-azido nucleotides, and 2'-O-methyl nucleotides.

In one embodiment, a multifunctional siNA molecule of the invention comprises a conjugate attached to the multifunctional siNA molecule. For example, the conjugate can be attached to the multifunctional siNA molecule via a covalent attachment. In one embodiment, the conjugate is attached to the multifunctional siNA molecule via a biodegradable linker. In one embodiment, the conjugate molecule is attached at the 3'-end of the multifunctional siNA molecule. In another embodiment, the conjugate molecule is attached at the 5'-end of the multifunctional siNA molecule. In yet another embodiment, the conjugate molecule is attached at both the 3'-end and 5'-end of the multifunctional siNA molecule, or any combination thereof. In one embodiment, the conjugate molecule of the invention comprises a molecule that facilitates delivery of a multifunctional siNA molecule into a biological system, such as a cell. In another embodiment, the conjugate molecule attached to the chemically-modified multifunctional siNA molecule is a polyethylene glycol, human serum albumin, or a ligand for a cellular receptor that can mediate cellular uptake. Examples of specific conjugate molecules contemplated by the instant invention that can be attached to multifunctional siNA molecules are described in Vargeese et al., U.S. Ser. No. 10/201,394, incorporated by reference herein. The type of conjugates used and the extent of conjugation of multifunctional siNA molecules of the invention can be evaluated for improved pharmacokinetic profiles, bioavailability, and/or stability of multifunctional siNA constructs while at the same time maintaining the ability of the multifunctional siNA to modulate gene expression. As such, one skilled in the art can screen multifunctional siNA constructs that are modified with various conjugates to determine whether the multifunctional siNA conjugate complex possesses improved properties while maintaining the ability to modulate gene expression, for example in animal models as are generally known in the art.

In one embodiment, a multifunctional siNA molecule of the invention comprises a non-nucleotide linker, such as an abasic nucleotide, polyether, polyamine, polyamide, peptide, carbohydrate, lipid, polyhydrocarbon, or other polymeric compounds (e.g. polyethylene glycols such as those having between 2 and 100 ethylene glycol units). Specific examples include those described by Seela and Kaiser, *Nucleic Acids Res.* 1990, 18:6353 and *Nucleic Acids Res.* 1987, 15:3113; Cload and Schepartz, *J. Am. Chem. Soc.* 1991, 113:6324; Richardson and Schepartz, *J. Am. Chem. Soc.* 1991, 113: 5109; Ma et al., *Nucleic Acids Res.* 1993, 21:2585 and *Biochemistry* 1993, 32:1751; Durand et al., *Nucleic Acids Res.* 1990, 18:6353; McCurdy et al., *Nucleosides & Nucleotides* 1991, 10:287; Jschke et al., *Tetrahedron Lett.* 1993, 34:301; Ono et al., *Biochemistry* 1991, 30:9914; Arnold et al., International Publication No. WO 89/02439; Usman et al., International Publication No. WO 95/06731; Dudycz et al., International Publication No. WO 95/11910 and Ferentz and Verdine, *J. Am. Chem. Soc.* 1991, 113:4000, all hereby incorporated by reference herein. A "non-nucleotide" further means any group or compound that can be incorporated into a nucleic acid chain in the place of one or more nucleotide units, including either sugar and/or phosphate substitutions, and allows the remaining bases to exhibit their enzymatic activity. The group or compound can be abasic in that it does not contain a commonly recognized nucleotide base, such as adenosine, guanine, cytosine, uracil or thymine, for example at the C1 position of the sugar.

In one embodiment, the invention features a multifunctional siNA molecule that does not require the presence of a 2'-OH group (ribonucleotide) to be present within the multifunctional siNA molecule to support inhibition or modulation of gene expression of target nucleic acids.

In one embodiment, the invention features a method for modulating the expression of one or more genes within a cell comprising: (a) synthesizing a multifunctional siNA molecule of the invention, which can be chemically-modified or unmodified, wherein the multifunctional siNA comprises sequences complementary to one or more RNAs of the gene(s) or portions thereof; and (b) introducing the multifunctional siNA molecule into a cell under conditions suitable to modulate the expression of the gene(s) in the cell.

In one embodiment, the invention features a method for modulating the expression of a gene within a cell comprising: (a) synthesizing a multifunctional siNA molecule of the invention, which can be chemically-modified or unmodified, wherein the multifunctional siNA comprises a first strand and a second strand that are complementary to each other, and wherein the first strand comprises a region having sequence complementarity to a first portion of a RNA of the gene or a portion thereof and the second strand comprises a region having sequence complementarity to a second portion of the RNA of the gene or a portion thereof; and (b) introducing the multifunctional siNA molecule into a cell under conditions suitable to modulate the expression of the gene in the cell. The first and second portions of the RNA can comprise, for example, coding and/or non-coding sequences of the gene.

In one embodiment, the invention features a method for modulating the expression of a gene within a cell comprising: (a) synthesizing a multifunctional siNA molecule of the invention, which can be chemically-modified or unmodified, wherein the multifunctional siNA comprises a first strand and a second strand that are complementary to each other, and wherein the first strand comprises a region having sequence complementarity to a first portion of a RNA of the gene or a portion thereof and the second strand comprises a region having sequence complementarity to a second RNA that regulates the expression of the gene or a portion thereof, and (b) introducing the multifunctional siNA molecule into a cell under conditions suitable to modulate the expression of the gene in the cell. The first RNA can comprise for example a coding or non-coding sequence of the gene. The second RNA can comprise for example an enhancer region, a tRNA, a RNA encoding an enhancer element, a RNA encoding a transcription factor, a micro RNA, stRNA, or other non-coding RNA that is involved in the expression of the target gene.

In one embodiment, the invention features a method for modulating the expression of more than one gene within a cell comprising: (a) synthesizing a multifunctional siNA molecule of the invention, which can be chemically-modified or unmodified, wherein the multifunctional siNA comprises a first strand and a second strand that are complementary to each other, and wherein the first strand comprises a region having sequence complementarity to a RNA of a first gene or a portion thereof and the second strand comprises a region having sequence complementarity to a RNA of a second gene or a portion thereof; and (b) introducing the multifunctional siNA molecule into a cell under conditions suitable to modulate the expression of the genes in the cell. The RNA of the first and second genes can independently comprise coding and/or non-coding sequences of the genes. In one embodiment, the first gene encodes one or more cytokines and the second gene encodes one or more receptors of the cytokine(s). In one embodiment, the first gene encodes one or more strains of a virus and the second gene encodes one or strains of the same virus. In one embodiment, the first gene encodes one or more strains of a virus and the second gene encodes one or strains of a different virus. In one embodiment, the first gene encodes one or more strains of a virus and the second gene encodes one or more cellular factors involved in infection or replication of the virus. In one embodiment, the first gene encodes a first protein and the second gene encodes a second protein that are involved in a common biologic pathway. In one embodiment, the first gene encodes a first protein and the second gene encodes a second protein that are involved in divergent biologic pathways.

In one embodiment, multifunctional siNA molecules of the invention are used as reagents in ex vivo applications. For example, multifunctional siNA reagents are introduced into tissue or cells that are transplanted into a subject for therapeutic effect. The cells and/or tissue can be derived from an organism or subject that later receives the explant, or can be derived from another organism or subject prior to transplantation. The multifunctional siNA molecules can be used to modulate the expression of one or more genes in the cells or tissue, such that the cells or tissue obtain a desired phenotype or are able to perform a function when transplanted in vivo. In one embodiment, certain target cells from a patient are extracted. These extracted cells are contacted with multifunctional siNAs targeting a specific nucleotide sequence within the cells under conditions suitable for uptake of the multifunctional siNAs by these cells (e.g., using delivery reagents such as cationic lipids, liposomes and the like or using techniques such as electroporation to facilitate the delivery of multifunctional siNAs into cells). The cells are then reintroduced back into the same patient or other patients. Non-limiting examples of ex vivo applications include use in organ/tissue transplant, tissue grafting, or treatment of pulmonary disease (e.g., restenosis) or prevent neointimal hyperplasia and atherosclerosis in vein grafts. Such ex vivo applications may also be used to treat conditions associated with coronary and peripheral bypass graft failure, for example, such methods can be used in conjunction with peripheral vascular bypass graft surgery and coronary artery bypass graft surgery. Additional applications include transplants to treat CNS lesions or injury, including use in treatment of neurodegenerative conditions such as Alzheimer's disease, Parkinson's Disease, Epilepsy, Dementia, Huntington's disease, or amyotrophic lateral sclerosis (ALS).

In one embodiment, the invention features a method of modulating the expression of one or more genes in a tissue explant comprising: (a) synthesizing a multifunctional siNA molecule of the invention, which can be chemically-modified or unmodified, wherein the multifunctional siNA comprises sequences complementary to one or more RNAs of the gene(s) or portions thereof; and (b) introducing the multifunctional siNA molecule into a cell of the tissue explant derived from a particular organism under conditions suitable to modulate the expression of the gene(s) in the tissue explant. In another embodiment, the method further comprises introducing the tissue explant back into the organism the tissue was derived from or into another organism under conditions suitable to modulate the expression of the gene(s) in that organism.

In one embodiment, the invention features a method of modulating the expression of a gene in a tissue explant comprising: (a) synthesizing a multifunctional siNA molecule of the invention, which can be chemically-modified or unmodified, wherein the multifunctional siNA comprises a first strand and a second strand that are complementary to each other, and wherein the first strand comprises a region having sequence complementarity to a first portion of a RNA of the gene or a portion thereof and the second strand comprises a region having sequence complementarity to a second portion of the RNA of the gene or a portion thereof; and (b) introducing the multifunctional siNA molecule into a cell of the tissue explant derived from a particular organism under conditions suitable to modulate the expression of the gene in the tissue explant. In another embodiment, the method further comprises introducing the tissue explant back into the organism the tissue was derived from or into another organism under conditions suitable to modulate the expression of the gene in that organism. The first and second portions of the RNA can comprise, for example, coding and/or non-coding sequences of the gene.

In another embodiment, the invention features a method of modulating the expression of more than one gene in a tissue explant comprising: (a) synthesizing a multifunctional siNA molecule of the invention, which can be chemically-modified or unmodified, wherein the multifunctional siNA comprises a first strand and a second strand that are complementary to each other, and wherein the first strand comprises a region having sequence complementarity to a RNA of a first gene or a portion thereof and the second strand comprises a region having sequence complementarity to a second gene or a portion thereof; and (b) introducing the multifunctional siNA molecule(s) into a cell of the tissue explant derived from a particular organism under conditions suitable to modulate the expression of the genes in the tissue explant. In another embodiment, the method further comprises introducing the tissue explant back into the organism the tissue was derived from or into another organism under conditions suitable to modulate the expression of the genes in that organism. The RNA of the first and second genes can independently comprise coding and/or non-coding sequences of the genes. In one embodiment, the first gene encodes one or more cytokines and the second gene encodes one or more receptors of the cytokine(s). In one embodiment, the first gene encodes one or more strains of a virus and the second gene encodes one or strains of the same virus. In one embodiment, the first gene encodes one or more strains of a virus and the second gene encodes one or strains of a different virus. In one embodiment, the first gene encodes one or more strains of a virus and the second gene encodes one or more cellular factors involved in infection or replication of the virus. In one embodiment, the first gene encodes a first protein and the second gene encodes a second protein that are involved in a common biologic pathway. In one embodiment, the first gene encodes a first protein and the second gene encodes a second protein that are involved in divergent biologic pathways.

In one embodiment, the invention features a method for modulating the expression of one or more genes within an organism comprising: (a) synthesizing a multifunctional siNA molecule of the invention, which can be chemically-modified or unmodified, wherein the multifunctional siNA comprises sequences complementary to one or more RNAs of the gene(s) or portions thereof; and (b) introducing the multifunctional siNA molecule into the organism under conditions suitable to modulate the expression of the gene(s) in the organism.

In one embodiment, the invention features a method for modulating the expression of a gene within an organism comprising: (a) synthesizing a multifunctional siNA molecule of the invention, which can be chemically-modified or unmodified, wherein the multifunctional siNA comprises a first strand and a second strand that are complementary to each other, and wherein the first strand comprises a region having sequence complementarity to a first portion of a RNA of the gene or a portion thereof and the second strand comprises a region having sequence complementarity to a second portion of the RNA of the gene or a portion thereof; and (b) introducing the multifunctional siNA molecule into the organism under conditions suitable to modulate the expression of the gene in the cell. The first and second portions of the RNA can comprise, for example, coding and/or non-coding sequences of the gene.

In one embodiment, the invention features a method for modulating the expression of a gene within an organism comprising: (a) synthesizing a multifunctional siNA molecule of the invention, which can be chemically-modified or unmodified, wherein the multifunctional siNA comprises a first strand and a second strand that are complementary to each other, and wherein the first strand comprises a region having sequence complementarity to a first portion of a RNA of the gene or a portion thereof and the second strand comprises a region having sequence complementarity to a second RNA that regulates the expression of the gene or a portion thereof; and (b) introducing the multifunctional siNA molecule into the organism under conditions suitable to modulate the expression of the gene in the organism. The first RNA can comprise for example a coding or non-coding sequence of the gene. The second RNA can comprise for example an enhancer region, a tRNA, a RNA encoding an enhancer element, a RNA encoding a transcription factor, a micro RNA, stRNA, or other non-coding RNA that is involved in the expression of the target gene.

In one embodiment, the invention features a method for modulating the expression of more than one gene within an organism comprising: (a) synthesizing a multifunctional siNA molecule of the invention, which can be chemically-modified or unmodified, wherein the multifunctional siNA comprises a first strand and a second strand that are complementary to each other, and wherein the first strand comprises a region having sequence complementarity to a RNA of a first gene or a portion thereof and the second strand comprises a region having sequence complementarity to a second gene or a portion thereof; and (b) introducing the multifunctional siNA molecule into the organism under conditions suitable to modulate the expression of the genes in the organism. The RNA of the first and second genes can independently comprise coding and/or non-coding sequences of the genes. In one embodiment, the first gene encodes one or more cytokines and the second gene encodes one or more receptors of the cytokine(s). In one embodiment, the first gene encodes one or more strains of a virus and the second gene encodes one or strains of the same virus. In one embodiment, the first gene encodes one or more strains of a virus and the second gene encodes one or strains of a different virus. In one embodiment, the first gene encodes one or more strains of a virus and the second gene encodes one or more cellular factors involved in infection or replication of the virus. In one embodiment, the first gene encodes a first protein and the second gene encodes a second protein that are involved in a common biologic pathway. In one embodiment, the first gene encodes a first protein and the second gene encodes a second protein that are involved in divergent biologic pathways.

In one embodiment, the invention features a method for modulating the expression of one or more genes within a tissue or organ comprising: (a) synthesizing a multifunctional siNA molecule of the invention, which can be chemically-modified or unmodified, wherein the multifunctional siNA comprises sequences complementary to one or more RNAs of the gene(s) or portions thereof; and (b) introducing the multifunctional siNA molecule into the tissue or organ under conditions suitable to modulate the expression of the gene(s) in the tissue or organ. In another embodiment, the tissue is ocular tissue and the organ is the eye. In another embodiment, the tissue comprises hepatocytes and/or hepatic tissue and the organ is the liver.

In one embodiment, the invention features a method for modulating the expression of a gene within a tissue or organ comprising: (a) synthesizing a multifunctional siNA molecule of the invention, which can be chemically-modified or unmodified, wherein the multifunctional siNA comprises a first strand and a second strand that are complementary to each other, and wherein the first strand comprises a region having sequence complementarity to a first portion of a RNA of the gene or a portion thereof and the second strand comprises a region having sequence complementarity to a second portion of the RNA of the gene or a portion thereof; and (b) introducing the multifunctional siNA molecule into the tissue or organ under conditions suitable to modulate the expression of the gene in the tissue or organ. The first and second portions of the RNA can comprise, for example, coding and/or non-coding sequences of the gene. In another embodiment, the tissue is ocular tissue and the organ is the eye. In another embodiment, the tissue comprises hepatocytes and/or hepatic tissue and the organ is the liver.

In one embodiment, the invention features a method for modulating the expression of more than one gene within a tissue or organ comprising: (a) synthesizing a multifunctional siNA molecule of the invention, which can be chemically-modified or unmodified, wherein the multifunctional siNA comprises a first strand and a second strand that are complementary to each other, and wherein the first strand comprises a region having sequence complementarity to a RNA of a first gene or a portion thereof and the second strand comprises a region having sequence complementarity to a RNA of a second gene or a portion thereof; and (b) introducing the multifunctional siNA molecule into the tissue or organ under conditions suitable to modulate the expression of the genes in the tissue or organ. The RNA of the first and second genes can independently comprise coding and/or non-coding sequences of the genes. In one embodiment, the first gene encodes one or more cytokines and the second gene encodes one or more receptors of the cytokine(s). In one embodiment, the first gene encodes one or more strains of a virus and the second gene encodes one or strains of the same virus. In one embodiment, the first gene encodes one or more strains of a virus and the second gene encodes one or strains of a different virus. In one embodiment, the first gene encodes one or more strains of a virus and the second gene encodes one or more cellular factors involved in infection or replication of the virus. In one embodiment, the first gene encodes a first protein and the second gene encodes a second protein that are involved in a common biologic pathway. In one embodiment, the first gene encodes a first protein and the second gene encodes a second protein that are involved in divergent biologic pathways. In another embodiment, the tissue is ocular tissue and the organ is the eye. In another embodiment, the tissue comprises hepatocytes and/or hepatic tissue and the organ is the liver.

The multifunctional siNA molecules of the invention can be designed to down regulate or inhibit target gene expression in a biological system by targeting of a variety of nucleic acid molecules (e.g., RNA). In one embodiment, the multifunctional siNA molecules of the invention are used to target various RNAs corresponding to a target gene. Non-limiting examples of such RNAs include messenger RNA (mRNA), alternate RNA splice variants of target gene(s), post-transcriptionally modified RNA of target gene(s), pre-mRNA of target gene(s), and/or RNA templates. If alternate splicing produces a family of transcripts that are distinguished by usage of appropriate exons, the instant invention can be used to inhibit gene expression through the appropriate exons to specifically inhibit or to distinguish among the functions of gene family members. For example, a protein that contains an alternatively spliced transmembrane domain can be expressed in both membrane bound and secreted forms. Use of the invention to target the exon containing the transmembrane domain can be used to determine the functional consequences of pharmaceutical targeting of membrane bound as opposed to the secreted form of the protein. Non-limiting examples of applications of the invention relating to targeting these RNA molecules include therapeutic pharmaceutical applications, pharmaceutical discovery applications, molecular diagnostic and gene function applications, and gene mapping, for example using single nucleotide polymorphism mapping with multifunctional siNA molecules of the invention. Such applications can be implemented using known gene sequences or from partial sequences available from an expressed sequence tag (EST).

In another embodiment, the multifunctional siNA molecules of the invention are used to target conserved sequences corresponding to a gene family or gene families (e.g., different isoforms or different members of a superfamily of genes, such as interleukin superfamily genes, tumor necrosis family superfamily genes, viral strains etc. (see for example McSwiggen et al., WO 03/74654). As such, multifunctional siNA molecules targeting multiple gene targets can provide increased therapeutic effect. In addition, multifunctional siNA can be used to characterize pathways of gene function in a variety of applications. For example, the present invention can be used to inhibit the activity of target gene(s) in a pathway to determine the function of uncharacterized gene(s) in gene function analysis, mRNA function analysis, or translational analysis. The invention can be used to determine potential target gene pathways involved in various diseases and conditions toward pharmaceutical development. The invention can be used to understand pathways of gene expression involved in, for example, in development, such as prenatal development and postnatal development, and/or the progression and/or maintenance of cancer, infectious disease, autoimmunity, inflammation, endocrine disorders, renal disease, ocular disease, pulmonary disease, neurologic disease, cardiovascular disease, birth defects, aging, any other disease or condition related to gene expression.

In one embodiment, multifunctional siNA molecule(s) and/or methods of the invention are used to down-regulate or inhibit the expression of gene(s) that encode RNA referred to by Genbank Accession, for example genes encoding RNA sequence(s) referred to herein by Genbank Accession number. See, for example, McSwiggen et al., WO 03/74654 incorporated by reference herein in its entirety for a list of mammalian and viral targets.

In one embodiment, the invention features a method comprising: (a) generating a library of multifunctional siNA constructs having a predetermined complexity; and (b) assaying the multifunctional siNA constructs of (a) above, under conditions suitable to determine accessible target sites within the target RNA sequence. In one embodiment, the multifunctional siNA molecules of (a) have strands of a fixed length, for example, about 28 nucleotides in length. In another embodiment, the multifunctional siNA molecules of (a) are of differing length, for example having strands of about 19 to about 34 (e.g., about 19, 20, 21, 22, 23, 24, 25, 26, 27, 28, 29, 30, 31, 32, 33, or 34) nucleotides in length. The assay can comprise a cell culture system in which target RNA is expressed. In another embodiment, fragments of target RNA are analyzed for detectable levels of cleavage, for example by gel electrophoresis, northern blot analysis, or RNAse protection assays, to determine the most suitable target site(s) within the target RNA sequence. The target RNA sequence can be obtained as is known in the art, for example, by cloning and/or transcription for in vitro systems, and by cellular expression in in vivo systems.

By "detectable level of cleavage" is meant cleavage of target RNA (and formation of cleaved product RNAs) to an extent sufficient to discern cleavage products above the background of RNAs produced by random degradation of the target RNA. Production of cleavage products from 1-5% of the target RNA is sufficient to detect above the background for most methods of detection.

In one embodiment, the invention features a composition comprising a multifunctional siNA molecule of the invention, which can be chemically-modified or unmodified, in a pharmaceutically acceptable carrier or diluent. In another embodiment, the invention features a pharmaceutical composition comprising multifunctional siNA molecules of the invention, which can be chemically-modified, targeting one or more genes in a pharmaceutically acceptable carrier or diluent. In another embodiment, the invention features a method for diagnosing a disease or condition in a subject comprising administering to the subject a composition of the invention under conditions suitable for the diagnosis of the disease or condition in the subject. In another embodiment, the invention features a method for treating or preventing a disease or condition in a subject, comprising administering to the subject a composition of the invention under conditions suitable for the treatment or prevention of the disease or condition in the subject, alone or in conjunction with one or more other therapeutic compounds. In yet another embodiment, the invention features a method for reducing or preventing tissue rejection in a subject comprising administering to the subject a composition of the invention under conditions suitable for the reduction or prevention of tissue rejection in the subject.

In another embodiment, the invention features a method for validating a gene target in a biological system comprising: (a) synthesizing a multifunctional siNA molecule of the invention, which can be chemically-modified or unmodified, wherein the multifunctional siNA comprises a first sequence and a second sequence that are complementary to each other, and wherein the first sequence is complementary to a first portion of a RNA of the gene or a portion thereof and the second sequence is complementary a second portion of the RNA of the gene or a portion thereof; and (b) introducing the multifunctional siNA molecule into a cell, tissue, or organism under conditions suitable for modulating expression of the target gene in the cell, tissue, or organism; and (c) determining the function of the gene by assaying for any phenotypic change in the cell, tissue, or organism.

In another embodiment, the invention features a method for validating a biologic pathway comprising two gene targets in a biological system comprising: (a) synthesizing a multifunctional siNA molecule of the invention, which can be chemically-modified or unmodified, wherein the multifunctional siNA comprises a first sequence and a second sequence that are complementary to each other, and wherein the first sequence is complementary to a RNA of a first gene or a portion thereof and the second sequence is complementary a RNA of a second gene or a portion thereof; and (b) introducing the multifunctional siNA molecule into a cell, tissue, or organism under conditions suitable for modulating expression of the target genes in the cell, tissue, or organism; and (c) determining the function of the biologic pathway by assaying for any phenotypic change in the cell, tissue, or organism.

In another embodiment, the invention features a method for validating a biologic pathway comprising two or more gene targets in a biological system comprising: (a) synthesizing a multifunctional siNA molecule of the invention, which can be chemically-modified or unmodified, wherein the multifunctional siNA comprises a first sequence and a second sequence that are complementary to each other, and wherein the first sequence is complementary to a RNA of a one or more first gene targets or a portion thereof and the second sequence is complementary a RNA of one or more second gene targets or a portion thereof; and (b) introducing the multifunctional siNA molecule into a cell, tissue, or organism under conditions suitable for modulating expression of the target genes in the cell, tissue, or organism; and (c) determining the function of the biologic pathway by assaying for any phenotypic change in the cell, tissue, or organism.

By "biological system" is meant, material, in a purified or unpurified form, from biological sources, including but not limited to human, animal, plant, insect, bacterial, viral or other sources, wherein the system comprises the components required for biologic activity (e.g., inhibition of gene expression). The term "biological system" includes, for example, a cell, tissue, or organism, or extract thereof.

By "phenotypic change" is meant any detectable change to a cell that occurs in response to contact or treatment with a nucleic acid molecule of the invention (e.g., multifunctional siNA). Such detectable changes include, but are not limited to, changes in shape, size, proliferation, motility, protein expression or RNA expression or other physical or chemical changes as can be assayed by methods known in the art. The detectable change can also include expression of reporter genes/molecules such as Green Florescent Protein (GFP) or various tags that are used to identify an expressed protein or any other cellular component that can be assayed.

In one embodiment, the invention features a kit containing a multifunctional siNA molecule of the invention, which can be chemically-modified or unmodified, that can be used to modulate the expression of a target gene in biological system, including, for example, in a cell, tissue, or organism. In one embodiment, the invention features a kit containing a multifunctional siNA molecule of the invention, which can be chemically-modified or unmodified, that can be used to modulate the expression of more than one target gene in biological system, including, for example, in a cell, tissue, or organism. In another embodiment, the invention features a kit containing more than one multifunctional siNA molecule of the invention, which can be chemically-modified, that can be used to modulate the expression of more than one target gene in a biological system, including, for example, in a cell, tissue, or organism.

In one embodiment, the invention features a cell containing one or more multifunctional siNA molecules of the invention, which can be chemically-modified or unmodified. In another embodiment, the cell containing a multifunctional siNA molecule of the invention is a mammalian cell. In yet another embodiment, the cell containing a multifunctional siNA molecule of the invention is a human cell.

In one embodiment, the synthesis of a multifunctional siNA duplex molecule of the invention, which can be chemically-modified or unmodified, comprises: (a) synthesizing a self complementary nucleic acid sequence comprising nucleic acid molecule, defined herein as multifunctional siNA molecule; (b) incubating the nucleic acid molecule of (a) under conditions suitable for the multifunctional siNA molecule to form a double-stranded multifunctional siNA molecule. In one embodiment, synthesis of the self complementary nucleic acid sequence containing oligonucleotide or multifunctional siNA is by solid phase oligonucleotide synthesis. In another embodiment the multifunctional siNA molecule is expressed from an expression vector or is enzymatically synthesized.

In another embodiment, the method of synthesis of multifunctional siNA molecules of the invention comprises the teachings of Scaringe et al., U.S. Pat. Nos. 5,889,136; 6,008,400; and 6,111,086, incorporated by reference herein in their entirety.

In one embodiment, the invention features a multifunctional siNA construct that mediates modulation or inhibition of gene expression in a cell or reconstituted system, wherein the multifunctional siNA construct comprises one or more chemical modifications, for example, one or more chemical modifications having any of Formulae III-IX or any combination thereof that increases the nuclease resistance and/or overall effectiveness or potency of the multifunctional siNA construct.

In another embodiment, the invention features a method for generating multifunctional siNA molecules with increased nuclease resistance comprising (a) introducing nucleotides having any of Formula III-IX or any combination thereof into a multifunctional siNA molecule, and (b) assaying the multifunctional siNA molecule of step (a) under conditions suitable for isolating multifunctional siNA molecules having increased nuclease resistance.

In another embodiment, the invention features a method for generating multifunctional siNA molecules with increased duration of effect comprising (a) introducing nucleotides having any of Formula III-IX or any combination thereof into a multifunctional siNA molecule, and (b) assaying the multifunctional siNA molecule of step (a) under conditions suitable for isolating multifunctional siNA molecules having increased duration of effect.

In another embodiment, the invention features a method for generating multifunctional siNA molecules with increased delivery into a target cell or tissue, such as hepatocytes, endothelial cells, T-cells, primary cells, and neuronal cells, comprising (a) introducing chemical modifications, conjugates, or nucleotides having any of Formula III-IX or any combination thereof into a multifunctional siNA molecule, and (b) assaying the multifunctional siNA molecule of step (a) under conditions suitable for isolating multifunctional siNA molecules having increased delivery into a target cell or tissue. In one embodiment, the invention features multifunctional siNA duplex constructs that mediate modulation or inhibition of gene expression against a target gene, wherein the multifunctional siNA construct comprises one or more chemical modifications described herein that modulates the binding affinity between the two strands of the multifunctional siNA construct.

In one embodiment, the binding affinity between the strands of the duplex formed by the multifunctional siNA of the invention is modulated to increase the activity of the multifunctional siNA molecule with regard to the ability of the multifunctional siNA to modulate gene expression. In another embodiment the binding affinity between the two strands of a multifunctional siNA duplex is decreased. The binding affinity between the strands of the multifunctional siNA construct can be decreased by introducing one or more chemically modified nucleotides in the multifunctional siNA sequence that disrupts the duplex stability of the multifunctional siNA (e.g., lowers the Tm of the duplex). The binding affinity between the strands of the multifunctional siNA construct can be decreased by introducing one or more nucleotides in the multifunctional siNA sequence that do not form Watson-Crick base pairs. The binding affinity between the strands of the multifunctional siNA construct can be decreased by introducing one or more wobble base pairs in the multifunctional siNA sequence. The binding affinity between the strands of the multifunctional siNA construct can be decreased by modifying the nucleobase composition of the multifunctional siNA, such as by altering the G-C content of the multifunctional siNA sequence (e.g., decreasing the number of G-C base pairs in the multifunctional siNA sequence). These modifications and alterations in sequence can be introduced selectively at pre-determined positions of the multifunctional siNA sequence to increase multifunctional siNA mediated modulation of gene expression. For example, such modifications and sequence alterations can be introduced to disrupt multifunctional siNA duplex stability between the 5'-end of one strand 3'-end of the other strand, the 3'-end of one strand and the 5'-end of the other strand, or alternately the middle of the multifunctional siNA duplex. In another embodiment, multifunctional siNA molecules are screened for optimized activity by introducing such modifications and sequence alterations either by rational design based upon observed rules or trends in increasing multifunctional siNA activity, or randomly via combinatorial selection processes that cover either partial or complete sequence space of the multifunctional siNA construct.

In another embodiment, the invention features a method for generating a multifunctional siNA duplex molecule with increased binding affinity between the strands of the multifunctional siNA molecule comprising (a) introducing nucleotides having any of Formula III-IX or any combination thereof into a multifunctional siNA molecule, and (b) assaying the multifunctional siNA molecule of step (a) under conditions suitable for isolating a multifunctional siNA molecule having increased binding affinity between the strands of the multifunctional siNA molecule.

In one embodiment, the invention features a multifunctional siNA construct that modulates the expression of a target RNA, wherein the multifunctional siNA construct comprises one or more chemical modifications described herein that modulates the binding affinity between the multifunctional siNA construct and a complementary target RNA sequence within a cell.

In one embodiment, the invention features a multifunctional siNA construct that modulates the expression of a target DNA, wherein the multifunctional siNA construct comprises one or more chemical modifications described herein that modulates the binding affinity between the multifunctional siNA construct and a complementary target DNA sequence within a cell.

In another embodiment, the invention features a method for generating a multifunctional siNA molecule with increased binding affinity between the multifunctional siNA molecule and a complementary target RNA sequence comprising (a) introducing nucleotides having any of Formula III-XI or any combination thereof into a multifunctional siNA molecule, and (b) assaying the multifunctional siNA molecule of step (a) under conditions suitable for isolating a multifunctional siNA molecule having increased binding affinity between the multifunctional siNA molecule and a complementary target RNA sequence.

In another embodiment, the invention features a method for generating a multifunctional siNA molecule with increased binding affinity between the multifunctional siNA molecule and a complementary target DNA sequence comprising (a) introducing nucleotides having any of Formula III-IX or any combination thereof into a multifunctional siNA molecule, and (b) assaying the multifunctional siNA molecule of step (a) under conditions suitable for isolating a multifunctional siNA molecule having increased binding affinity between the multifunctional siNA molecule and a complementary target DNA sequence.

In one embodiment, the invention features a multifunctional siNA construct that modulates the expression of a target gene in a cell or reconstituted system, wherein the multifunctional siNA construct comprises one or more chemical modifications described herein that modulates the cellular uptake of the multifunctional siNA construct.

In another embodiment, the invention features a method for generating a multifunctional siNA molecule against a target gene with improved cellular uptake comprising (a) introducing nucleotides having any of Formula III-IX or any combination thereof into a multifunctional siNA molecule, and (b) assaying the multifunctional siNA molecule of step (a) under conditions suitable for isolating a multifunctional siNA molecule having improved cellular uptake.

In one embodiment, the invention features a multifunctional siNA construct that modulates the expression of a target gene, wherein the multifunctional siNA construct comprises one or more chemical modifications described herein that increases the bioavailability of the multifunctional siNA construct, for example, by attaching polymeric conjugates such as polyethyleneglycol or equivalent conjugates that improve the pharmacokinetics of the multifunctional siNA construct, or by attaching conjugates that target specific tissue types or cell types in vivo. Non-limiting examples of such conjugates are described in Vargeese et al., U.S. Ser. No. 10/201,394 incorporated by reference herein.

In one embodiment, the invention features a method for generating a multifunctional siNA molecule of the invention with improved bioavailability comprising (a) introducing a conjugate into the structure of a multifunctional siNA molecule, and (b) assaying the multifunctional siNA molecule of step (a) under conditions suitable for isolating multifunctional siNA molecules having improved bioavailability. Such conjugates can include ligands for cellular receptors, such as peptides derived from naturally occurring protein ligands; protein localization sequences, including cellular ZIP code sequences; antibodies; nucleic acid aptamers; vitamins and other co-factors, such as folate and N-acetylgalactosamine; polymers, such as polyethyleneglycol (PEG); phospholipids; cholesterol; polyamines, such as spermine or spermidine; and others.

In one embodiment, the invention features a method for screening multifunctional siNA molecules against a target nucleic acid sequence comprising, (a) generating a plurality of unmodified multifunctional siNA molecules, (b) assaying the multifunctional siNA molecules of step (a) under conditions suitable for isolating multifunctional siNA molecules that are active in modulating expression of the target nucleic acid sequence, (c) optionally introducing chemical modifications (e.g. chemical modifications as described herein or as otherwise known in the art) into the active multifunctional siNA molecules of (b), and (d) optionally re-screening the chemically modified multifunctional siNA molecules of (c) under conditions suitable for isolating chemically modified multifunctional siNA molecules that are active in modulating expression of the target nucleic acid sequence, for example in a biological system.

In one embodiment, the invention features a method for screening multifunctional siNA molecules against more than one target nucleic acid sequence comprising, (a) generating a plurality of unmodified multifunctional siNA molecules, (b) assaying the multifunctional siNA molecules of step (a) under conditions suitable for isolating multifunctional siNA molecules that are active in modulating expression of the target nucleic acid sequences, (c) optionally introducing chemical modifications (e.g. chemical modifications as described herein or as otherwise known in the art) into the active multifunctional siNA molecules of (b), and (d) optionally re-screening the chemically modified multifunctional siNA molecules of (c) under conditions suitable for isolating chemically modified multifunctional siNA molecules that are active in modulating expression of the target nucleic acid sequences, for example in a biological system.

In one embodiment, the invention features a method for screening multifunctional siNA molecules against a target nucleic acid sequence comprising (a) generating a plurality of chemically modified multifunctional siNA molecules (e.g. multifunctional siNA molecules as described herein or as otherwise known in the art), and (b) assaying the multifunctional siNA molecules of step (a) under conditions suitable for isolating chemically modified multifunctional siNA molecules that are active in modulating expression of the target nucleic acid sequence.

In one embodiment, the invention features a method for screening multifunctional siNA molecules against more than one target nucleic acid sequence comprising (a) generating a plurality of chemically modified multifunctional siNA molecules (e.g. multifunctional siNA molecules as described herein or as otherwise known in the art), and (b) assaying the multifunctional siNA molecules of step (a) under conditions suitable for isolating chemically modified multifunctional siNA molecules that are active in modulating expression of the target nucleic acid sequences.

In another embodiment, the invention features a method for generating multifunctional siNA molecules of the invention with improved bioavailability comprising (a) introducing an excipient formulation to a multifunctional siNA molecule, and (b) assaying the multifunctional siNA molecule of step (a) under conditions suitable for isolating multifunctional siNA molecules having improved bioavailability. Such excipients include polymers such as cyclodextrins, lipids, cationic lipids, polyamines, phospholipids, nanoparticles, receptors, ligands, and others.

In another embodiment, the invention features a method for generating a multifunctional siNA molecule of the invention with improved bioavailability comprising (a) introducing an excipient formulation to a multifunctional siNA molecule, and (b) assaying the multifunctional siNA molecule of step (a) under conditions suitable for isolating multifunctional siNA molecules having improved bioavailability. Such excipients include polymers such as cyclodextrins, lipids, cationic lipids, polyamines, phospholipids, and others.

In another embodiment, the invention features a method for generating a multifunctional siNA molecule of the invention with improved bioavailability comprising (a) introducing nucleotides having any of Formulae III-IX, a conjugate, or any combination thereof into a multifunctional siNA molecule, and (b) assaying the multifunctional siNA molecule of step (a) under conditions suitable for isolating multifunctional siNA molecules having improved bioavailability.

In another embodiment, polyethylene glycol (PEG) can be covalently attached to multifunctional siNA compounds of the present invention. The attached PEG can be any molecular weight, preferably from about 2,000 to about 50,000 daltons (Da).

The present invention can be used alone or as a component of a kit having at least one of the reagents necessary to carry out the in vitro or in vivo introduction of RNA to test samples and/or subjects. For example, preferred components of the kit include a multifunctional siNA molecule of the invention and a vehicle that promotes introduction of the multifunctional siNA into cells of interest as described herein (e.g., using lipids and other methods of transfection known in the art, see for example Beigelman et al, U.S. Pat. No. 6,395,713). The kit can be used, for example, for target validation, such as in determining gene function and/or activity, in drug optimization, and in drug discovery (see for example Usman et al., U.S. Ser. No. 60/402,996). Such a kit can also include instructions to allow a user of the kit to practice the invention.

The term "multifunctional short interfering nucleic acid" or "multifunctional siNA" as used herein refers to any short interfering nucleic acid molecule comprising a first region of one strand having nucleic acid sequence complementary to a first target nucleic acid sequence and a first region of the second strand having nucleic acid sequence complementary to a second target nucleic acid sequence, wherein the first regions of each strand are not complementary to each other or if complementary then do not share more than 75% complementarity.

The term "short interfering nucleic acid", "siNA", "short interfering RNA", "siRNA", "short interfering nucleic acid molecule", "short interfering oligonucleotide molecule", or "chemically-modified short interfering nucleic acid molecule" as used herein refers to any nucleic acid molecule capable of inhibiting or down regulating gene expression or viral replication, for example by mediating RNA interference "RNAi" or gene silencing in a sequence-specific manner; see for example Zamore et al., 2000, Cell, 101, 25-33; Bass, 2001, Nature, 411, 428-429; Elbashir et al., 2001, Nature, 411, 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237; Hutvagner and Zamore, 2002, Science, 297, 2056-60; McManus et al., 2002, RNA, 8, 842-850; Reinhart et al., 2002, Gene & Dev., 16, 1616-1626; and Reinhart & Bartel, 2002, Science, 297, 1831). Non limiting examples of siNA molecules of the invention are shown in Beigelman et al. WO 03/070918. For example the siNA can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The siNA can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double stranded structure, for example wherein the double stranded region is about 19 base pairs); the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof. Alternatively, the siNA is assembled from a single oligonucleotide, where the self-complementary sense and antisense regions of the siNA are linked by means of a nucleic acid based or non-nucleic acid-based linker(s). The siNA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The siNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (for example, where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al., 2002, Cell., 110, 563-574 and Schwarz et al., 2002, Molecular Cell, 10, 537-568), or 5',3'-diphosphate. In certain embodiments, the siNA molecule of the invention comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic intercations, and/or stacking interactions. In certain embodiments, the siNA molecules of the invention comprise nucleotide sequence that is complementary to nucleotide sequence of a target gene. In another embodiment, the siNA molecule of the invention interacts with nucleotide sequence of a target gene in a manner that causes inhibition of expression of the target gene. As used herein, siNA molecules need not be limited to those molecules containing only RNA, but further encompasses chemically-modified nucleotides and non-nucleotides. In certain embodiments, the short interfering nucleic acid molecules of the invention lack 2'-hydroxy (2'-OH) containing nucleotides. Applicant describes in certain embodiments short interfering nucleic acids that do not require the presence of nucleotides having a 2'-hydroxy group for mediating RNAi and as such, short interfering nucleic acid molecules of the invention optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. The modified short interfering nucleic acid molecules of the invention can also be referred to as short interfering modified oligonucleotides "siMON." As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, siNA molecules of the invention can be used to epigenetically silence genes at both the post-transcriptional level or the pre-transcriptional level. In a non-limiting example, epigenetic regulation of gene expression by siNA molecules of the invention can result from siNA mediated modification of chromatin structure to alter gene expression (see, for example, Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

By "modulate" is meant that the expression of the gene, or level of RNA molecule or equivalent RNA molecules encoding one or more proteins or protein subunits, or activity of one or more proteins or protein subunits is up regulated or down regulated, such that expression, level, or activity is greater than or less than that observed in the absence of the modulator. For example, the term "modulate" can mean "inhibit," but the use of the word "modulate" is not limited to this definition.

By "inhibit", "down-regulate", or "reduce", it is meant that the expression of the gene, or level of RNA molecules or equivalent RNA molecules encoding one or more proteins or protein subunits, or activity of one or more proteins or protein subunits, is reduced below that observed in the absence of the nucleic acid molecules (e.g., multifunctional siNA) of the invention. In one embodiment, inhibition, down-regulation or reduction with an multifunctional siNA molecule is below that level observed in the presence of an inactive or attenuated molecule. In another embodiment, inhibition, down-regulation, or reduction with multifunctional siNA molecules is below that level observed in the presence of, for example, an multifunctional siNA molecule with scrambled sequence or with mismatches. In another embodiment, inhibition, down-regulation, or reduction of gene expression with a nucleic acid molecule of the instant invention is greater in the presence of the nucleic acid molecule than in its absence.

By "palindrome" or "repeat" nucleic acid sequence is meant, a nucleic acid sequence whose 5'-to-3' sequence is identical when present in a duplex. For example, a palindrome sequence of the invention in a duplex can comprise sequence having the same sequence when one strand of the duplex is read in the 5'-to-3' direction (left to right) and the other strand is read 3'-to-5' direction (right to left). In another example, a repeat sequence of the invention can comprise a sequence having repeated nucleotides so arranged as to provide self complementarity (e.g. 5'-AUAU . . . -3'; 5'-AAUU . . . -3'; 5'-UAUA . . . -3'; 5'-UUAA . . . -3'; 5'-CGCG . . . -3'; 5'-CCGG . . . -3', 5'-GGCC . . . -3'; 5'-CCGG . . . -3'; or any expanded repeat thereof etc.). The palindrome or repeat sequence can comprise about 2 to about 24 nucleotides in even numbers, (e.g., 2, 4, 6, 8, 10, 12, 14, 16, 18, 20, 22, or 24 nucleotides). All that is required of the palindrome or repeat sequence is that it comprises nucleic acid sequence whose 5'-to-3' sequence is identical when present in a duplex, either alone or as part of a longer nucleic acid sequence. The palindrome or repeat sequence of the invention can comprise chemical modifications as described herein that can form, for example, Watson Crick or non-Watson Crick base pairs.

By "gene", or "target gene", is meant, a nucleic acid that encodes an RNA, for example, nucleic acid sequences including, but not limited to, structural genes encoding a polypeptide. A gene or target gene can also encode a functional RNA (fRNA) or non-coding RNA (ncRNA), such as small temporal RNA (stRNA), micro RNA (miRNA), small nuclear RNA (snRNA), short interfering RNA (siRNA), small nucleolar RNA (snRNA), ribosomal RNA (rRNA), transfer RNA (tRNA) and precursor RNAs thereof. Such non-coding RNAs can serve as target nucleic acid molecules for multifunctional siNA mediated RNA interference in modulating the activity of fRNA or ncRNA involved in functional or regulatory cellular processes. Abberant fRNA or ncRNA activity leading to disease can therefore be modulated by multifunctional siNA molecules of the invention. multifunctional siNA molecules targeting fRNA and ncRNA can also be used to manipulate or alter the genotype or phenotype of an organism or cell, by intervening in cellular processes such as genetic imprinting, transcription, translation, or nucleic acid processing (e.g., transamination, methylation etc.). The target gene can be a gene derived from a cell, an endogenous gene, a transgene, or exogenous genes such as genes of a pathogen, for example a virus, which is present in the cell after infection thereof. The cell containing the target gene can be derived from or contained in any organism, for example a plant, animal, protozoan, virus, bacterium, or fungus. Non-limiting examples of plants include monocots, dicots, or gymnosperms. Non-limiting examples of animals include vertebrates or invertebrates (see for example Zwick et al., U.S. Pat. No. 6,350,934, incorporated by reference herein). Non-limiting examples of fungi include molds or yeasts. Examples of target genes can be found generally in the art, see for example McSwiggen et al., WO 03/74654 and Zwick et al., U.S. Pat. No. 6,350,934, incorporated by reference herein.

By "highly conserved sequence region" is meant, a nucleotide sequence of one or more regions in a target gene does not vary significantly from one generation to the other or from one biological system to the other.

By "cancer" is meant a group of diseases characterized by uncontrolled growth and/or spread of abnormal cells.

By "target nucleic acid" is meant any nucleic acid sequence whose expression or activity is to be modulated. The target nucleic acid can be DNA or RNA, such as endogenous DNA or RNA, viral DNA or viral RNA, or other RNA encoded by a gene, virus, bacteria, fungus, mammal, or plant.

By "complementarity" is meant that a nucleic acid can form hydrogen bond(s) with another nucleic acid sequence by either traditional Watson-Crick or other non-traditional types. In reference to the nucleic molecules of the present invention, the binding free energy for a nucleic acid molecule with its complementary sequence is sufficient to allow the relevant function of the nucleic acid to proceed, e.g., RNAi activity or inhibition of gene expression or formation of double stranded oligonucleotides by the multifunctional siNA molecules. Determination of binding free energies for nucleic acid molecules is well known in the art (see, e.g., Turner et al., 1987, CSH Symp. Quant. Biol. LII pp. 123-133; Frier et al., 1986, Proc. Nat. Acad. Sci. USA 83:9373-9377; Turner et al., 1987, J. Am. Chem. Soc. 109:3783-3785). A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, or 10 nucleotides out of a total of 10 nucleotides in the first oligonucleotide being based paired to a second nucleic acid sequence having 10 nucleotides represents 50%, 60%, 70%, 80%, 90%, and 100% complementary respectively). "Perfectly complementary" or "perfect complementarity" means that all the contiguous residues of a nucleic acid sequence will hydrogen bond with the same number of contiguous residues in a second nucleic acid sequence.

The multifunctional siNA molecules of the invention represent a novel therapeutic approach to a broad spectrum of diseases and conditions, including cancer or cancerous disease, infectious disease, ocular disease, cardiovascular disease, neurological disease, prion disease, inflammatory disease, autoimmune disease, pulmonary disease, renal disease, liver disease, mitochondrial disease, endocrine disease, reproduction related diseases and conditions, and any other indications that can respond to the level of an expressed gene product or a foreign nucleic acid, such as viral, fungal or bacterial genome, in a cell or organism.

In one embodiment of the present invention, each strand of a multifunctional siNA molecule of the invention is independently about 21 to about 44 nucleotides in length, in specific embodiments about 21, 22, 23, 24, 25, 26, 27, 28, 29 30, 31, 32, 33, 34, 35, 36, 37, 38, 39, 40, 41, 42, 43, or 44 nucleotides in length. In another embodiment, the multifunctional multifunctional siNA duplexes of the invention independently comprise about 17 to about 44 base pairs (e.g., about 17, 18, 19, 20, 21, 22, 23, 24, 25, 26, 27, 28, 29 30, 31, 32, 33, 34, 35, 36, 37, 38, 39, 40, 41, 42, 43 or 44 base pairs). Exemplary multifunctional multifunctional siNA molecules of the invention are shown in FIGS. 1-4.

As used herein "cell" is used in its usual biological sense, and does not refer to an entire multicellular organism, e.g., specifically does not refer to a human. The cell can be present in an organism, e.g., birds, plants and mammals such as humans, cows, sheep, apes, monkeys, swine, dogs, and cats. The cell can be prokaryotic (e.g., bacterial cell) or eukaryotic (e.g., mammalian or plant cell). The cell can be of somatic or germ line origin, totipotent or hybrid, dividing or non-dividing. The cell can also be derived from or can comprise a gamete or embryo, a stem cell, or a fully differentiated cell.

The multifunctional siNA molecules of the invention are added directly, or can be complexed with cationic lipids, packaged within liposomes, or otherwise delivered to target cells or tissues. The nucleic acid or nucleic acid complexes can be locally administered to relevant tissues ex vivo, or in vivo through injection, infusion pump or stent, with or without their incorporation in biopolymers.

In another aspect, the invention provides mammalian cells containing one or more multifunctional siNA molecules of this invention. The one or more multifunctional siNA molecules can independently be targeted to the same or different sites.

By "RNA" is meant a molecule comprising at least one ribonucleotide residue. By "ribonucleotide" is meant a nucleotide with a hydroxyl group at the 2' position of a β-D-ribofuranose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the multifunctional siNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

By "subject" is meant an organism, which is a donor or recipient of explanted cells or the cells themselves. "Subject" also refers to an organism to which the nucleic acid molecules of the invention can be administered. A subject can be a mammal or mammalian cells, including a human or human cells.

The term "ligand" refers to any compound or molecule, such as a drug, peptide, hormone, or neurotransmitter, that is capable of interacting with another compound, such as a receptor, either directly or indirectly. The receptor that interacts with a ligand can be present on the surface of a cell or can alternately be an intracellular receptor. Interaction of the ligand with the receptor can result in a biochemical reaction, or can simply be a physical interaction or association.

The term "phosphorothioate" as used herein refers to an internucleotide linkage having Formula I, wherein Z and/or W comprise a sulfur atom. Hence, the term phosphorothioate refers to both phosphorothioate and phosphorodithioate internucleotide linkages.

The term "phosphonoacetate" as used herein refers to an internucleotide linkage having Formula I, wherein Z and/or W comprise an acetyl or protected acetyl group.

The term "thiophosphonoacetate" as used herein refers to an internucleotide linkage having Formula I, wherein Z comprises an acetyl or protected acetyl group and W comprises a sulfur atom or alternately W comprises an acetyl or protected acetyl group and Z comprises a sulfur atom.

The term "universal base" as used herein refers to nucleotide base analogs that form base pairs with each of the natural DNA/RNA bases with little discrimination between them. Non-limiting examples of universal bases include C-phenyl, C-naphthyl and other aromatic derivatives, inosine, azole carboxamides, and nitroazole derivatives such as 3-nitropyrrole, 4-nitroindole, 5-nitroindole, and 6-nitroindole as known in the art (see for example Loakes, 2001, *Nucleic Acids Research,* 29, 2437-2447).

The term "acyclic nucleotide" as used herein refers to any nucleotide having an acyclic ribose sugar, for example where any of the ribose carbons (C1, C2, C3, C4, or C5), are independently or in combination absent from the nucleotide.

The nucleic acid molecules of the instant invention, individually, or in combination or in conjunction with other drugs, can be used to treat diseases or conditions discussed herein (e.g., cancers and other proliferative conditions, viral infection, inflammatory disease, autoimmunity, pulmonary disease, renal disease, ocular disease, etc.). For example, to treat a particular disease or condition, the multifunctional siNA molecules can be administered to a subject or can be administered to other appropriate cells evident to those skilled in the art, individually or in combination with one or more drugs under conditions suitable for the treatment.

In one embodiment, the invention features a method for treating or preventing a disease or condition in a subject, wherein the disease or condition is related to angiogenesis or neovascularization, comprising administering to the subject a multifunctional siNA molecule of the invention under conditions suitable for the treatment or prevention of the disease or condition in the subject, alone or in conjunction with one or more other therapeutic compounds. In another embodiment, the disease or condition resulting from angiogenesis, such as tumor angiogenesis leading to cancer, such as without limitation to breast cancer, lung cancer (including non-small cell lung carcinoma), prostate cancer, colorectal cancer, brain cancer, esophageal cancer, bladder cancer, pancreatic cancer, cervical cancer, head and neck cancer, skin cancers, nasopharyngeal carcinoma, liposarcoma, epithelial carcinoma, renal cell carcinoma, gallbladder adeno carcinoma, parotid adenocarcinoma, ovarian cancer, melanoma, lymphoma, glioma, endometrial sarcoma, and multidrug resistant cancers, diabetic retinopathy, macular degeneration, age related macular degeneration, macular adema, neovascular glaucoma, myopic degeneration, arthritis, psoriasis, endometriosis, female reproduction, verruca vulgaris, angiofibroma of tuberous sclerosis, pot-wine stains, Sturge Weber syndrome, Kippel-Trenaunay-Weber syndrome, Osler-Weber-Rendu syndrome, renal disease such as Autosomal dominant polycystic kidney disease (ADPKD), restenosis, arteriosclerosis, and any other diseases or conditions that are related to gene expression or will respond to RNA interference in a cell or tissue, alone or in combination with other therapies.

In one embodiment, the invention features a method for treating or preventing an ocular disease or condition in a subject, wherein the ocular disease or condition is related to angiogenesis or neovascularization (such as those involving genes in the vascular endothelial growth factor, VEGF pathway or TGF-beta pathway), comprising administering to the subject a multifunctional siNA molecule of the invention under conditions suitable for the treatment or prevention of the disease or condition in the subject, alone or in conjunction with one or more other therapeutic compounds. In another embodiment, the ocular disease or condition comprises macular degeneration, age related macular degeneration, diabetic retinopathy, macular adema, neovascular glaucoma, myopic degeneration, trachoma, scarring of the eye, cataract, ocular inflammation and/or ocular infections.

In one embodiment, the invention features a method of locally administering (e.g. by injection, such as intraocular, intratumoral, periocular, intracranial, etc., topical administration, catheter or the like) to a tissue or cell (e.g., ocular or retinal, brain, CNS) a double stranded RNA formed by a multifunctional siNA molecule or a vector expressing multifunctional siNA molecule, comprising nucleotide sequence that is complementary to nucleotide sequence of target RNA, or a portion thereof, (e.g., target RNA encoding VEGF or a VEGF receptor) comprising contacting said tissue of cell with said double stranded RNA under conditions suitable for said local administration.

In one embodiment, the invention features a method of systemically administering (e.g. by injection, such as subcutaneous, intravenous, topical administration, or the like) to a tissue or cell in a subject, a double stranded RNA formed by a multifunctional siNA molecule or a vector expressing multifunctional siNA molecule comprising nucleotide sequence that is complementary to nucleotide sequence of target RNA, or a portion thereof, (e.g., target RNA encoding VEGF or a VEGF receptor) comprising contacting said subject with said double stranded RNA under conditions suitable for said systemic administration.

In one embodiment, the invention features a method for treating or preventing tumor angiogenesis in a subject comprising administering to the subject a multifunctional siNA molecule of the invention under conditions suitable for the treatment or prevention of tumor angiogenesis in the subject, alone or in conjunction with one or more other therapeutic compounds.

In one embodiment, the invention features a method for treating or preventing viral infection or replication in a subject comprising administering to the subject a multifunctional siNA molecule of the invention under conditions suitable for the treatment or prevention of viral infection or replication in the subject, alone or in conjunction with one or more other therapeutic compounds.

In one embodiment, the invention features a method for treating or preventing autoimmune disease in a subject comprising administering to the subject a multifunctional siNA molecule of the invention under conditions suitable for the treatment or prevention of autoimmune disease in the subject, alone or in conjunction with one or more other therapeutic compounds.

In one embodiment, the invention features a method for treating or preventing neurologic disease (e.g., Alzheimer's disease, Huntington disease, Parkinson disease, ALS, multiple sclerosis, epilepsy, etc.) in a subject comprising administering to the subject a multifunctional siNA molecule of the invention under conditions suitable for the treatment or prevention of neurologic disease in the subject, alone or in conjunction with one or more other therapeutic compounds.

In one embodiment, the invention features a method for treating or preventing inflammation in a subject comprising administering to the subject a multifunctional siNA molecule of the invention under conditions suitable for the treatment or prevention of inflammation in the subject, alone or in conjunction with one or more other therapeutic compounds.

In a further embodiment, the multifunctional siNA molecules can be used in combination with other known treatments to treat conditions or diseases discussed above. For example, the described molecules could be used in combination with one or more known therapeutic agents to treat a disease or condition. Non-limiting examples of other therapeutic agents that can be readily combined with a multifunctional siNA molecule of the invention are enzymatic nucleic acid molecules, allosteric nucleic acid molecules, antisense, decoy, or aptamer nucleic acid molecules, antibodies such as monoclonal antibodies, small molecules, and other organic and/or inorganic compounds including metals, salts and ions.

In another aspect of the invention, multifunctional siNA molecules that interact with target RNA molecules and down-regulate gene encoding target RNA molecules (for example target RNA molecules referred to by Genbank Accession numbers herein) are expressed from transcription units inserted into DNA or RNA vectors. The recombinant vectors can be DNA plasmids or viral vectors. multifunctional siNA expressing viral vectors can be constructed based on, but not limited to, adeno-associated virus, retrovirus, adenovirus, or alphavirus. The recombinant vectors capable of expressing the multifunctional siNA molecules can be delivered as described herein, and persist in target cells. Alternatively, viral vectors can be used that provide for transient expression of multifunctional siNA molecules. Such vectors can be repeatedly administered as necessary. Once expressed, the multifunctional siNA molecules interact with target nucleic acids and down-regulate gene function or expression. Delivery of multifunctional siNA expressing vectors can be systemic, such as by intravenous or intramuscular administration, by administration to target cells ex-planted from a subject followed by reintroduction into the subject, or by any other means that would allow for introduction into the desired target cell.

In one embodiment, the expression vector comprises a transcription initiation region, a transcription termination region, and a gene encoding at least one multifunctional siNA. The gene can be operably linked to the initiation region and the termination region, in a manner which allows expression and/or delivery of the multifunctional siNA. In another embodiment, the expression vector can comprises a transcription initiation region, a transcription termination region, an open reading frame and a gene encoding at least one multifunctional siNA, wherein the gene is operably linked to the 3'-end of the open reading frame. The gene can be operably linked to the initiation region, the open reading frame and the termination region in a manner which allows expression and/or delivery of the multifunctional siNA. In another embodiment, the expression vector comprises a transcription initiation region, a transcription termination region, an intron, and a gene encoding at least one multifunctional siNA. The gene can be operably linked to the initiation region, the intron, and the termination region in a manner which allows expression and/or delivery of the multifunctional siNA. In yet another embodiment, the expression vector comprises a transcription initiation region, a transcription termination region, an intron, an open reading frame, and a gene encoding at least one multifunctional siNA, wherein the gene is operably linked to the 3'-end of the open reading frame. The gene can be operably linked to the initiation region, the intron, the open reading frame and the termination region in a manner which allows expression and/or delivery of the multifunctional siNA.

The expression vector can be derived from, for example, a retrovirus, an adenovirus, an adeno-associated virus, an alphavirus or a bacterial plasmid as well as other known vectors. The expression vector can be operably linked to a RNA polymerase II promoter element or a RNA polymerase III promoter element. The RNA polymerase III promoter can be derived from, for example, a transfer RNA gene, a U6 small nuclear RNA gene, or a TRZ RNA gene. The multifunctional siNA transcript can comprise a sequence at its 5'-end homologous to the terminal 27 nucleotides encoded by the U6 small nuclear RNA gene. The library of multifunctional siNA constructs can be a multimer random library. The multimer random library can comprise at least one multifunctional siNA.

The multifunctional siNA of the instant invention can be chemically synthesized, expressed from a vector, or enzymatically synthesized.

By "vectors" is meant any nucleic acid- and/or viral-based technique used to produce, express and/or deliver a desired nucleic acid, such as the multifunctional siNA molecule of the invention.

Other features and advantages of the invention will be apparent from the following description of the preferred embodiments thereof, and from the claims.

BRIEF DESCRIPTION OF THE DRAWINGS

FIG. 1 shows non-limiting examples of multifunctional siNA molecules of the invention comprising two separate polynucleotide sequences that are each capable of mediating RNAi directed cleavage of differing target nucleic acid sequences. FIG. 1A shows a non-limiting example of a multifunctional siNA molecule having a first region that is complementary to a first target nucleic acid sequence (complementary region 1) and a second region that is complementary to a second target nucleic acid sequence (complementary region 2), wherein the first and second complementary regions are situated at the 3'-ends of each polynucleotide sequence in the multifunctional siNA. The dashed portions of each polynucleotide sequence of the multifunctional siNA construct have complementarity with regard to corresponding portions of the siNA duplex, but do not have complementarity to the target nucleic acid sequences. FIG. 1B shows a non-limiting example of a multifunctional siNA molecule having a first region that is complementary to a first target nucleic acid sequence (complementary region 1) and a second region that is complementary to a second target nucleic acid sequence (complementary region 2), wherein the first and second complementary regions are situated at the 5'-ends of each polynucleotide sequence in the multifunctional siNA. The dashed portions of each polynucleotide sequence of the multifunctional siNA construct have complementarity with regard to corresponding portions of the siNA duplex, but do not have complementarity to the target nucleic acid sequences.

FIG. 2 shows non-limiting examples of multifunctional siNA molecules of the invention comprising a single polynucleotide sequence comprising distinct regions that are each capable of mediating RNAi directed cleavage of differing target nucleic acid sequences. FIG. 2A shows a non-limiting example of a multifunctional siNA molecule having a first region that is complementary to a first target nucleic acid sequence (complementary region 1) and a second region that is complementary to a second target nucleic acid sequence (complementary region 2), wherein the second complementary region is situated at the 3'-end of the polynucleotide sequence in the multifunctional siNA. The dashed portions of each polynucleotide sequence of the multifunctional siNA construct have complementarity with regard to corresponding portions of the siNA duplex, but do not have complementarity to the target nucleic acid sequences. FIG. 2B shows a non-limiting example of a multifunctional siNA molecule having a first region that is complementary to a first target nucleic acid sequence (complementary region 1) and a second region that is complementary to a second target nucleic acid sequence (complementary region 2), wherein the first complementary region is situated at the 5'-end of the polynucleotide sequence in the multifunctional siNA. The dashed portions of each polynucleotide sequence of the multifunctional siNA construct have complementarity with regard to corresponding portions of the siNA duplex, but do not have complementarity to the target nucleic acid sequences. In one embodiment, these multifunctional siNA constructs are processed in vivo or in vitro to generate multifunctional siNA constructs as shown in FIG. 1.

FIG. 3 shows non-limiting examples of multifunctional siNA molecules of the invention comprising two separate polynucleotide sequences that are each capable of mediating RNAi directed cleavage of differing target nucleic acid sequences and wherein the multifunctional siNA construct further comprises a self complementary, palindrome, or repeat region, thus enabling shorter bifunctional siNA constructs that can mediate RNA interference against differing target nucleic acid sequences. FIG. 3A shows a non-limiting example of a multifunctional siNA molecule having a first region that is complementary to a first target nucleic acid sequence (complementary region 1) and a second region that is complementary to a second target nucleic acid sequence (complementary region 2), wherein the first and second complementary regions are situated at the 3'-ends of each polynucleotide sequence in the multifunctional siNA, and wherein the first and second complementary regions further comprise a self complementary, palindrome, or repeat region. The dashed portions of each polynucleotide sequence of the multifunctional siNA construct have complementarity with regard to corresponding portions of the siNA duplex, but do not have complementarity to the target nucleic acid sequences. FIG. 3B shows a non-limiting example of a multifunctional siNA molecule having a first region that is complementary to a first target nucleic acid sequence (complementary region 1) and a second region that is complementary to a second target nucleic acid sequence (complementary region 2), wherein the first and second complementary regions are situated at the 5'-ends of each polynucleotide sequence in the multifunctional siNA, and wherein the first and second complementary regions further comprise a self complementary, palindrome, or repeat region. The dashed portions of each polynucleotide sequence of the multifunctional siNA construct have complementarity with regard to corresponding portions of the siNA duplex, but do not have complementarity to the target nucleic acid sequences.

FIG. 4 shows non-limiting examples of multifunctional siNA molecules of the invention comprising a single polynucleotide sequence comprising distinct regions that are each capable of mediating RNAi directed cleavage of differing target nucleic acid sequences and wherein the multifunctional siNA construct further comprises a self complementary, palindrome, or repeat region, thus enabling shorter bifunctional siNA constructs that can mediate RNA interference against differing target nucleic acid sequences. FIG. 4A shows a non-limiting example of a multifunctional siNA molecule having a first region that is complementary to a first target nucleic acid sequence (complementary region 1) and a second region that is complementary to a second target nucleic acid sequence (complementary region 2), wherein the second complementary region is situated at the 3'-end of the polynucleotide sequence in the multifunctional siNA, and wherein the first and second complementary regions further comprise a self complementary, palindrome, or repeat region. The dashed portions of each polynucleotide sequence of the multifunctional siNA construct have complementarity with regard to corresponding portions of the siNA duplex, but do not have complementarity to the target nucleic acid sequences. FIG. 2B shows a non-limiting example of a multifunctional siNA molecule having a first region that is complementary to a first target nucleic acid sequence (complementary region 1) and a second region that is complementary to a second target nucleic acid sequence (complementary region 2), wherein the first complementary region is situated at the 5'-end of the polynucleotide sequence in the multifunctional siNA, and wherein the first and second complementary regions further comprise a self complementary, palindrome, or repeat region. The dashed portions of each polynucleotide sequence of the multifunctional siNA construct have complementarity with regard to corresponding portions of the siNA duplex, but do not have complementarity to the target nucleic acid sequences. In one embodiment, these multifunctional siNA constructs are processed in vivo or in vitro to generate multifunctional siNA constructs as shown in FIG. 3.

FIG. 5 shows a non-limiting example of how multifunctional siNA molecules of the invention can target two separate target nucleic acid molecules, such as separate RNA molecules encoding differing proteins, for example a cytokine and its corresponding receptor, differing viral strains, a virus and a cellular protein involved in viral infection or replication, or differing proteins involved in a common or divergent biologic pathway that is implicated in the maintenance of progression of disease. Each strand of the multifunctional siNA construct comprises a region having complementarity to separate target nucleic acid molecules. The multifunctional siNA molecule is designed such that each strand of the siNA can be utilized by the RISC complex to initiate RNA interferance mediated cleavage of its corresponding target. These design parameters can include destabilization of each end of the siNA construct (see for example Schwarz et al., 2003, Cell, 115, 199-208). Such destabilization can be accomplished for example by using guanosine-cytidine base pairs, alternate base pairs (e.g., wobbles), or destabilizing chemically modified nucleotides at terminal nucleotide positions as is known in the art.

FIG. 6 shows a non-limiting example of how multifunctional siNA molecules of the invention can target two separate target nucleic acid sequences within the same target nucleic acid molecule, such as alternate coding regions of a RNA, coding and non-coding regions of a RNA, or alternate splice variant regions of a RNA. Each strand of the multifunctional siNA construct comprises a region having complementarity to the separate regions of the target nucleic acid molecule. The multifunctional siNA molecule is designed such that each strand of the siNA can be utilized by the RISC complex to initiate RNA interference mediated cleavage of its corresponding target region. These design parameters can include destabilization of each end of the siNA construct (see for example Schwarz et al., 2003, Cell, 115, 199-208). Such destabilization can be accomplished for example by using guanosine-cytidine base pairs, alternate base pairs (e.g., wobbles), or destabilizing chemically modified nucleotides at terminal nucleotide positions as is known in the art.

FIG. 7 shows non-limiting examples of non-Watson Crick base pairs that can be utilized in generating artificial self complementary, palindrome, or repeat sequences for designing siNA molecules of the invention.

FIG. 8 shows a non-limiting proposed mechanistic representation of target RNA degradation involved in RNAi. Double-stranded RNA (dsRNA), which is generated by RNA-dependent RNA polymerase (RdRP) from foreign single-stranded RNA, for example viral, transposon, or other exogenous RNA, activates the DICER enzyme that in turn generates siNA duplexes. Alternately, synthetic or expressed siNA can be introduced directly into a cell by appropriate means. An active siNA complex forms which recognizes a target RNA, resulting in degradation of the target RNA by the RISC endonuclease complex or in the synthesis of additional RNA by RNA-dependent RNA polymerase (RdRP), which can activate DICER and result in additional siNA molecules, thereby amplifying the RNAi response.

FIG. 11A: A DNA oligomer is synthesized with a 5'-restriction (R1) site sequence followed by a region having sequence identical to a predetermined target sequence, wherein the sense region comprises, for example, about 19, 20, 21, 22, 23, 24, 25, 26, 27, 28, 29, or 30 nucleotides (N) in length, and which is followed by a 3'-restriction site (R2) which is adjacent to a loop sequence of defined sequence (X). FIG. 11B: The synthetic construct is then extended by DNA polymerase to generate a hairpin structure having self-complementary sequence. FIG. 11C: The construct is processed by restriction enzymes specific to R1 and R2 to generate a double-stranded DNA which is then inserted into an appropriate vector for expression in cells. The transcription cassette is designed such that a U6 promoter region flanks each side of the dsDNA which generates the strands of the siNA. Poly T termination sequences can be added to the constructs to generate U overhangs in the resulting transcript.

DETAILED DESCRIPTION OF THE INVENTION

Synthesis of Nucleic Acid Molecules

Figure 9:
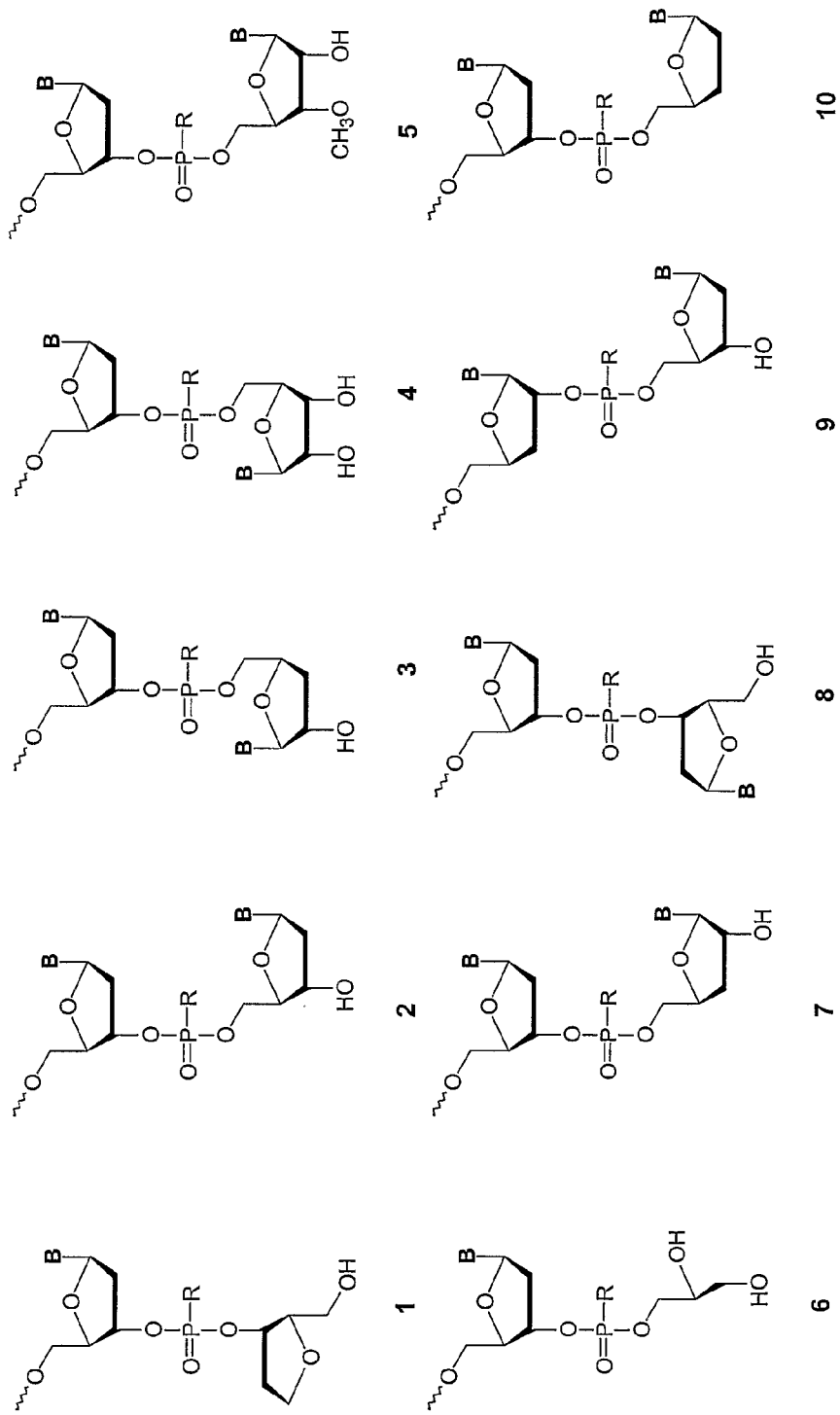
FIG. 9 shows non-limiting examples of different stabilization chemistries (1-10) that can be used, for example, to stabilize the 3'-end of siNA sequences of the invention against degradation, including (1) [3-3']-inverted deoxyribose; (2) deoxyribonucleotide; (3) [5'-3']-3'-deoxyribonucleotide; (4) [5'-3']-ribonucleotide; (5) [5'-3']-3'-O-methyl ribonucleotide; (6) 3'-glyceryl; (7) [3'-5']-3'-deoxyribonucleotide; (8) [3'-3']-deoxyribonucleotide; (9) [5'-2']-deoxyribonucleotide; and (10) [5-3']-dideoxyribonucleotide. In addition to modified and unmodified backbone chemistries indicated in the figure, these chemistries can be combined with different backbone modifications as described herein, for example, backbone modifications having Formula III herein. In addition, the 2'-deoxy nucleotide shown 5' to the terminal modifications shown can be another modified or unmodified nucleotide or non-nucleotide described herein, for example modifications having any of Formulae III-IX herein or any combination thereof.
Figure 10:
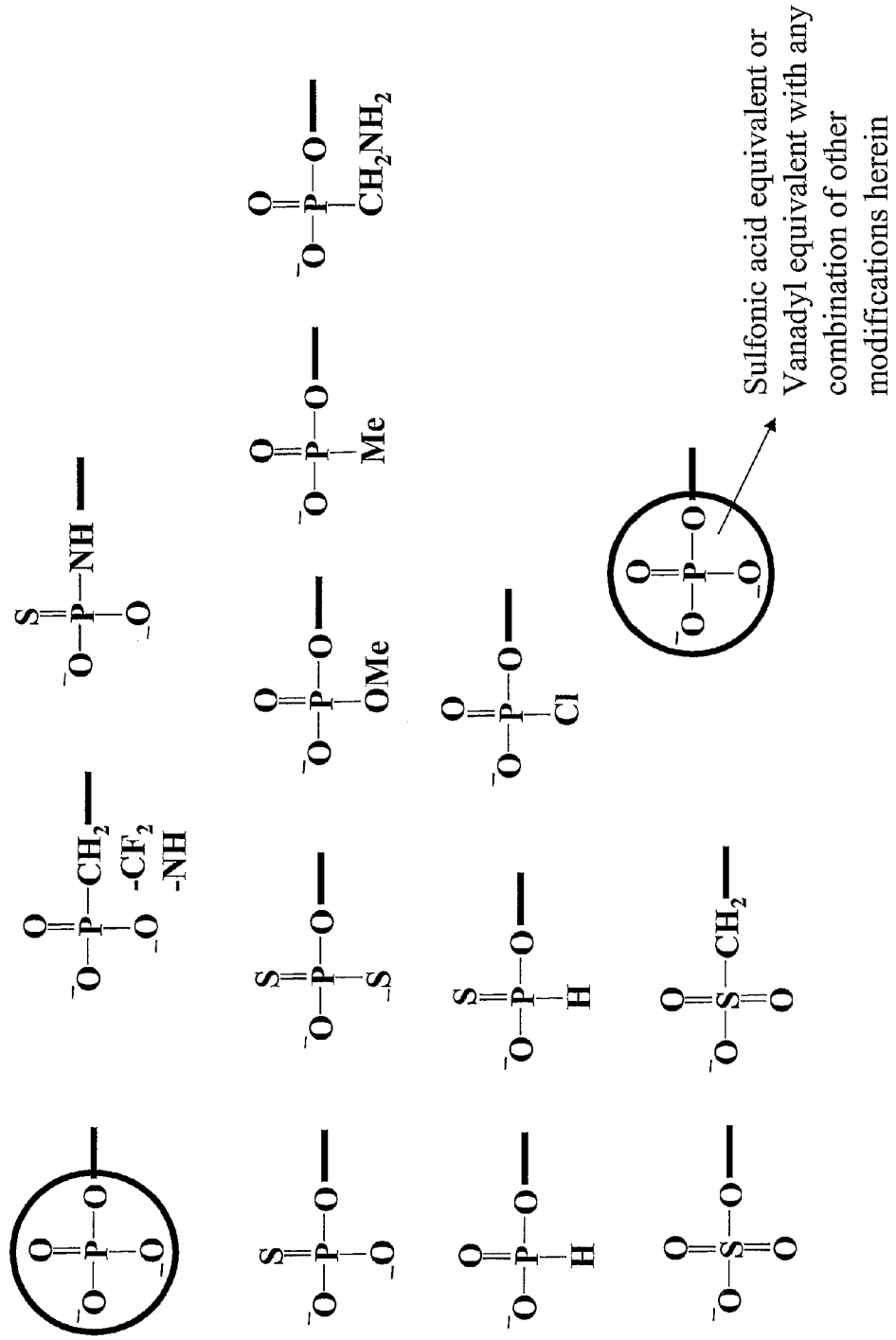
FIG. 10 shows non-limiting examples of chemically modified terminal phosphate groups of the invention.
Figure 11:
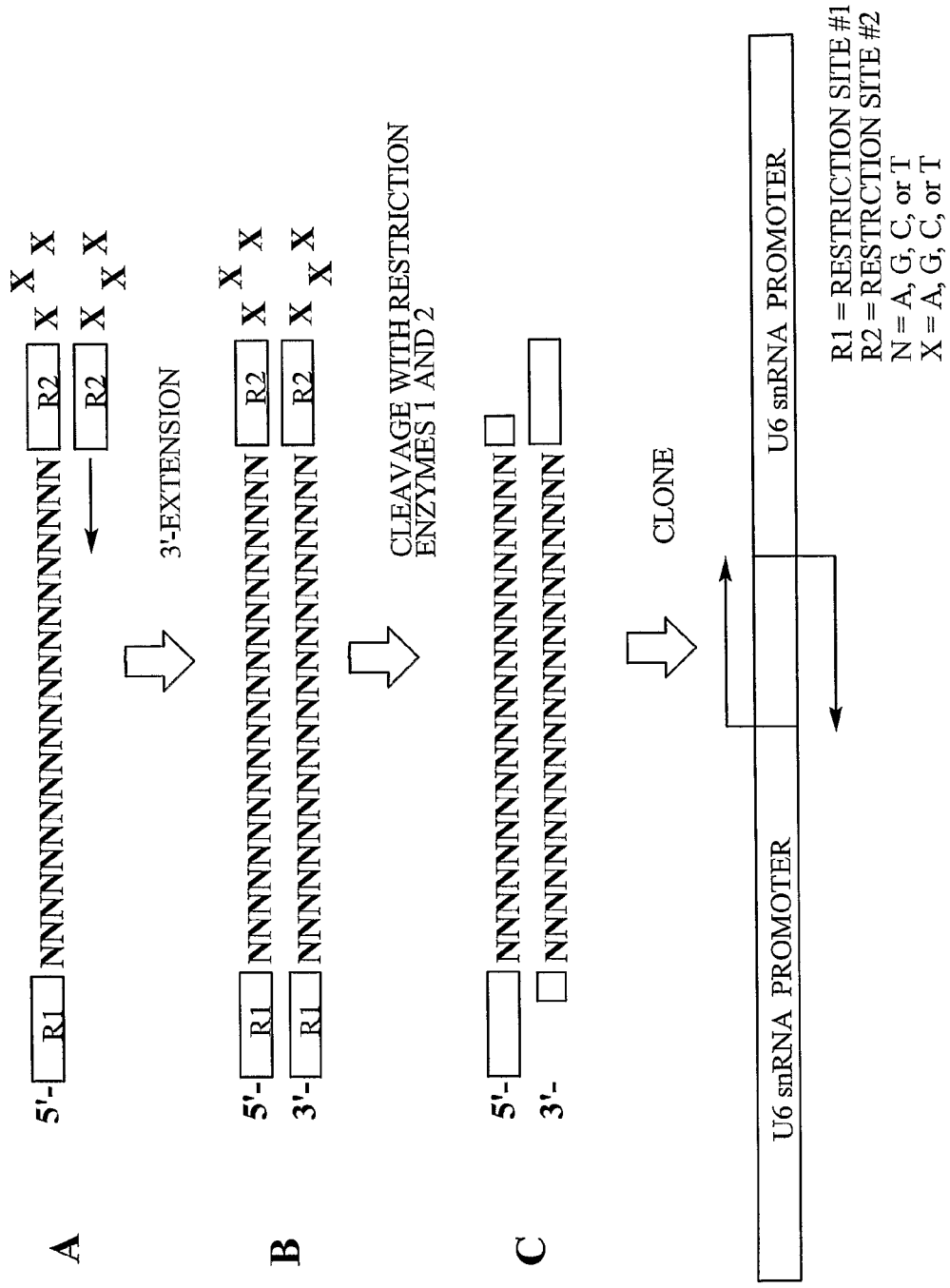
FIG. 11A-C is a diagrammatic representation of a scheme utilized in generating an expression cassette to generate siNA constructs.

Synthesis of nucleic acids greater than 100 nucleotides in length is difficult using automated methods, and the therapeutic cost of such molecules is prohibitive. In this invention, small nucleic acid motifs ("small" refers to nucleic acid motifs no more than 100 nucleotides in length, preferably no more than 80 nucleotides in length, and most preferably no more than 50 nucleotides in length; e.g., individual siNA oligonucleotide sequences) are preferably used for exogenous delivery. The simple structure of these molecules increases the ability of the nucleic acid to invade targeted regions of protein and/or RNA structure. Exemplary molecules of the instant invention are chemically synthesized, and others can similarly be synthesized.

Oligonucleotides (e.g., certain modified oligonucleotides or portions of oligonucleotides lacking ribonucleotides) are synthesized using protocols known in the art, for example as described in Caruthers et al., 1992, Methods in Enzymology 211, 3-19, Thompson et al., International PCT Publication No. WO 99/54459, Wincott et al., 1995, Nucleic Acids Res. 23, 2677-2684, Wincott et al., 1997, Methods Mol. Bio., 74, 59, Brennan et al., 1998, Biotechnol Bioeng., 61, 33-45, and Brennan, U.S. Pat. No. 6,001,311. All of these references are incorporated herein by reference. The synthesis of oligonucleotides makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer using a 0.2 µmol scale protocol with a 2.5 min coupling step for 2'-O-methylated nucleotides and a 45 second coupling step for 2'-deoxy nucleotides or 2'-deoxy-2'-fluoro nucleotides. Table VII outlines the amounts and the contact times of the reagents used in the synthesis cycle. Alternatively, syntheses at the 0.2 µmol scale can be performed on a 96-well plate synthesizer, such as the instrument produced by Protogene (Palo Alto, Calif.) with minimal modification to the cycle. A 33-fold excess (60 µL of 0.11 M=6.6 µmol) of 2'-O-methyl phosphoramidite and a 105-fold excess of S-ethyl tetrazole (60 µL of 0.25 M=15 µmol) can be used in each coupling cycle of 2'-O-methyl residues relative to polymer-bound 5'-hydroxyl. A 22-fold excess (40 µL of 0.11 M=4.4 µmol) of deoxy phosphoramidite and a 70-fold excess of S-ethyl tetrazole (40 µL of 0.25 M=10 µmol) can be used in each coupling cycle of deoxy residues relative to polymer-bound 5'-hydroxyl. Average coupling yields on the 394 Applied Biosystems, Inc. synthesizer, determined by colorimetric quantitation of the trityl fractions, are typically 97.5-99%. Other oligonucleotide synthesis reagents for the 394 Applied Biosystems, Inc. synthesizer include the following: detritylation solution is 3% TCA in methylene chloride (ABI); capping is performed with 16% N-methyl imidazole in THF (ABI) and 10% acetic anhydride/10% 2,6-lutidine in THF (ABI); and oxidation solution is 16.9 mM I$_2$, 49 mM pyridine, 9% water in THF (PERSEPTIVE™). Burdick & Jackson Synthesis Grade acetonitrile is used directly from the reagent bottle. S-Ethyltetrazole solution (0.25 M in acetonitrile) is made up from the solid obtained from American International Chemical, Inc. Alternately, for the introduction of phosphorothioate linkages, Beaucage reagent (3H-1,2-Benzodithiol-3-one 1,1-dioxide, 0.05 M in acetonitrile) is used.

Deprotection of the DNA-based oligonucleotides is performed as follows: the polymer-bound trityl-on oligoribonucleotide is transferred to a 4 mL glass screw top vial and suspended in a solution of 40% aqueous methylamine (1 mL) at 65° C. for 10 minutes. After cooling to −20° C., the supernatant is removed from the polymer support. The support is washed three times with 1.0 mL of EtOH:MeCN:H2O/3:1:1, vortexed and the supernatant is then added to the first supernatant. The combined supernatants, containing the oligoribonucleotide, are dried to a white powder.

The method of synthesis used for RNA including certain siNA molecules of the invention follows the procedure as described in Usman et al., 1987, J. Am. Chem. Soc., 109, 7845; Scaringe et al., 1990, Nucleic Acids Res., 18, 5433; and Wincott et al., 1995, Nucleic Acids Res. 23, 2677-2684 Wincott et al., 1997, Methods Mol. Bio., 74, 59, and makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer using a 0.2 µmol scale protocol with a 7.5 min coupling step for alkylsilyl protected nucleotides and a 2.5 min coupling step for 2'-O-methylated nucleotides. Table VII outlines the amounts and the contact times of the reagents used in the synthesis cycle. Alternatively, syntheses at the 0.2 µmol scale can be done on a 96-well plate synthesizer, such as the instrument produced by Protogene (Palo Alto, Calif.) with minimal modification to the cycle. A 33-fold excess (60 µL of 0.11 M=6.6 µmol) of 2'-O-methyl phosphoramidite and a 75-fold excess of S-ethyl tetrazole (60 µL of 0.25 M=15 µmol) can be used in each coupling cycle of 2'-O-methyl residues relative to polymer-bound 5'-hydroxyl. A 66-fold excess (120 µL of 0.11 M=13.2 µmol) of alkylsilyl (ribo) protected phosphoramidite and a 150-fold excess of S-ethyl tetrazole (120 µL of 0.25 M=30 µmol) can be used in each coupling cycle of ribo residues relative to polymer-bound 5'-hydroxyl. Average coupling yields on the 394 Applied Biosystems, Inc. synthesizer, determined by colorimetric quantitation of the trityl fractions, are typically 97.5-99%. Other oligonucleotide synthesis reagents for the 394 Applied Biosystems, Inc. synthesizer include the following: detritylation solution is 3% TCA in methylene chloride (ABI); capping is performed with 16% N-methyl imidazole in THF (ABI) and 10% acetic anhydride/10% 2,6-lutidine in THF (ABI); oxidation solution is 16.9 mM I$_2$, 49 mM pyridine, 9% water in THF (PERSEPTIVE™). Burdick & Jackson Synthesis Grade acetonitrile is used directly from the reagent bottle. S-Ethyltetrazole solution (0.25 M in acetonitrile) is made up from the solid obtained from American International Chemical, Inc. Alternately, for the introduction of phosphorothioate linkages, Beaucage reagent (3H-1,2-Benzodithiol-3-one 1,1-dioxide 0.05 M in acetonitrile) is used.

Deprotection of the RNA is performed using either a two-pot or one-pot protocol. For the two-pot protocol, the polymer-bound trityl-on oligoribonucleotide is transferred to a 4 mL glass screw top vial and suspended in a solution of 40% aq. methylamine (1 mL) at 65° C. for 10 minutes. After cooling to −20° C., the supernatant is removed from the polymer support. The support is washed three times with 1.0 mL of EtOH:MeCN:H2O/3:1:1, vortexed and the supernatant is then added to the first supernatant. The combined supernatants, containing the oligoribonucleotide, are dried to a white powder. The base deprotected oligoribonucleotide is resuspended in anhydrous TEA/HF/NMP solution (300 µL of a solution of 1.5 mL N-methylpyrrolidinone, 750 µL TEA and 1 mL TEA.3HF to provide a 1.4 M HF concentration) and heated to 65° C. After 1.5 h, the oligomer is quenched with 1.5 M $NH_4HCO_3$.

Alternatively, for the one-pot protocol, the polymer-bound trityl-on oligoribonucleotide is transferred to a 4 mL glass screw top vial and suspended in a solution of 33% ethanolic methylamine/DMSO: 1/1 (0.8 mL) at 65° C. for 15 minutes. The vial is brought to room temperature TEA.3HF (0.1 mL) is added and the vial is heated at 65° C. for 15 minutes. The sample is cooled at −20° C. and then quenched with 1.5 M $NH_4HCO_3$.

For purification of the trityl-on oligomers, the quenched $NH_4HCO_3$ solution is loaded onto a C-18 containing cartridge that had been prewashed with acetonitrile followed by 50 mM TEAA. After washing the loaded cartridge with water, the RNA is detritylated with 0.5% TFA for 13 minutes. The cartridge is then washed again with water, salt exchanged with 1 M NaCl and washed with water again. The oligonucleotide is then eluted with 30% acetonitrile.

The average stepwise coupling yields are typically >98% (Wincott et al., 1995 *Nucleic Acids Res.* 23, 2677-2684). Those of ordinary skill in the art will recognize that the scale of synthesis can be adapted to be larger or smaller than the example described above including but not limited to 96-well format.

Alternatively, the nucleic acid molecules of the present invention can be synthesized separately and assembled together to form a duplex or joined together post-synthetically, for example, by ligation (Moore et al., 1992, *Science* 256, 9923; Draper et al., International PCT publication No. WO 93/23569; Shabarova et al., 1991, *Nucleic Acids Research* 19, 4247; Bellon et al., 1997, *Nucleosides & Nucleotides*, 16, 951; Bellon et al., 1997, *Bioconjugate Chem.* 8, 204), or by hybridization following synthesis and/or deprotection.

A siNA molecule can also be assembled from two distinct nucleic acid strands or fragments wherein the two fragments comprise the same nucleic acid sequence and are self complementary.

siNA constructs can be purified by gel electrophoresis using general methods or can be purified by high pressure liquid chromatography (HPLC; see Wincott et al., supra, the totality of which is hereby incorporated herein by reference) and re-suspended in water.

In another aspect of the invention, siNA molecules of the invention are expressed from transcription units inserted into DNA or RNA vectors. The recombinant vectors can be DNA plasmids or viral vectors. siNA expressing viral vectors can be constructed based on, but not limited to, adeno-associated virus, retrovirus, adenovirus, or alphavirus. The recombinant vectors capable of expressing the siNA molecules can be delivered as described herein, and persist in target cells. Alternatively, viral vectors can be used that provide for transient expression of siNA molecules.

Alternatively, certain siNA molecules of the instant invention can be expressed within cells from eukaryotic promoters (e.g., Izant and Weintraub, 1985, *Science*, 229, 345; McGarry and Lindquist, 1986, *Proc. Natl. Acad. Sci., USA* 83, 399; Thompson et al., 1995, *Nucleic Acids Res.*, 23, 2259; Good et al., 1997, *Gene Therapy*, 4, 45). Those skilled in the art realize that any nucleic acid can be expressed in eukaryotic cells from the appropriate DNA/RNA vector. The activity of such nucleic acids can be augmented by their release from the primary transcript by a enzymatic nucleic acid (Draper et al., PCT WO 93/23569, and Sullivan et al., PCT WO 94/02595; Ohkawa et al., 1992, *Nucleic Acids Symp. Ser.*, 27, 15-6; Taira et al., 1991, *Nucleic Acids Res.*, 19, 5125-30; Ventura et al., 1993, *Nucleic Acids Res.*, 21, 3249-55; Chowrira et al., 1994, *J. Biol. Chem.*, 269, 25856).

In another aspect of the invention, siNA molecules of the present invention can be expressed from transcription units (see for example Couture et al., 1996, *TIG.*, 12, 510) inserted into DNA or RNA vectors. The recombinant vectors can be DNA plasmids or viral vectors. siNA expressing viral vectors can be constructed based on, but not limited to, adeno-associated virus, retrovirus, adenovirus, or alphavirus. In another embodiment, pol III based constructs are used to express nucleic acid molecules of the invention (see for example Noonberg et al., 5,624,803; Thompson, U.S. Pat. Nos. 5,902,880 and 6,146,886). The recombinant vectors capable of expressing the siNA molecules can be delivered as described above, and persist in target cells. Alternatively, viral vectors can be used that provide for transient expression of nucleic acid molecules. Such vectors can be repeatedly administered as necessary. Once expressed, the siNA molecule interacts with the target mRNA and generates an RNAi response. Delivery of siNA molecule expressing vectors can be systemic, such as by intravenous or intra-muscular administration, by administration to target cells ex-planted from a subject followed by reintroduction into the subject, or by any other means that would allow for introduction into the desired target cell (for a review see Couture et al., 1996, *TIG.*, 12, 510).

In one aspect the invention features an expression vector comprising a nucleic acid sequence encoding at least one siNA molecule of the instant invention. The expression vector can encode the self complementary siNA sequence that can self assemble upon expression from the vector into a duplex oligonucleotide. The nucleic acid sequences encoding the siNA molecules of the instant invention can be operably linked in a manner that allows expression of the siNA molecule (see for example Noonberg et al., 5,624,803; Thompson, U.S. Pat. Nos. 5,902,880 and 6,146,886; Paul et al., 2002, *Nature Biotechnology*, 19, 505; Miyagishi and Taira, 2002, *Nature Biotechnology*, 19, 497; Lee et al., 2002, *Nature Biotechnology*, 19, 500; and Novina et al., 2002, *Nature Medicine*, 8, 681-686).

In another aspect, the invention features an expression vector comprising: a) a transcription initiation region (e.g., eukaryotic pol I, II or III initiation region); b) a transcription termination region (e.g., eukaryotic pol I, II or III termination region); and c) a nucleic acid sequence encoding at least one of the siNA molecules of the instant invention, wherein said sequence is operably linked to said initiation region and said termination region, in a manner that allows expression and/or delivery of the siNA molecule. The vector can optionally include an open reading frame (ORF) for a protein operably linked on the 5' side or the 3'-side of the sequence encoding the siNA of the invention; and/or an intron (intervening sequences).

Transcription of the siNA molecule sequences can be driven from a promoter for eukaryotic RNA polymerase I (pol I), RNA polymerase II (pol II), or RNA polymerase III (pol III). Transcripts from pol II or pol III promoters are expressed at high levels in all cells; the levels of a given pol II promoter in a given cell type depends on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990, *Proc. Natl. Acad. Sci. USA*, 87, 6743-7; Gao and Huang 1993, *Nucleic Acids Res.*, 21, 2867-72; Lieber et al., 1993, *Methods Enzymol.*, 217, 47-66; Zhou et al., 1990, *Mol. Cell.*

*Biol.*, 10, 4529-37). Several investigators have demonstrated that nucleic acid molecules expressed from such promoters can function in mammalian cells (e.g. Kashani-Sabet et al., 1992, *Antisense Res. Dev.*, 2, 3-15; Ojwang et al., 1992, *Proc. Natl. Acad. Sci. USA*, 89, 10802-6; Chen et al., 1992, *Nucleic Acids Res.*, 20, 4581-9; Yu et al., 1993, *Proc. Natl. Acad. Sci. USA*, 90, 6340-4; L'Huillier et al., 1992, *EMBO J.*, 11, 4411-8; Lisziewicz et al., 1993, *Proc. Natl. Acad. Sci. U.S. A*, 90, 8000-4; Thompson et al., 1995, *Nucleic Acids Res.*, 23, 2259; Sullenger & Cech, 1993, *Science*, 262, 1566). More specifically, transcription units such as the ones derived from genes encoding U6 small nuclear (snRNA), transfer RNA (tRNA) and adenovirus VA RNA are useful in generating high concentrations of desired RNA molecules such as siNA in cells (Thompson et al., supra; Couture and Stinchcomb, 1996, supra; Noonberg et al., 1994, *Nucleic Acid Res.*, 22, 2830; Noonberg et al., U.S. Pat. No. 5,624,803; Good et al., 1997, *Gene Ther.*, 4, 45; Beigelman et al., International PCT Publication No. WO 96/18736. The above siNA transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors) (for a review see Couture and Stinchcomb, 1996, supra).

In another aspect, the invention features an expression vector comprising a nucleic acid sequence encoding at least one of the siNA molecules of the invention, in a manner that allows expression of that siNA molecule. The expression vector comprises in one embodiment; a) a transcription initiation region; b) a transcription termination region; and c) a nucleic acid sequence encoding at least one strand of the siNA molecule, wherein the sequence is operably linked to the initiation region and the termination region in a manner that allows expression and/or delivery of the siNA molecule.

In another embodiment, the expression vector comprises: a) a transcription initiation region; b) a transcription termination region; c) an open reading frame; and d) a nucleic acid sequence encoding at least one strand of a siNA molecule, wherein the sequence is operably linked to the 3'-end of the open reading frame and wherein the sequence is operably linked to the initiation region, the open reading frame and the termination region in a manner that allows expression and/or delivery of the siNA molecule. In yet another embodiment, the expression vector comprises: a) a transcription initiation region; b) a transcription termination region; c) an intron; and d) a nucleic acid sequence encoding at least one siNA molecule, wherein the sequence is operably linked to the initiation region, the intron and the termination region in a manner which allows expression and/or delivery of the nucleic acid molecule.

In another embodiment, the expression vector comprises: a) a transcription initiation region; b) a transcription termination region; c) an intron; d) an open reading frame; and e) a nucleic acid sequence encoding at least one strand of a siNA molecule, wherein the sequence is operably linked to the 3'-end of the open reading frame and wherein the sequence is operably linked to the initiation region, the intron, the open reading frame and the termination region in a manner which allows expression and/or delivery of the siNA molecule.

Optimizing Activity of the Nucleic Acid Molecule of the Invention.

Chemically synthesizing nucleic acid molecules with modifications (base, sugar and/or phosphate) can prevent their degradation by serum ribonucleases, which can increase their potency (see e.g., Eckstein et al., International Publication No. WO 92/07065; Perrault et al., 1990 *Nature* 344, 565; Pieken et al., 1991, *Science* 253, 314; Usman and Cedergren, 1992, *Trends in Biochem. Sci.* 17, 334; Usman et al., International Publication No. WO 93/15187; and Rossi et al., International Publication No. WO 91/03162; Sproat, U.S. Pat. No. 5,334,711; Gold et al., U.S. Pat. No. 6,300,074; Burgin et al., supra; and Beigelman et al., WO 03/70918, all of which are incorporated by reference herein). All of the above references describe various chemical modifications that can be made to the base, phosphate and/or sugar moieties of the nucleic acid molecules described herein. Modifications that enhance their efficacy in cells, and removal of bases from nucleic acid molecules to shorten oligonucleotide synthesis times and reduce chemical requirements are desired.

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-fluoro, 2'-O-methyl, 2'-O-allyl, 2'-H, nucleotide base modifications (for a review see Usman and Cedergren, 1992, *TIBS.* 17, 34; Usman et al., 1994, *Nucleic Acids Symp. Ser.* 31, 163; Burgin et al., 1996, *Biochemistry*, 35, 14090). Sugar modification of nucleic acid molecules have been extensively described in the art (see Eckstein et al., International Publication PCT No. WO 92/07065; Usman and Cedergren, *Trends in Biochem. Sci.*, 1992, 17, 334-339; Usman et al. International Publication PCT No. WO 93/15187; Sproat, U.S. Pat. No. 5,334,711 and Beigelman et al., 1995, *J. Biol. Chem.*, 270, 25702; Beigelman et al., International PCT publication No. WO 97/26270; Beigelman et al., U.S. Pat. No. 5,716,824; Beigelman et al., WO 03/70918; Usman et al., U.S. Pat. No. 5,627,053; Thompson et al., U.S. Ser. No. 60/082,404 which was filed on Apr. 20, 1998; Karpeisky et al., 1998, *Tetrahedron Lett.*, 39, 1131; Earnshaw and Gait, 1998, *Biopolymers (Nucleic Acid Sciences)*, 48, 39-55; Verma and Eckstein, 1998, *Annu. Rev. Biochem.*, 67, 99-134; and Burlina et al., 1997, *Bioorg. Med. Chem.*, 5, 1999-2010; all of the references are hereby incorporated in their totality by reference herein). Such publications describe general methods and strategies to determine the location of incorporation of sugar, base and/or phosphate modifications and the like into nucleic acid molecules without modulating catalysis, and are incorporated by reference herein. In view of such teachings, similar modifications can be used as described herein to modify the siNA nucleic acid molecules of the instant invention so long as the ability of siNA to promote RNAi is cells is not significantly inhibited.

While chemical modification of oligonucleotide internucleotide linkages with phosphorothioate, phosphorodithioate, and/or 5'-methylphosphonate linkages improves stability, excessive modifications can cause some toxicity or decreased activity. Therefore, when designing nucleic acid molecules, the amount of these internucleotide linkages should be minimized. The reduction in the concentration of these linkages should lower toxicity, resulting in increased efficacy and higher specificity of these molecules.

siNA molecules having chemical modifications that maintain or enhance activity are provided. Such a nucleic acid is also generally more resistant to nucleases than an unmodified nucleic acid. Accordingly, the in vitro and/or in vivo activity should not be significantly lowered. In cases in which modulation is the goal, therapeutic nucleic acid molecules delivered exogenously should optimally be stable within cells until translation of the target RNA has been modulated long enough to reduce the levels of the undesirable protein. This period of time varies between hours to days depending upon the disease state. Improvements in the chemical synthesis of RNA and DNA (Wincott et al., 1995, Nucleic Acids Res. 23, 2677; Caruthers et al., 1992, *Methods in Enzymology* 211, 3-19 (incorporated by reference herein)) have expanded the ability to modify nucleic acid molecules by introducing nucleotide modifications to enhance their nuclease stability, as described above.

In one embodiment, nucleic acid molecules of the invention include one or more (e.g., about 1, 2, 3, 4, 5, 6, 7, 8, 9, 10, or more) G-clamp nucleotides. A G-clamp nucleotide is a modified cytosine analog wherein the modifications confer the ability to hydrogen bond both Watson-Crick and Hoogsteen faces of a complementary guanine within a duplex, see for example Lin and Matteucci, 1998, *J. Am. Chem. Soc.*, 120, 8531-8532. A single G-clamp analog substitution within an oligonucleotide can result in substantially enhanced helical thermal stability and mismatch discrimination when hybridized to complementary oligonucleotides. The inclusion of such nucleotides in nucleic acid molecules of the invention results in both enhanced affinity and specificity to nucleic acid targets, complementary sequences, or template strands. In another embodiment, nucleic acid molecules of the invention include one or more (e.g., about 1, 2, 3, 4, 5, 6, 7, 8, 9, 10, or more) LNA "locked nucleic acid" nucleotides such as a 2',4'-C methylene bicyclo nucleotide (see for example Wengel et al., International PCT Publication No. WO 00/66604 and WO 99/14226, and McSwiggen et al., WO 03/70918).

In another embodiment, the invention features conjugates and/or complexes of siNA molecules of the invention. Such conjugates and/or complexes can be used to facilitate delivery of siNA molecules into a biological system, such as a cell. The conjugates and complexes provided by the instant invention can impart therapeutic activity by transferring therapeutic compounds across cellular membranes, altering the pharmacokinetics, and/or modulating the localization of nucleic acid molecules of the invention (see for example WO 02/094185 and U.S. Ser. No. 10/427,160 both incorporated by reference herein in their entirety including the drawings). The present invention encompasses the design and synthesis of novel conjugates and complexes for the delivery of molecules, including, but not limited to, small molecules, lipids, cholesterol, phospholipids, nucleosides, nucleotides, nucleic acids, antibodies, toxins, negatively charged polymers and other polymers, for example, proteins, peptides, hormones, carbohydrates, polyethylene glycols, or polyamines, across cellular membranes. In general, the transporters described are designed to be used either individually or as part of a multi-component system, with or without degradable linkers. These compounds are expected to improve delivery and/or localization of nucleic acid molecules of the invention into a number of cell types originating from different tissues, in the presence or absence of serum (see Sullenger and Cech, U.S. Pat. No. 5,854,038). Conjugates of the molecules described herein can be attached to biologically active molecules via linkers that are biodegradable, such as biodegradable nucleic acid linker molecules.

The present invention features compositions and conjugates to facilitate delivery of molecules into a biological system such as cells. The conjugates provided by the instant invention can impart therapeutic activity by transferring therapeutic compounds across cellular membranes. The present invention encompasses the design and synthesis of novel agents for the delivery of molecules, including but not limited to siNA molecules. In general, the transporters described are designed to be used either individually or as part of a multi-component system. The compounds of the invention generally shown in Formulae herein are expected to improve delivery of molecules into a number of cell types originating from different tissues, in the presence or absence of serum.

In another embodiment, the compounds of the invention are provided as a surface component of a lipid aggregate, such as a liposome encapsulated with the predetermined molecule to be delivered. Liposomes, which can be unilamellar or multilamellar, can introduce encapsulated material into a cell by different mechanisms. For example, the liposome can directly introduce its encapsulated material into the cell cytoplasm by fusing with the cell membrane. Alternatively, the liposome can be compartmentalized into an acidic vacuole (i.e., an endosome) and its contents released from the liposome and out of the acidic vacuole into the cellular cytoplasm.

In one embodiment the invention features a lipid aggregate formulation of the compounds described herein, including phosphatidylcholine (of varying chain length; e.g., egg yolk phosphatidylcholine), cholesterol, a cationic lipid, and 1,2-distearoyl-sn-glycero-3-phosphoethanolamine-polythylene-glycol-2000 (DSPE-PEG2000). The cationic lipid component of this lipid aggregate can be any cationic lipid known in the art such as dioleoyl 1,2,-diacyl-3-trimethylammoniumpropane (DOTAP). In another embodiment this cationic lipid aggregate comprises a covalently bound compound described in any of the Formulae herein.

In another embodiment, polyethylene glycol (PEG) is covalently attached to the compounds of the present invention. The attached PEG can be any molecular weight but is preferably between 2000-50,000 daltons.

The compounds and methods of the present invention are useful for introducing nucleotides, nucleosides, nucleic acid molecules, lipids, peptides, proteins, and/or non-nucleosidic small molecules into a cell. For example, the invention can be used for nucleotide, nucleoside, nucleic acid, lipids, peptides, proteins, and/or non-nucleosidic small molecule delivery where the corresponding target site of action exists intracellularly.

In one embodiment, the compounds of the instant invention provide conjugates of molecules that can interact with cellular receptors, such as high affinity folate receptors and ASGPr receptors, and provide a number of features that allow the efficient delivery and subsequent release of conjugated compounds across biological membranes. The compounds utilize chemical linkages between the receptor ligand and the compound to be delivered of length that can interact preferentially with cellular receptors. Furthermore, the chemical linkages between the ligand and the compound to be delivered can be designed as degradable linkages, for example by utilizing a phosphate linkage that is proximal to a nucleophile, such as a hydroxyl group. Deprotonation of the hydroxyl group or an equivalent group, as a result of pH or interaction with a nuclease, can result in nucleophilic attack of the phosphate resulting in a cyclic phosphate intermediate that can be hydrolyzed. This cleavage mechanism is analogous RNA cleavage in the presence of a base or RNA nuclease. Alternately, other degradable linkages can be selected that respond to various factors such as UV irradiation, cellular nucleases, pH, temperature etc. The use of degradable linkages allows the delivered compound to be released in a predetermined system, for example in the cytoplasm of a cell, or in a particular cellular organelle.

The present invention also provides ligand derived phosphoramidites that are readily conjugated to compounds and molecules of interest. Phosphoramidite compounds of the invention permit the direct attachment of conjugates to molecules of interest without the need for using nucleic acid phosphoramidite species as scaffolds. As such, the used of phosphoramidite chemistry can be used directly in coupling the compounds of the invention to a compound of interest, without the need for other condensation reactions, such as condensation of the ligand to an amino group on the nucleic acid, for example at the N6 position of adenosine or a 2'-deoxy-2'-amino function. Additionally, compounds of the invention can be used to introduce non-nucleic acid based conjugated linkages into oligonucleotides that can provide more efficient coupling during oligonucleotide synthesis than the use of nucleic acid-based phosphoramidites. This improved coupling can take into account improved steric considerations of abasic or non-nucleosidic scaffolds bearing pendant alkyl linkages.

Compounds of the invention utilizing triphosphate groups can be utilized in the enzymatic incorporation of conjugate molecules into oligonucleotides. Such enzymatic incorporation is useful when conjugates are used in post-synthetic enzymatic conjugation or selection reactions, (see for example Matulic-Adamic et al., 2000, *Bioorg. Med. Chem. Lett.,* 10, 1299-1302; Lee et al., 2001, *NAR.,* 29, 1565-1573; Joyce, 1989, *Gene,* 82, 83-87; Beaudry et al., 1992, *Science* 257, 635-641; Joyce, 1992, *Scientific American* 267, 90-97; Breaker et al., 1994, *TIBTECH* 12, 268; Bartel et al., 1993, *Science* 261:1411-1418; Szostak, 1993, *TIBS* 17, 89-93; Kumar et al., 1995, *FASEB J.,* 9, 1183; Breaker, 1996, *Curr. Op. Biotech.,* 7, 442; Santoro et al., 1997, *Proc. Natl. Acad. Sci.,* 94, 4262; Tang et al., 1997, *RNA* 3, 914; Nakamaye & Eckstein, 1994, supra; Long & Uhlenbeck, 1994, supra; Ishizaka et al., 1995, supra; Vaish et al., 1997, *Biochemistry* 36, 6495; Kuwabara et al., 2000, *Curr. Opin. Chem. Biol.,* 4, 669).

The term "biodegradable linker" as used herein, refers to a nucleic acid or non-nucleic acid linker molecule that is designed as a biodegradable linker to connect one molecule to another molecule, for example, a biologically active molecule to a siNA molecule of the invention or the strands of a siNA molecule of the invention. The biodegradable linker is designed such that its stability can be modulated for a particular purpose, such as delivery to a particular tissue or cell type. The stability of a nucleic acid-based biodegradable linker molecule can be modulated by using various chemistries, for example combinations of ribonucleotides, deoxyribonucleotides, and chemically-modified nucleotides, such as 2'-O-methyl, 2'-fluoro, 2'-amino, 2'-O-amino, 2'-C-allyl, 2'-O-allyl, and other 2'-modified or base modified nucleotides. The biodegradable nucleic acid linker molecule can be a dimer, trimer, tetramer or longer nucleic acid molecule, for example, an oligonucleotide of about 2, 3, 4, 5, 6, 7, 8, 9, 10, 11, 12, 13, 14, 15, 16, 17, 18, 19, or 20 nucleotides in length, or can comprise a single nucleotide with a phosphorus-based linkage, for example, a phosphoramidate or phosphodiester linkage. The biodegradable nucleic acid linker molecule can also comprise nucleic acid backbone, nucleic acid sugar, or nucleic acid base modifications (see for example McSwiggen et al., WO 03/70918 and Vargeese et al., U.S. Ser. No. 10/201, 394 and 10/427,160).

The term "biodegradable" as used herein, refers to degradation in a biological system, for example enzymatic degradation or chemical degradation.

The term "biologically active molecule" as used herein, refers to compounds or molecules that are capable of eliciting or modifying a biological response in a system. Non-limiting examples of biologically active siNA molecules either alone or in combination with other molecules contemplated by the instant invention include therapeutically active molecules such as antibodies, cholesterol, hormones, antivirals, peptides, proteins, chemotherapeutics, small molecules, vitamins, co-factors, nucleosides, nucleotides, oligonucleotides, enzymatic nucleic acids, antisense nucleic acids, triplex forming oligonucleotides, 2,5-A chimeras, siNA, dsRNA, allozymes, aptamers, decoys and analogs thereof. Biologically active molecules of the invention also include molecules capable of modulating the pharmacokinetics and/or pharmacodynamics of other biologically active molecules, for example, lipids and polymers such as polyamines, polyamides, polyethylene glycol and other polyethers.

The term "phospholipid" as used herein, refers to a hydrophobic molecule comprising at least one phosphorus group. For example, a phospholipid can comprise a phosphorus-containing group and saturated or unsaturated alkyl group, optionally substituted with OH, COOH, oxo, amine, or substituted or unsubstituted aryl groups.

The term "alkyl" as used herein refers to a saturated aliphatic hydrocarbon, including straight-chain, branched-chain "isoalkyl", and cyclic alkyl groups. The term "alkyl" also comprises alkoxy, alkyl-thio, alkyl-thio-alkyl, alkoxyalkyl, alkylamino, alkenyl, alkynyl, alkoxy, cycloalkenyl, cycloalkyl, cycloalkylalkyl, heterocycloalkyl, heteroaryl, C1-C6 hydrocarbyl, aryl or substituted aryl groups. Preferably, the alkyl group has 1 to 12 carbons. More preferably it is a lower alkyl of from about 1 to about 7 carbons, more preferably about 1 to about 4 carbons. The alkyl group can be substituted or unsubstituted. When substituted the substituted group(s) preferably comprise hydroxy, oxy, thio, amino, nitro, cyano, alkoxy, alkyl-thio, alkyl-thio-alkyl, alkoxyalkyl, alkylamino, silyl, alkenyl, alkynyl, alkoxy, cycloalkenyl, cycloalkyl, cycloalkylalkyl, heterocycloalkyl, heteroaryl, C1-C6 hydrocarbyl, aryl or substituted aryl groups. The term "alkyl" also includes alkenyl groups containing at least one carbon-carbon double bond, including straight-chain, branched-chain, and cyclic groups. Preferably, the alkenyl group has about 2 to about 12 carbons. More preferably it is a lower alkenyl of from about 2 to about 7 carbons, more preferably about 2 to about 4 carbons. The alkenyl group can be substituted or unsubstituted. When substituted the substituted group(s) preferably comprise hydroxy, oxy, thio, amino, nitro, cyano, alkoxy, alkyl-thio, alkyl-thio-alkyl, alkoxyalkyl, alkylamino, silyl, alkenyl, alkynyl, alkoxy, cycloalkenyl, cycloalkyl, cycloalkylalkyl, heterocycloalkyl, heteroaryl, C1-C6 hydrocarbyl, aryl or substituted aryl groups. The term "alkyl" also includes alkynyl groups containing at least one carbon-carbon triple bond, including straight-chain, branched-chain, and cyclic groups. Preferably, the alkynyl group has about 2 to about 12 carbons. More preferably it is a lower alkynyl of from about 2 to about 7 carbons, more preferably about 2 to about 4 carbons. The alkynyl group can be substituted or unsubstituted. When substituted the substituted group(s) preferably comprise hydroxy, oxy, thio, amino, nitro, cyano, alkoxy, alkyl-thio, alkyl-thio-alkyl, alkoxyalkyl, alkylamino, silyl, alkenyl, alkynyl, alkoxy, cycloalkenyl, cycloalkyl, cycloalkylalkyl, heterocycloalkyl, heteroaryl, C1-C6 hydrocarbyl, aryl or substituted aryl groups. Alkyl groups or moieties of the invention can also include aryl, alkylaryl, carbocyclic aryl, heterocyclic aryl, amide and ester groups. The preferred substituent(s) of aryl groups are halogen, trihalomethyl, hydroxyl, SH, OH, cyano, alkoxy, alkyl, alkenyl, alkynyl, and amino groups. An "alkylaryl" group refers to an alkyl group (as described above) covalently joined to an aryl group (as described above). Carbocyclic aryl groups are groups wherein the ring atoms on the aromatic ring are all carbon atoms. The carbon atoms are optionally substituted. Heterocyclic aryl groups are groups having from about 1 to about 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl and the like, all optionally substituted. An "amide" refers to an —C(O)—NH—R, where R is either alkyl, aryl, alkylaryl or hydrogen. An "ester" refers to an —C(O)—OR', where R is either alkyl, aryl, alkylaryl or hydrogen.

The term "alkoxyalkyl" as used herein refers to an alkyl-O-alkyl ether, for example, methoxyethyl or ethoxymethyl.

The term "alkyl-thio-alkyl" as used herein refers to an alkyl-5-alkyl thioether, for example, methylthiomethyl or methylthioethyl.

The term "amino" as used herein refers to a nitrogen containing group as is known in the art derived from ammonia by the replacement of one or more hydrogen radicals by organic radicals. For example, the terms "aminoacyl" and "aminoalkyl" refer to specific N-substituted organic radicals with acyl and alkyl substituent groups respectively.

The term "alkenyl" as used herein refers to a straight or branched hydrocarbon of a designed number of carbon atoms containing at least one carbon-carbon double bond. Examples of "alkenyl" include vinyl, allyl, and 2-methyl-3-heptene.

The term "alkoxy" as used herein refers to an alkyl group of indicated number of carbon atoms attached to the parent molecular moiety through an oxygen bridge. Examples of alkoxy groups include, for example, methoxy, ethoxy, propoxy and isopropoxy.

The term "alkynyl" as used herein refers to a straight or branched hydrocarbon of a designed number of carbon atoms containing at least one carbon-carbon triple bond. Examples of "alkynyl" include propargyl, propyne, and 3-hexyne.

The term "aryl" as used herein refers to an aromatic hydrocarbon ring system containing at least one aromatic ring. The aromatic ring can optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene and biphenyl. Preferred examples of aryl groups include phenyl and naphthyl.

The term "cycloalkenyl" as used herein refers to a C3-C8 cyclic hydrocarbon containing at least one carbon-carbon double bond. Examples of cycloalkenyl include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "cycloalkyl" as used herein refers to a C3-C8 cyclic hydrocarbon. Examples of cycloalkyl include cyclopropyl, cyclobutyl, cyclopentyl, cyclohexyl, cycloheptyl and cyclooctyl.

The term "cycloalkylalkyl," as used herein, refers to a C3-C7 cycloalkyl group attached to the parent molecular moiety through an alkyl group, as defined above. Examples of cycloalkylalkyl groups include cyclopropylmethyl and cyclopentylethyl.

The terms "halogen" or "halo" as used herein refers to indicate fluorine, chlorine, bromine, and iodine.

The term "heterocycloalkyl," as used herein refers to a non-aromatic ring system containing at least one heteroatom selected from nitrogen, oxygen, and sulfur. The heterocycloalkyl ring can be optionally fused to or otherwise attached to other heterocycloalkyl rings and/or non-aromatic hydrocarbon rings. Preferred heterocycloalkyl groups have from 3 to 7 members. Examples of heterocycloalkyl groups include, for example, piperazine, morpholine, piperidine, tetrahydrofuran, pyrrolidine, and pyrazole. Preferred heterocycloalkyl groups include piperidinyl, piperazinyl, morpholinyl, and pyrrolidinyl.

The term "heteroaryl" as used herein refers to an aromatic ring system containing at least one heteroatom selected from nitrogen, oxygen, and sulfur. The heteroaryl ring can be fused or otherwise attached to one or more heteroaryl rings, aromatic or non-aromatic hydrocarbon rings or heterocycloalkyl rings. Examples of heteroaryl groups include, for example, pyridine, furan, thiophene, 5,6,7,8-tetrahydroisoquinoline and pyrimidine. Preferred examples of heteroaryl groups include thienyl, benzothienyl, pyridyl, quinolyl, pyrazinyl, pyrimidyl, imidazolyl, benzimidazolyl, furanyl, benzofuranyl, thiazolyl, benzothiazolyl, isoxazolyl, oxadiazolyl, isothiazolyl, benzisothiazolyl, triazolyl, tetrazolyl, pyrrolyl, indolyl, pyrazolyl, and benzopyrazolyl.

The term "C1-C6 hydrocarbyl" as used herein refers to straight, branched, or cyclic alkyl groups having 1-6 carbon atoms, optionally containing one or more carbon-carbon double or triple bonds. Examples of hydrocarbyl groups include, for example, methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, vinyl, 2-pentene, cyclopropylmethyl, cyclopropyl, cyclohexylmethyl, cyclohexyl and propargyl. When reference is made herein to C1-C6 hydrocarbyl containing one or two double or triple bonds it is understood that at least two carbons are present in the alkyl for one double or triple bond, and at least four carbons for two double or triple bonds.

The term "phosphorus containing group" as used herein, refers to a chemical group containing a phosphorus atom. The phosphorus atom can be trivalent or pentavalent, and can be substituted with O, H, N, S, C or halogen atoms. Examples of phosphorus containing groups of the instant invention include but are not limited to phosphorus atoms substituted with O, H, N, S, C or halogen atoms, comprising phosphonate, alkylphosphonate, phosphate, diphosphate, triphosphate, pyrophosphate, phosphorothioate, phosphorodithioate, phosphoramidate, phosphoramidite groups, nucleotides and nucleic acid molecules.

The term "degradable linker" as used herein, refers to linker moieties that are capable of cleavage under various conditions. Conditions suitable for cleavage can include but are not limited to pH, UV irradiation, enzymatic activity, temperature, hydrolysis, elimination, and substitution reactions, and thermodynamic properties of the linkage.

The term "photolabile linker" as used herein, refers to linker moieties as are known in the art, that are selectively cleaved under particular UV wavelengths. Compounds of the invention containing photolabile linkers can be used to deliver compounds to a target cell or tissue of interest, and can be subsequently released in the presence of a UV source.

The term "nucleic acid conjugates" as used herein, refers to nucleoside, nucleotide and oligonucleotide conjugates.

The term "lipid" as used herein, refers to any lipophilic compound. Non-limiting examples of lipid compounds include fatty acids and their derivatives, including straight chain, branched chain, saturated and unsaturated fatty acids, carotenoids, terpenes, bile acids, and steroids, including cholesterol and derivatives or analogs thereof.

The term "folate" as used herein, refers to analogs and derivatives of folic acid, for example antifolates, dihydrofolates, tetrahydrofolates, tetrahydrorpterins, folinic acid, pteropolyglutamic acid, 1-deza, 3-deaza, 5-deaza, 8-deaza, 10-deaza, 1,5-deaza, 5,10 dideaza, 8,10-dideaza, and 5,8-dideaza folates, antifolates, and pteroic acid derivatives.

The term "compounds with neutral charge" as used herein, refers to compositions which are neutral or uncharged at neutral or physiological pH. Examples of such compounds are cholesterol and other steroids, cholesteryl hemisuccinate (CHEMS), dioleoyl phosphatidyl choline, distearoylphosphotidyl choline (DSPC), fatty acids such as oleic acid, phosphatidic acid and its derivatives, phosphatidyl serine, polyethylene glycol-conjugated phosphatidylamine, phosphatidylcholine, phosphatidylethanolamine and related variants, prenylated compounds including farnesol, polyprenols, tocopherol, and their modified forms, diacylsuccinyl glycerols, fusogenic or pore forming peptides, dioleoylphosphotidylethanolamine (DOPE), ceramide and the like.

The term "lipid aggregate" as used herein refers to a lipid-containing composition wherein the lipid is in the form of a liposome, micelle (non-lamellar phase) or other aggregates with one or more lipids.

The term "nitrogen containing group" as used herein refers to any chemical group or moiety comprising a nitrogen or substituted nitrogen. Non-limiting examples of nitrogen containing groups include amines, substituted amines, amides, alkylamines, amino acids such as arginine or lysine, polyamines such as spermine or spermidine, cyclic amines such as pyridines, pyrimidines including uracil, thymine, and cytosine, morpholines, phthalimides, and heterocyclic amines such as purines, including guanine and adenine.

Therapeutic nucleic acid molecules (e.g., siNA molecules) delivered exogenously optimally are stable within cells until reverse transcription of the RNA has been modulated long enough to reduce the levels of the RNA transcript. The nucleic acid molecules are resistant to nucleases in order to function as effective intracellular therapeutic agents. Improvements in the chemical synthesis of nucleic acid molecules described in the instant invention and in the art have expanded the ability to modify nucleic acid molecules by introducing nucleotide modifications to enhance their nuclease stability as described above.

Use of the nucleic acid-based molecules of the invention will lead to better treatment of the disease progression by affording the possibility of combination therapies (e.g., multiple siNA molecules targeted to different genes; nucleic acid molecules coupled with known small molecule modulators; or intermittent treatment with combinations of molecules, including different motifs and/or other chemical or biological molecules). The treatment of subjects with siNA molecules can also include combinations of different types of nucleic acid molecules, such as enzymatic nucleic acid molecules (ribozymes), allozymes, antisense, 2,5-A oligoadenylate, decoys, and aptamers.

In another aspect a siNA molecule of the invention comprises one or more 3'-cap structures.

By "cap structure" is meant chemical modifications, which have been incorporated at either terminus of the oligonucleotide (see, for example, Adamic et al., U.S. Pat. No. 5,998,203, and Beigelman et al., WO 03/70918 incorporated by reference herein). These terminal modifications protect the nucleic acid molecule from exonuclease degradation, and can help in delivery and/or localization within a cell. The cap can be present at the 3'-terminus of one or both strands of the multifunctional siNA (3'-cap). Non-limiting examples of the 3'-cap include, but are not limited to, glyceryl, inverted deoxy abasic residue (moiety), 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Iyer, 1993, *Tetrahedron* 49, 1925; incorporated by reference herein).

By the term "non-nucleotide" is meant any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenosine, guanine, cytosine, uracil or thymine and therefore lacks a base at the 1'-position.

By "nucleotide" as used herein is as recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see, for example, Usman and McSwiggen, supra; Eckstein et al., International PCT Publication No. WO 92/07065; Usman et al., International PCT Publication No. WO 93/15187; Uhlman & Peyman, supra, all are hereby incorporated by reference herein). There are several examples of modified nucleic acid bases known in the art as summarized by Limbach et al., 1994, *Nucleic Acids Res.* 22, 2183. Some of the non-limiting examples of base modifications that can be introduced into nucleic acid molecules include, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, and others (Burgin et al., 1996, *Biochemistiy,* 35, 14090; Uhlman & Peyman, supra). By "modified bases" in this aspect is meant nucleotide bases other than adenine, guanine, cytosine and uracil at 1' position or their equivalents.

In one embodiment, the invention features modified siNA molecules, with phosphate backbone modifications comprising one or more phosphorothioate, phosphonoacetate, and/or thiophosphonoacetate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications, see Hunziker and Leumann, 1995, *Nucleic Acid Analogues: Synthesis and Properties,* in *Modern Synthetic Methods*, VCH, 331-417, and Mesmaeker et al., 1994, *Novel Backbone Replacements for Oligonucleotides,* in *Carbohydrate Modifications in Antisense Research*, ACS, 24-39.

By "abasic" is meant sugar moieties lacking a base or having other chemical groups in place of a base at the 1' position, see for example Adamic et al., U.S. Pat. No. 5,998, 203.

By "unmodified nucleoside" is meant one of the bases adenine, cytosine, guanine, thymine, or uracil joined to the 1' carbon of β-D-ribo-furanose.

By "modified nucleoside" is meant any nucleotide base which contains a modification in the chemical structure of an unmodified nucleotide base, sugar and/or phosphate. Non-limiting examples of modified nucleotides are shown by Formulae I-VII and/or other modifications described herein.

In connection with 2'-modified nucleotides as described for the present invention, by "amino" is meant 2'-NH$_2$ or 2'-O—NH$_2$, which can be modified or unmodified. Such modified groups are described, for example, in Eckstein et al., U.S. Pat. No. 5,672,695 and Matulic-Adamic et al., U.S. Pat. No. 6,248,878, which are both incorporated by reference in their entireties.

Various modifications to nucleic acid siNA structure can be made to enhance the utility of these molecules. Such modifications will enhance shelf-life, half-life in vitro, stability, and ease of introduction of such oligonucleotides to the target site, e.g., to enhance penetration of cellular membranes, and confer the ability to recognize and bind to targeted cells.

Administration of Nucleic Acid Molecules

A siNA molecule of the invention can be adapted for use to treat any disease, infection or condition associated with gene expression, and other indications that can respond to the level of gene product in a cell or tissue, alone or in combination with other therapies. For example, a siNA molecule can comprise a delivery vehicle, including liposomes, for administration to a subject, carriers and diluents and their salts, and/or can be present in pharmaceutically acceptable formulations. Methods for the delivery of nucleic acid molecules are described in Akhtar et al., 1992, *Trends Cell Bio.,* 2, 139; *Delivery Strategies for Antisense Oligonucleotide Therapeutics,* ed. Akhtar, 1995, Maurer et al., 1999, *Mol. Membr. Biol.,* 16, 129-140; Hofland and Huang, 1999, *Handb. Exp. Pharmacol.,* 137, 165-192; and Lee et al., 2000, *ACS Symp. Ser.,* 752, 184-192, all of which are incorporated herein by reference. Beigelman et al., U.S. Pat. No. 6,395,713 and Sullivan et al., PCT WO 94/02595 further describe the general methods for delivery of nucleic acid molecules. These protocols can be utilized for the delivery of virtually any nucleic acid molecule. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see for example Gonzalez et al., 1999, *Bioconjugate Chem.,* 10, 1068-1074; Wang et al., International PCT publication Nos. WO 03/47518 and WO 03/46185), poly(lactic-co-glycolic)acid (PLGA) and PLCA microspheres (see for example U.S. Pat. No. 6,447,796 and US Patent Application Publication No. US 2002130430), biodegradable nanocapsules, and bioadhesive microspheres, or by proteinaceous vectors (O'Hare and Normand, International PCT Publication No. WO 00/53722). In one embodiment, nucleic acid molecules or the invention are administered via biodegradable implant materials, such as elastic shape memory polymers (see for example Lendelein and Langer, 2002, Science, 296, 1673). Alternatively, the nucleic acid/vehicle combination is locally delivered by direct injection or by use of an infusion pump. Direct injection of the nucleic acid molecules of the invention, whether subcutaneous, intramuscular, or intradermal, can take place using standard needle and syringe methodologies, or by needle-free technologies such as those described in Conry et al., 1999, *Clin. Cancer Res.,* 5, 2330-2337 and Barry et al., International PCT Publication No. WO 99/31262. Many examples in the art describe CNS delivery methods of oligonucleotides by osmotic pump, (see Chun et al., 1998, *Neuroscience Letters,* 257, 135-138, D'Aldin et al., 1998, *Mol. Brain. Research,* 55, 151-164, Dryden et al., 1998, *J. Endocrinol.,* 157, 169-175, Ghirnikar et al., 1998, *Neuroscience Letters,* 247, 21-24) or direct infusion (Broaddus et al., 1997, *Neurosurg. Focus,* 3, article 4). Other routes of delivery include, but are not limited to oral (tablet or pill form) and/or intrathecal delivery (Gold, 1997, Neuroscience, 76, 1153-1158). More detailed descriptions of nucleic acid delivery and administration are provided in Sullivan et al., supra, Draper et al., PCT WO93/23569, Beigelman et al., PCT WO99/05094, and Klimuk et al., PCT WO99/04819 all of which have been incorporated by reference herein. The molecules of the instant invention can be used as pharmaceutical agents. Pharmaceutical agents prevent, modulate the occurrence, or treat (alleviate a symptom to some extent, preferably all of the symptoms) of a disease state in a subject.

In addition, the invention features the use of methods to deliver the nucleic acid molecules of the instant invention to hematopoietic cells, including monocytes and lymphocytes. These methods are described in detail by Hartmann et al., 1998, *J. Pharmacol. Exp. Ther.,* 285(2), 920-928; Kronenwett et al., 1998, *Blood,* 91(3), 852-862; Filion and Phillips, 1997, *Biochim. Biophys. Acta.,* 1329(2), 345-356; Ma and Wei, 1996, *Leuk. Res.,* 20(11/12), 925-930; and Bongartz et al., 1994, *Nucleic Acids Research,* 22(22), 4681-8. Such methods, as described above, include the use of free oligonucleotide, cationic lipid formulations, liposome formulations including pH sensitive liposomes and immunoliposomes, and bioconjugates including oligonucleotides conjugated to fusogenic peptides, for the transfection of hematopoietic cells with oligonucleotides.

In one embodiment, a compound, molecule, or composition for the treatment of ocular conditions (e.g., macular degeneration, diabetic retinopathy etc.) is administered to a subject intraocularly or by intraocular means. In another embodiment, a compound, molecule, or composition for the treatment of ocular conditions (e.g., macular degeneration, diabetic retinopathy etc.) is administered to a subject periocularly or by periocular means (see for example Ahlheim et al., International PCT publication No. WO 03/24420). In one embodiment, a siNA molecule and/or formulation or composition thereof is administered to a subject intraocularly or by intraocular means. In another embodiment, a siNA molecule and/or formulation or composition thereof is administered to a subject periocularly or by periocular means. Periocular administration generally provides a less invasive approach to administering siNA molecules and formulation or composition thereof to a subject (see for example Ahlheim et al., International PCT publication No. WO 03/24420). The use of periocular administration also minimizes the risk of retinal detachment, allows for more frequent dosing or administration, provides a clinically relevant route of administration for macular degeneration and other optic conditions, and also provides the possibility of using reservoirs (e.g., implants, pumps or other devices) for drug delivery.

In one embodiment, a siNA molecule of the invention is complexed with membrane disruptive agents such as those described in U.S. Patent Application Publication No. 20010007666, incorporated by reference herein in its entirety including the drawings. In another embodiment, the membrane disruptive agent or agents and the siNA molecule are also complexed with a cationic lipid or helper lipid molecule, such as those lipids described in U.S. Pat. No. 6,235,310, incorporated by reference herein in its entirety including the drawings.

In one embodiment, siNA molecules of the invention are formulated or complexed with polyethylenimine (e.g., linear or branched PEI) and/or polyethylenimine derivatives, including for example grafted PEIs such as galactose PEI, cholesterol PEI, antibody derivatized PEI, and polyethylene glycol PEI (PEG-PEI) derivatives thereof (see for example Ogris et al., 2001, *AAPA PharmSci*, 3, 1-11; Furgeson et al., 2003, Bioconjugate Chem., 14, 840-847; Kunath et al., 2002, Pharmaceutical Research, 19, 810-817; Choi et al., 2001, Bull. Korean Chem. Soc., 22, 46-52; Bettinger et al., 1999, Bioconjugate Chem., 10, 558-561; Peterson et al., 2002, Bioconjugate Chem., 13, 845-854; Erbacher et al., 1999, Journal of Gene Medicine Preprint, 1, 1-18; Godbey et al., 1999., PNAS USA, 96, 5177-5181; Godbey et al., 1999, Journal of Controlled Release, 60, 149-160; Diebold et al., 1999, Journal of Biological Chemistry, 274, 19087-19094; Thomas and Klibanov, 2002, PNAS USA, 99, 14640-14645; and Sagara, U.S. Pat. No. 6,586,524, incorporated by reference herein.

In one embodiment, a siNA molecule of the invention comprises a bioconjugate, for example a nucleic acid conjugate as described in Vargeese et al., U.S. Ser. No. 10/427,160, filed Apr. 30, 2003; U.S. Pat. No. 6,528,631; U.S. Pat. No. 6,335,434; U.S. Pat. No. 6,235,886; U.S. Pat. No. 6,153,737; U.S. Pat. No. 5,214,136; U.S. Pat. No. 5,138,045, all incorporated by reference herein.

Thus, the invention features a pharmaceutical composition comprising one or more nucleic acid(s) of the invention in an acceptable carrier, such as a stabilizer, buffer, and the like. The polynucleotides of the invention can be administered (e.g., RNA, DNA or protein) and introduced into a subject by any standard means, with or without stabilizers, buffers, and the like, to form a pharmaceutical composition. When it is desired to use a liposome delivery mechanism, standard protocols for formation of liposomes can be followed. The compositions of the present invention can also be formulated and used as tablets, capsules or elixirs for oral administration, suppositories for rectal administration, sterile solutions, suspensions for injectable administration, and the other compositions known in the art.

The present invention also includes pharmaceutically acceptable formulations of the compounds described. These formulations include salts of the above compounds, e.g., acid addition salts, for example, salts of hydrochloric, hydrobromic, acetic acid, and benzene sulfonic acid.

A pharmacological composition or formulation refers to a composition or formulation in a form suitable for administration, e.g., systemic administration, into a cell or subject, including for example a human. Suitable forms, in part, depend upon the use or the route of entry, for example oral, transdermal, or by injection. Such forms should not prevent the composition or formulation from reaching a target cell (i.e., a cell to which the negatively charged nucleic acid is desirable for delivery). For example, pharmacological compositions injected into the blood stream should be soluble. Other factors are known in the art, and include considerations such as toxicity and forms that prevent the composition or formulation from exerting its effect.

By "systemic administration" is meant in vivo systemic absorption or accumulation of drugs in the blood stream followed by distribution throughout the entire body. Administration routes that lead to systemic absorption include, without limitation: intravenous, subcutaneous, intraperitoneal, inhalation, oral, intrapulmonary and intramuscular. Each of these administration routes exposes the siNA molecules of the invention to an accessible diseased tissue. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation that can facilitate the association of drug with the surface of cells, such as, lymphocytes and macrophages is also useful. This approach can provide enhanced delivery of the drug to target cells by taking advantage of the specificity of macrophage and lymphocyte immune recognition of abnormal cells, such as cancer cells.

By "pharmaceutically acceptable formulation" is meant a composition or formulation that allows for the effective distribution of the nucleic acid molecules of the instant invention in the physical location most suitable for their desired activity. Non-limiting examples of agents suitable for formulation with the nucleic acid molecules of the instant invention include: P-glycoprotein inhibitors (such as Pluronic P85), which can enhance entry of drugs into the CNS (Jolliet-Riant and Tillement, 1999, *Fundam. Clin. Pharmacol.*, 13, 16-26); biodegradable polymers, such as poly (DL-lactide-coglycolide) microspheres for sustained release delivery after intracerebral implantation (Emerich, D F et al, 1999, *Cell Transplant*, 8, 47-58) (Alkermes, Inc. Cambridge, Mass.); and loaded nanoparticles, such as those made of polybutylcyanoacrylate, which can deliver drugs across the blood brain barrier and can alter neuronal uptake mechanisms (*Prog Neuropsychopharmacol Biol Psychiatry*, 23, 941-949, 1999). Other non-limiting examples of delivery strategies for the nucleic acid molecules of the instant invention include material described in Boado et al., 1998, *J. Pharm. Sci.*, 87, 1308-1315; Tyler et al., 1999, *FEBS Lett.*, 421, 280-284; Pardridge et al., 1995, *PNAS USA.*, 92, 5592-5596; Boado, 1995, *Adv. Drug Delivery Rev.*, 15, 73-107; Aldrian-Herrada et al., 1998, *Nucleic Acids Res.*, 26, 4910-4916; and Tyler et al., 1999, *PNAS USA.*, 96, 7053-7058.

The invention also features the use of the composition comprising surface-modified liposomes containing poly (ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. *Chem. Rev.* 1995, 95, 2601-2627; Ishiwata et al., *Chem. Pharm. Bull.* 1995, 43, 1005-1011). Such liposomes have been shown to accumulate selectively in tumors, presumably by extravasation and capture in the neovascularized target tissues (Lasic et al., *Science* 1995, 267, 1275-1276; Oku et al., 1995, *Biochim. Biophys. Acta*, 1238, 86-90). The long-circulating liposomes enhance the pharmacokinetics and pharmacodynamics of DNA and RNA, particularly compared to conventional cationic liposomes which are known to accumulate in tissues of the MPS (Liu et al., *J. Biol. Chem.* 1995, 42, 24864-24870; Choi et al., International PCT Publication No. WO 96/10391; Ansell et al., International PCT Publication No. WO 96/10390; Holland et al., International PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

The present invention also includes compositions prepared for storage or administration that include a pharmaceutically effective amount of the desired compounds in a pharmaceutically acceptable carrier or diluent. Acceptable carriers or diluents for therapeutic use are well known in the pharmaceutical art, and are described, for example, in *Remington's Pharmaceutical Sciences*, Mack Publishing Co. (A. R. Gennaro edit. 1985), hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.1 mg/kg and 100 mg/kg body weight/day of active ingredients is administered dependent upon potency of the negatively charged polymer.

The nucleic acid molecules of the invention and formulations thereof can be administered orally, topically, parenterally, by inhalation or spray, or rectally in dosage unit formulations containing conventional non-toxic pharmaceutically acceptable carriers, adjuvants and/or vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a nucleic acid molecule of the invention and a pharmaceutically acceptable carrier. One or more nucleic acid molecules of the invention can be present in association with one or more non-toxic pharmaceutically acceptable carriers and/or diluents and/or adjuvants, and if desired other active ingredients. The pharmaceutical compositions containing nucleic acid molecules of the invention can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

The nucleic acid molecules of the invention can also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nucleic acid molecules of the invention can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per subject per day). The amount of active ingredient that can be combined with the carrier materials to produce a single dosage form varies depending upon the host treated and the particular mode of administration. Dosage unit forms generally contain between from about 1 mg to about 500 mg of an active ingredient.

It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

The nucleic acid molecules of the present invention can also be administered to a subject in combination with other therapeutic compounds to increase the overall therapeutic effect. The use of multiple compounds to treat an indication can increase the beneficial effects while reducing the presence of side effects.

In one embodiment, the invention comprises compositions suitable for administering nucleic acid molecules of the invention to specific cell types. For example, the asialoglycoprotein receptor (ASGPr) (Wu and Wu, 1987, *J. Biol. Chem.* 262, 4429-4432) is unique to hepatocytes and binds branched galactose-terminal glycoproteins, such as asialoorosomucoid (ASOR). In another example, the folate receptor is overexpressed in many cancer cells. Binding of such glycoproteins, synthetic glycoconjugates, or folates to the receptor takes place with an affinity that strongly depends on the degree of branching of the oligosaccharide chain, for example, triatennary structures are bound with greater affinity than biatenarry or monoatennary chains (Baenziger and Fiete, 1980, *Cell*, 22, 611-620; Connolly et al., 1982, *J. Biol. Chem.*, 257, 939-945). Lee and Lee, 1987, *Glycoconjugate J.*, 4, 317-328, obtained this high specificity through the use of N-acetyl-D-galactosamine as the carbohydrate moiety, which has higher affinity for the receptor, compared to galactose. This "clustering effect" has also been described for the binding and uptake of mannosyl-terminating glycoproteins or glycoconjugates (Ponpipom et al., 1981, *J. Med. Chem.*, 24, 1388-1395). The use of galactose, galactosamine, or folate based conjugates to transport exogenous compounds across cell membranes can provide a targeted delivery approach to, for example, the treatment of liver disease, cancers of the liver, or other cancers. The use of bioconjugates can also provide a reduction in the required dose of therapeutic compounds required for treatment. Furthermore, therapeutic bioavailability, pharmacodynamics, and pharmacokinetic parameters can be modulated through the use of nucleic acid bioconjugates of the invention. Non-limiting examples of such bioconjugates are described in Vargeese et al., U.S. Ser. No. 10/201,394, filed Aug. 13, 2001; and Matulic-Adamic et al., U.S. Ser. No. 10/151,116, filed May 17, 2002. In one embodiment, nucleic acid molecules of the invention are complexed with or covalently attached to nanoparticles, such as Hepatitis B virus S, M, or L envelope proteins (see for example Yamado et al., 2003, *Nature Biotechnology*, 21, 885).

In one embodiment, nucleic acid molecules of the invention are delivered with specificity for human tumor cells, specifically non-apoptotic human tumor cells including for example T-cells, hepatocytes, breast carcinoma cells, ovarian carcinoma cells, melanoma cells, intestinal epithelial cells, prostate cells, testicular cells, non-small cell lung cancers, small cell lung cancers, etc.

Alternatively, certain siNA molecules of the instant invention can be expressed within cells from eukaryotic promoters (e.g., Izant and Weintraub, 1985, *Science*, 229, 345; McGarry and Lindquist, 1986, *Proc. Natl. Acad. Sci.*, USA 83, 399; Thompson et al., 1995, *Nucleic Acids Res.*, 23, 2259; Good et al., 1997, *Gene Therapy*, 4, 45; Noonberg et al., U.S. Pat. No. 5,624,803; Thompson, U.S. Pat. Nos. 5,902,880 and 6,146,886; Paul et al., 2002, *Nature Biotechnology*, 19, 505; Miyagishi and Taira, 2002, *Nature Biotechnology*, 19, 497; Lee et al., 2002, *Nature Biotechnology*, 19, 500; for a review see Couture et al., 1996, *TIG.*, 12, 510). Those skilled in the art realize that any nucleic acid can be expressed in eukaryotic cells from the appropriate DNA/RNA vector. The activity of such nucleic acids can be augmented by their release from the primary transcript by a enzymatic nucleic acid (Draper et al., PCT WO 93/23569, and Sullivan et al., PCT WO 94/02595; Ohkawa et al., 1992, *Nucleic Acids Symp. Ser.*, 27, 15-6; Taira et al., 1991, *Nucleic Acids Res.*, 19, 5125-30; Ventura et al., 1993, *Nucleic Acids Res.*, 21, 3249-55; Chowrira et al., 1994, *J. Biol. Chem.*, 269, 25856).

In another aspect of the invention, siNA molecules of the present invention can be expressed from transcription units (see for example Couture et al., 1996, *TIG.*, 12, 510) inserted into DNA or RNA vectors. The recombinant vectors can be DNA plasmids or viral vectors. siNA expressing viral vectors can be constructed based on, but not limited to, adeno-associated virus, retrovirus, adenovirus, or alphavirus. In another embodiment, pol III based constructs are used to express nucleic acid molecules of the invention (see for example Thompson, U.S. Pat. Nos. 5,902,880 and 6,146,886). The recombinant vectors capable of expressing the siNA molecules can be delivered as described above, and persist in target cells. Alternatively, viral vectors can be used that provide for transient expression of nucleic acid molecules. Such vectors can be repeatedly administered as necessary. Once expressed, the siNA molecule interacts with the target mRNA and generates an RNAi response. Delivery of siNA molecule expressing vectors can be systemic, such as by intravenous or intra-muscular administration, by administration to target cells ex-planted from a subject followed by reintroduction into the subject, or by any other means that would allow for introduction into the desired target cell (for a review see Couture et al., 1996, *TIG.*, 12, 510).

EXAMPLES

The following are non-limiting examples showing the selection, isolation, synthesis and activity of nucleic acids of the instant invention.

Example 1

Serum Stability of Chemically Modified siNA Constructs

Chemical modifications are introduced into siNA constructs to determine the stability of these constructs compared to native siNA oligonucleotides (or those containing for example two thymidine nucleotide overhangs) in human serum. RNAi stability tests are performed by internally labeling siNA and duplexing by incubating in appropriate buffers to facilitate the formation of duplexes by the siNA. Duplexed siNA constructs are then tested for stability by incubating at a final concentration of 2 µM siNA (strand 2 concentration) in 90% mouse or human serum for time-points of 30 sec, 1 min, 5 min, 30 min, 90 min, 4 hrs 10 min, 16 hrs 24 min, and 49 hrs. Time points are run on a 15% denaturing polyacrylamide gels and analyzed on a phosphoimager.

Internal labeling is performed via kinase reactions with polynucleotide kinase (PNK) and $^{32}$P-γ-ATP, with addition of radiolabeled phosphate at a nucleotide position (e.g. nucleotide 13) of strand 2, counting in from the 3' side. Ligation of the remaining fragments with T4 RNA ligase results in the full length strand 2. Duplexing of siNA is accomplished for example by adding an appropriate concentration of the siNA oligonucleotide and heating to 95° C. for 5 minutes followed by slow cooling to room temperature. Reactions are performed by adding 100% serum to the siNA duplexes and incubating at 37° C., then removing aliquots at desired time-points.

Example 2

Identification of Potential siNA Target Sites in any RNA Sequence

The sequence of an RNA target of interest, such as a viral or human mRNA transcript, is screened for target sites, for example by using a computer folding algorithm. Such target sites can contain complementary, palindrome or repeat sequences that are shared by more than one target nucleic acid sequence such that multifunctional siNA molecules can be designed to target differing nucleic acid sequences sharing common palindrome or repeat sequences or having some degree of self complementarity. In addition, the use of non-naturally occurring nucleotides or non-nucleotides can be utilized to generate artificial complementary, palindrome, or repeat regions within a multifunctional siNA molecule of the invention (see for example FIG. 7). In a non-limiting example, the sequence of a gene or RNA gene transcript derived from a database, such as Genbank, is used to generate siNA sequences having complementarity to the target. Such sequences can be obtained from a database, or can be determined experimentally as known in the art. Target sites that are known, for example, those target sites determined to be effective target sites based on studies with other nucleic acid molecules, for example ribozymes or antisense, or those targets known to be associated with a disease or condition such as those sites containing mutations or deletions, can be used to design siNA molecules targeting those sites. Various parameters can be used to determine which sites are the most suitable target sites within the target RNA sequence. These parameters include but are not limited to secondary or tertiary RNA structure, the nucleotide base composition of the target sequence, the degree of homology between various regions of the target sequence, or the relative position of the target sequence within the RNA transcript. Based on these determinations, any number of target sites within the RNA transcript can be chosen to screen siNA molecules for efficacy, for example by using in vitro RNA cleavage assays, cell culture, or animal models. In a non-limiting example, anywhere from 1 to 1000 target sites are chosen within the transcript based on the size of the siNA construct to be used. High throughput screening assays can be developed for screening siNA molecules using methods known in the art, such as with multi-well or multi-plate assays or combinatorial/siNA library screening assays to determine efficient reduction in target gene expression.

In a non-limiting example, a multifunctional siNA is designed to target two separate nucleic acid sequences. The goal is to combine two different siNAs together in one siNA that is active against two different targets. The siNAs are joined in a way that the 5' of each strand starts with the "antisense" sequence of one of two siRNAs as shown in italics below.

```
                                             SEQ ID NO: 1
3'TTAGAAACCAGACGUAAGUGU GGUACGACCUGACGACCGU 5'

SEQ ID NO: 2
5' UCUUUGGUCUGCAUUCACAC CAUGCUGGACUGCUGGCATT3'
```

RISC is expected to incorporate either of the two strands from 5' end. This would lead to two types of active RISC populations carrying either strand. The 5' 19 nt of each strand will act as guide sequence for degradation of separate target sequences.

In another example, the size of multifunctional siNA molecules is reduced by either finding overlaps or truncating the individual siNA length. The exemplary exercise described below indicates that for any given first target sequence, a shared complementary sequence in a second target sequence is likely to be found.

The number of spontaneous matches of short polynucleotide sequences (e.g., less than 14 nucleotides) that are expected to occur between two longer sequences generated independent of one another was investigated. A simulation using the uniform random generator SAS V8.1 utilized a 4,000 character string that was generated as a random repeating occurrence of the letters {ACGU}. This sequence was then broken into the nearly 4000 overlapping sets formed by taking S1 as the characters from positions (1, 2 ... n), S2 from positions (2, 3 ..., n+1) completely through the sequence to the last set, S 4000-n+1 from position (4000-n+1, ..., 4000). This process was then repeated for a second 4000 character string. Occurrence of same sets (of size n) were then checked for sequence identity between the two strings by a sorting and match-merging routine. This procedure was repeated for sets of 9-11 characters. Results were an average of 55 matching sequences of length n=9 characters (range 39 to 72); 13 common sets (range 6 to 18) for size n=10, and 4 matches on average (range 0 to 6) for sets of 11 characters. The choice of 4000 for the original string length is approximately the length of the coding region of both VEGFR1 and VEGFR2. This simple simulation suggests that any two long coding regions formed independent of one-another will share common short sequences that can be used to shorten the length of multifunctional siNA constructs. In this example, common sequences of size 9 occurred by chance alone in >1% frequency.

Below is an example of a multifunctional siNA construct that targets VEGFR1 and VEGFR2 in which each strand has a total length of 24 nt with a 14 nt self complementary region (underline). The antisense region of each siNA '1' targeting VEGFR1 and siNA '2' targeting VEGFR2 (complementary regions are shown in italic) are used

```
siNA '1'
5' CAAUUAGAGUGGCAGUGAG       (SEQ ID NO: 3)
3' GUUAAUCUCACCGUCACUC       (SEQ ID NO: 4)

siNA '2'
AGAGUGGCAGUGAGCAAAG 5'       (SEQ ID NO: 5)
UCUCACCGUCACUCGUUUC 3'       (SEQ ID NO: 6)

Multifunctional siNA
CAAUUAGAGUGGCAGUGAGCAAAG     (SEQ ID NO: 7)
GUUAAUCUCACCGUCACUCGUUUC     (SEQ ID NO: 8)
```

In another example, the length of a multifunctional siNA construct is reduced by determining whether fewer base pairs of sequence homology to each target sequence can be tolerated for effective RNAi activity. If so, the overall length of multifunctional siNA can be reduced as shown below. In the following hypothetical example, 4 nucleotides (bold) are reduced from each 19 nucleotide siNA '1' and siNA '2' constructs. The resulting multifunctional siNA is 30 base pairs long.

```
siNA '1'
5' CAAUUAGAGUGGCAGUGAG       (SEQ ID NO: 3)
3' GUUAAUCUCACCGUCACUC       (SEQ ID NO: 4)

siNA '2'
AGAGUGGCAGUGAGCAAAG 5'       (SEQ ID NO: 5)
UCUCACCGUCACUCGUUUC 3'       (SEQ ID NO: 6)

Multifunctional siNA
CAAUUAGAGUGGCAGUGGCAGUGAGCAAAG    (SEQ ID NO: 9)
GUUAAUCUCACCGUCACCGUCACUCGUUUC    (SEQ ID NO: 10)
```

Example 3

Selection of siNA Molecule Target Sites in a RNA

The following non-limiting steps can be used to carry out the selection of siNAs targeting a given gene sequence or transcript.

The target sequence is parsed in silico into a list of all fragments or subsequences of a particular length, for example 23 nucleotide fragments, contained within the target sequence. This step is typically carried out using a custom Perl script, but commercial sequence analysis programs such as Oligo, MacVector, or the GCG Wisconsin Package can be employed as well.

In some instances, the siNAs correspond to more than one target sequence; such would be the case for example in targeting different transcripts of the same gene, targeting different transcripts of more than one gene, or for targeting both the human gene and an animal homolog. In this case, a subsequence list of a particular length is generated for each of the targets, and then the lists are compared to find matching sequences in each list. The subsequences are then ranked according to the number of target sequences that contain the given subsequence. The goal is to find subsequences that are present in most or all of the target sequences. Alternately, the ranking can identify subsequences that are unique to a target sequence, such as a mutant target sequence. Such an approach would enable the use of siNA to target specifically the mutant sequence and not effect the expression of the normal sequence.

In some instances, the siNA subsequences are absent in one or more sequences while present in the desired target sequence; such would be the case if the siNA targets a gene with a paralogous family member that is to remain untargeted. As in case 2 above, a subsequence list of a particular length is generated for each of the targets, and then the lists are compared to find sequences that are present in the target gene but are absent in the untargeted paralog.

The ranked siNA subsequences can be further analyzed and ranked according to GC content. A preference can be given to sites containing 30-70% GC, with a further preference to sites containing 40-60% GC.

The ranked siNA subsequences can be further analyzed and ranked according to whether they have runs of GGG or CCC in the sequence. GGG (or even more Gs) in either strand can make oligonucleotide synthesis problematic and can potentially interfere with activity, so it is avoided when other appropriately suitable sequences are available. CCC is searched in the target strand because that will place GGG in the siNA strand.

The ranked siNA subsequences can be further analyzed and ranked according to whether they have the dinucleotide UU (uridine dinucleotide) on the 3'-end of the sequence, and/or AA on the 5'-end of the sequence (to yield 3' UU on the siNA sequence). These sequences allow one to design siNA molecules with terminal TT thymidine dinucleotides.

Other design considerations can be used when selecting target nucleic acid sequences, see for example Reynolds et al., 2004, *Nature Biotechnology Advanced Online Publication*, 1 Feb. 2004, doi:10.1038/nbt936.

The siNA molecules are screened in an appropriate in vitro, cell culture or animal model system, such as the systems described herein or otherwise known in the art, to identify the most active siNA molecule or the most preferred target sites within the target RNA sequences.

Example 4 siNA Design siNA target sites were chosen by analyzing sequences of the target RNA and optionally prioritizing the target sites on the basis of preferred sequence motifs, such as predicted duplex stability, GC content, folding (structure of any given sequence analyzed to determine siNA accessibility to the target), other parameters as are known in the art (see for example Reynolds et al., 2004, *Nature Biotechnology Advanced Online Publication*, 1 Feb. 2004, doi:10.1038/nbt936), or by using a library of siNA molecules.

Once target sites have been identified for multifunctional siNA constructs, each strand of the siNA is designed with a complementary region of length, for example, between about 18 and about 28 nucleotides, that is complementary to a different target nucleic acid sequence. Each complementary region is designed with an adjacent flanking region of about 4 to about 22 nucleotides that is not complementary to the target sequence, but which comprises complementarity to the complementary region of the other sequence (see for example FIG. 1). Hairpin constructs can likewise be designed (see for example FIG. 2). Identification of complementary, palindrome or repeat sequences that are shared between the different target nucleic acid sequences can be used to shorten the overall length of the multifunctional siNA constructs (see for example FIGS. 3 and 4).

siNA molecules are designed that could bind each target and are optionally individually analyzed by computer folding to assess whether the siNA molecule can interact with the target sequence. Varying the length of the siNA molecules can be chosen to optimize activity. Generally, a sufficient number of complementary nucleotide bases are chosen to bind to, or otherwise interact with, the target RNA sequences, but the degree of complementarity can be modulated to accommodate siNA duplexes or varying length or base composition. By using such methodologies, siNA molecules can be designed to target sites within any combination of known RNA sequences, for example those RNA sequences corresponding to the any gene transcript.

Chemically modified siNA constructs are designed to provide nuclease stability for systemic administration in vivo and/or improved pharmacokinetic, localization, and delivery properties while preserving the ability to mediate gene inhibition activity. Chemical modifications as described herein are introduced synthetically using synthetic methods described herein and those generally known in the art. The synthetic siNA constructs are then assayed for nuclease stability in serum and/or cellular/tissue extracts (e.g. liver extracts). The synthetic siNA constructs are also tested in parallel for activity using an appropriate assay, such as a luciferase reporter assay as described herein or another suitable assay that can quantity inhibitory activity. Synthetic siNA constructs that possess both nuclease stability and activity can be further modified and re-evaluated in stability and activity assays. The chemical modifications of the stabilized active siNA constructs can then be applied to any siNA sequence targeting any chosen RNA and used, for example, in target screening assays to pick lead siNA compounds for therapeutic development. Alternately, chemically modified siNA constructs can be screened directly for activity in an appropriate assay system (e.g., cell culture, animal models etc.).

Example 5

Chemical Synthesis and Purification of siNA siNA molecules can be designed to interact with various sites in the RNA message (see for example FIG. 6), for example, target sequences within the RNA sequences described herein or with various sites in different RNA sequences (see for example FIG. 5). The sequence of the siNA molecule(s) is complementary to the target site sequences described above. The siNA molecules can be chemically synthesized using methods described herein. Inactive siNA molecules that are used as control sequences can be synthesized by scrambling the sequence of the siNA molecules such that it is not complementary to the target sequence. Generally, siNA constructs can by synthesized using solid phase oligonucleotide synthesis methods as described herein (see for example Usman et al., U.S. Pat. Nos. 5,804,683; 5,831,071; 5,998,203; 6,117,657; 6,353,098; 6,362,323; 6,437,117; 6,469,158; Scaringe et al., U.S. Pat. Nos. 6,111,086; 6,008,400; 6,111,086 all incorporated by reference herein in their entirety).

In a non-limiting example, RNA oligonucleotides are synthesized in a stepwise fashion using the phosphoramidite chemistry described herein and as is known in the art. Standard phosphoramidite chemistry involves the use of nucleosides comprising any of 5'-O-dimethoxytrityl, 2'-O-tert-butyldimethylsilyl, 3'-O-2-Cyanoethyl N,N-diisopropylphosphoroamidite groups, and exocyclic amine protecting groups (e.g. N6-benzoyl adenosine, N4 acetyl cytidine, and N2-isobutyryl guanosine). Alternately, 2'-O-Silyl ethers can be used in conjunction with acid-labile 2'-O-orthoester protecting groups in the synthesis of RNA as described by Scaringe supra. Differing 2' chemistries can require different protecting groups, for example, 2'-deoxy-2'-amino nucleosides can utilize N-phthaloyl protection as described by Usman et al., U.S. Pat. No. 5,631,360, incorporated by reference herein in its entirety).

During solid phase synthesis, each nucleotide is added sequentially (3'- to 5'-direction) to the solid support-bound oligonucleotide. The first nucleoside at the 3'-end of the chain is covalently attached to a solid support (e.g., controlled pore glass or polystyrene) using various linkers. The nucleotide precursor, a ribonucleoside phosphoramidite, and activator are combined resulting in the coupling of the second nucleoside phosphoramidite onto the 5'-end of the first nucleoside. The support is then washed and any unreacted 5'-hydroxyl groups are capped with a capping reagent such as acetic anhydride to yield inactive 5'-acetyl moieties. The trivalent phosphorus linkage is then oxidized to a more stable phosphate linkage. At the end of the nucleotide addition cycle, the 5'-O-protecting group is cleaved under suitable conditions (e.g., acidic conditions for trityl-based groups and Fluoride for silyl-based groups). The cycle is repeated for each subsequent nucleotide.

Modification of synthesis conditions can be used to optimize coupling efficiency, for example, by using differing coupling times, differing reagent/phosphoramidite concentrations, differing contact times, differing solid supports and solid support linker chemistries depending on the particular chemical composition of the siNA to be synthesized. Deprotection and purification of the siNA can be performed as is generally described in Usman et al., U.S. Pat. No. 5,831,071, U.S. Pat. No. 6,353,098, U.S. Pat. No. 6,437,117, and Bellon et al., U.S. Pat. No. 6,054,576, U.S. Pat. No. 6,162,909, U.S. Pat. No. 6,303,773, or Scaringe supra, incorporated by reference herein in their entireties. Additionally, deprotection conditions can be modified to provide the best possible yield and purity of siNA constructs. For example, applicant has observed that oligonucleotides comprising 2'-deoxy-2'-fluoro nucleotides can degrade under inappropriate deprotection conditions. Such oligonucleotides are deprotected using aqueous methylamine at about 35° C. for 30 minutes. If the 2'-deoxy-2'-fluoro containing oligonucleotide also comprises ribonucleotides, after deprotection with aqueous methylamine at about 35° C. for 30 minutes, TEA-HF is added and the reaction maintained at about 65° C. for an additional 15 minutes.

Example 6

Nucleic Acid Inhibition of Target RNA In Vivo siNA molecules targeted to the target RNA are designed and synthesized as described above. These nucleic acid molecules can be tested for cleavage activity in vivo, for example, using the following procedure.

Two formats are used to test the efficacy of siNAs targeting a particular gene transcript. First, the reagents are tested on target expressing cells (e.g., HeLa), to determine the extent of RNA and protein inhibition. siNA reagents are selected against the RNA target. RNA inhibition is measured after delivery of these reagents by a suitable transfection agent to cells. Relative amounts of target RNA are measured versus actin using real-time PCR monitoring of amplification (eg., ABI 7700 Taqman®). A comparison is made to a mixture of oligonucleotide sequences made to unrelated targets or to a randomized siNA control with the same overall length and chemistry, but with randomly substituted nucleotides at each position. Primary and secondary lead reagents are chosen for the target and optimization performed. After an optimal transfection agent concentration is chosen, a RNA time-course of inhibition is performed with the lead siNA molecule. In addition, a cell-plating format can be used to determine RNA inhibition.

Delivery of siNA to Cells

Cells (e.g., HeLa) are seeded, for example, at $1\times10^5$ cells per well of a six-well dish in EGM-2 (BioWhittaker) the day before transfection. siNA (final concentration, for example 20 nM) and cationic lipid (e.g., final concentration 2 µg/ml) are complexed in EGM basal media (Biowhittaker) at 37° C. for 30 mins in polystyrene tubes. Following vortexing, the complexed siNA is added to each well and incubated for the times indicated. For initial optimization experiments, cells are seeded, for example, at $1\times10^3$ in 96 well plates and siNA complex added as described. Efficiency of delivery of siNA to cells is determined using a fluorescent siNA complexed with lipid. Cells in 6-well dishes are incubated with siNA for 24 hours, rinsed with PBS and fixed in 2% paraformaldehyde for 15 minutes at room temperature. Uptake of siNA is visualized using a fluorescent microscope.

Tagman and Lightcycler Quantification of mRNA

Total RNA is prepared from cells following siNA delivery, for example, using Qiagen RNA purification kits for 6-well or Rneasy extraction kits for 96-well assays. For Taqman analysis, dual-labeled probes are synthesized with the reporter dye, FAM or JOE, covalently linked at the 5'-end and the quencher dye TAMRA conjugated to the 3'-end. One-step RT-PCR amplifications are performed on, for example, an ABI PRISM 7700 Sequence Detector using 50 µl reactions consisting of 10 µl total RNA, 100 nM forward primer, 900 nM reverse primer, 100 nM probe, 1× TaqMan PCR reaction buffer (PE-Applied Biosystems), 5.5 mM $MgCl_2$, 300 µM each dATP, dCTP, dGTP, and dTTP, 10 U RNase Inhibitor (Promega), 1.25 U AmpliTaq Gold (PE-Applied Biosystems) and 10 U M-MLV Reverse Transcriptase (Promega). The thermal cycling conditions can consist of 30 min at 48° C., 10 min at 95° C., followed by 40 cycles of 15 sec at 95° C. and 1 min at 60° C. Quantitation of mRNA levels is determined relative to standards generated from serially diluted total cellular RNA (300, 100, 33, 11 ng/rxn) and normalizing to β-actin or GAPDH mRNA in parallel TaqMan reactions. For each gene of interest an upper and lower primer and a fluorescently labeled probe are designed. Real time incorporation of SYBR Green I dye into a specific PCR product can be measured in glass capillary tubes using a lightcyler. A standard curve is generated for each primer pair using control cRNA. Values are represented as relative expression to GAPDH in each sample.

Western Blotting

Nuclear extracts can be prepared using a standard micro preparation technique (see for example Andrews and Faller, 1991, *Nucleic Acids Research*, 19, 2499). Protein extracts from supernatants are prepared, for example, using TCA precipitation. An equal volume of 20% TCA is added to the cell supernatant, incubated on ice for 1 hour and pelleted by centrifugation for 5 minutes. Pellets are washed in acetone, dried and resuspended in water. Cellular protein extracts are run on a 10% Bis-Tris NuPage (nuclear extracts) or 4-12% Tris-Glycine (supernatant extracts) polyacrylamide gel and transferred onto nitro-cellulose membranes. Non-specific binding can be blocked by incubation, for example, with 5% non-fat milk for 1 hour followed by primary antibody for 16 hour at 4° C. Following washes, the secondary antibody is applied, for example, (1:10,000 dilution) for 1 hour at room temperature and the signal detected with SuperSignal reagent (Pierce).

Example 7

Multifunctional siNA Constructs Targeting VEGF and VEGF Receptors

Using the methods described herein, multifunctional siNA constructs are designed against VEGF and VEGFR (e.g. VEGFR1 and/or VEGFR2) target RNA sequences. These siNA constructs can utilize tandem sequences of both targets that do not share any complemetarity (see for example FIGS. 1 and 2). Alternately, the siNA constructs can utilize the identification of complementary, palindromic or repeat sequences (for example Z in Formula I herein) in target nucleic acid sequences of interest (see for example FIGS. 3 and 4). Generally these complementary palindrome/repeat sequences comprise about 2 to about 12 nucleotides in length, but can vary according to a particular multifunctional siNA construct. In one example, a nucleotide sequence that is complementary to the VEGF target nucleic acid sequence is incorporated at the 3'-end of the first strand of the siNA molecule and a nucleotide sequence that is complementary to the VEGFR target nucleic acid sequence is incorporated at the 3'-end of the second strand of the siNA molecule (e.g., FIG. 1A). Alternately, the nucleotide sequence that is complementary to the VEGF target nucleic acid sequence is incorporated at the 5'-end of the first strand of the siNA molecule and a nucleotide sequence that is complementary to the VEGFR target nucleic acid sequence is incorporated at the 5'-end of the second strand of the siNA molecule (e.g., FIG. 1B). If self complementary, palindrome or repeat sequences are used, then generally, the longer the repeat identified in the target nucleic acid sequence, the shorter the resulting siNA sequence will be. For example, if each target sequence is 21 nucleotides in length and there is no repeat found in the sequence, the resulting siNA construct will be, for example, 21+0+21=42 nucleotides in length. The first 21 nucleotides represent sequence complementary to the first target nucleic acid sequence, the 0 represents the lack of a self complementary, palindrome, or repeat sequence, and the second 21 nucleotides represent sequence complementary to the second target nucleic acid sequence. If a 2 nucleotide repeat is utilized, the resulting siNA construct will be, for example, 19+2+19=40 nucleotides in length. If a 4 nucleotide repeat is utilized, the resulting siNA construct will be, for example, 17+4+17=38 nucleotides in length. If a 6 nucleotide repeat is utilized, the resulting siNA construct will be, for example, 15+6+15=36 nucleotides in length. If an 8 nucleotide repeat is utilized, the resulting siNA construct will be, for example, 13+8+13=34 nucleotides in length. If a 10 nucleotide repeat is utilized, the resulting siNA construct will be, for example, 11+10+11=32 nucleotides in length. If a 12 nucleotide repeat is utilized, the resulting siNA construct will be, for example, 9+12+9=30 nucleotides in length and so forth. Thus, for each nucleotide reduction in the target site, the siNA length can be shortened by 2 nucleotides. These same principles can be utilized for a target site having different length nucleotide sequences, such as target sites comprising 14 to 28 nucleotides. In addition, various combinations of 5' and 3' overhang sequences (e.g., TT) can be introduced to the siNA constructs designed with self complementary, palindrome, or repeat sequences.

In one example, multifunctional siNA are designed against VEGFR1 and VEGFR2 RNA targets and are screened in cell culture experiments along with chemically modified siNA constructs with known activity with matched chemistry inverted controls and untreated cells along with a transfection control (LF2K). In a non-limiting example, multifunctional siNA sequences targeting VEGFR1 and VEGFR2 comprise sequences shown in Table I. HAEC cells are transfected with 0.25 ug/well of lipid complexed with 25 nM multifunctional siNA targeting for example VEGFR1 site 1501 and VEGFR2 site 5760. Cells are incubated at 37° for 24 h in the continued presence of the siNA transfection mixture. At 24 h, RNA is prepared from each well of treated cells. The supernatants with the transfection mixtures are first removed and discarded, then the cells are lysed and RNA prepared from each well. Target gene expression following treatment is evaluated by RT-PCR for the VEGFR1 and VEGFR2 mRNA and for a control gene (36B4, an RNA polymerase subunit) for normalization.

In one example, multifunctional siNA are designed against VEGF and VEGFR1 RNA targets and are screened in cell culture experiments along with chemically modified siNA constructs with known activity with matched chemistry inverted controls and untreated cells along with a transfection control (LF2K). In a non-limiting example, multifunctional siNA sequences targeting VEGF and VEGFR1 comprise sequences shown in Table II. HAEC cells are transfected with 0.25 ug/well of lipid complexed with 25 nM multifunctional siNA targeting for example VEGFR1 site 5353 and VEGF site 360. Cells are incubated at 37° for 24 h in the continued presence of the siNA transfection mixture. At 24 h, RNA is prepared from each well of treated cells. The supernatants with the transfection mixtures are first removed and discarded, then the cells are lysed and RNA prepared from each well. Target gene expression following treatment is evaluated by RT-PCR for the VEGFR1 and VEGF mRNA and for a control gene (36B4, an RNA polymerase subunit) for normalization.

In one example, multifunctional siNA are designed against VEGF and VEGFR2 RNA targets and are screened in cell culture experiments along with chemically modified siNA constructs with known activity with matched chemistry inverted controls and untreated cells along with a transfection control (LF2K). In a non-limiting example, multifunctional siNA sequences targeting VEGF and VEGFR2 comprise sequences shown in Table III. HAEC cells are transfected with 0.25 ug/well of lipid complexed with 25 nM multifunctional siNA targeting for example VEGFR2 site 905 and VEGF site 220. Cells are incubated at 37° for 24 h in the continued presence of the siNA transfection mixture. At 24 h, RNA is prepared from each well of treated cells. The supernatants with the transfection mixtures are first removed and discarded, then the cells are lysed and RNA prepared from each well. Target gene expression following treatment is evaluated by RT-PCR for the VEGFR2 and VEGF mRNA and for a control gene (36B4, an RNA polymerase subunit) for normalization.

In one example, multifunctional siNA are designed against VEGF RNA targets and conserved sites within VEGFR1/VEGFR RNA targets and are screened in cell culture experiments along with chemically modified siNA constructs with known activity with matched chemistry inverted controls and untreated cells along with a transfection control (LF2K). In a non-limiting example, multifunctional siNA sequences targeting VEGF, VEGFR1, and VEGFR comprise sequences shown in Table IV. HAEC cells are transfected with 0.25 ug/well of lipid complexed with 25 nM multifunctional siNA targeting for example VEGFR1/R2 hybrid site 3646 and VEGF site 349. Cells are incubated at 37° for 24 h in the continued presence of the siNA transfection mixture. At 24 h, RNA is prepared from each well of treated cells. The supernatants with the transfection mixtures are first removed and discarded, then the cells are lysed and RNA prepared from each well. Target gene expression following treatment is evaluated by RT-PCR for the VEGFR1, VEGFR2 and VEGF mRNA and for a control gene (36B4, an RNA polymerase subunit) for normalization.

Example 8

Multifunctional siNA Constructs Targeting HBV and FAS RNA

Using the methods described herein, multifunctional siNA constructs are designed against HBV and FAS target RNA sequences. These siNA constructs can utilize tandem sequences of both targets that do not share any complemetarity (see for example FIGS. 1 and 2). Alternately, the siNA constructs can utilize the identification of complementary, palindromic or repeat sequences (for example Z in Formula I herein) in target nucleic acid sequences of interest (see for example FIGS. 3 and 4). Generally these complementary palindrome/repeat sequences comprise about 2 to about 12 nucleotides in length, but can vary according to a particular multifunctional siNA construct. In one example, a nucleotide sequence that is complementary to the HBV target nucleic acid sequence is incorporated at the 3'-end of the first strand of the siNA molecule and a nucleotide sequence that is complementary to the FAS target nucleic acid sequence is incorporated at the 3'-end of the second strand of the siNA molecule (e.g., FIG. 1A). Alternately, the nucleotide sequence that is complementary to the HBV target nucleic acid sequence is incorporated at the 5'-end of the first strand of the siNA molecule and a nucleotide sequence that is complementary to the FAS receptor target nucleic acid sequence is incorporated at the 5'-end of the second strand of the siNA molecule (e.g., FIG. 1B). If self complementary, palindrome or repeat sequences are used, then generally, the longer the repeat identified in the target nucleic acid sequence, the shorter the resulting siNA sequence will be. For example, if each target sequence is 21 nucleotides in length and there is no repeat found in the sequence, the resulting siNA construct will be, for example, 21+0+21=42 nucleotides in length. The first 21 nucleotides represent sequence complementary to the first target nucleic acid sequence, the 0 represents the lack of a self complementary, palindrome, or repeat sequence, and the second 21 nucleotides represent sequence complementary to the second target nucleic acid sequence. If a 2 nucleotide repeat is utilized, the resulting siNA construct will be, for example, 19+2+19=40 nucleotides in length. If a 4 nucleotide repeat is utilized, the resulting siNA construct will be, for example, 17+4+17=38 nucleotides in length. If a 6 nucleotide repeat is utilized, the resulting siNA construct will be, for example, 15+6+15=36 nucleotides in length. If an 8 nucleotide repeat is utilized, the resulting siNA construct will be, for example, 13+8+13=34 nucleotides in length. If a 10 nucleotide repeat is utilized, the resulting siNA construct will be, for example, 11+10+11=32 nucleotides in length. If a 12 nucleotide repeat is utilized, the resulting siNA construct will be, for example, 9+12+9=30 nucleotides in length and so forth. Thus, for each nucleotide reduction in the target site, the siNA length can be shortened by 2 nucleotides. These same principles can be utilized for a target site having different length nucleotide sequences, such as target sites comprising 14 to 28 nucleotides. In addition, various combinations of 5' and 3' overhang sequences (e.g., TT) can be introduced to the siNA constructs designed with self complementary, palindrome, or repeat sequences.

In one example, multifunctional siNA are designed against HBV and FAS RNA targets as described herein and are screened in HepG2 cells. Transfection of the human hepatocellular carcinoma cell line, Hep G2, with replication-competent HBV DNA results in the expression of HBV proteins and the production of virions. The human hepatocellular carcinoma cell line Hep G2 is grown in Dulbecco's modified Eagle media supplemented with 10% fetal calf serum, 2 mM glutamine, 0.1 mM nonessential amino acids, 1 mM sodium pyruvate, 25 mM Hepes, 100 units penicillin, and 100 µg/ml streptomycin. To generate a replication competent cDNA, prior to transfection the HBV genomic sequences are excised from the bacterial plasmid sequence contained in the psHBV-1 vector. Other methods known in the art can be used to generate a replication competent cDNA. This can be done with an EcoRI and Hind III restriction digest. Following completion of the digest, a ligation is performed under dilute conditions (20 µg/ml) to favor intermolecular ligation. The total ligation mixture is then concentrated using Qiagen spin columns. To test the efficacy of siNAs targeted against both HBV and FAS RNA, multifunctional siNA duplexes targeting HBV pregenomic RNA and FAS RNA are co-transfected with HBV genomic DNA once at 25 nM with lipid at 12.5 ug/ml into Hep G2 cells, and the subsequent levels of secreted HBV surface antigen (HBsAg) is analyzed by ELISA and FAS RNA is quantitated by RT-PCR.

Example 9

Multifunctional siNA Constructs Targeting HCV and FAS RNA

Using the methods described herein, multifunctional siNA constructs are designed against HCV and FAS target RNA sequences. These siNA constructs can utilize tandem sequences of both targets that do not share any complemetarity (see for example FIGS. 1 and 2). Alternately, the siNA constructs can utilize the identification of complementary, palindromic or repeat sequences (for example Z in Formula I herein) in target nucleic acid sequences of interest (see for example FIGS. 3 and 4). Generally these complementary palindrome/repeat sequences comprise about 2 to about 12 nucleotides in length, but can vary according to a particular multifunctional siNA construct. In one example, a nucleotide sequence that is complementary to the HCV target nucleic acid sequence is incorporated at the 3'-end of the first strand of the siNA molecule and a nucleotide sequence that is complementary to the FAS target nucleic acid sequence is incorporated at the 3'-end of the second strand of the siNA molecule (e.g., FIG. 1A). Alternately, the nucleotide sequence that is complementary to the HCV target nucleic acid sequence is incorporated at the 5'-end of the first strand of the siNA molecule and a nucleotide sequence that is complementary to the FAS receptor target nucleic acid sequence is incorporated at the 5'-end of the second strand of the siNA molecule (e.g., FIG. 1B). If self complementary, palindrome or repeat sequences are used, then generally, the longer the repeat identified in the target nucleic acid sequence, the shorter the resulting siNA sequence will be. For example, if each target sequence is 21 nucleotides in length and there is no repeat found in the sequence, the resulting siNA construct will be, for example, 21+0+21=42 nucleotides in length. The first 21 nucleotides represent sequence complementary to the first target nucleic acid sequence, the 0 represents the lack of a self complementary, palindrome, or repeat sequence, and the second 21 nucleotides represent sequence complementary to the second target nucleic acid sequence. If a 2 nucleotide repeat is utilized, the resulting siNA construct will be, for example, 19+2+19=40 nucleotides in length. If a 4 nucleotide repeat is utilized, the resulting siNA construct will be, for example, 17+4+17=38 nucleotides in length. If a 6 nucleotide repeat is utilized, the resulting siNA construct will be, for example, 15+6+15=36 nucleotides in length. If an 8 nucleotide repeat is utilized, the resulting siNA construct will be, for example, 13+8+13=34 nucleotides in length. If a 10 nucleotide repeat is utilized, the resulting siNA construct will be, for example, 11+10+11=32 nucleotides in length. If a 12 nucleotide repeat is utilized, the resulting siNA construct will be, for example, 9+12+9=30 nucleotides in length and so forth. Thus, for each nucleotide reduction in the target site, the siNA length can be shortened by 2 nucleotides. These same principles can be utilized for a target site having different length nucleotide sequences, such as target sites comprising 14 to 28 nucleotides. In addition, various combinations of 5' and 3' overhang sequences (e.g., TT) can be introduced to the siNA constructs designed with self complementary, palindrome, or repeat sequences.

In one example, a HCV replicon system is used to test the efficacy of siNAs targeting HCV target RNA and FAS target RNA. The reagents are tested in cell culture using Huh7 cells (see for example Randall et al., 2003, *PNAS USA*, 100, 235-240) to determine the extent of HCV and FAS RNA and/or protein inhibition. Multifunctional siNAs are selected against the HCV and FAS nucleic acid targets as described herein. In a non-limiting example, multifunctional siNA sequences targeting HCV RNA and FAS RNA comprise sequences shown in Table V. RNA inhibition is measured after delivery of these reagents by a suitable transfection agent to Huh7 cells. Relative amounts of target RNA are measured versus actin using real-time PCR monitoring of amplification (eg., ABI 7700 Taqman®). A comparison is made to a mixture of oligonucleotide sequences designed to target unrelated targets or to a randomized siNA control with the same overall length and chemistry, but with randomly substituted nucleotides at each position. Primary and secondary lead reagents are chosen for the target and optimization performed. After an optimal transfection agent concentration is chosen, a RNA time-course of inhibition is performed with the lead multifunctional siNA molecule. In addition, a cell-plating format can be used to determine RNA inhibition. Generally, siNA reagents are transfected at 25 nM into Huh7 cells and HCV RNA and FAS RNA is quantitated compared to untreated cells and cells transfected with lipofectamine ("LFA2K") as a transfection control.

Example 10

Multifunctional siNA Constructs Targeting TGF-Beta and TGF-Beta Receptor RNA

Using the methods described herein, multifunctional siNA constructs are designed against TGF-beta and TGF-beta receptor target RNA sequences. These siNA constructs can utilize tandem sequences of both targets that do not share any complemetarity (see for example FIGS. 1 and 2). Alternately, the siNA constructs can utilize the identification of complementary, palindromic or repeat sequences (for example Z in Formula I herein) in target nucleic acid sequences of interest (see for example FIGS. 3 and 4). Generally these complementary palindrome/repeat sequences comprise about 2 to about 12 nucleotides in length, but can vary according to a particular multifunctional siNA construct. In one example, a nucleotide sequence that is complementary to the TGF-beta target nucleic acid sequence is incorporated at the 3'-end of the first strand of the siNA molecule and a nucleotide sequence that is complementary to the TGF-beta receptor target nucleic acid sequence is incorporated at the 3'-end of the second strand of the siNA molecule (e.g., FIG. 1A). Alternately, the nucleotide sequence that is complementary to the TGF-beta target nucleic acid sequence is incorporated at the 5'-end of the first strand of the siNA molecule and a nucleotide sequence that is complementary to the TGF-beta receptor target nucleic acid sequence is incorporated at the 5'-end of the second strand of the siNA molecule (e.g., FIG. 1B). If self complementary, palindrome or repeat sequences are used, then generally, the longer the repeat identified in the target nucleic acid sequence, the shorter the resulting siNA sequence will be. For example, if each target sequence is 21 nucleotides in length and there is no repeat found in the sequence, the resulting siNA construct will be, for example, 21+0+21=42 nucleotides in length. The first 21 nucleotides represent sequence complementary to the first target nucleic acid sequence, the 0 represents the lack of a self complementary, palindrome, or repeat sequence, and the second 21 nucleotides represent sequence complementary to the second target nucleic acid sequence. If a 2 nucleotide repeat is utilized, the resulting siNA construct will be, for example, 19+2+19=40 nucleotides in length. If a 4 nucleotide repeat is utilized, the resulting siNA construct will be, for example, 17+4+17=38 nucleotides in length. If a 6 nucleotide repeat is utilized, the resulting siNA construct will be, for example, 15+6+15=36 nucleotides in length. If an 8 nucleotide repeat is utilized, the resulting siNA construct will be, for example, 13+8+13=34 nucleotides in length. If a 10 nucleotide repeat is utilized, the resulting siNA construct will be, for example, 11+10+11=32 nucleotides in length. If a 12 nucleotide repeat is utilized, the resulting siNA construct will be, for example, 9+12+9=30 nucleotides in length and so forth. Thus, for each nucleotide reduction in the target site, the siNA length can be shortened by 2 nucleotides. These same principles can be utilized for a target site having different length nucleotide sequences, such as target sites comprising 14 to 28 nucleotides. In addition, various combinations of 5' and 3' overhang sequences (e.g., TT) can be introduced to the siNA constructs designed with self complementary, palindrome, or repeat sequences.

In one example, multifunctional siNA are designed against TGF-beta and TGF-beta receptor targets and are screened in cell culture experiments along with chemically modified siNA constructs with known activity using matched chemistry inverted controls and untreated cells along with a transfection control (LF2K). In a non-limiting example, multifunctional siNA sequences targeting TGF-beta and TGF-beta receptor comprise sequences shown in Table VI. A549 cells are transfected with 0.25 ug/well of lipid complexed with 25 nM multifunctional siNA targeting for example TGF-beta site 169 and TGF-beta receptor site 127. Cells are incubated at 37° for 24 h in the continued presence of the siNA transfection mixture. At 24 h, RNA is prepared from each well of treated cells. The supernatants with the transfection mixtures are first removed and discarded, then the cells are lysed and RNA prepared from each well. Target gene expression following treatment is evaluated by RT-PCR for the TGF-beta and TGF-beta receptor mRNA and for a control gene (36B4, an RNA polymerase subunit) for normalization.

Example 11

Multifunctional siNA Constructs Targeting HIV and Cellular RNA

Using the methods described herein, multifunctional siNA constructs are designed against HIV and cellular target RNA sequences. Non-limiting examples of HIV targets include HIV LTR, HIV-TAT, HIV-REV, HIV-NEF, HIV-RRE, HIV-TAR, HIV-VIF, and HIV-ENF. Non-limiting examples of cellular targets include CD4 receptors, CXCR4, CCR5, CCR3, CCR2, CCR1, CCR4, CCR8, CCR9, CXCR2, STRL33 and others described herein. These siNA constructs can utilize tandem sequences of both targets that do not share any complementarity (see for example FIGS. 1 and 2). Alternately, the siNA constructs can utilize the identification of complementary, palindromic or repeat sequences (for example Z in Formula I herein) in target nucleic acid sequences of interest (see for example FIGS. 3 and 4). Generally these complementary palindrome/repeat sequences comprise about 2 to about 12 nucleotides in length, but can vary according to a particular multifunctional siNA construct. In one example, a nucleotide sequence that is complementary to the HIV target nucleic acid sequence is incorporated at the 3'-end of the first strand of the siNA molecule and a nucleotide sequence that is complementary to the cellular target nucleic acid sequence is incorporated at the 3'-end of the second strand of the siNA molecule (e.g., FIG. 1A). Alternately, the nucleotide sequence that is complementary to the HIV target nucleic acid sequence is incorporated at the 5'-end of the first strand of the siNA molecule and a nucleotide sequence that is complementary to the cellular target nucleic acid sequence is incorporated at the 5'-end of the second strand of the siNA molecule (e.g., FIG. 1B). If self complementary, palindrome or repeat sequences are used, then generally, the longer the repeat identified in the target nucleic acid sequence, the shorter the resulting siNA sequence will be. For example, if each target sequence is 21 nucleotides in length and there is no repeat found in the sequence, the resulting siNA construct will be, for example, 21+0+21=42 nucleotides in length. The first 21 nucleotides represent sequence complementary to the first target nucleic acid sequence, the 0 represents the lack of a self complementary, palindrome, or repeat sequence, and the second 21 nucleotides represent sequence complementary to the second target nucleic acid sequence. If a 2 nucleotide repeat is utilized, the resulting siNA construct will be, for example, 19+2+19=40 nucleotides in length. If a 4 nucleotide repeat is utilized, the resulting siNA construct will be, for example, 17+4+17=38 nucleotides in length. If a 6 nucleotide repeat is utilized, the resulting siNA construct will be, for example, 15+6+15=36 nucleotides in length. If an 8 nucleotide repeat is utilized, the resulting siNA construct will be, for example, 13+8+13=34 nucleotides in length. If a 10 nucleotide repeat is utilized, the resulting siNA construct will be, for example, 11+10+11=32 nucleotides in length. If a 12 nucleotide repeat is utilized, the resulting siNA construct will be, for example, 9+12+9=30 nucleotides in length and so forth. Thus, for each nucleotide reduction in the target site, the siNA length can be shortened by 2 nucleotides. These same principles can be utilized for a target site having different length nucleotide sequences, such as target sites comprising 14 to 28 nucleotides. In addition, various combinations of 5' and 3' overhang sequences (e.g., TT) can be introduced to the siNA constructs designed with self complementary, palindrome, or repeat sequences.

In one example, multifunctional siNA are designed against HIV and cellular targets and are screened in cell culture experiments along with chemically modified siNA constructs with known activity using matched chemistry inverted controls and untreated cells along with a transfection control (LF2K). The siNA constructs of the invention can be used in various cell culture systems as are commonly known in the art to screen for compounds having anti-HIV activity. B cell, T cell, macrophage and endothelial cell culture systems are non-limiting examples of cell culture systems that can be readily adapted for screening siNA molecules of the invention. In a non-limiting example, siNA molecules of the invention are co-transfected with HIV-1 pNL4-3 proviral DNA into 293/EcR cells as described by Lee et al., 2002, *Nature Biotechnology*, 19, 500-505, using a U6 snRNA promoter driven expression system.

In a non-limiting example, the siNA expression vectors are prepared using the pTZ U6+1 vector described in Lee et al. supra. as follows. One cassette harbors the first siNA strand and the other the second siNA strand. These sequences are designed to target HIV and cellular RNA targets described herein. As a control to verify a siNA mechanism, irrelevant sequences lacking complementarity to HIV and cellular targets are subcloned in pTZ U6+1. RNA samples are prepared from 293/EcR cells transiently co-transfected with siNA or control constructs, and subjected to Ponasterone A induction. RNAs are also prepared from 293 cells co-transfected with HIV-1 pNL4-3 proviral DNA and siNA or control constructs. For determination of anti-HIV activity of the siNAs, transient assays are done by co-transfection of siNA constructs and infectious HIV proviral DNA, pNL4-3 into 293 cells as described above, followed by Northern analysis as known in the art. The p24 values are calculated with the aid of, for example, a Dynatech MR5000 ELISA plate reader (Dynatech Labs Inc., Chantilly, Va.). Cell viability can also be assessed using a Trypan Blue dye exclusion count at four days after transfection.

Other cell culture model systems for screening compounds having anti-HIV activity are generally known in the art. For example, Duzgunes et al., 2001, *Nucleosides, Nucleotides & Nucleic Acids*, 20(4-7), 515-523; Cagnun et al., 2000, *Antisense Nucleic Acid Drug Dev.*, 10, 251; Ho et al., 1995, *Stem Cells*, 13 supp 3, 100; and Baur et al., 1997, *Blood*, 89, 2259 describe cell culture systems that can be readily adapted for use with both synthetic and vector expressed multifunctional siNA compositions of the instant invention and the assays described herein.

Example 12

Animal Models

Various animal models can be used to screen multifunctional siNA constructs in vivo as are known in the art, for example those animal models that are used to evaluate other nucleic acid technologies such as enzymatic nucleic acid molecules (ribozymes) and/or antisense. Such animal models are used to test the efficacy of siNA molecules described herein. In a non-limiting example, siNA molecules that are designed as anti-angiogenic agents can be screened using animal models. There are several animal models available in which to test the anti-angiogenesis effect of nucleic acids of the present invention, such as siNA, directed against genes associated with angiogenesis and/or metastasis, such as VEGF and VEGFR (e.g., VEGFR1, VEGFR2, and/or VEGFR3) or various combinations of VEGFR (e.g., VEGFR1, VEGFR2, and/or VEGFR3) genes.

Several animal models exist for screening of anti-angiogenic agents. These include corneal vessel formation following corneal injury (Burger et al., 1985 Cornea 4: 35-41; Lepri, et al., 1994 *J. Ocular Pharmacol.* 10: 273-280; Ormerod et al., 1990 *Am. J. Pathol.* 137: 1243-1252) or intracorneal growth factor implant (Grant et al., 1993 *Diabetologia* 36: 282-291; Pandey et al. 1995 supra; Zieche et al., 1992 *Lab. Invest.* 67: 711-715), vessel growth into Matrigel matrix containing growth factors (Passaniti et al., 1992 supra), female reproductive organ neovascularization following hormonal manipulation (Shweiki et al., 1993 *Clin. Invest.* 91: 2235-2243), several models involving inhibition of tumor growth in highly vascularized solid tumors (O'Reilly et al., 1994 *Cell* 79: 315-328; Senger et al., 1993 *Cancer and Metas. Rev.* 12: 303-324; Takahasi et al., 1994 *Cancer Res.* 54: 4233-4237; Kim et al., 1993 supra), and transient hypoxia-induced neovascularization in the mouse retina (Pierce et al., 1995 *Proc. Natl. Acad. Sci. USA.* 92: 905-909).

Ocular Models of Angiogenesis

The cornea model, described in Pandey et al. supra, is the most common and well characterized model for screening anti-angiogenic agent efficacy. This model involves an avascular tissue into which vessels are recruited by a stimulating agent (growth factor, thermal or alkalai burn, endotoxin). The corneal model utilizes the intrastromal corneal implantation of a Teflon pellet soaked in a VEGF-Hydron solution to recruit blood vessels toward the pellet, which can be quantitated using standard microscopic and image analysis techniques. To evaluate their anti-angiogenic efficacy, nucleic acids are applied topically to the eye or bound within Hydron on the Teflon pellet itself. This avascular cornea as well as the Matrigel (see below) provide for low background assays. While the corneal model has been performed extensively in the rabbit, studies in the rat have also been conducted.

The mouse model (Passaniti et al., supra) is a non-tissue model that utilizes Matrigel, an extract of basement membrane (Kleinman et al., 1986) or Millipore® filter disk, which can be impregnated with growth factors and anti-angiogenic agents in a liquid form prior to injection. Upon subcutaneous administration at body temperature, the Matrigel or Millipore® filter disk forms a solid implant. VEGF embedded in the Matrigel or Millipore® filter disk is used to recruit vessels within the matrix of the Matrigel or Millipore® filter disk which can be processed histologically for endothelial cell specific vWF (factor VIII antigen) immunohistochemistry, Trichrome-Masson stain, or hemoglobin content. Like the cornea, the Matrigel or Millipore® filter disk is avascular; however, it is not tissue. In the Matrigel or Millipore® filter disk model, nucleic acids are administered within the matrix of the Matrigel or Millipore® filter disk to test their anti-angiogenic efficacy. Thus, delivery issues in this model, as with delivery of nucleic acids by Hydron-coated Teflon pellets in the rat cornea model, may be less problematic due to the homogeneous presence of the nucleic acid within the respective matrix.

Additionally, siNA molecules of the invention targeting VEGF and/or VEGFR (e.g. VEGFR1, VEGFR2, and/or VEGFR3) can be assessed for activity transgenic mice to determine whether modulation of VEGF and/or VEGFR can inhibit optic neovascularisation. Animal models of choroidal neovascularization are described in, for example, Mori et al., 2001, *Journal of Cellular Physiology*, 188, 253; Mori et al., 2001, *American Journal of Pathology*, 159, 313; Ohno-Matsui et al., 2002, *American Journal of Pathology*, 160, 711; and Kwak et al., 2000, *Investigative Opthalmology & Visual Science*, 41, 3158. VEGF plays a central role in causing retinal neovascularization. Increased expression of VEGFR2 in retinal photoreceptors of transgenic mice stimulates neovascularization within the retina, and a blockade of VEGFR2 signaling has been shown to inhibit retinal choroidal neovascularization (CNV) (Mori et al., 2001, *J. Cell. Physiol.*, 188, 253).

CNV is laser induced in, for example, adult C57BL/6 mice. The mice are also given an intravitreous, periocular or a subretinal injection of VEGF and/or VEGFr (e.g., VEGFR2) siNA in each eye. Intravitreous injections are made using a Harvard pump microinjection apparatus and pulled glass micropipets. Then a micropipette is passed through the sclera just behind the limbus into the vitreous cavity. The subretinal injections are made using a condensing lens system on a dissecting microscope. The pipet tip is then passed through the sclera posterior to the limbus and positioned above the retina. Five days after the injection of the vector the mice are anesthetized with ketamine hydrochloride (100 mg/kg body weight), 1% tropicamide is also used to dilate the pupil, and a diode laser photocoagulation is used to rupture Bruch's membrane at three locations in each eye. A slit lamp delivery system and a hand-held cover slide are used for laser photocoagulation. Burns are made in the 9, 12, and 3 o'clock positions 2-3 disc diameters from the optic nerve (Mori et al., supra).

The mice typically develop subretinal neovascularisation due to the expression of VEGF in photoreceptors beginning at prenatal day 7. At prenatal day 21, the mice are anesthetized and perfused with 1 ml of phosphate-buffered saline containing 50 mg/ml of fluorescein-labeled dextran. Then the eyes are removed and placed for 1 hour in a 10% phosphate-buffered formalin. The retinas are removed and examined by fluorescence microscopy (Mori et al., supra).

Fourteen days after the laser induced rupture of Bruch's membrane, the eyes that received intravitreous and subretinal injection of siNA are evaluated for smaller appearing areas of CNV, while control eyes are evaluated for large areas of CNV. The eyes that receive intravitreous injections or a subretinal injection of siNA are also evaluated for fewer areas of neovascularisation on the outer surface of the retina and potential abortive sprouts from deep retinal capillaries that do not reach the retinal surface compared to eyes that did not receive an injection of siNA.

Tumor Models of Angiogenesis

Use of Murine Models

For a typical systemic study involving 10 mice (20 g each) per dose group, 5 doses (1, 3, 10, 30 and 100 mg/kg daily over 14 days continuous administration), approximately 400 mg of siRNA, formulated in saline is used. A similar study in young adult rats (200 g) requires over 4 g. Parallel pharmacokinetic studies involve the use of similar quantities of siRNA further justifying the use of murine models.

Lewis Lung Carcinoma and B-16 Melanoma Murine Models

Identifying a common animal model for systemic efficacy testing of nucleic acids is an efficient way of screening siNA for systemic efficacy.

The Lewis lung carcinoma and B-16 murine melanoma models are well accepted models of primary and metastatic cancer and are used for initial screening of anti-cancer agents. These murine models are not dependent upon the use of immunodeficient mice, are relatively inexpensive, and minimize housing concerns. Both the Lewis lung and B-16 melanoma models involve subcutaneous implantation of approximately 106 tumor cells from metastatically aggressive tumor cell lines (Lewis lung lines 3LL or D122, LLc-LN7; B-16-BL6 melanoma) in C57BL/6J mice. Alternatively, the Lewis lung model can be produced by the surgical implantation of tumor spheres (approximately 0.8 mm in diameter). Metastasis also can be modeled by injecting the tumor cells directly intravenously. In the Lewis lung model, microscopic metastases can be observed approximately 14 days following implantation with quantifiable macroscopic metastatic tumors developing within 21-25 days. The B-16 melanoma exhibits a similar time course with tumor neovascularization beginning 4 days following implantation. Since both primary and metastatic tumors exist in these models after 21-25 days in the same animal, multiple measurements can be taken as indices of efficacy. Primary tumor volume and growth latency as well as the number of micro- and macroscopic metastatic lung foci or number of animals exhibiting metastases can be quantitated. The percent increase in lifespan can also be measured. Thus, these models provide suitable primary efficacy assays for screening systemically administered siRNA nucleic acids and siRNA nucleic acid formulations.

In the Lewis lung and B-16 melanoma models, systemic pharmacotherapy with a wide variety of agents usually begins 1-7 days following tumor implantation/inoculation with either continuous or multiple administration regimens. Concurrent pharmacokinetic studies can be performed to determine whether sufficient tissue levels of siRNA can be achieved for pharmacodynamic effect to be expected. Furthermore, primary tumors and secondary lung metastases can be removed and subjected to a variety of in vitro studies (i.e. target RNA reduction).

Models of Angiogenesis Related Kidney Disease

In addition, animal models are useful in screening compounds, eg. siNA molecules, for efficacy in treating renal failure, such as a result of autosomal dominant polycystic kidney disease (ADPKD). The Han:SPRD rat model, mice with a targeted mutation in the Pkd2 gene and congenital polycystic kidney (cpk) mice, closely resemble human ADPKD and provide animal models to evaluate the therapeutic effect of siNA constructs that have the potential to interfere with one or more of the pathogenic elements of ADPKD mediated renal failure, such as angiogenesis. Angiogenesis may be necessary in the progression of ADPKD for growth of cyst cells as well as increased vascular permeability promoting fluid secretion into cysts. Proliferation of cystic epithelium is also a feature of ADPKD because cyst cells in culture produce soluble vascular endothelial growth factor (VEGF). VEGFr1 has also been detected in epithelial cells of cystic tubules but not in endothelial cells in the vasculature of cystic kidneys or normal kidneys. VEGFr2 expression is increased in endothelial cells of cyst vessels and in endothelial cells during renal ischemia-reperfusion. It is proposed that inhibition of VEGF receptors with anti-VEGFr1 and anti-VEGFr2 siNA molecules would attenuate cyst formation, renal failure and mortality in ADPKD. Anti-VEGFr2 siNA molecules would therefore be designed to inhibit angiogenesis involved in cyst formation. As VEGFr1 is present in cystic epithelium and not in vascular endothelium of cysts, it is proposed that anti-VEGFr1 siNA molecules would attenuate cystic epithelial cell proliferation and apoptosis which would in turn lead to less cyst formation. Further, it is proposed that VEGF produced by cystic epithelial cells is one of the stimuli for angiogenesis as well as epithelial cell proliferation and apoptosis. The use of Han:SPRD rats (see for example Kaspareit-Rittinghausen et al., 1991, *Am. J. Pathol.* 139, 693-696), mice with a targeted mutation in the Pkd2 gene (Pkd2−/− mice, see for example Wu et al., 2000, *Nat. Genet.* 24, 75-78) and cpk mice (see for example Woo et al., 1994, *Nature*, 368, 750-

753) all provide animal models to study the efficacy of siNA molecules of the invention against VEGFr1 and VEGFr2 mediated renal failure.

VEGF, VEGFr1 VGFR2 and/or VEGFr3 protein levels can be measured clinically or experimentally by FACS analysis. VEGF, VEGFr1 VGFR2 and/or VEGFr3 encoded mRNA levels are assessed by Northern analysis, RNase-protection, primer extension analysis and/or quantitative RT-PCR. siNA nucleic acids that block VEGF, VEGFr1 VGFR2 and/or VEGFr3 protein encoding mRNAs and therefore result in decreased levels of VEGF, VEGFr1 VGFR2 and/or VEGFr3 activity by more than 20% in vitro can be identified.

TGF-Beta and TGF-Beta Receptor Animal Models

Evaluating the efficacy of anti-TGF-beta and/or TGF-betaR agents in animal models is an important prerequisite to human clinical trials. The following description provides animal models for non-limiting examples of diseases and conditions contemplated by the instant invention.

Diabetic Nephropathy

The db/db mouse, which expresses a mutant form of the full length leptin receptor in the hypothalamus, is a genetic model of type 2 diabetes that develops hyperglycemia in the second month of age and overt nephropathy by four months of age. Additional animal models include the streptozotocin diabetic rat or mouse, the spontaneously diabetic BioBreeding rat, and the nonobese diabetic mouse. These models are useful in evaluating nucleic acid molecules of the invention targeting TGF-beta and TGF-betaR for efficacy in treating diabetic nephropathy.

Chronic Liver Disease

The carbon tetrachloride-induced cirrhosis model in mice or rats is a useful model in studying chronic liver disease. In the mouse model, standard therapeutic regimens begin at week 12 and continue for at least 10 weeks. Endpoints include serum chemistry (liver enzymes, direct bilirubin), histopath evaluation with morphometric analysis of collagen content, and liver hydroxyproline content. In the rat model, therapeutic regimens commence at week 6 and continue for up to week 16. Primary endpoints are elevated liver enzyme profile and histopathologic evidence of advanced fibrosis or frank cirrhosis. Phenobarbital can be added to the induction regime and will up-regulate liver enzymes, allowing for a faster induction of the disease state. Liver panels are performed weekly to monitor progression of the disease process. These models are useful in evaluating nucleic acid molecules of the invention targeting TGF-beta and TGF-betaR for efficacy in treating chronic liver disease.

Pulmonary Fibrosis

A rapid (14 day) bleomycin (Bleo)-induced pulmonary injury model is available in mice and in rats. This model is useful in evaluating nucleic acid molecules of the invention targeting TGF-beta and TGF-betaR for efficacy in treating pulmonary fibrosis.

HCV Animal Models

Evaluating the efficacy of anti-HCV agents in animal models is an important prerequisite to human clinical trials. The best characterized animal system for HCV infection is the chimpanzee. Moreover, the chronic hepatitis that results from HCV infection in chimpanzees and humans is very similar. Although clinically relevant, the chimpanzee model suffers from several practical impediments that make use of this model difficult. These include high cost, long incubation requirements and lack of sufficient quantities of animals. Due to these factors, a number of groups have attempted to develop rodent models of chronic hepatitis C infection. While direct infection has not been possible, several groups have reported on the stable transfection of either portions or entire HCV genomes into rodents (Yamamoto et al., Hepatology 1995 22(3): 847-855; Galun et al., Journal of Infectious Disease 1995 172(1):25-30; Koike et al., Journal of general Virology 1995 76(12)3031-3038; Pasquinelli et al., Hepatology 1997 25(3): 719-727; Hayashi et al., Princess Takamatsu Symp 1995 25:1430149; Mariya et al., Journal of General Virology 1997 78(7) 1527-1531; Takehara et al., Hepatology 1995 21(3):746-751; Kawamura et al., Hepatology 1997 25(4): 1014-1021). In addition, transplantation of HCV infected human liver into immunocompromised mice results in prolonged detection of HCV RNA in the animal's blood.

A method for expressing hepatitis C virus in an in vivo animal model has been developed (Vierling, International PCT Publication No. WO 99/16307). Viable, HCV infected human hepatocytes are transplanted into a liver parenchyma of a scid/scid mouse host. The scid/scid mouse host is then maintained in a viable state, whereby viable, morphologically intact human hepatocytes persist in the donor tissue and hepatitis C virus is replicated in the persisting human hepatocytes. This model provides an effective means for the study of HCV inhibition by enzymatic nucleic acids in vivo.

HIV Animal Models

Evaluating the efficacy of anti-HIV agents in animal models is an important prerequisite to human clinical trials. The siNA constructs of the invention can be evaluated in a variety of animal models including, for example, a hollow fiber HIV model (see, for example, Gruenberg, U.S. Pat. No. 5,627,070), mouse models for AIDS using transgenic mice expressing HIV-1 genes from CD4 promoters and enhancers (see, for example, Jolicoeur, International PCT Publication No. WO 98/50535) and/or the HIV/SIV/SHIV non-human primate models (see, for example, Narayan, U.S. Pat. No. 5,849,994). The siNA compounds and virus can be administered by a variety of methods and routes as described herein and as known in the art. Quantitation of results in these models can be performed by a variety of methods, including quantitative PCR, quantitative and bulk co-cultivation assays, plasma co-cultivation assays, antigen and antibody detection assays, lymphocyte proliferation, intracellular cytokines, flow cytometry, as well as hematology and CBC evaluation. Additional animal models are generally known in the art, see for example Bai et al., 2000, *Mol. Ther.,* 1, 244.

HBV Animal Models

Non-limiting examples of HBV animal models useful in evaluating siNA molecules of the invention are described in McSwiggen et al., U.S. Ser. No. 10/757,803 and U.S. Ser. No. 10/669,841, incorporated by reference herein.

Example 10

Indications

The siNA molecules of the invention can be used to treat a variety of diseases and conditions through modulation of gene expression. Using the methods described herein, chemically modified siNA molecules can be designed to modulate the expression of any number of target genes, including but not limited to genes associated with cancer, metabolic diseases, infectious diseases such as viral, bacterial or fungal infections, neurologic diseases, musculoskeletal diseases, diseases of the immune system, diseases associated with signaling pathways and cellular messengers, and diseases associated with transport systems including molecular pumps and channels.

Non-limiting examples of various viral genes that can be targeted using siNA molecules of the invention include Hepatitis C. Virus (HCV, for example Genbank Accession Nos: D11168, D50483.1, L38318 and S82227), Hepatitis B Virus (HBV, for example GenBank Accession No. AF100308.1), Human Immunodeficiency Virus type 1 (HIV-1, for example GenBank Accession No. U51188), Human Immunodeficiency Virus type 2 (HIV-2, for example GenBank Accession No. X60667), West Nile Virus (WNV for example GenBank accession No. NC_001563), cytomegalovirus (CMV for example GenBank Accession No. NC_001347), respiratory syncytial virus (RSV for example GenBank Accession No. NC_001781), influenza virus (for example GenBank Accession No. AF037412, rhinovirus (for example, GenBank accession numbers: D00239, X02316, X01087, L24917, M16248, K02121, X01087), papillomavirus (for example GenBank Accession No. NC_001353), Herpes Simplex Virus (HSV for example GenBank Accession No. NC_001345), and other viruses such as HTLV (for example GenBank Accession No. AJ4300458) and SARS (for example GenBank, Accession No. NC_004718). Due to the high sequence variability of many viral genomes, selection of siNA molecules for broad therapeutic applications would likely involve the conserved regions of the viral genome. Nonlimiting examples of conserved regions of the viral genomes include but are not limited to 5'-Non Coding Regions (NCR), 3'-Non Coding Regions (NCR) LTR regions and/or internal ribosome entry sites (IRES). siNA molecules designed against conserved regions of various viral genomes will enable efficient inhibition of viral replication in diverse patient populations and may ensure the effectiveness of the siNA molecules against viral quasi species which evolve due to mutations in the non-conserved regions of the viral genome.

Non-limiting examples of human genes that can be targeted using siNA molecules of the invention using methods described herein include any human RNA sequence, for example those commonly referred to by Genbank Accession Number. These RNA sequences can be used to design siNA molecules that inhibit gene expression and therefore abrogate diseases, conditions, or infections associated with expression of those genes. Such non-limiting examples of human genes that can be targeted using siNA molecules of the invention include VEGF (for example GenBank Accession No. NM_003376.3), VEGFr (VEGFR1 for example GenBank Accession No. XM_067723, VEGFR2 for example GenBank Accession No. AF063658), HER1, HER2, HER3, and HER4 (for example Genbank Accession Nos: NM_005228, NM_004448, NM_001982, and NM_005235 respectively), telomerase (TERT, for example GenBank Accession No. NM_003219), telomerase RNA (for example GenBank Accession No. U86046), NFkappaB, Rel-A (for example GenBank Accession No. NM_005228), NOGO (for example GenBank Accession No. AB020693), NOGOr (for example GenBank Accession No. XM_015620), RAS (for example GenBank Accession No. NM_004283), RAF (for example GenBank Accession No. XM_033884), CD20 (for example GenBank Accession No. X07203), METAP2 (for example GenBank Accession No. NM_003219), CLCA1 (for example GenBank Accession No. NM_001285), phospholamban (for example GenBank Accession No. NM_002667), PTP1B (for example GenBank Accession No. M31724), PCNA (for example GenBank Accession No. NM_002592.1), PKC-alpha (for example GenBank Accession No. NM_002737) and others. The genes described herein are provided as non-limiting examples of genes that can be targeted using siNA molecules of the invention. Additional examples of such genes are described by accession number in Beigelman et al., U.S. Ser. No. 60/363,124, filed Mar. 11, 2002 and incorporated by reference herein in its entirety.

The siNA molecule of the invention can also be used in a variety of agricultural applications involving modulation of endogenous or exogenous gene expression in plants using siNA, including use as insecticidal, antiviral and anti-fungal agents or modulate plant traits such as oil and starch profiles and stress resistance.

Example 11

Diagnostic Uses

The siNA molecules of the invention can be used in a variety of diagnostic applications, such as in the identification of molecular targets (e.g., RNA) in a variety of applications, for example, in clinical, industrial, environmental, agricultural and/or research settings. Such diagnostic use of siNA molecules involves utilizing reconstituted RNAi systems, for example, using cellular lysates or partially purified cellular lysates. siNA molecules of this invention can be used as diagnostic tools to examine genetic drift and mutations within diseased cells or to detect the presence of endogenous or exogenous, for example viral, RNA in a cell. The close relationship between siNA activity and the structure of the target RNA allows the detection of mutations in any region of the molecule, which alters the base-pairing and three-dimensional structure of the target RNA. By using multiple siNA molecules described in this invention, one can map nucleotide changes, which are important to RNA structure and function in vitro, as well as in cells and tissues. Cleavage of target RNAs with siNA molecules can be used to inhibit gene expression and define the role of specified gene products in the progression of disease or infection. In this manner, other genetic targets can be defined as important mediators of the disease. These experiments will lead to better treatment of the disease progression by affording the possibility of combination therapies (e.g., multiple siNA molecules targeted to different genes, siNA molecules coupled with known small molecule inhibitors, or intermittent treatment with combinations siNA molecules and/or other chemical or biological molecules). Other in vitro uses of siNA molecules of this invention are well known in the art, and include detection of the presence of mRNAs associated with a disease, infection, or related condition. Such RNA is detected by determining the presence of a cleavage product after treatment with a siNA using standard methodologies, for example, fluorescence resonance emission transfer (FRET).

In a specific example, siNA molecules that cleave only wild-type or mutant forms of the target RNA are used for the assay. The first siNA molecules (i.e., those that cleave only wild-type forms of target RNA) are used to identify wild-type RNA present in the sample and the second siNA molecules (i.e., those that cleave only mutant forms of target RNA) are used to identify mutant RNA in the sample. As reaction controls, synthetic substrates of both wild-type and mutant RNA are cleaved by both siNA molecules to demonstrate the relative siNA efficiencies in the reactions and the absence of cleavage of the "non-targeted" RNA species. The cleavage products from the synthetic substrates also serve to generate size markers for the analysis of wild-type and mutant RNAs in the sample population. Thus, each analysis requires two siNA molecules, two substrates and one unknown sample, which is combined into six reactions. The presence of cleavage products is determined using an RNase protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype (i.e., disease related or infection related) is adequate to establish risk. If probes of comparable specific activity are used for both transcripts, then a qualitative comparison of RNA levels is adequate and decreases the cost of the initial diagnosis. Higher mutant form to wild-type ratios are correlated with higher risk whether RNA levels are compared qualitatively or quantitatively.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications can be made to the invention disclosed herein without departing from the scope and spirit of the invention. Thus, such additional embodiments are within the scope of the present invention and the following claims. The present invention teaches one skilled in the art to test various combinations and/or substitutions of chemical modifications described herein toward generating nucleic acid constructs with improved activity for mediating RNAi activity. Such improved activity can comprise improved stability, improved bioavailability, and/or improved activation of cellular responses mediating RNAi. Therefore, the specific embodiments described herein are not limiting and one skilled in the art can readily appreciate that specific combinations of the modifications described herein can be tested without undue experimentation toward identifying siNA molecules with improved RNAi activity.

The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

TABLE I

Multifunctional siNA sequences

| Target1 | Pos1 | Target1 Sequence | Seq ID | Target1 Complement | Seq ID |
|---|---|---|---|---|---|
| VEGFR1 | 349 | CUGAGUUUAAAAGGCACCC | 8 | GGGUGCCUUUUAAACUCAG | 66 |
| VEGFR1 | 1175 | AUACUUGUCGUGUAAGGAG | 9 | CUCCUUACACGACAAGUAU | 67 |
| VEGFR1 | 1501 | CUCACUGCCACUCUAAUUG | 10 | CAAUUAGAGUGGCAGUGAG | 68 |
| VEGFR1 | 1502 | UCACUGCCACUCUAAUUGU | 11 | ACAAUUAGAGUGGCAGUGA | 69 |
| VEGFR1 | 1503 | CACUGCCACUCUAAUUGUC | 12 | GACAAUUAGAGUGGCAGUG | 70 |
| VEGFR1 | 1504 | ACUGCCACUCUAAUUGUCA | 13 | UGACAAUUAGAGUGGCAGU | 71 |
| VEGFR1 | 3646 | AUGCUGGACUGCUGGCACA | 14 | UGUGCCAGCAGUCCAGCAU | 72 |

| Target2 | Pos2 | Target2 Sequence | Seq ID | Target2 Complement | Seq ID |
|---|---|---|---|---|---|
| VEGFR2 | 3715 | ACCAUGCUGGACUGCUGGC | 26 | GCCAGCAGUCCAGCAUGGU | 84 |
| VEGFR2 | 2332 | ACGACAAGUAUUGGGGAAA | 121 | UUUCCCCAAUACUUGUCGU | 142 |
| VEGFR2 | 503 | AGAGUGGCAGUGAGCAAAG | 122 | CUUUGCUCACUGCCACUCU | 143 |
| VEGFR2 | 503 | AGAGUGGCAGUGAGCAAAG | 122 | CUUUGCUCACUGCCACUCU | 143 |
| VEGFR2 | 503 | AGAGUGGCAGUGAGCAAAG | 122 | CUUUGCUCACUGCCACUCU | 143 |

TABLE I-continued

Multifunctional siNA sequences

| Target1 | Pos1 | Target1 Sequence | Seq ID | Target1 Complement | Seq ID |
|---|---|---|---|---|---|
| VEGFR2 | 503 | AGAGUGGCAGUGAGCAAAG | 122 | CUUUGCUCACUGCCACUCU | 143 |
| VEGFR2 | 3716 | CCAUGCUGGACUGCUGGCA | 27 | UGCCAGCAGUCCAGCAUGG | 85 |

| Multifunctional Strand 1 (VEGFR2) | Seq ID | Multifunctional Strand 2 (VEGFR1) | Seq ID |
|---|---|---|---|
| UCAUCAUUAAUUUUUGCUUGCCAUUCCC | 180 | GGGAAUGGCAAGCAAAAAUUAAUGAUGA | 232 |
| AGUGGAUGUGAUGCGGGGGCUGCUGCAA | 181 | UUGCAGCAGCCCCCGCAUCACAUCCACU | 233 |
| ACAUGAUCUGUGGAGGGGUCGGGCUC | 182 | GAGCCCCGACCCCUCCACAGAUCAUGU | 234 |
| CCUGCAAGUUGCUGUCUUGGGUGCAUUG | 183 | CAAUGCACCCAAGACAGCAACUUGCAGG | 235 |
| GCCAGCAGUCCAGCAUGGUUGGACAUCUUCCAGGAGUA | 184 | UACUCCUGGAAGAUGUCCAACCAUGCUGGACUGCUGGC | 236 |
| UGCCAGCAGUCCAGCAUGGUGUGAAUGCAGACCAAAGA | 185 | UCUUUGGUCUGCAUUCACACCAUGCUGGACUGCUGGCA | 237 |
| GUGCCAGCAGUCCAGCAUGGUGAAUGCAGACCAAAGAA | 186 | UUCUUUGGUCUGCAUUCACCAUGCUGGACUGCUGGCAC | 238 |
| CACAGACUCCCUGCUUUUGGGGUGACC | 187 | GGUCACCCCAAAAGCAGGGAGUCUGUG | 239 |

TABLE II

| Target1 | Pos1 | Target1 Sequence | Seq ID | Target1 Complement | Seq ID |
|---|---|---|---|---|---|
| VEGF | 143 | CAUUGAUCCGGGUUUUAUC | 41 | GAUAAAACCCGGAUCAAUG | 99 |
| VEGF | 181 | CAUUUUUUUUUAAAACUGU | 42 | ACAGUUUUAAAAAAAAAUG | 100 |
| VEGF | 221 | UUUUUGCUUGCCAUUCCCC | 43 | GGGGAAUGGCAAGCAAAAA | 101 |
| VEGF | 360 | AGAGACGGGGUCAGAGAGA | 44 | UCUCUCUGACCCCGUCUCU | 102 |
| VEGF | 361 | GAGACGGGGUCAGAGAGAG | 45 | CUCUCUCUGACCCCGUCUC | 103 |
| VEGF | 598 | CCGGAGCCCGCGCCCGGAG | 46 | CUCCGGGCGCGGGCUCCGG | 104 |
| VEGF | 758 | GGGAGGAGCCGCAGCCGGA | 47 | UCCGGCUGCGGCUCCUCCC | 105 |
| VEGF | 1062 | GCAUUGGAGCCUUGCCUUG | 48 | CAAGGCAAGGCUCCAAUGC | 106 |
| VEGF | 1214 | UGGACAUCUUCGAGGAGUA | 49 | UACUCCUGGAAGAUGUCCA | 107 |
| VEGF | 1420 | UGUGAAUGCAGACCAAAGA | 50 | UCUUUGGUCUGCAUUCACA | 108 |
| VEGF | 1421 | GUGAAUGCAGACCAAAGAA | 51 | UUCUUUGGUCUGCAUUCAC | 109 |
| VEGF | 1562 | AGCAUUUGUUUGUACAAGA | 52 | UCUUGUACAAACAAAUGCU | 110 |
| VEGF | 1563 | GCAUUUGUUUGUACAAGAU | 53 | AUCUUGUACAAACAAAUGC | 111 |

| Target2 | Pos2 | Target2 Sequence | Seq ID | Target2 Complement | Seq ID |
|---|---|---|---|---|---|
| VEGFR1 | 3646 | AUGCUGGACUGCUGGCACA | 14 | UGUGCCAGCAGUCCAGCAU | 72 |
| VEGFR1 | 3646 | AUGCUGGACUGCUGGCACA | 14 | UGUGCCAGCAGUCCAGCAU | 72 |
| VEGFR1 | 2063 | GCAAGCAAAAAUGGCAU | 134 | AUGGCAUUUUUUGCUUGC | 155 |
| VEGFR1 | 5353 | GACCCCGUCUCUAUACCAA | 135 | UUGGUAUAGAGACGGGGUC | 156 |
| VEGFR1 | 5353 | GACCCCGUCUCUAUACCAA | 135 | UUGGUAUAGAGACGGGGUC | 156 |
| VEGFR1 | 47 | GCGGGCUCCGGGGCUCGGG | 136 | CCCGAGCCCCGGAGCCCGC | 157 |

TABLE II-continued

| | | | | | |
|---|---|---|---|---|---|
| VEGFR1 | 15 | CGGCUCCUCCCCGGCAGCG | 137 | CGCUGCCGGGGAGGAGCCG | 158 |
| VEGFR1 | 3646 | AUGCUGGACUGCUGGCACA | 14 | UGUGCCAGCAGUCCAGCAU | 72 |
| VEGFR1 | 349 | CUGAGUUUAAAAGGCACCC | 8 | GGGUGCCUUUUAAACUCAG | 66 |
| VEGFR1 | 3646 | AUGCUGGACUGCUGGCACA | 14 | UGUGCCAGCAGUCCAGCAU | 72 |
| VEGFR1 | 349 | CUGAGUUUAAAAGGCACCC | 8 | GGGUGCCUUUUAAACUCAG | 66 |
| VEGFR1 | 3646 | AUGCUGGACUGCUGGCACA | 14 | UGUGCCAGCAGUCCAGCAU | 72 |
| VEGFR1 | 3646 | AUGCUGGACUGCUGGCACA | 14 | UGUGCCAGCAGUCCAGCAU | 72 |

| Multifunctional Strand 1 (VEGFR1) | Seq ID | Multifunctional Strand 2 (VEGF) | Seq ID |
|---|---|---|---|
| UGUGCCAGCAGUCCAGCAUUGAUCCGGGUUUUAUC | 199 | GAUAAAACCCGGAUCAAUGCUGGACUGCUGGCACA | 249 |
| UGUGCCAGCAGUCCAGCAUUUUUUUUUAAAACUGU | 200 | ACAGUUUUAAAAAAAAAUGCUGGACUGCUGGCACA | 250 |
| GGGGAAUGGCAAGCAAAAAUGGCCAU | 201 | AUGGCCAUUUUUUGCUUGCCAUUCCCC | 251 |
| UCUCUCUGACCCCGUCUCUAUACCAA | 202 | UUGGUAUAGAGACGGGGUCAGAGAGA | 252 |
| CUCUCUCUGACCCCGUCUCUAUACCAA | 203 | UUGGUAUAGAGACGGGGUCAGAGAGAG | 253 |
| CUCCGGGCGCGGGCUCCGGGGCUCGGG | 204 | CCCGAGCCCCGGAGCCCGCGCCCGGAG | 254 |
| UCCGGCUGCGGCUCCUCCCCGGCAGCG | 205 | CGCUGCCGGGGAGGAGCCGCAGCCGGA | 255 |
| UGUGCCAGCAGUCCAGCAUUGGAGCCUUGCCUUG | 206 | CAAGGCAAGGCUCCAAUGCUGGACUGCUGGCACA | 256 |
| UACUCCUGGAAGAUGUCCACUGAGUUUAAAAGGCACCC | 207 | GGGUGCCUUUUAAACUCAGUGGACAUCUUCCAGGAGUA | 257 |
| UCUUUGGUCUGCAUUCACAAUGCUGGACUGCUGGCACA | 208 | UGUGCCAGCAGUCCAGCAUUGUGAAUGCAGACCAAAGA | 258 |
| UUCUUUGGUCUGCAUUCACCUGAGUUUAAAAGGCACCC | 209 | GGGUGCCUUUUAAACUCAGGUGAAUGCAGACCAAAGAA | 259 |
| UGUGCCAGCAGUCCAGCAUUUGUUUGUACAAGA | 210 | UCUUGUACAAACAAAUGCUGGACUGCUGGCACA | 260 |
| UGUGCCAGCAGUCCAGCAUUUGUUUGUACAAGAU | 211 | AUCUUGUACAAACAAAUGCUGGACUGCUGGCACA | 261 |

TABLE III

| Target1 | Pos1 | Target1 Sequence | Seq ID | Target1 Complement | Seq ID |
|---|---|---|---|---|---|
| VEGF | 851 | CAUGGACGGGUGAGGCGGC | 54 | GCCGCCUCACCCGUCCAUG | 112 |
| VEGF | 852 | AUGGACGGGUGAGGCGGCG | 55 | CGCCGCCUCACCCGUCCAU | 113 |
| VEGF | 1122 | CAUGGCAGAAGGAGGAGGG | 56 | CCCUCCUCCUUCUGCCAUG | 114 |
| VEGF | 1123 | AUGGCAGAAGGAGGAGGGC | 57 | GCCCUCCUCCUUCUGCCAU | 115 |
| VEGF | 1167 | CAUGGAUGUCUAUCAGCGC | 58 | GCGCUGAUAGACAUCCAUG | 116 |

| Target2 | Pos2 | Target2 Sequence | Seq ID | Target2 Complement | Seq ID |
|---|---|---|---|---|---|
| VEGFR2 | 3716 | CCAUGCUGGACUGCUGGCA | 27 | UGCCAGCAGUCCAGCAUGG | 85 |
| VEGFR2 | 3716 | CCAUGCUGGACUGCUGGCA | 27 | UGCCAGCAGUCCAGCAUGG | 85 |
| VEGFR2 | 3716 | CCAUGCUGGACUGCUGGCA | 27 | UGCCAGCAGUCCAGCAUGG | 85 |
| VEGFR2 | 3716 | CCAUGCUGGACUGCUGGCA | 27 | UGCCAGCAGUCCAGCAUGG | 85 |
| VEGFR2 | 3716 | CCAUGCUGGACUGCUGGCA | 27 | UGCCAGCAGUCCAGCAUGG | 85 |

TABLE III-continued

| Multifunctional Strand 1 (VEGFR2) | Seq ID | Multifunctional Strand 2 (VEGF) | Seq ID |
|---|---|---|---|
| UGCCAGCAGUCCAGCAUGGACGGGUGAGGCGGC | 212 | GCCGCCUCACCCGUCCAUGCUGGACUGCUGGCA | 262 |
| UGCCAGCAGUCCAGCAUGGACGGGUGAGGCGGCG | 213 | CGCCGCCUCACCCGUCCAUGCUGGACUGCUGGCA | 263 |
| UGCCAGCAGUCCAGCAUGGCAGAAGGAGGAGGG | 214 | CCCUCCUCCUUCUGCCAUGCUGGACUGCUGGCA | 264 |
| UGCCAGCAGUCCAGCAUGGCAGAAGGAGGAGGGC | 215 | GCCCUCCUCCUUCUGCCAUGCUGGACUGCUGGCA | 265 |
| UGCCAGCAGUCCAGCAUGGAUGUCUAUCAGCGC | 216 | GCGCUGAUAGACAUCCAUGCUGGACUGCUGGCA | 266 |

TABLE IV

| Target1 | Pos1 | Target1 Sequence | Seq ID | Target1 Complement | Seq ID |
|---|---|---|---|---|---|
| VEGF | 143 | CAUUGAUCCGGGUUUUAUC | 41 | GAUAAAACCCGGAUCAAUG | 99 |
| VEGF | 181 | CAUUUUUUUUUAAAACUGU | 42 | ACAGUUUUAAAAAAAAAUG | 100 |
| VEGF | 1062 | GCAUUGGAGCCUUGCCUUG | 48 | CAAGGCAAGGCUCCAAUGC | 106 |
| VEGF | 1420 | UGUGAAUGCAGACCAAAGA | 50 | UCUUUGGUCUGCAUUCACA | 108 |
| VEGF | 1562 | AGCAUUUGUUUGUACAAGA | 52 | UCUUGUACAAACAAAUGCU | 110 |
| VEGF | 1563 | GCAUUUGUUUGUACAAGAU | 53 | AUCUUGUACAAACAAAUGC | 111 |
| VEGF | 851 | CAUGGACGGGUGAGGCGGC | 54 | GCCGCCUCACCCGUCCAUG | 112 |
| VEGF | 852 | AUGGACGGGUGAGGCGGCG | 55 | CGCCGCCUCACCCGUCCAU | 113 |
| VEGF | 1122 | CAUGGCAGAAGGAGGAGGG | 56 | CCCUCCUCCUUCUGCCAUG | 114 |
| VEGF | 1123 | AUGGCAGAAGGAGGAGGGC | 57 | GCCCUCCUCCUUCUGCCAU | 115 |
| VEGF | 1167 | CAUGGAUGUCUAUCAGCGC | 58 | GCGCUGAUAGACAUCCAUG | 116 |

| Target2 | Pos2 | Target2 Sequence | Seq ID | Target2 Complement | Seq ID |
|---|---|---|---|---|---|
| VEGFR1/R2 | 3646 | AUGCUGGACUGCUGGCACA | 14 | UGUGCCAGCAGUCCAGCAU | 72 |
| VEGFR1/R2 | 3646 | AUGCUGGACUGCUGGCACA | 14 | UGUGCCAGCAGUCCAGCAU | 72 |
| VEGFR1/R2 | 3646 | AUGCUGGACUGCUGGCACA | 14 | UGUGCCAGCAGUCCAGCAU | 72 |
| VEGFR1/R2 | 3646 | AUGCUGGACUGCUGGCACA | 14 | UGUGCCAGCAGUCCAGCAU | 72 |
| VEGFR1/R2 | 3646 | AUGCUGGACUGCUGGCACA | 14 | UGUGCCAGCAGUCCAGCAU | 72 |
| VEGFR1/R2 | 3646 | AUGCUGGACUGCUGGCACA | 14 | UGUGCCAGCAGUCCAGCAU | 72 |
| VEGFR1/R2 | 3716 | CCAUGCUGGACUGCUGGCA | 27 | UGCCAGCAGUCCAGCAUGG | 85 |
| VEGFR1/R2 | 3716 | CCAUGCUGGACUGCUGGCA | 27 | UGCCAGCAGUCCAGCAUGG | 85 |
| VEGFR1/R2 | 3716 | CCAUGCUGGACUGCUGGCA | 27 | UGCCAGCAGUCCAGCAUGG | 85 |
| VEGFR1/R2 | 3716 | CCAUGCUGGACUGCUGGCA | 27 | UGCCAGCAGUCCAGCAUGG | 85 |
| VEGFR1/R2 | 3716 | CCAUGCUGGACUGCUGGCA | 27 | UGCCAGCAGUCCAGCAUGG | 85 |

| Multifunctional Strand 1 (VEGFR1/R2) | Seq ID | Multifunctional Strand 2 (VEGF) | Seq ID |
|---|---|---|---|
| UGUGCCAGCAGUCCAGCAUUGAUCCGGGUUUUAUC | 199 | GAUAAAACCCGGAUCAAUGCUGGACUGCUGGCACA | 249 |
| UGUGCCAGCAGUCCAGCAUUUUUUUUUAAAACUGU | 200 | ACAGUUUUAAAAAAAAAUGCUGGACUGCUGGCACA | 250 |
| UGUGCCAGCAGUCCAGCAUUGGAGCCUUGCCUUG | 206 | CAAGGCAAGGCUCCAAUGCUGGACUGCUGGCACA | 256 |
| UCUUUGGUCUGCAUUCACAAUGCUGGACUGCUGGCACA | 208 | UGUGCCAGCAGUCCAGCAUUGUGAAUGCAGACCAAAGA | 258 |

TABLE IV-continued

| | | |
|---|---|---|
| UGUGCCAGCAGUCCAGCAUUUGUUUGUACAAGA | 210 UCUUGUACAAACAAAUGCUGGACUGCUGGCACA | 260 |
| UGUGCCAGCAGUCCAGCAUUUGUUUGUACAAGAU | 211 AUCUUGUACAAACAAAUGCUGGACUGCUGGCACA | 261 |
| UGCCAGCAGUCCAGCAUGGACGGGUGAGGCGGC | 212 GCCGCCUCACCCGUCCAUGCUGGACUGCUGGCA | 262 |
| UGCCAGCAGUCCAGCAUGGACGGGUGAGGCGGCG | 213 CGCCGCCUCACCCGUCCAUGCUGGACUGCUGGCA | 263 |
| UGCCAGCAGUCCAGCAUGGCAGAAGGAGGAGGG | 214 CCCUCCUCCUUCUGCCAUGCUGGACUGCUGGCA | 264 |
| UGCCAGCAGUCCAGCAUGGCAGAAGGAGGAGGGC | 215 GCCCUCCUCCUUCUGCCAUGCUGGACUGCUGGCA | 265 |
| UGCCAGCAGUCCAGCAUGGAUGUCUAUCAGCGC | 216 GCGCUGAUAGACAUCCAUGCUGGACUGCUGGCA | 266 |

TABLE V

| Target1 | Pos1 | Target1 Sequence | Seq ID | Target1 Complement | Seq ID |
|---|---|---|---|---|---|
| HCV | 141 | CGGGAGAGCCAUAGUGGUC | 15 | GACCACUAUGGCUCUCCCG | 73 |
| HCV | 151 | AUAGUGGUCUGCGGAACCG | 16 | CGGUUCCGCAGACCACUAU | 74 |
| HCV | 152 | UAGUGGUCUGCGGAACCGG | 17 | CCGGUUCCGCAGACCACUA | 75 |
| HCV | 287 | AGGCCUUGUGGUACUGCCU | 18 | AGGCAGUACCACAAGGCCU | 76 |
| HCV | 300 | CUGCCUGAUAGGGUGCUUG | 19 | CAAGCACCCUAUCAGGCAG | 77 |
| HCV | 304 | CUGAUAGGGUGCUUGCGAG | 20 | CUCGCAAGCACCCUAUCAG | 78 |
| HCV | 327 | CCGGGAGGUCUCGUAGACC | 21 | GGUCUACGAGACCUCCCGG | 79 |

| Target2 | Pos2 | Target2 Sequence | Seq ID | Target2 Complement | Seq ID |
|---|---|---|---|---|---|
| FAS | 272 | UCUCCCGCGGGUUGGUGGA | 3 | UCCACCAACCCGCGGGAGA | 61 |
| FAS | 1046 | ACCACUAUUGCUGGAGUCA | 5 | UGACUCCAGCAAUAGUGGU | 63 |
| FAS | 1046 | ACCACUAUUGCUGGAGUCA | 5 | UGACUCCAGCAAUAGUGGU | 63 |
| FAS | 495 | AAGGCCUGCAUCAUGAUGG | 4 | CCAUCAUGAUGCAGGCCUU | 62 |
| FAS | 1771 | CAGGCAGGCCACUUUGCCU | 123 | AGGCAAAGUGGCCUGCCUG | 144 |
| FAS | 1757 | UAUCAGUUACUGAACAGGC | 124 | GCCUGUUCAGUAACUGAUA | 145 |
| FAS | 49 | CCCGGGCGUUCCCCAGCGA | 125 | UCGCUGGGGAACGCCCGGG | 146 |

| Multifunctional Strand 1 (FAS) | Seq ID | Multifunctional Strand 2 (HCV) | Seq ID |
|---|---|---|---|
| GACCACUAUGGCUCUCCCGCGGGUUGGUGGA | 173 | UCCACCAACCCGCGGGAGAGCCAUAGUGGUC | 161 |
| CGGUUCCGCAGACCACUAUUGCUGGAGUCA | 174 | UGACUCCAGCAAUAGUGGUCUGCGGAACCG | 163 |
| CCGGUUCCGCAGACCACUAUUGCUGGAGUCA | 175 | UGACUCCAGCAAUAGUGGUCUGCGGAACCGG | 228 |
| AGGCAGUACCACAAGGCCUGCAUCAUGAUGG | 176 | CCAUCAUGAUGCAGGCCUUGUGGUACUGCCU | 162 |
| CAAGCACCCUAUCAGGCAGGCCACUUUGCCU | 177 | AGGCAAAGUGGCCUGCCUGAUAGGGUGCUUG | 229 |
| CUCGCAAGCACCCUAUCAGUUACUGAACAGGC | 178 | GCCUGUUCAGUAACUGAUAGGGUGCUUGCGAG | 230 |
| GGUCUACGAGACCUCCCGGGCGUUCCCCAGCGA | 179 | UCGCUGGGGAACGCCCGGGAGGUCUCGUAGACC | 231 |

TABLE VI

| Target1 | Pos1 | Target1 Sequence | Seq ID | Target1 Complement | Seq ID |
|---|---|---|---|---|---|
| TGFB1 | 10 | CGCGGAGCAGCCAGACAGC | 30 | GCUGUCUGGCUGCUCCGCG | 88 |
| TGFB1 | 135 | GAGGAGCAGCCUGAGGCCC | 31 | GGGCCUCAGGCUGCUCCUC | 89 |
| TGFB1 | 169 | GCCGCCGCCGCCCCCGCCA | 32 | UGGCGGGGCGGCGGCGGC | 90 |
| TGFB1 | 170 | CCGCCGCCGCCCCCGCCAC | 33 | GUGGCGGGGCGGCGGCGG | 91 |
| TGFB1 | 364 | GCCGGGGACGCUUGCUCCC | 34 | GGGAGCAAGCGUCCCCGGC | 92 |
| TGFB1 | 1528 | GGAUAACACACUGCAAGUG | 35 | CACUUGCAGUGUGUUAUCC | 93 |
| TGFB1 | 2385 | AUAGCAACACUCUGAGAUG | 36 | CAUCUCAGAGUGUUGCUAU | 94 |

| Target2 | Pos2 | Target2 Sequence | Seq ID | Target2 Complement | Seq ID |
|---|---|---|---|---|---|
| TGFBR1 | 92 | GCUGCUCCGCGUCCCCGGC | 131 | GCCGGGGACGCGGAGCAGC | 152 |
| TGFBR1 | 108 | GGCUGCUCCUCCUCGUGCU | 132 | AGCACGAGGAGGAGCAGCC | 153 |
| TGFBR1 | 127 | GGCGGCGGCGGCGGCGGCG | 37 | CGCCGCCGCCGCCGCCGCC | 95 |
| TGFBR1 | 127 | GGCGGCGGCGGCGGCGGCG | 37 | CGCCGCCGCCGCCGCCGCC | 95 |
| TGFBR1 | 100 | GCGUCCCCGGCUGCUCCUC | 133 | GAGGAGCAGCCGGGGACGC | 154 |
| TGFBR1 | 1770 | GGGUCCUUUCUGUGCACUA | 40 | UAGUGCACAGAAAGGACCC | 98 |
| TGFBR1 | 1565 | CAACAGGAAGGCAUCAAAA | 39 | UUUUGAUGCCUUCCUGUUG | 97 |

| Multifunctional Strand 1 (TGFBR1) | Seq ID | Multifunctional Strand 2 (TGFB1) | Seq ID |
|---|---|---|---|
| GCUGUCUGGCUGCUCCGCGUCCCCGGC | 188 | GCCGGGGACGCGGAGCAGCCAGACAGC | 240 |
| GGGCCUCAGGCUGCUCCUCCUCGUGCU | 189 | AGCACGAGGAGGAGCAGCCUGAGGCCC | 241 |
| UGGCGGGGCGGCGGCGGCGGCGGCG | 190 | CGCCGCCGCCGCCGCCGCCCCCGCCA | 195 |
| GUGGCGGGGCGGCGGCGGCGGCGGCG | 191 | CGCCGCCGCCGCCGCCGCCCCCGCCAC | 242 |
| GGGAGCAAGCGUCCCCGGCUGCUCCUC | 192 | GAGGAGCAGCCGGGGACGCUUGCUCCC | 243 |
| CACUUGCAGUGUGUUAUCCGGGUCCUUUCUGUGCACUA | 193 | UAGUGCACAGAAAGGACCCGGAUAACACACUGCAAGUG | 244 |
| CAUCUCAGAGUGUUGCUAUCAACAGGAAGGCAUCAAAA | 194 | UUUUGAUGCCUUCCUGUUGAUAGCAACACUCUGAGAUG | 245 |

TABLE VII

| Reagent | Equivalents | Amount | Wait Time* DNA | Wait Time* 2'-O-methyl | Wait Time* RNA |
|---|---|---|---|---|---|
| A. 2.5 μmol Synthesis Cycle ABI 394 Instrument | | | | | |
| Phosphoramidites | 6.5 | 163 μL | 45 sec | 2.5 min | 7.5 min |
| S-Ethyl Tetrazole | 23.8 | 238 μL | 45 sec | 2.5 min | 7.5 min |
| Acetic Anhydride | 100 | 233 μL | 5 sec | 5 sec | 5 sec |
| N-Methyl Imidazole | 186 | 233 μL | 5 sec | 5 sec | 5 sec |
| TCA | 176 | 2.3 mL | 21 sec | 21 sec | 21 sec |
| Iodine | 11.2 | 1.7 mL | 45 sec | 45 sec | 45 sec |
| Beaucage | 12.9 | 645 μL | 100 sec | 300 sec | 300 sec |
| Acetonitrile | NA | 6.67 mL | NA | NA | NA |

TABLE VII-continued

B. 0.2 μmol Synthesis Cycle ABI 394 Instrument

| Phosphoramidites | 15 | 31 μL | 45 sec | 233 sec | 465 sec |
| S-Ethyl Tetrazole | 38.7 | 31 μL | 45 sec | 233 min | 465 sec |
| Acetic Anhydride | 655 | 124 μL | 5 sec | 5 sec | 5 sec |
| N-Methyl Imidazole | 1245 | 124 μL | 5 sec | 5 sec | 5 sec |
| TCA | 700 | 732 μL | 10 sec | 10 sec | 10 sec |
| Iodine | 20.6 | 244 μL | 15 sec | 15 sec | 15 sec |
| Beaucage | 7.7 | 232 μL | 100 sec | 300 sec | 300 sec |
| Acetonitrile | NA | 2.64 mL | NA | NA | NA |

C. 0.2 μmol Synthesis Cycle 96 well Instrument

| Reagent | Equivalents: DNA/2'-O-methyl/Ribo | Amount: DNA/2'-O-methyl/Ribo | Wait Time* DNA | Wait Time* 2'-O-methyl | Wait Time* Ribo |
|---|---|---|---|---|---|
| Phosphoramidites | 22/33/66 | 40/60/120 μL | 60 sec | 180 sec | 360 sec |
| S-Ethyl Tetrazole | 70/105/210 | 40/60/120 μL | 60 sec | 180 min | 360 sec |
| Acetic Anhydride | 265/265/265 | 50/50/50 μL | 10 sec | 10 sec | 10 sec |
| N-Methyl Imidazole | 502/502/502 | 50/50/50 μL | 10 sec | 10 sec | 10 sec |
| TCA | 238/475/475 | 250/500/500 μL | 15 sec | 15 sec | 15 sec |
| Iodine | 6.8/6.8/6.8 | 80/80/80 μL | 30 sec | 30 sec | 30 sec |
| Beaucage | 34/51/51 | 80/120/120 μL | 100 sec | 200 sec | 200 sec |
| Acetonitrile | NA | 1150/1150/1150 μL | NA | NA | NA |

*Wait time does not include contact time during delivery.
*Tandem synthesis utilizes double coupling of linker molecule

TABLE VIII

Non-limiting examples of Stabilization Chemistries for chemically modified multifunctional siNA constructs

| Chemistry | pyrimidine | Purine | cap | p=S |
|---|---|---|---|---|
| "Stab 00" | Ribo | Ribo | TT at 3'-ends | |
| "Stab 1" | Ribo | Ribo | — | 5 at 5'-end 1 at 3'-end |
| "Stab 2" | Ribo | Ribo | — | All linkages |
| "Stab 3" | 2'-fluoro | Ribo | — | 4 at 5'-end 4 at 3'-end |
| "Stab 4" | 2'-fluoro | Ribo | 3'-end | — |
| "Stab 5" | 2'-fluoro | Ribo | — | 1 at 3'-end |
| "Stab 6" | 2'-O-Methyl | Ribo | 3'-end | — |
| "Stab 7" | 2'-fluoro | 2'-deoxy | 3'-end | — |
| "Stab 8" | 2'-fluoro | 2'-O-Methyl | — | 1 at 3'-end |
| "Stab 9" | Ribo | Ribo | 3'-end | — |
| "Stab 10" | Ribo | Ribo | — | 1 at 3'-end |
| "Stab 11" | 2'-fluoro | 2'-deoxy | — | 1 at 3'-end |
| "Stab 12" | 2'-fluoro | LNA | 3'-end | |
| "Stab 13" | 2'-fluoro | LNA | | 1 at 3'-end |
| "Stab 14" | 2'-fluoro | 2'-deoxy | | 2 at 5'-end 1 at 3'-end |
| "Stab 15" | 2'-deoxy | 2'-deoxy | | 2 at 5'-end 1 at 3'-end |
| "Stab 16" | Ribo | 2'-O-Methyl | 3'-end | |

TABLE VIII-continued

Non-limiting examples of Stabilization Chemistries for chemically modified multifunctional siNA constructs

| Chemistry | pyrimidine | Purine | cap | p=S |
|---|---|---|---|---|
| "Stab 17" | 2'-O-Methyl | 2'-O-Methyl | 3'-end | |
| "Stab 18" | 2'-fluoro | 2'-O-Methyl | 3'-end | 1 at 3'-end |
| "Stab 19" | 2'-fluoro | 2'-O-Methyl | 3'-end | |
| "Stab 20" | 2'-fluoro | 2'-deoxy | 3'-end | |
| "Stab 21" | 2'-fluoro | Ribo | 3'-end | |
| "Stab 22" | Ribo | Ribo | 3'-end | |

CAP = any terminal cap, see for example FIG. 9.
All Stab 1-22 chemistries can comprise 3'-terminal thymidine (TT) residues

What we claim is:

1. A multifunctional siNA molecule of Formula I:

5'-p-XZX'-3'

3'-Y'ZY-p-5' wherein each 5'-p-XZX'-3' and 5'-p-YZY'-3' independently comprise an oligonucleotide of length between 24 and 38 nucleotides, XZ comprises a nucleic acid sequence that is complementary to a first target nucleic acid sequence, YZ comprises an oligonucleotide comprising nucleic acid sequence that is complementary to a second target nucleic acid sequence, Z comprises nucleotide sequence of length 1 to 24 nucleotides that is complementary between regions XZ and YZ, X comprises nucleotide sequence of length 1 to 21 nucleotides that is complementary to nucleotide sequence present in region Y', Y comprises nucleotide sequence of length 1 to 21 nucleotides that is complementary to nucleotide sequence present in region X', p comprises a terminal phosphate group that can independently be present or absent, and wherein each said XZ and said YZ are independently of length sufficient to stably interact with said first and said second target nucleic acid sequence, respectively, or a portion thereof.

2. The siNA molecule of claim 1, wherein said siNA comprises a 3'-terminal cap moiety.

3. The siNA molecule of claim 2, wherein said terminal cap moiety is an inverted deoxyabasic moiety.

4. The siNA molecule of claim 2, wherein said terminal cap moiety is an inverted deoxynucleotide moiety.

5. The siNA molecule of claim 2, wherein said terminal cap moiety is a dinucleotide moiety.

6. The siNA molecule of claim 5, wherein said dinucleotide is dithymidine (TT).

7. The siNA molecule of claim 1, wherein said siNA molecule comprises no ribonucleotides.

8. The siNA molecule of claim 1, wherein said siNA molecule comprises ribonucleotides.

9. The siNA molecule of claim 1, wherein any purine nucleotide in said siNA is a 2'-0-methyl pyrimidine nucleotide.

10. The siNA molecule of claim 1, wherein any purine nucleotide in said siNA is a 2'-deoxy purine nucleotide.

11. The siNA molecule of claim 1, wherein any pyrimidine nucleotide in said siNA is a 2'-deoxy-2'-fluoro pyrimidine nucleotide.

12. The siNA molecule of claim 1, wherein said siNA molecule comprises 3'-nucleotide overhangs.

13. The siNA molecule of claim 12, wherein said 3'-overhangs comprise about 1 to about 4 nucleotides.

14. The siNA molecule of claim 13, wherein said nucleotides comprise deoxynucleotides.

15. The siNA molecule of claim 14, wherein said deoxynucleotides are thymidine nucleotides.

16. A composition comprising the siNA molecule of claim 1 in a pharmaceutically acceptable carrier or diluent.

* * * * *

SEQUENCE LISTING

```
<160> NUMBER OF SEQ ID NOS: 270

<210> SEQ ID NO 1
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(38)
<223> OTHER INFORMATION: RNA

<400> SEQUENCE: 1
ugccagcagu ccagcauggu gugaaugcag accaaagatt                        40

<210> SEQ ID NO 2
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(38)
<223> OTHER INFORMATION: RNA

<400> SEQUENCE: 2
ucuuuggucu gcauucacac caugcuggac ugcuggcatt                        40

<210> SEQ ID NO 3
<211> LENGTH: 19
<212> TYPE: RNA
<213> ORGANISM: Artificial Sequence
<220> FEATURE:
<223> OTHER INFORMATION: Synthetic

<400> SEQUENCE: 3
caauuagagu ggcagugag                                                19

<210> SEQ ID NO 4
<211> LENGTH: 19
<212> TYPE: RNA
<213> ORGANISM: Artificial Sequence
<220> FEATURE:
<223> OTHER INFORMATION: Synthetic

<400> SEQUENCE: 4
```
cucacugcca cucuaauug                                                19

<210> SEQ ID NO 5
<211> LENGTH: 19
<212> TYPE: RNA
<213> ORGANISM: Artificial Sequence
<220> FEATURE:
<223> OTHER INFORMATION: Synthetic

<400> SEQUENCE: 5
gaaacgagug acggugaga                                                19

<210> SEQ ID NO 6
<211> LENGTH: 19
<212> TYPE: RNA
<213> ORGANISM: Artificial Sequence
<220> FEATURE:
<223> OTHER INFORMATION: Synthetic

<400> SEQUENCE: 6
ucucaccguc acucguuuc                                                19

<210> SEQ ID NO 7
<211> LENGTH: 24
<212> TYPE: RNA
<213> ORGANISM: Artificial Sequence
<220> FEATURE:
<223> OTHER INFORMATION: Synthetic

<400> SEQUENCE: 7
gaaacgagug acggugagau uaac                                          24

<210> SEQ ID NO 8
<211> LENGTH: 24
<212> TYPE: RNA
<213> ORGANISM: Artificial Sequence
<220> FEATURE:
<223> OTHER INFORMATION: Synthetic

<400> SEQUENCE: 8
guuaaucuca ccgucacucg uuuc                                          24

<210> SEQ ID NO 9
<211> LENGTH: 19
<212> TYPE: RNA
<213> ORGANISM: Artificial Sequence
<220> FEATURE:
<223> OTHER INFORMATION: Synthetic

<400> SEQUENCE: 9
auacuugucg uguaaggag                                                19

<210> SEQ ID NO 10
<211> LENGTH: 19
<212> TYPE: RNA
<213> ORGANISM: Artificial Sequence
<220> FEATURE:
<223> OTHER INFORMATION: Synthetic

<400> SEQUENCE: 10
cucacugcca cucuaauug                                                19

<210> SEQ ID NO 11
<211> LENGTH: 19
<212> TYPE: RNA

```
<213> ORGANISM: Artificial Sequence
<220> FEATURE:
<223> OTHER INFORMATION: Synthetic

<400> SEQUENCE: 11
ucacugccac ucuaauugu                                                    19

<210> SEQ ID NO 12
<211> LENGTH: 19
<212> TYPE: RNA
<213> ORGANISM: Artificial Sequence
<220> FEATURE:
<223> OTHER INFORMATION: Synthetic

<400> SEQUENCE: 12
cacugccacu cuaauuguc                                                    19

<210> SEQ ID NO 13
<211> LENGTH: 19
<212> TYPE: RNA
<213> ORGANISM: Artificial Sequence
<220> FEATURE:
<223> OTHER INFORMATION: Synthetic

<400> SEQUENCE: 13
acugccacuc uaauuguca                                                    19

<210> SEQ ID NO 14
<211> LENGTH: 19
<212> TYPE: RNA
<213> ORGANISM: Artificial Sequence
<220> FEATURE:
<223> OTHER INFORMATION: Synthetic

<400> SEQUENCE: 14
augcuggacu gcuggcaca                                                    19

<210> SEQ ID NO 15
<211> LENGTH: 19
<212> TYPE: RNA
<213> ORGANISM: Artificial Sequence
<220> FEATURE:
<223> OTHER INFORMATION: Synthetic

<400> SEQUENCE: 15
cgggagagcc auagugguc                                                    19

<210> SEQ ID NO 16
<211> LENGTH: 19
<212> TYPE: RNA
<213> ORGANISM: Artificial Sequence
<220> FEATURE:
<223> OTHER INFORMATION: Synthetic

<400> SEQUENCE: 16
auaguggucu gcggaaccg                                                    19

<210> SEQ ID NO 17
<211> LENGTH: 19
<212> TYPE: RNA
<213> ORGANISM: Artificial Sequence
<220> FEATURE:
<223> OTHER INFORMATION: Synthetic

<400> SEQUENCE: 17
uaguggucug cggaaccgg                                                    19
```

-continued

```
<210> SEQ ID NO 18
<211> LENGTH: 19
<212> TYPE: RNA
<213> ORGANISM: Artificial Sequence
<220> FEATURE:
<223> OTHER INFORMATION: Synthetic

<400> SEQUENCE: 18
aggccuugug guacugccu                                                    19

<210> SEQ ID NO 19
<211> LENGTH: 19
<212> TYPE: RNA
<213> ORGANISM: Artificial Sequence
<220> FEATURE:
<223> OTHER INFORMATION: Synthetic

<400> SEQUENCE: 19
cugccugaua gggugcuug                                                    19

<210> SEQ ID NO 20
<211> LENGTH: 19
<212> TYPE: RNA
<213> ORGANISM: Artificial Sequence
<220> FEATURE:
<223> OTHER INFORMATION: Synthetic

<400> SEQUENCE: 20
cugauagggu gcuugcgag                                                    19

<210> SEQ ID NO 21
<211> LENGTH: 19
<212> TYPE: RNA
<213> ORGANISM: Artificial Sequence
<220> FEATURE:
<223> OTHER INFORMATION: Synthetic

<400> SEQUENCE: 21
ccgggagguc ucguagacc                                                    19

<210> SEQ ID NO 22
<211> LENGTH: 19
<212> TYPE: RNA
<213> ORGANISM: Artificial Sequence
<220> FEATURE:
<223> OTHER INFORMATION: Synthetic

<400> SEQUENCE: 22
aagcaaaaau uaaugauga                                                    19

<210> SEQ ID NO 23
<211> LENGTH: 19
<212> TYPE: RNA
<213> ORGANISM: Artificial Sequence
<220> FEATURE:
<223> OTHER INFORMATION: Synthetic

<400> SEQUENCE: 23
cccccgcauc acauccacu                                                    19

<210> SEQ ID NO 24
<211> LENGTH: 19
<212> TYPE: RNA
<213> ORGANISM: Artificial Sequence
<220> FEATURE:
```

-continued

<223> OTHER INFORMATION: Synthetic

<400> SEQUENCE: 24
cccccuccac agaucaugu                                               19

<210> SEQ ID NO 25
<211> LENGTH: 19
<212> TYPE: RNA
<213> ORGANISM: Artificial Sequence
<220> FEATURE:
<223> OTHER INFORMATION: Synthetic

<400> SEQUENCE: 25
caagacagca acuugcagg                                               19

<210> SEQ ID NO 26
<211> LENGTH: 19
<212> TYPE: RNA
<213> ORGANISM: Artificial Sequence
<220> FEATURE:
<223> OTHER INFORMATION: Synthetic

<400> SEQUENCE: 26
accaugcugg acugcuggc                                               19

<210> SEQ ID NO 27
<211> LENGTH: 19
<212> TYPE: RNA
<213> ORGANISM: Artificial Sequence
<220> FEATURE:
<223> OTHER INFORMATION: Synthetic

<400> SEQUENCE: 27
ccaugcugga cugcuggca                                               19

<210> SEQ ID NO 28
<211> LENGTH: 19
<212> TYPE: RNA
<213> ORGANISM: Artificial Sequence
<220> FEATURE:
<223> OTHER INFORMATION: Synthetic

<400> SEQUENCE: 28
caugcuggac ugcuggcac                                               19

<210> SEQ ID NO 29
<211> LENGTH: 19
<212> TYPE: RNA
<213> ORGANISM: Artificial Sequence
<220> FEATURE:
<223> OTHER INFORMATION: Synthetic

<400> SEQUENCE: 29
caaaagcagg gagucugug                                               19

<210> SEQ ID NO 30
<211> LENGTH: 19
<212> TYPE: RNA
<213> ORGANISM: Artificial Sequence
<220> FEATURE:
<223> OTHER INFORMATION: Synthetic

<400> SEQUENCE: 30
cgcggagcag ccagacagc                                               19

```
<210> SEQ ID NO 31
<211> LENGTH: 19
<212> TYPE: RNA
<213> ORGANISM: Artificial Sequence
<220> FEATURE:
<223> OTHER INFORMATION: Synthetic

<400> SEQUENCE: 31
gaggagcagc cugaggccc                                                  19

<210> SEQ ID NO 32
<211> LENGTH: 19
<212> TYPE: RNA
<213> ORGANISM: Artificial Sequence
<220> FEATURE:
<223> OTHER INFORMATION: Synthetic

<400> SEQUENCE: 32
gccgccgccg ccccgcca                                                   19

<210> SEQ ID NO 33
<211> LENGTH: 19
<212> TYPE: RNA
<213> ORGANISM: Artificial Sequence
<220> FEATURE:
<223> OTHER INFORMATION: Synthetic

<400> SEQUENCE: 33
ccgccgccgc ccccgccac                                                  19

<210> SEQ ID NO 34
<211> LENGTH: 19
<212> TYPE: RNA
<213> ORGANISM: Artificial Sequence
<220> FEATURE:
<223> OTHER INFORMATION: Synthetic

<400> SEQUENCE: 34
gccggggacg cuugcuccc                                                  19

<210> SEQ ID NO 35
<211> LENGTH: 19
<212> TYPE: RNA
<213> ORGANISM: Artificial Sequence
<220> FEATURE:
<223> OTHER INFORMATION: Synthetic

<400> SEQUENCE: 35
ggauaacaca cugcaagug                                                  19

<210> SEQ ID NO 36
<211> LENGTH: 19
<212> TYPE: RNA
<213> ORGANISM: Artificial Sequence
<220> FEATURE:
<223> OTHER INFORMATION: Synthetic

<400> SEQUENCE: 36
auagcaacac ucugagaug                                                  19

<210> SEQ ID NO 37
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 37
ggcggcggcg gcggcggcg                                                    19

<210> SEQ ID NO 38
<211> LENGTH: 19
<212> TYPE: RNA
<213> ORGANISM: Artificial Sequence
<220> FEATURE:
<223> OTHER INFORMATION: Synthetic

<400> SEQUENCE: 38
ggcggcggcg gcggcgcug                                                    19

<210> SEQ ID NO 39
<211> LENGTH: 19
<212> TYPE: RNA
<213> ORGANISM: Artificial Sequence
<220> FEATURE:
<223> OTHER INFORMATION: Synthetic

<400> SEQUENCE: 39
caacaggaag gcaucaaaa                                                    19

<210> SEQ ID NO 40
<211> LENGTH: 19
<212> TYPE: RNA
<213> ORGANISM: Artificial Sequence
<220> FEATURE:
<223> OTHER INFORMATION: Synthetic

<400> SEQUENCE: 40
ggguccuuuc ugugcacua                                                    19

<210> SEQ ID NO 41
<211> LENGTH: 19
<212> TYPE: RNA
<213> ORGANISM: Artificial Sequence
<220> FEATURE:
<223> OTHER INFORMATION: Synthetic

<400> SEQUENCE: 41
cauugauccg gguuuuauc                                                    19

<210> SEQ ID NO 42
<211> LENGTH: 19
<212> TYPE: RNA
<213> ORGANISM: Artificial Sequence
<220> FEATURE:
<223> OTHER INFORMATION: Synthetic

<400> SEQUENCE: 42
cauuuuuuuu uaaaacugu                                                    19

<210> SEQ ID NO 43
<211> LENGTH: 19
<212> TYPE: RNA
<213> ORGANISM: Artificial Sequence
<220> FEATURE:
<223> OTHER INFORMATION: Synthetic

<400> SEQUENCE: 43
uuuuugcuug ccauucccc                                                    19

<210> SEQ ID NO 44
<211> LENGTH: 19
```

```
<212> TYPE: RNA
<213> ORGANISM: Artificial Sequence
<220> FEATURE:
<223> OTHER INFORMATION: Synthetic

<400> SEQUENCE: 44
agagacgggg ucagagaga                                                    19

<210> SEQ ID NO 45
<211> LENGTH: 19
<212> TYPE: RNA
<213> ORGANISM: Artificial Sequence
<220> FEATURE:
<223> OTHER INFORMATION: Synthetic

<400> SEQUENCE: 45
gagacggggu cagagagag                                                    19

<210> SEQ ID NO 46
<211> LENGTH: 19
<212> TYPE: RNA
<213> ORGANISM: Artificial Sequence
<220> FEATURE:
<223> OTHER INFORMATION: Synthetic

<400> SEQUENCE: 46
ccggagcccg cgcccggag                                                    19

<210> SEQ ID NO 47
<211> LENGTH: 19
<212> TYPE: RNA
<213> ORGANISM: Artificial Sequence
<220> FEATURE:
<223> OTHER INFORMATION: Synthetic

<400> SEQUENCE: 47
gggaggagcc gcagccgga                                                    19

<210> SEQ ID NO 48
<211> LENGTH: 19
<212> TYPE: RNA
<213> ORGANISM: Artificial Sequence
<220> FEATURE:
<223> OTHER INFORMATION: Synthetic

<400> SEQUENCE: 48
gcauuggagc cuugccuug                                                    19

<210> SEQ ID NO 49
<211> LENGTH: 19
<212> TYPE: RNA
<213> ORGANISM: Artificial Sequence
<220> FEATURE:
<223> OTHER INFORMATION: Synthetic

<400> SEQUENCE: 49
uggacaucuu ccaggagua                                                    19

<210> SEQ ID NO 50
<211> LENGTH: 19
<212> TYPE: RNA
<213> ORGANISM: Artificial Sequence
<220> FEATURE:
<223> OTHER INFORMATION: Synthetic

<400> SEQUENCE: 50
```
ugugaaugca gaccaaaga                             19

<210> SEQ ID NO 51
<211> LENGTH: 19
<212> TYPE: RNA
<213> ORGANISM: Artificial Sequence
<220> FEATURE:
<223> OTHER INFORMATION: Synthetic

<400> SEQUENCE: 51
gugaaugcag accaaagaa                             19

<210> SEQ ID NO 52
<211> LENGTH: 19
<212> TYPE: RNA
<213> ORGANISM: Artificial Sequence
<220> FEATURE:
<223> OTHER INFORMATION: Synthetic

<400> SEQUENCE: 52
agcauuuguu uguacaaga                             19

<210> SEQ ID NO 53
<211> LENGTH: 19
<212> TYPE: RNA
<213> ORGANISM: Artificial Sequence
<220> FEATURE:
<223> OTHER INFORMATION: Synthetic

<400> SEQUENCE: 53
gcauuuguuu guacaagau                             19

<210> SEQ ID NO 54
<211> LENGTH: 19
<212> TYPE: RNA
<213> ORGANISM: Artificial Sequence
<220> FEATURE:
<223> OTHER INFORMATION: Synthetic

<400> SEQUENCE: 54
cauggacggg ugaggcggc                             19

<210> SEQ ID NO 55
<211> LENGTH: 19
<212> TYPE: RNA
<213> ORGANISM: Artificial Sequence
<220> FEATURE:
<223> OTHER INFORMATION: Synthetic

<400> SEQUENCE: 55
auggacgggu gaggcggcg                             19

<210> SEQ ID NO 56
<211> LENGTH: 19
<212> TYPE: RNA
<213> ORGANISM: Artificial Sequence
<220> FEATURE:
<223> OTHER INFORMATION: Synthetic

<400> SEQUENCE: 56
cauggcagaa ggaggaggg                             19

<210> SEQ ID NO 57
<211> LENGTH: 19
<212> TYPE: RNA
<213> ORGANISM: Artificial Sequence

```
<220> FEATURE:
<223> OTHER INFORMATION: Synthetic

<400> SEQUENCE: 57
auggcagaag gaggagggc                                                    19

<210> SEQ ID NO 58
<211> LENGTH: 19
<212> TYPE: RNA
<213> ORGANISM: Artificial Sequence
<220> FEATURE:
<223> OTHER INFORMATION: Synthetic

<400> SEQUENCE: 58
cauggauguc uaucagcgc                                                    19

<210> SEQ ID NO 59
<211> LENGTH: 19
<212> TYPE: RNA
<213> ORGANISM: Artificial Sequence
<220> FEATURE:
<223> OTHER INFORMATION: Synthetic

<400> SEQUENCE: 59
agcucacgaa aagccccgg                                                    19

<210> SEQ ID NO 60
<211> LENGTH: 19
<212> TYPE: RNA
<213> ORGANISM: Artificial Sequence
<220> FEATURE:
<223> OTHER INFORMATION: Synthetic

<400> SEQUENCE: 60
guguuccgug ccagugccc                                                    19

<210> SEQ ID NO 61
<211> LENGTH: 19
<212> TYPE: RNA
<213> ORGANISM: Artificial Sequence
<220> FEATURE:
<223> OTHER INFORMATION: Synthetic

<400> SEQUENCE: 61
uccaccaacc cgcgggaga                                                    19

<210> SEQ ID NO 62
<211> LENGTH: 19
<212> TYPE: RNA
<213> ORGANISM: Artificial Sequence
<220> FEATURE:
<223> OTHER INFORMATION: Synthetic

<400> SEQUENCE: 62
ccaucaugau gcaggccuu                                                    19

<210> SEQ ID NO 63
<211> LENGTH: 19
<212> TYPE: RNA
<213> ORGANISM: Artificial Sequence
<220> FEATURE:
<223> OTHER INFORMATION: Synthetic

<400> SEQUENCE: 63
ugacuccagc aauaguggu                                                    19
```

```
<210> SEQ ID NO 64
<211> LENGTH: 19
<212> TYPE: RNA
<213> ORGANISM: Artificial Sequence
<220> FEATURE:
<223> OTHER INFORMATION: Synthetic

<400> SEQUENCE: 64
aaaggucuuu gagguagag                                                   19

<210> SEQ ID NO 65
<211> LENGTH: 19
<212> TYPE: RNA
<213> ORGANISM: Artificial Sequence
<220> FEATURE:
<223> OTHER INFORMATION: Synthetic

<400> SEQUENCE: 65 gugguccag guaucugcu                                                    19

<210> SEQ ID NO 66
<211> LENGTH: 19
<212> TYPE: RNA
<213> ORGANISM: Artificial Sequence
<220> FEATURE:
<223> OTHER INFORMATION: Synthetic

<400> SEQUENCE: 66
gggugccuuu uaaacucag                                                   19

<210> SEQ ID NO 67
<211> LENGTH: 19
<212> TYPE: RNA
<213> ORGANISM: Artificial Sequence
<220> FEATURE:
<223> OTHER INFORMATION: Synthetic

<400> SEQUENCE: 67
cuccuuacac gacaaguau                                                   19

<210> SEQ ID NO 68
<211> LENGTH: 19
<212> TYPE: RNA
<213> ORGANISM: Artificial Sequence
<220> FEATURE:
<223> OTHER INFORMATION: Synthetic

<400> SEQUENCE: 68
caauuagagu ggcagugag                                                   19

<210> SEQ ID NO 69
<211> LENGTH: 19
<212> TYPE: RNA
<213> ORGANISM: Artificial Sequence
<220> FEATURE:
<223> OTHER INFORMATION: Synthetic

<400> SEQUENCE: 69
acaauuagag uggcaguga                                                   19

<210> SEQ ID NO 70
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 70
gacaauuaga guggcagug                                                19

<210> SEQ ID NO 71
<211> LENGTH: 19
<212> TYPE: RNA
<213> ORGANISM: Artificial Sequence
<220> FEATURE:
<223> OTHER INFORMATION: Synthetic

<400> SEQUENCE: 71
ugacaauuag aguggcagu                                                19

<210> SEQ ID NO 72
<211> LENGTH: 19
<212> TYPE: RNA
<213> ORGANISM: Artificial Sequence
<220> FEATURE:
<223> OTHER INFORMATION: Synthetic

<400> SEQUENCE: 72
ugugccagca guccagcau                                                19

<210> SEQ ID NO 73
<211> LENGTH: 19
<212> TYPE: RNA
<213> ORGANISM: Artificial Sequence
<220> FEATURE:
<223> OTHER INFORMATION: Synthetic

<400> SEQUENCE: 73
gaccacuaug gcucucccg                                                19

<210> SEQ ID NO 74
<211> LENGTH: 19
<212> TYPE: RNA
<213> ORGANISM: Artificial Sequence
<220> FEATURE:
<223> OTHER INFORMATION: Synthetic

<400> SEQUENCE: 74
cgguuccgca gaccacuau                                                19

<210> SEQ ID NO 75
<211> LENGTH: 19
<212> TYPE: RNA
<213> ORGANISM: Artificial Sequence
<220> FEATURE:
<223> OTHER INFORMATION: Synthetic

<400> SEQUENCE: 75
ccgguuccgc agaccacua                                                19

<210> SEQ ID NO 76
<211> LENGTH: 19
<212> TYPE: RNA
<213> ORGANISM: Artificial Sequence
<220> FEATURE:
<223> OTHER INFORMATION: Synthetic

<400> SEQUENCE: 76
aggcaguacc acaaggccu                                                19

<210> SEQ ID NO 77
```

```
<211> LENGTH: 19
<212> TYPE: RNA
<213> ORGANISM: Artificial Sequence
<220> FEATURE:
<223> OTHER INFORMATION: Synthetic

<400> SEQUENCE: 77
caagcacccu aucaggcag                                                    19

<210> SEQ ID NO 78
<211> LENGTH: 19
<212> TYPE: RNA
<213> ORGANISM: Artificial Sequence
<220> FEATURE:
<223> OTHER INFORMATION: Synthetic

<400> SEQUENCE: 78
cucgcaagca cccuaucag                                                    19

<210> SEQ ID NO 79
<211> LENGTH: 19
<212> TYPE: RNA
<213> ORGANISM: Artificial Sequence
<220> FEATURE:
<223> OTHER INFORMATION: Synthetic

<400> SEQUENCE: 79
ggucuacgag accucccgg                                                    19

<210> SEQ ID NO 80
<211> LENGTH: 19
<212> TYPE: RNA
<213> ORGANISM: Artificial Sequence
<220> FEATURE:
<223> OTHER INFORMATION: Synthetic

<400> SEQUENCE: 80
ucaucauuaa uuuuugcuu                                                    19

<210> SEQ ID NO 81
<211> LENGTH: 19
<212> TYPE: RNA
<213> ORGANISM: Artificial Sequence
<220> FEATURE:
<223> OTHER INFORMATION: Synthetic

<400> SEQUENCE: 81
aguggaugug augcggggg                                                    19

<210> SEQ ID NO 82
<211> LENGTH: 19
<212> TYPE: RNA
<213> ORGANISM: Artificial Sequence
<220> FEATURE:
<223> OTHER INFORMATION: Synthetic

<400> SEQUENCE: 82
acaugaucug uggaggggg                                                    19

<210> SEQ ID NO 83
<211> LENGTH: 19
<212> TYPE: RNA
<213> ORGANISM: Artificial Sequence
<220> FEATURE:
<223> OTHER INFORMATION: Synthetic

<400> SEQUENCE: 83
```
ccugcaaguu gcugucuug                                                19

<210> SEQ ID NO 84
<211> LENGTH: 19
<212> TYPE: RNA
<213> ORGANISM: Artificial Sequence
<220> FEATURE:
<223> OTHER INFORMATION: Synthetic

<400> SEQUENCE: 84
gccagcaguc cagcauggu                                                19

<210> SEQ ID NO 85
<211> LENGTH: 19
<212> TYPE: RNA
<213> ORGANISM: Artificial Sequence
<220> FEATURE:
<223> OTHER INFORMATION: Synthetic

<400> SEQUENCE: 85
ugccagcagu ccagcaugg                                                19

<210> SEQ ID NO 86
<211> LENGTH: 19
<212> TYPE: RNA
<213> ORGANISM: Artificial Sequence
<220> FEATURE:
<223> OTHER INFORMATION: Synthetic

<400> SEQUENCE: 86
gugccagcag uccagcaug                                                19

<210> SEQ ID NO 87
<211> LENGTH: 19
<212> TYPE: RNA
<213> ORGANISM: Artificial Sequence
<220> FEATURE:
<223> OTHER INFORMATION: Synthetic

<400> SEQUENCE: 87
cacagacucc cugcuuuug                                                19

<210> SEQ ID NO 88
<211> LENGTH: 19
<212> TYPE: RNA
<213> ORGANISM: Artificial Sequence
<220> FEATURE:
<223> OTHER INFORMATION: Synthetic

<400> SEQUENCE: 88
gcugucuggc ugcuccgcg                                                19

<210> SEQ ID NO 89
<211> LENGTH: 19
<212> TYPE: RNA
<213> ORGANISM: Artificial Sequence
<220> FEATURE:
<223> OTHER INFORMATION: Synthetic

<400> SEQUENCE: 89
gggccucagg cugcuccuc                                                19

<210> SEQ ID NO 90
<211> LENGTH: 19
<212> TYPE: RNA

```
<213> ORGANISM: Artificial Sequence
<220> FEATURE:
<223> OTHER INFORMATION: Synthetic

<400> SEQUENCE: 90
uggcgggggc ggcggcggc                                                    19

<210> SEQ ID NO 91
<211> LENGTH: 19
<212> TYPE: RNA
<213> ORGANISM: Artificial Sequence
<220> FEATURE:
<223> OTHER INFORMATION: Synthetic

<400> SEQUENCE: 91
guggcggggg cggcggcgg                                                    19

<210> SEQ ID NO 92
<211> LENGTH: 19
<212> TYPE: RNA
<213> ORGANISM: Artificial Sequence
<220> FEATURE:
<223> OTHER INFORMATION: Synthetic

<400> SEQUENCE: 92
gggagcaagc gucccccggc                                                   19

<210> SEQ ID NO 93
<211> LENGTH: 19
<212> TYPE: RNA
<213> ORGANISM: Artificial Sequence
<220> FEATURE:
<223> OTHER INFORMATION: Synthetic

<400> SEQUENCE: 93
cacuugcagu guguuaucc                                                    19

<210> SEQ ID NO 94
<211> LENGTH: 19
<212> TYPE: RNA
<213> ORGANISM: Artificial Sequence
<220> FEATURE:
<223> OTHER INFORMATION: Synthetic

<400> SEQUENCE: 94
caucucagag uguugcuau                                                    19

<210> SEQ ID NO 95
<211> LENGTH: 19
<212> TYPE: RNA
<213> ORGANISM: Artificial Sequence
<220> FEATURE:
<223> OTHER INFORMATION: Synthetic

<400> SEQUENCE: 95
cgccgccgcc gccgccgcc                                                    19

<210> SEQ ID NO 96
<211> LENGTH: 19
<212> TYPE: RNA
<213> ORGANISM: Artificial Sequence
<220> FEATURE:
<223> OTHER INFORMATION: Synthetic

<400> SEQUENCE: 96
cagcgccgcc gccgccgcc                                                    19
```

```
<210> SEQ ID NO 97
<211> LENGTH: 19
<212> TYPE: RNA
<213> ORGANISM: Artificial Sequence
<220> FEATURE:
<223> OTHER INFORMATION: Synthetic

<400> SEQUENCE: 97
uuuugaugcc uuccuguug                                           19

<210> SEQ ID NO 98
<211> LENGTH: 19
<212> TYPE: RNA
<213> ORGANISM: Artificial Sequence
<220> FEATURE:
<223> OTHER INFORMATION: Synthetic

<400> SEQUENCE: 98
uagugcacag aaaggaccc                                           19

<210> SEQ ID NO 99
<211> LENGTH: 19
<212> TYPE: RNA
<213> ORGANISM: Artificial Sequence
<220> FEATURE:
<223> OTHER INFORMATION: Synthetic

<400> SEQUENCE: 99
gauaaaaccc ggaucaaug                                           19

<210> SEQ ID NO 100
<211> LENGTH: 19
<212> TYPE: RNA
<213> ORGANISM: Artificial Sequence
<220> FEATURE:
<223> OTHER INFORMATION: Synthetic

<400> SEQUENCE: 100
acaguuuuaa aaaaaaaug                                           19

<210> SEQ ID NO 101
<211> LENGTH: 19
<212> TYPE: RNA
<213> ORGANISM: Artificial Sequence
<220> FEATURE:
<223> OTHER INFORMATION: Synthetic

<400> SEQUENCE: 101
ggggaauggc aagcaaaaa                                           19

<210> SEQ ID NO 102
<211> LENGTH: 19
<212> TYPE: RNA
<213> ORGANISM: Artificial Sequence
<220> FEATURE:
<223> OTHER INFORMATION: Synthetic

<400> SEQUENCE: 102
ucucucugac cccgucucu                                           19

<210> SEQ ID NO 103
<211> LENGTH: 19
<212> TYPE: RNA
<213> ORGANISM: Artificial Sequence
<220> FEATURE:
```

<223> OTHER INFORMATION: Synthetic

<400> SEQUENCE: 103
cucucucuga ccccgucuc                                              19

<210> SEQ ID NO 104
<211> LENGTH: 19
<212> TYPE: RNA
<213> ORGANISM: Artificial Sequence
<220> FEATURE:
<223> OTHER INFORMATION: Synthetic

<400> SEQUENCE: 104
cuccgggcgc gggcuccgg                                              19

<210> SEQ ID NO 105
<211> LENGTH: 19
<212> TYPE: RNA
<213> ORGANISM: Artificial Sequence
<220> FEATURE:
<223> OTHER INFORMATION: Synthetic

<400> SEQUENCE: 105
uccggcugcg gcuccuccc                                              19

<210> SEQ ID NO 106
<211> LENGTH: 19
<212> TYPE: RNA
<213> ORGANISM: Artificial Sequence
<220> FEATURE:
<223> OTHER INFORMATION: Synthetic

<400> SEQUENCE: 106
caaggcaagg cuccaaugc                                              19

<210> SEQ ID NO 107
<211> LENGTH: 19
<212> TYPE: RNA
<213> ORGANISM: Artificial Sequence
<220> FEATURE:
<223> OTHER INFORMATION: Synthetic

<400> SEQUENCE: 107
uacuccugga agaugucca                                              19

<210> SEQ ID NO 108
<211> LENGTH: 19
<212> TYPE: RNA
<213> ORGANISM: Artificial Sequence
<220> FEATURE:
<223> OTHER INFORMATION: Synthetic

<400> SEQUENCE: 108
ucuuuggucu gcauucaca                                              19

<210> SEQ ID NO 109
<211> LENGTH: 19
<212> TYPE: RNA
<213> ORGANISM: Artificial Sequence
<220> FEATURE:
<223> OTHER INFORMATION: Synthetic

<400> SEQUENCE: 109
uucuuugguc ugcauucac                                              19

```
<210> SEQ ID NO 110
<211> LENGTH: 19
<212> TYPE: RNA
<213> ORGANISM: Artificial Sequence
<220> FEATURE:
<223> OTHER INFORMATION: Synthetic

<400> SEQUENCE: 110
ucuuguacaa acaaaugcu                                                19

<210> SEQ ID NO 111
<211> LENGTH: 19
<212> TYPE: RNA
<213> ORGANISM: Artificial Sequence
<220> FEATURE:
<223> OTHER INFORMATION: Synthetic

<400> SEQUENCE: 111
aucuuguaca aacaaaugc                                                19

<210> SEQ ID NO 112
<211> LENGTH: 19
<212> TYPE: RNA
<213> ORGANISM: Artificial Sequence
<220> FEATURE:
<223> OTHER INFORMATION: Synthetic

<400> SEQUENCE: 112
gccgccucac ccguccaug                                                19

<210> SEQ ID NO 113
<211> LENGTH: 19
<212> TYPE: RNA
<213> ORGANISM: Artificial Sequence
<220> FEATURE:
<223> OTHER INFORMATION: Synthetic

<400> SEQUENCE: 113
cgccgccuca cccguccau                                                19

<210> SEQ ID NO 114
<211> LENGTH: 19
<212> TYPE: RNA
<213> ORGANISM: Artificial Sequence
<220> FEATURE:
<223> OTHER INFORMATION: Synthetic

<400> SEQUENCE: 114
cccuccuccu ucugccaug                                                19

<210> SEQ ID NO 115
<211> LENGTH: 19
<212> TYPE: RNA
<213> ORGANISM: Artificial Sequence
<220> FEATURE:
<223> OTHER INFORMATION: Synthetic

<400> SEQUENCE: 115
gcccuccucc uucugccau                                                19

<210> SEQ ID NO 116
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 116
gcgcugauag acauccaug                                              19

<210> SEQ ID NO 117
<211> LENGTH: 19
<212> TYPE: RNA
<213> ORGANISM: Artificial Sequence
<220> FEATURE:
<223> OTHER INFORMATION: Synthetic

<400> SEQUENCE: 117
gccccgggag gucucguag                                              19

<210> SEQ ID NO 118
<211> LENGTH: 19
<212> TYPE: RNA
<213> ORGANISM: Artificial Sequence
<220> FEATURE:
<223> OTHER INFORMATION: Synthetic

<400> SEQUENCE: 118
agugccccgg gaggucucg                                              19

<210> SEQ ID NO 119
<211> LENGTH: 19
<212> TYPE: RNA
<213> ORGANISM: Artificial Sequence
<220> FEATURE:
<223> OTHER INFORMATION: Synthetic

<400> SEQUENCE: 119
ugcuugcgag ugccccggg                                              19

<210> SEQ ID NO 120
<211> LENGTH: 19
<212> TYPE: RNA
<213> ORGANISM: Artificial Sequence
<220> FEATURE:
<223> OTHER INFORMATION: Synthetic

<400> SEQUENCE: 120
agagccauag uggucugcg                                              19

<210> SEQ ID NO 121
<211> LENGTH: 19
<212> TYPE: RNA
<213> ORGANISM: Artificial Sequence
<220> FEATURE:
<223> OTHER INFORMATION: Synthetic

<400> SEQUENCE: 121
acgacaagua uuggggaaa                                              19

<210> SEQ ID NO 122
<211> LENGTH: 19
<212> TYPE: RNA
<213> ORGANISM: Artificial Sequence
<220> FEATURE:
<223> OTHER INFORMATION: Synthetic

<400> SEQUENCE: 122
agaguggcag ugagcaaag                                              19

<210> SEQ ID NO 123
<211> LENGTH: 19
```

```
<212> TYPE: RNA
<213> ORGANISM: Artificial Sequence
<220> FEATURE:
<223> OTHER INFORMATION: Synthetic

<400> SEQUENCE: 123
caggcaggcc acuuugccu                                                    19

<210> SEQ ID NO 124
<211> LENGTH: 19
<212> TYPE: RNA
<213> ORGANISM: Artificial Sequence
<220> FEATURE:
<223> OTHER INFORMATION: Synthetic

<400> SEQUENCE: 124
uaucaguuac ugaacaggc                                                    19

<210> SEQ ID NO 125
<211> LENGTH: 19
<212> TYPE: RNA
<213> ORGANISM: Artificial Sequence
<220> FEATURE:
<223> OTHER INFORMATION: Synthetic

<400> SEQUENCE: 125
cccgggcguu ccccagcga                                                    19

<210> SEQ ID NO 126
<211> LENGTH: 19
<212> TYPE: RNA
<213> ORGANISM: Artificial Sequence
<220> FEATURE:
<223> OTHER INFORMATION: Synthetic

<400> SEQUENCE: 126
auuuuugcuu gccauuccc                                                    19

<210> SEQ ID NO 127
<211> LENGTH: 19
<212> TYPE: RNA
<213> ORGANISM: Artificial Sequence
<220> FEATURE:
<223> OTHER INFORMATION: Synthetic

<400> SEQUENCE: 127
gaugcggggg cugcugcaa                                                    19

<210> SEQ ID NO 128
<211> LENGTH: 19
<212> TYPE: RNA
<213> ORGANISM: Artificial Sequence
<220> FEATURE:
<223> OTHER INFORMATION: Synthetic

<400> SEQUENCE: 128
guggaggggg ucggggcuc                                                    19

<210> SEQ ID NO 129
<211> LENGTH: 19
<212> TYPE: RNA
<213> ORGANISM: Artificial Sequence
<220> FEATURE:
<223> OTHER INFORMATION: Synthetic

<400> SEQUENCE: 129
```

-continued

```
ugcugucuug ggugcauug                                                       19

<210> SEQ ID NO 130
<211> LENGTH: 19
<212> TYPE: RNA
<213> ORGANISM: Artificial Sequence
<220> FEATURE:
<223> OTHER INFORMATION: Synthetic

<400> SEQUENCE: 130
ccugcuuuug ggggugacc                                                       19

<210> SEQ ID NO 131
<211> LENGTH: 19
<212> TYPE: RNA
<213> ORGANISM: Artificial Sequence
<220> FEATURE:
<223> OTHER INFORMATION: Synthetic

<400> SEQUENCE: 131
gcugcuccgc gucccoggc                                                       19

<210> SEQ ID NO 132
<211> LENGTH: 19
<212> TYPE: RNA
<213> ORGANISM: Artificial Sequence
<220> FEATURE:
<223> OTHER INFORMATION: Synthetic

<400> SEQUENCE: 132
ggcugcuccu ccucgugcu                                                       19

<210> SEQ ID NO 133
<211> LENGTH: 19
<212> TYPE: RNA
<213> ORGANISM: Artificial Sequence
<220> FEATURE:
<223> OTHER INFORMATION: Synthetic

<400> SEQUENCE: 133 gcgucccogg cugcuccuc                                                       19

<210> SEQ ID NO 134
<211> LENGTH: 19
<212> TYPE: RNA
<213> ORGANISM: Artificial Sequence
<220> FEATURE:
<223> OTHER INFORMATION: Synthetic

<400> SEQUENCE: 134
gcaagcaaaa aauggccau                                                       19

<210> SEQ ID NO 135
<211> LENGTH: 19
<212> TYPE: RNA
<213> ORGANISM: Artificial Sequence
<220> FEATURE:
<223> OTHER INFORMATION: Synthetic

<400> SEQUENCE: 135
gaccccgucu cuauaccaa                                                       19

<210> SEQ ID NO 136
<211> LENGTH: 19
<212> TYPE: RNA
<213> ORGANISM: Artificial Sequence
```

```
<220> FEATURE:
<223> OTHER INFORMATION: Synthetic

<400> SEQUENCE: 136
gcgggcuccg gggcucggg                                                     19

<210> SEQ ID NO 137
<211> LENGTH: 19
<212> TYPE: RNA
<213> ORGANISM: Artificial Sequence
<220> FEATURE:
<223> OTHER INFORMATION: Synthetic

<400> SEQUENCE: 137
cggcuccucc ccggcagcg                                                     19

<210> SEQ ID NO 138
<211> LENGTH: 19
<212> TYPE: RNA
<213> ORGANISM: Artificial Sequence
<220> FEATURE:
<223> OTHER INFORMATION: Synthetic

<400> SEQUENCE: 138
cuacgagacc ucccggggc                                                     19

<210> SEQ ID NO 139
<211> LENGTH: 19
<212> TYPE: RNA
<213> ORGANISM: Artificial Sequence
<220> FEATURE:
<223> OTHER INFORMATION: Synthetic

<400> SEQUENCE: 139
cgagaccucc cggggcacu                                                     19

<210> SEQ ID NO 140
<211> LENGTH: 19
<212> TYPE: RNA
<213> ORGANISM: Artificial Sequence
<220> FEATURE:
<223> OTHER INFORMATION: Synthetic

<400> SEQUENCE: 140
cccggggcac ucgcaagca                                                     19

<210> SEQ ID NO 141
<211> LENGTH: 19
<212> TYPE: RNA
<213> ORGANISM: Artificial Sequence
<220> FEATURE:
<223> OTHER INFORMATION: Synthetic

<400> SEQUENCE: 141
cgcagaccac uauggcucu                                                     19

<210> SEQ ID NO 142
<211> LENGTH: 19
<212> TYPE: RNA
<213> ORGANISM: Artificial Sequence
<220> FEATURE:
<223> OTHER INFORMATION: Synthetic

<400> SEQUENCE: 142
uuuccccaau acuugucgu                                                     19
```

```
<210> SEQ ID NO 143
<211> LENGTH: 19
<212> TYPE: RNA
<213> ORGANISM: Artificial Sequence
<220> FEATURE:
<223> OTHER INFORMATION: Synthetic

<400> SEQUENCE: 143
cuuugcucac ugccacucu                                                      19

<210> SEQ ID NO 144
<211> LENGTH: 19
<212> TYPE: RNA
<213> ORGANISM: Artificial Sequence
<220> FEATURE:
<223> OTHER INFORMATION: Synthetic

<400> SEQUENCE: 144
aggcaaagug gccugccug                                                      19

<210> SEQ ID NO 145
<211> LENGTH: 19
<212> TYPE: RNA
<213> ORGANISM: Artificial Sequence
<220> FEATURE:
<223> OTHER INFORMATION: Synthetic

<400> SEQUENCE: 145
gccuguucag uaacugaua                                                      19

<210> SEQ ID NO 146
<211> LENGTH: 19
<212> TYPE: RNA
<213> ORGANISM: Artificial Sequence
<220> FEATURE:
<223> OTHER INFORMATION: Synthetic

<400> SEQUENCE: 146
ucgcugggga acgcccggg                                                      19

<210> SEQ ID NO 147
<211> LENGTH: 19
<212> TYPE: RNA
<213> ORGANISM: Artificial Sequence
<220> FEATURE:
<223> OTHER INFORMATION: Synthetic

<400> SEQUENCE: 147
gggaauggca agcaaaaau                                                      19

<210> SEQ ID NO 148
<211> LENGTH: 19
<212> TYPE: RNA
<213> ORGANISM: Artificial Sequence
<220> FEATURE:
<223> OTHER INFORMATION: Synthetic

<400> SEQUENCE: 148
uugcagcagc ccccgcauc                                                      19

<210> SEQ ID NO 149
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 149
gagccccgac ccccuccac                                                  19

<210> SEQ ID NO 150
<211> LENGTH: 19
<212> TYPE: RNA
<213> ORGANISM: Artificial Sequence
<220> FEATURE:
<223> OTHER INFORMATION: Synthetic

<400> SEQUENCE: 150
caaugcaccc aagacagca                                                  19

<210> SEQ ID NO 151
<211> LENGTH: 19
<212> TYPE: RNA
<213> ORGANISM: Artificial Sequence
<220> FEATURE:
<223> OTHER INFORMATION: Synthetic

<400> SEQUENCE: 151
ggucaccccc aaaagcagg                                                  19

<210> SEQ ID NO 152
<211> LENGTH: 19
<212> TYPE: RNA
<213> ORGANISM: Artificial Sequence
<220> FEATURE:
<223> OTHER INFORMATION: Synthetic

<400> SEQUENCE: 152
gccggggacg cggagcagc                                                  19

<210> SEQ ID NO 153
<211> LENGTH: 19
<212> TYPE: RNA
<213> ORGANISM: Artificial Sequence
<220> FEATURE:
<223> OTHER INFORMATION: Synthetic

<400> SEQUENCE: 153
agcacgagga ggagcagcc                                                  19

<210> SEQ ID NO 154
<211> LENGTH: 19
<212> TYPE: RNA
<213> ORGANISM: Artificial Sequence
<220> FEATURE:
<223> OTHER INFORMATION: Synthetic

<400> SEQUENCE: 154
gaggagcagc cggggacgc                                                  19

<210> SEQ ID NO 155
<211> LENGTH: 19
<212> TYPE: RNA
<213> ORGANISM: Artificial Sequence
<220> FEATURE:
<223> OTHER INFORMATION: Synthetic

<400> SEQUENCE: 155
auggccauuu uuugcuugc                                                  19

<210> SEQ ID NO 156
```

```
<211> LENGTH: 19
<212> TYPE: RNA
<213> ORGANISM: Artificial Sequence
<220> FEATURE:
<223> OTHER INFORMATION: Synthetic

<400> SEQUENCE: 156
uugguauaga gacgggguc                                                       19

<210> SEQ ID NO 157
<211> LENGTH: 19
<212> TYPE: RNA
<213> ORGANISM: Artificial Sequence
<220> FEATURE:
<223> OTHER INFORMATION: Synthetic

<400> SEQUENCE: 157
cccgagcccc ggagcccgc                                                       19

<210> SEQ ID NO 158
<211> LENGTH: 19
<212> TYPE: RNA
<213> ORGANISM: Artificial Sequence
<220> FEATURE:
<223> OTHER INFORMATION: Synthetic

<400> SEQUENCE: 158
cgcugccggg gaggagccg                                                       19

<210> SEQ ID NO 159
<211> LENGTH: 31
<212> TYPE: RNA
<213> ORGANISM: Artificial Sequence
<220> FEATURE:
<223> OTHER INFORMATION: Synthetic

<400> SEQUENCE: 159
agcucacgaa aagccccggg aggucucgua g                                         31

<210> SEQ ID NO 160
<211> LENGTH: 31
<212> TYPE: RNA
<213> ORGANISM: Artificial Sequence
<220> FEATURE:
<223> OTHER INFORMATION: Synthetic

<400> SEQUENCE: 160
guguuccgug ccagugcccc gggaggucuc g                                         31

<210> SEQ ID NO 161
<211> LENGTH: 31
<212> TYPE: RNA
<213> ORGANISM: Artificial Sequence
<220> FEATURE:
<223> OTHER INFORMATION: Synthetic

<400> SEQUENCE: 161
uccaccaacc cgcgggagag ccauaguggu c                                         31

<210> SEQ ID NO 162
<211> LENGTH: 31
<212> TYPE: RNA
<213> ORGANISM: Artificial Sequence
<220> FEATURE:
<223> OTHER INFORMATION: Synthetic

<400> SEQUENCE: 162
```
ccaucaugau gcaggccuug ugguacugcc u                                    31

<210> SEQ ID NO 163
<211> LENGTH: 30
<212> TYPE: RNA
<213> ORGANISM: Artificial Sequence
<220> FEATURE:
<223> OTHER INFORMATION: Synthetic

<400> SEQUENCE: 163
ugacuccagc aauagugguc ugcggaaccg                                      30

<210> SEQ ID NO 164
<211> LENGTH: 34
<212> TYPE: RNA
<213> ORGANISM: Artificial Sequence
<220> FEATURE:
<223> OTHER INFORMATION: Synthetic

<400> SEQUENCE: 164
aaaggucuuu gagguagagc cauaguhhuc ugcg                                 34

<210> SEQ ID NO 165
<211> LENGTH: 34
<212> TYPE: RNA
<213> ORGANISM: Artificial Sequence
<220> FEATURE:
<223> OTHER INFORMATION: Synthetic

<400> SEQUENCE: 165
gugguuccag guaucugcuu gcgagugccc cggg                                 34

<210> SEQ ID NO 166
<211> LENGTH: 38
<212> TYPE: RNA
<213> ORGANISM: Artificial Sequence
<220> FEATURE:
<223> OTHER INFORMATION: Synthetic

<400> SEQUENCE: 166
gggugccuuu uaaacucaga ccaugcugga cugcuggc                             38

<210> SEQ ID NO 167
<211> LENGTH: 27
<212> TYPE: RNA
<213> ORGANISM: Artificial Sequence
<220> FEATURE:
<223> OTHER INFORMATION: Synthetic

<400> SEQUENCE: 167
cuccuuacac gacaaguauu ggggaaa                                         27

<210> SEQ ID NO 168
<211> LENGTH: 24
<212> TYPE: RNA
<213> ORGANISM: Artificial Sequence
<220> FEATURE:
<223> OTHER INFORMATION: Synthetic

<400> SEQUENCE: 168
caauuagagu ggcagugagc aaag                                            24

<210> SEQ ID NO 169
<211> LENGTH: 25
<212> TYPE: RNA

```
<213> ORGANISM: Artificial Sequence
<220> FEATURE:
<223> OTHER INFORMATION: Synthetic

<400> SEQUENCE: 169
acaauuagag uggcagugag caaag                                          25

<210> SEQ ID NO 170
<211> LENGTH: 26
<212> TYPE: RNA
<213> ORGANISM: Artificial Sequence
<220> FEATURE:
<223> OTHER INFORMATION: Synthetic

<400> SEQUENCE: 170
gacaauuaga guggcaguga gcaaag                                         26

<210> SEQ ID NO 171
<211> LENGTH: 27
<212> TYPE: RNA
<213> ORGANISM: Artificial Sequence
<220> FEATURE:
<223> OTHER INFORMATION: Synthetic

<400> SEQUENCE: 171
ugacaauuag aguggcagug agcaaag                                        27

<210> SEQ ID NO 172
<211> LENGTH: 38
<212> TYPE: RNA
<213> ORGANISM: Artificial Sequence
<220> FEATURE:
<223> OTHER INFORMATION: Synthetic

<400> SEQUENCE: 172
ugugccagca guccagcauc caugcuggac ugcuggca                            38

<210> SEQ ID NO 173
<211> LENGTH: 31
<212> TYPE: RNA
<213> ORGANISM: Artificial Sequence
<220> FEATURE:
<223> OTHER INFORMATION: Synthetic

<400> SEQUENCE: 173
gaccacuaug gcucucccgc ggguuggugg a                                   31

<210> SEQ ID NO 174
<211> LENGTH: 30
<212> TYPE: RNA
<213> ORGANISM: Artificial Sequence
<220> FEATURE:
<223> OTHER INFORMATION: Synthetic

<400> SEQUENCE: 174
cgguuccgca gaccacuauu gcuggaguca                                     30

<210> SEQ ID NO 175
<211> LENGTH: 31
<212> TYPE: RNA
<213> ORGANISM: Artificial Sequence
<220> FEATURE:
<223> OTHER INFORMATION: Synthetic

<400> SEQUENCE: 175
ccgguuccgc agaccacuau ugcuggaguc a                                   31
```

<210> SEQ ID NO 176
<211> LENGTH: 31
<212> TYPE: RNA
<213> ORGANISM: Artificial Sequence
<220> FEATURE:
<223> OTHER INFORMATION: Synthetic

<400> SEQUENCE: 176
aggcaguacc acaaggccug caucaugaug g            31

<210> SEQ ID NO 177
<211> LENGTH: 31
<212> TYPE: RNA
<213> ORGANISM: Artificial Sequence
<220> FEATURE:
<223> OTHER INFORMATION: Synthetic

<400> SEQUENCE: 177
caagcacccu aucaggcagg ccacuuugcc u            31

<210> SEQ ID NO 178
<211> LENGTH: 32
<212> TYPE: RNA
<213> ORGANISM: Artificial Sequence
<220> FEATURE:
<223> OTHER INFORMATION: Synthetic

<400> SEQUENCE: 178
cucgcaagca cccuaucagu uacugaacag gc           32

<210> SEQ ID NO 179
<211> LENGTH: 33
<212> TYPE: RNA
<213> ORGANISM: Artificial Sequence
<220> FEATURE:
<223> OTHER INFORMATION: Synthetic

<400> SEQUENCE: 179
ggucuacgag accucccggg cguccccag cga           33

<210> SEQ ID NO 180
<211> LENGTH: 28
<212> TYPE: RNA
<213> ORGANISM: Artificial Sequence
<220> FEATURE:
<223> OTHER INFORMATION: Synthetic

<400> SEQUENCE: 180
ucaucauuaa uuuuugcuug ccauuccc              28

<210> SEQ ID NO 181
<211> LENGTH: 28
<212> TYPE: RNA
<213> ORGANISM: Artificial Sequence
<220> FEATURE:
<223> OTHER INFORMATION: Synthetic

<400> SEQUENCE: 181
aguggaugug augcgggggc ugcugcaa              28

<210> SEQ ID NO 182
<211> LENGTH: 28
<212> TYPE: RNA
<213> ORGANISM: Artificial Sequence
<220> FEATURE:

<223> OTHER INFORMATION: Synthetic

<400> SEQUENCE: 182
acaugaucug uggagggggu cggggcuc                                              28

<210> SEQ ID NO 183
<211> LENGTH: 28
<212> TYPE: RNA
<213> ORGANISM: Artificial Sequence
<220> FEATURE:
<223> OTHER INFORMATION: Synthetic

<400> SEQUENCE: 183
ccugcaaguu gcugucuugg gugcauug                                              28

<210> SEQ ID NO 184
<211> LENGTH: 38
<212> TYPE: RNA
<213> ORGANISM: Artificial Sequence
<220> FEATURE:
<223> OTHER INFORMATION: Synthetic

<400> SEQUENCE: 184
gccagcaguc cagcaugguu ggacaucuuc caggagua                                   38

<210> SEQ ID NO 185
<211> LENGTH: 38
<212> TYPE: RNA
<213> ORGANISM: Artificial Sequence
<220> FEATURE:
<223> OTHER INFORMATION: Synthetic

<400> SEQUENCE: 185
ugccagcagu ccagcauggu gugaaugcag accaaaga                                   38

<210> SEQ ID NO 186
<211> LENGTH: 38
<212> TYPE: RNA
<213> ORGANISM: Artificial Sequence
<220> FEATURE:
<223> OTHER INFORMATION: Synthetic

<400> SEQUENCE: 186
gugccagcag uccagcaugg ugaaugcaga ccaaagaa                                   38

<210> SEQ ID NO 187
<211> LENGTH: 28
<212> TYPE: RNA
<213> ORGANISM: Artificial Sequence
<220> FEATURE:
<223> OTHER INFORMATION: Synthetic

<400> SEQUENCE: 187
cacagacucc cugcuuuugg gggugacc                                              28

<210> SEQ ID NO 188
<211> LENGTH: 27
<212> TYPE: RNA
<213> ORGANISM: Artificial Sequence
<220> FEATURE:
<223> OTHER INFORMATION: Synthetic

<400> SEQUENCE: 188
gcugucuggc ugcuccgcgu ccccggc                                               27

```
<210> SEQ ID NO 189
<211> LENGTH: 27
<212> TYPE: RNA
<213> ORGANISM: Artificial Sequence
<220> FEATURE:
<223> OTHER INFORMATION: Synthetic

<400> SEQUENCE: 189
gggccucagg cugcuccucc ucgugcu                                          27

<210> SEQ ID NO 190
<211> LENGTH: 26
<212> TYPE: RNA
<213> ORGANISM: Artificial Sequence
<220> FEATURE:
<223> OTHER INFORMATION: Synthetic

<400> SEQUENCE: 190
uggcgggggc ggcggcggcg gcggcg                                           26

<210> SEQ ID NO 191
<211> LENGTH: 27
<212> TYPE: RNA
<213> ORGANISM: Artificial Sequence
<220> FEATURE:
<223> OTHER INFORMATION: Synthetic

<400> SEQUENCE: 191
guggcggggg cggcggcggc ggcggcg                                          27

<210> SEQ ID NO 192
<211> LENGTH: 27
<212> TYPE: RNA
<213> ORGANISM: Artificial Sequence
<220> FEATURE:
<223> OTHER INFORMATION: Synthetic

<400> SEQUENCE: 192
gggagcaagc gucccggcu gcuccuc                                           27

<210> SEQ ID NO 193
<211> LENGTH: 38
<212> TYPE: RNA
<213> ORGANISM: Artificial Sequence
<220> FEATURE:
<223> OTHER INFORMATION: Synthetic

<400> SEQUENCE: 193
cacuugcagu guguuauccg gguccuuucu gugcacua                              38

<210> SEQ ID NO 194
<211> LENGTH: 38
<212> TYPE: RNA
<213> ORGANISM: Artificial Sequence
<220> FEATURE:
<223> OTHER INFORMATION: Synthetic

<400> SEQUENCE: 194
caucucagag uguugcuauc aacaggaagg caucaaaa                              38

<210> SEQ ID NO 195
<211> LENGTH: 26
<212> TYPE: RNA
<213> ORGANISM: Artificial Sequence
<220> FEATURE:
<223> OTHER INFORMATION: Synthetic
```

```
<400> SEQUENCE: 195
cgccgccgcc gccgccgccc ccgcca                                         26

<210> SEQ ID NO 196
<211> LENGTH: 26
<212> TYPE: RNA
<213> ORGANISM: Artificial Sequence
<220> FEATURE:
<223> OTHER INFORMATION: Synthetic

<400> SEQUENCE: 196
cagcgccgcc gccgccgccc ccgcca                                         26

<210> SEQ ID NO 197
<211> LENGTH: 38
<212> TYPE: RNA
<213> ORGANISM: Artificial Sequence
<220> FEATURE:
<223> OTHER INFORMATION: Synthetic

<400> SEQUENCE: 197
uuuugaugcc uuccuguugg gauaacacac ugcaagug                            38

<210> SEQ ID NO 198
<211> LENGTH: 38
<212> TYPE: RNA
<213> ORGANISM: Artificial Sequence
<220> FEATURE:
<223> OTHER INFORMATION: Synthetic

<400> SEQUENCE: 198
uagugcacag aaaggaccca uagcaacacu cugagaug                            38

<210> SEQ ID NO 199
<211> LENGTH: 35
<212> TYPE: RNA
<213> ORGANISM: Artificial Sequence
<220> FEATURE:
<223> OTHER INFORMATION: Synthetic

<400> SEQUENCE: 199
ugugccagca guccagcauu gauccggguu uuauc                               35

<210> SEQ ID NO 200
<211> LENGTH: 35
<212> TYPE: RNA
<213> ORGANISM: Artificial Sequence
<220> FEATURE:
<223> OTHER INFORMATION: Synthetic

<400> SEQUENCE: 200
ugugccagca guccagcauu uuuuuuaaa acugu                                35

<210> SEQ ID NO 201
<211> LENGTH: 27
<212> TYPE: RNA
<213> ORGANISM: Artificial Sequence
<220> FEATURE:
<223> OTHER INFORMATION: Synthetic

<400> SEQUENCE: 201
ggggaauggc aagcaaaaaa uggccau                                        27

<210> SEQ ID NO 202
<211> LENGTH: 26
```

```
<212> TYPE: RNA
<213> ORGANISM: Artificial Sequence
<220> FEATURE:
<223> OTHER INFORMATION: Synthetic

<400> SEQUENCE: 202
ucucucugac cccgucucua uaccaa                                           26

<210> SEQ ID NO 203
<211> LENGTH: 27
<212> TYPE: RNA
<213> ORGANISM: Artificial Sequence
<220> FEATURE:
<223> OTHER INFORMATION: Synthetic

<400> SEQUENCE: 203
cucucucuga ccccgucucu auaccaa                                          27

<210> SEQ ID NO 204
<211> LENGTH: 27
<212> TYPE: RNA
<213> ORGANISM: Artificial Sequence
<220> FEATURE:
<223> OTHER INFORMATION: Synthetic

<400> SEQUENCE: 204
cuccgggcgc gggcuccggg gcucggg                                          27

<210> SEQ ID NO 205
<211> LENGTH: 27
<212> TYPE: RNA
<213> ORGANISM: Artificial Sequence
<220> FEATURE:
<223> OTHER INFORMATION: Synthetic

<400> SEQUENCE: 205
uccggcugcg gcuccucccc ggcagcg                                          27

<210> SEQ ID NO 206
<211> LENGTH: 34
<212> TYPE: RNA
<213> ORGANISM: Artificial Sequence
<220> FEATURE:
<223> OTHER INFORMATION: Synthetic

<400> SEQUENCE: 206
ugugccagca guccagcauu ggagccuugc cuug                                  34

<210> SEQ ID NO 207
<211> LENGTH: 38
<212> TYPE: RNA
<213> ORGANISM: Artificial Sequence
<220> FEATURE:
<223> OTHER INFORMATION: Synthetic

<400> SEQUENCE: 207
uacuccugga agauguccac ugaguuuaaa aggcaccc                              38

<210> SEQ ID NO 208
<211> LENGTH: 38
<212> TYPE: RNA
<213> ORGANISM: Artificial Sequence
<220> FEATURE:
<223> OTHER INFORMATION: Synthetic

<400> SEQUENCE: 208
```

-continued ucuuuggucu gcauucacaa ugcuggacug cuggcaca       38

<210> SEQ ID NO 209
<211> LENGTH: 38
<212> TYPE: RNA
<213> ORGANISM: Artificial Sequence
<220> FEATURE:
<223> OTHER INFORMATION: Synthetic

<400> SEQUENCE: 209
uucuuugguc ugcauucacc ugaguuuaaa aggcaccc       38

<210> SEQ ID NO 210
<211> LENGTH: 33
<212> TYPE: RNA
<213> ORGANISM: Artificial Sequence
<220> FEATURE:
<223> OTHER INFORMATION: Synthetic

<400> SEQUENCE: 210
ugugccagca guccagcauu uguuuguaca aga            33

<210> SEQ ID NO 211
<211> LENGTH: 34
<212> TYPE: RNA
<213> ORGANISM: Artificial Sequence
<220> FEATURE:
<223> OTHER INFORMATION: Synthetic

<400> SEQUENCE: 211
ugugccagca guccagcauu uguuuguaca agau           34

<210> SEQ ID NO 212
<211> LENGTH: 33
<212> TYPE: RNA
<213> ORGANISM: Artificial Sequence
<220> FEATURE:
<223> OTHER INFORMATION: Synthetic

<400> SEQUENCE: 212
ugccagcagu ccagcaugga cgggugaggc ggc            33

<210> SEQ ID NO 213
<211> LENGTH: 34
<212> TYPE: RNA
<213> ORGANISM: Artificial Sequence
<220> FEATURE:
<223> OTHER INFORMATION: Synthetic

<400> SEQUENCE: 213
ugccagcagu ccagcaugga cgggugaggc ggcg           34

<210> SEQ ID NO 214
<211> LENGTH: 33
<212> TYPE: RNA
<213> ORGANISM: Artificial Sequence
<220> FEATURE:
<223> OTHER INFORMATION: Synthetic

<400> SEQUENCE: 214
ugccagcagu ccagcauggc agaaggagga ggg            33

<210> SEQ ID NO 215
<211> LENGTH: 34
<212> TYPE: RNA
<213> ORGANISM: Artificial Sequence -continued
<220> FEATURE:
<223> OTHER INFORMATION: Synthetic

<400> SEQUENCE: 215
ugccagcagu ccagcauggc agaaggagga gggc                               34

<210> SEQ ID NO 216
<211> LENGTH: 33
<212> TYPE: RNA
<213> ORGANISM: Artificial Sequence
<220> FEATURE:
<223> OTHER INFORMATION: Synthetic

<400> SEQUENCE: 216
ugccagcagu ccagcaugga ugucuaucag cgc                                33

<210> SEQ ID NO 217
<211> LENGTH: 31
<212> TYPE: RNA
<213> ORGANISM: Artificial Sequence
<220> FEATURE:
<223> OTHER INFORMATION: Synthetic

<400> SEQUENCE: 217
cuacgagacc ucccggggcu uuucgugagc u                                  31

<210> SEQ ID NO 218
<211> LENGTH: 31
<212> TYPE: RNA
<213> ORGANISM: Artificial Sequence
<220> FEATURE:
<223> OTHER INFORMATION: Synthetic

<400> SEQUENCE: 218
cgagaccucc cggggcacug gcacggaaca c                                  31

<210> SEQ ID NO 219
<211> LENGTH: 34
<212> TYPE: RNA
<213> ORGANISM: Artificial Sequence
<220> FEATURE:
<223> OTHER INFORMATION: Synthetic

<400> SEQUENCE: 219
cgcagaccac uauggcucua ccucaaagac cuuu                               34

<210> SEQ ID NO 220
<211> LENGTH: 34
<212> TYPE: RNA
<213> ORGANISM: Artificial Sequence
<220> FEATURE:
<223> OTHER INFORMATION: Synthetic

<400> SEQUENCE: 220
cccggggcac ucgcaagcag auaccuggaa ccac                               34

<210> SEQ ID NO 221
<211> LENGTH: 38
<212> TYPE: RNA
<213> ORGANISM: Artificial Sequence
<220> FEATURE:
<223> OTHER INFORMATION: Synthetic

<400> SEQUENCE: 221
gccagcaguc cagcaugguc ugaguuuaaa aggcaccc                           38

-continued

<210> SEQ ID NO 222
<211> LENGTH: 27
<212> TYPE: RNA
<213> ORGANISM: Artificial Sequence
<220> FEATURE:
<223> OTHER INFORMATION: Synthetic

<400> SEQUENCE: 222
uuuccccaau acugucgug uaaggag         27

<210> SEQ ID NO 223
<211> LENGTH: 24
<212> TYPE: RNA
<213> ORGANISM: Artificial Sequence
<220> FEATURE:
<223> OTHER INFORMATION: Synthetic

<400> SEQUENCE: 223
cuuugcucac ugccacucua auug            24

<210> SEQ ID NO 224
<211> LENGTH: 25
<212> TYPE: RNA
<213> ORGANISM: Artificial Sequence
<220> FEATURE:
<223> OTHER INFORMATION: Synthetic

<400> SEQUENCE: 224
cuuugcucac ugccacucua auugu           25

<210> SEQ ID NO 225
<211> LENGTH: 26
<212> TYPE: RNA
<213> ORGANISM: Artificial Sequence
<220> FEATURE:
<223> OTHER INFORMATION: Synthetic

<400> SEQUENCE: 225
cuuugcucac ugccacucua auguc           26

<210> SEQ ID NO 226
<211> LENGTH: 27
<212> TYPE: RNA
<213> ORGANISM: Artificial Sequence
<220> FEATURE:
<223> OTHER INFORMATION: Synthetic

<400> SEQUENCE: 226
cuuugcucac ugccacucua auguca          27

<210> SEQ ID NO 227
<211> LENGTH: 38
<212> TYPE: RNA
<213> ORGANISM: Artificial Sequence
<220> FEATURE:
<223> OTHER INFORMATION: Synthetic

<400> SEQUENCE: 227
ugccagcagu ccagcaugga ugcuggacug cuggcaca    38

<210> SEQ ID NO 228
<211> LENGTH: 31
<212> TYPE: RNA
<213> ORGANISM: Artificial Sequence
<220> FEATURE:
<223> OTHER INFORMATION: Synthetic -continued

```
<400> SEQUENCE: 228
ugacuccagc aauagugguc ugcggaaccg g                                        31

<210> SEQ ID NO 229
<211> LENGTH: 31
<212> TYPE: RNA
<213> ORGANISM: Artificial Sequence
<220> FEATURE:
<223> OTHER INFORMATION: Synthetic

<400> SEQUENCE: 229
aggcaaagug gccugccuga uagggugcuu g                                        31

<210> SEQ ID NO 230
<211> LENGTH: 32
<212> TYPE: RNA
<213> ORGANISM: Artificial Sequence
<220> FEATURE:
<223> OTHER INFORMATION: Synthetic

<400> SEQUENCE: 230
gccuguucag uaacugauag ggugcuugcg ag                                       32

<210> SEQ ID NO 231
<211> LENGTH: 33
<212> TYPE: RNA
<213> ORGANISM: Artificial Sequence
<220> FEATURE:
<223> OTHER INFORMATION: Synthetic

<400> SEQUENCE: 231
ucgcugggga acgcccggga ggucucguag acc                                      33

<210> SEQ ID NO 232
<211> LENGTH: 28
<212> TYPE: RNA
<213> ORGANISM: Artificial Sequence
<220> FEATURE:
<223> OTHER INFORMATION: Synthetic

<400> SEQUENCE: 232
gggaauggca agcaaaaauu aaugauga                                            28

<210> SEQ ID NO 233
<211> LENGTH: 28
<212> TYPE: RNA
<213> ORGANISM: Artificial Sequence
<220> FEATURE:
<223> OTHER INFORMATION: Synthetic

<400> SEQUENCE: 233
uugcagcagc ccccgcauca cauccacu                                            28

<210> SEQ ID NO 234
<211> LENGTH: 28
<212> TYPE: RNA
<213> ORGANISM: Artificial Sequence
<220> FEATURE:
<223> OTHER INFORMATION: Synthetic

<400> SEQUENCE: 234
gagccccgac ccccuccaca gaucaugu                                            28

<210> SEQ ID NO 235
```

```
<211> LENGTH: 28
<212> TYPE: RNA
<213> ORGANISM: Artificial Sequence
<220> FEATURE:
<223> OTHER INFORMATION: Synthetic

<400> SEQUENCE: 235
caaugcaccc aagacagcaa cuugcagg                                              28

<210> SEQ ID NO 236
<211> LENGTH: 38
<212> TYPE: RNA
<213> ORGANISM: Artificial Sequence
<220> FEATURE:
<223> OTHER INFORMATION: Synthetic

<400> SEQUENCE: 236
uacuccugga agauguccaa ccaugcugga cugcuggc                                   38

<210> SEQ ID NO 237
<211> LENGTH: 38
<212> TYPE: RNA
<213> ORGANISM: Artificial Sequence
<220> FEATURE:
<223> OTHER INFORMATION: Synthetic

<400> SEQUENCE: 237
ucuuuggucu gcauucacac caugcuggac ugcuggca                                   38

<210> SEQ ID NO 238
<211> LENGTH: 38
<212> TYPE: RNA
<213> ORGANISM: Artificial Sequence
<220> FEATURE:
<223> OTHER INFORMATION: Synthetic

<400> SEQUENCE: 238
uucuuugguc ugcauucacc augcuggacu gcuggcac                                   38

<210> SEQ ID NO 239
<211> LENGTH: 28
<212> TYPE: RNA
<213> ORGANISM: Artificial Sequence
<220> FEATURE:
<223> OTHER INFORMATION: Synthetic

<400> SEQUENCE: 239
ggucaccccc aaaagcaggg agucugug                                              28

<210> SEQ ID NO 240
<211> LENGTH: 27
<212> TYPE: RNA
<213> ORGANISM: Artificial Sequence
<220> FEATURE:
<223> OTHER INFORMATION: Synthetic

<400> SEQUENCE: 240
gccggggacg cggagcagcc agacagc                                               27

<210> SEQ ID NO 241
<211> LENGTH: 27
<212> TYPE: RNA
<213> ORGANISM: Artificial Sequence
<220> FEATURE:
<223> OTHER INFORMATION: Synthetic

<400> SEQUENCE: 241
```

```
agcacgagga ggagcagccu gaggccc                                27
```

<210> SEQ ID NO 242
<211> LENGTH: 27
<212> TYPE: RNA
<213> ORGANISM: Artificial Sequence
<220> FEATURE:
<223> OTHER INFORMATION: Synthetic

<400> SEQUENCE: 242

```
cgccgccgcc gccgccgccc ccgccac                                27
```

<210> SEQ ID NO 243
<211> LENGTH: 27
<212> TYPE: RNA
<213> ORGANISM: Artificial Sequence
<220> FEATURE:
<223> OTHER INFORMATION: Synthetic

<400> SEQUENCE: 243

```
gaggagcagc cggggacgcu ugcuccc                                27
```

<210> SEQ ID NO 244
<211> LENGTH: 38
<212> TYPE: RNA
<213> ORGANISM: Artificial Sequence
<220> FEATURE:
<223> OTHER INFORMATION: Synthetic

<400> SEQUENCE: 244

```
uagugcacag aaaggacccg gauaacacac ugcaagug                    38
```

<210> SEQ ID NO 245
<211> LENGTH: 38
<212> TYPE: RNA
<213> ORGANISM: Artificial Sequence
<220> FEATURE:
<223> OTHER INFORMATION: Synthetic

<400> SEQUENCE: 245

```
uuuugaugcc uuccuguuga uagcaacacu cugagaug                    38
```

<210> SEQ ID NO 246
<211> LENGTH: 26
<212> TYPE: RNA
<213> ORGANISM: Artificial Sequence
<220> FEATURE:
<223> OTHER INFORMATION: Synthetic

<400> SEQUENCE: 246

```
uggcgggggc ggcggcggcg gcgcug                                 26
```

<210> SEQ ID NO 247
<211> LENGTH: 38
<212> TYPE: RNA
<213> ORGANISM: Artificial Sequence
<220> FEATURE:
<223> OTHER INFORMATION: Synthetic

<400> SEQUENCE: 247

```
cacuugcagu guguuauccc aacaggaagg caucaaaa                    38
```

<210> SEQ ID NO 248
<211> LENGTH: 38
<212> TYPE: RNA

```
<213> ORGANISM: Artificial Sequence
<220> FEATURE:
<223> OTHER INFORMATION: Synthetic

<400> SEQUENCE: 248
caucucagag uguugcuaug gguccuuucu gugcacua                                    38

<210> SEQ ID NO 249
<211> LENGTH: 35
<212> TYPE: RNA
<213> ORGANISM: Artificial Sequence
<220> FEATURE:
<223> OTHER INFORMATION: Synthetic

<400> SEQUENCE: 249
gauaaaaccc ggaucaaugc uggacugcug gcaca                                      35

<210> SEQ ID NO 250
<211> LENGTH: 35
<212> TYPE: RNA
<213> ORGANISM: Artificial Sequence
<220> FEATURE:
<223> OTHER INFORMATION: Synthetic

<400> SEQUENCE: 250
acaguuuuaa aaaaaaaugc uggacugcug gcaca                                      35

<210> SEQ ID NO 251
<211> LENGTH: 27
<212> TYPE: RNA
<213> ORGANISM: Artificial Sequence
<220> FEATURE:
<223> OTHER INFORMATION: Synthetic

<400> SEQUENCE: 251
auggccauuu uuugcuugcc auucccc                                               27

<210> SEQ ID NO 252
<211> LENGTH: 26
<212> TYPE: RNA
<213> ORGANISM: Artificial Sequence
<220> FEATURE:
<223> OTHER INFORMATION: Synthetic

<400> SEQUENCE: 252
uugguauaga dacgggguca gagaga                                                26

<210> SEQ ID NO 253
<211> LENGTH: 27
<212> TYPE: RNA
<213> ORGANISM: Artificial Sequence
<220> FEATURE:
<223> OTHER INFORMATION: Synthetic

<400> SEQUENCE: 253
uugguauaga gacgggguca gagagag                                               27

<210> SEQ ID NO 254
<211> LENGTH: 27
<212> TYPE: RNA
<213> ORGANISM: Artificial Sequence
<220> FEATURE:
<223> OTHER INFORMATION: Synthetic

<400> SEQUENCE: 254
cccgagcccc ggagcccgcg cccggag                                               27
```

<210> SEQ ID NO 255
<211> LENGTH: 27
<212> TYPE: RNA
<213> ORGANISM: Artificial Sequence
<220> FEATURE:
<223> OTHER INFORMATION: Synthetic

<400> SEQUENCE: 255
cgcugccggg gaggagccgc agccgga                                        27

<210> SEQ ID NO 256
<211> LENGTH: 34
<212> TYPE: RNA
<213> ORGANISM: Artificial Sequence
<220> FEATURE:
<223> OTHER INFORMATION: Synthetic

<400> SEQUENCE: 256
caaggcaagg cuccaaugcu ggacugcugg caca                                34

<210> SEQ ID NO 257
<211> LENGTH: 38
<212> TYPE: RNA
<213> ORGANISM: Artificial Sequence
<220> FEATURE:
<223> OTHER INFORMATION: Synthetic

<400> SEQUENCE: 257
gggugccuuu uaaacucagu ggacaucuuc caggagua                            38

<210> SEQ ID NO 258
<211> LENGTH: 38
<212> TYPE: RNA
<213> ORGANISM: Artificial Sequence
<220> FEATURE:
<223> OTHER INFORMATION: Synthetic

<400> SEQUENCE: 258
ugugccagca guccagcauu gugaaugcag accaaaga                            38

<210> SEQ ID NO 259
<211> LENGTH: 38
<212> TYPE: RNA
<213> ORGANISM: Artificial Sequence
<220> FEATURE:
<223> OTHER INFORMATION: Synthetic

<400> SEQUENCE: 259
gggugccuuu uaaacucagg ugaaugcaga ccaaagaa                            38

<210> SEQ ID NO 260
<211> LENGTH: 33
<212> TYPE: RNA
<213> ORGANISM: Artificial Sequence
<220> FEATURE:
<223> OTHER INFORMATION: Synthetic

<400> SEQUENCE: 260
ucuuguacaa acaaaugcug gacugcuggc aca                                 33

<210> SEQ ID NO 261
<211> LENGTH: 34
<212> TYPE: RNA
<213> ORGANISM: Artificial Sequence
<220> FEATURE:

```
<223> OTHER INFORMATION: Synthetic

<400> SEQUENCE: 261
aucuuguaca aacaaaugcu ggacugcugg caca                                  34

<210> SEQ ID NO 262
<211> LENGTH: 33
<212> TYPE: RNA
<213> ORGANISM: Artificial Sequence
<220> FEATURE:
<223> OTHER INFORMATION: Synthetic

<400> SEQUENCE: 262
gccgccucac ccguccaugc uggacugcug gca                                   33

<210> SEQ ID NO 263
<211> LENGTH: 34
<212> TYPE: RNA
<213> ORGANISM: Artificial Sequence
<220> FEATURE:
<223> OTHER INFORMATION: Synthetic

<400> SEQUENCE: 263
cgccgccuca cccguccaug cuggacugcu ggca                                  34

<210> SEQ ID NO 264
<211> LENGTH: 33
<212> TYPE: RNA
<213> ORGANISM: Artificial Sequence
<220> FEATURE:
<223> OTHER INFORMATION: Synthetic

<400> SEQUENCE: 264
cccuccuccu ucugccaugc uggacugcug gca                                   33

<210> SEQ ID NO 265
<211> LENGTH: 34
<212> TYPE: RNA
<213> ORGANISM: Artificial Sequence
<220> FEATURE:
<223> OTHER INFORMATION: Synthetic

<400> SEQUENCE: 265
gcccuccucc uucugccaug cuggacugcu ggca                                  34

<210> SEQ ID NO 266
<211> LENGTH: 33
<212> TYPE: RNA
<213> ORGANISM: Artificial Sequence
<220> FEATURE:
<223> OTHER INFORMATION: Synthetic

<400> SEQUENCE: 266
gcgcugauag acauccaugc uggacugcug gca                                   33

<210> SEQ ID NO 267
<211> LENGTH: 19
<212> TYPE: RNA
<213> ORGANISM: Artificial Sequence
<220> FEATURE:
<223> OTHER INFORMATION: Synthetic

<400> SEQUENCE: 267
ucucccgcgg guuggugga                                                   19
```

```
<210> SEQ ID NO 268
<211> LENGTH: 19
<212> TYPE: RNA
<213> ORGANISM: Artificial Sequence
<220> FEATURE:
<223> OTHER INFORMATION: Synthetic

<400> SEQUENCE: 268
aaggccugca ucaugaugg                                                     19

<210> SEQ ID NO 269
<211> LENGTH: 19
<212> TYPE: RNA
<213> ORGANISM: Artificial Sequence
<220> FEATURE:
<223> OTHER INFORMATION: Synthetic

<400> SEQUENCE: 269
accacuauug cuggaguca                                                     19

<210> SEQ ID NO 270
<211> LENGTH: 19
<212> TYPE: RNA
<213> ORGANISM: Artificial Sequence
<220> FEATURE:
<223> OTHER INFORMATION: Synthetic

<400> SEQUENCE: 270
cugaguuuaa aaggcaccc                                                     19
```